US008980890B2

(12) United States Patent
Hangauer, Jr.

(10) Patent No.: US 8,980,890 B2
(45) Date of Patent: *Mar. 17, 2015

(54) COMPOSITIONS AND METHODS OF TREATING CELL PROLIFERATION DISORDERS

(75) Inventor: David G. Hangauer, Jr., Lancaster, NY (US)

(73) Assignee: Kinex Pharmaceuticals, LLC, Buffalo, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/950,764

(22) Filed: Nov. 19, 2010

(65) Prior Publication Data

US 2011/0065705 A1   Mar. 17, 2011

Related U.S. Application Data

(63) Continuation of application No. 11/796,200, filed on Apr. 26, 2007, which is a continuation of application No. 11/321,419, filed on Dec. 28, 2005, now Pat. No. 7,300,931.

(60) Provisional application No. 60/639,834, filed on Dec. 28, 2004, provisional application No. 60/704,551, filed on Aug. 1, 2005, provisional application No. 60/727,341, filed on Oct. 17, 2005.

(51) Int. Cl.
| | |
|---|---|
| C07D 213/56 | (2006.01) |
| C07D 213/61 | (2006.01) |
| C07D 213/64 | (2006.01) |
| C07D 213/89 | (2006.01) |
| C07D 239/26 | (2006.01) |
| C07D 239/30 | (2006.01) |
| C07D 401/12 | (2006.01) |
| C07D 403/04 | (2006.01) |
| A61K 31/4418 | (2006.01) |
| A61K 31/4545 | (2006.01) |
| A61K 31/496 | (2006.01) |
| A61K 31/506 | (2006.01) |
| A61K 31/5377 | (2006.01) |
| C07C 233/13 | (2006.01) |
| C07C 233/22 | (2006.01) |
| C07D 213/74 | (2006.01) |
| C07D 239/34 | (2006.01) |

(52) U.S. Cl.
CPC .......... *C07D 213/56* (2013.01); *C07C 233/13* (2013.01); *C07C 233/22* (2013.01); *C07D 213/64* (2013.01); *C07D 213/74* (2013.01); *C07D 213/89* (2013.01); *C07D 239/26* (2013.01); *C07D 239/34* (2013.01); *C07D 401/12* (2013.01); *C07D 403/04* (2013.01)
USPC ............... 514/235.5; 514/235.8; 514/252.14; 514/253.12; 514/318; 514/357; 544/122; 544/123; 544/131; 544/295; 544/360; 546/194; 546/329

(58) Field of Classification Search
USPC ................ 544/360, 361, 124, 131, 295, 357; 514/253.01, 235.5, 252.14, 318, 357; 546/194, 337
See application file for complete search history.

(56) References Cited

U.S. PATENT DOCUMENTS

| | | | |
|---|---|---|---|
| 3,761,477 A | 9/1973 | Schwartz et al. | |
| 3,868,380 A | 2/1975 | Molteni et al. | |
| 4,010,279 A | 3/1977 | Griss et al. | |
| 5,827,887 A | 10/1998 | Gourvest et al. | |
| 5,849,912 A | 12/1998 | Akasaka et al. | |
| 6,538,960 B1 | 3/2003 | Sabi et al. | |
| 6,624,180 B2 | 9/2003 | South et al. | |
| 6,844,367 B1 | 1/2005 | Zhu et al. | |
| 6,969,726 B2 | 11/2005 | Lou et al. | |
| 7,300,931 B2* | 11/2007 | Hangauer, Jr. ............. | 514/235.5 |
| 7,312,227 B2 | 12/2007 | Ledeboer et al. | |
| 7,521,461 B2 | 4/2009 | Li | |
| 7,851,470 B2 | 12/2010 | Hangauer, Jr. et al. | |
| 7,935,697 B2 | 5/2011 | Hangauer, Jr. et al. | |
| 7,939,529 B2 | 5/2011 | Hangauer, Jr. et al. | |
| 7,968,574 B2* | 6/2011 | Hangauer, Jr. ................ | 514/357 |
| 8,236,799 B2 | 8/2012 | Hangauer, Jr. | |
| 8,293,739 B2* | 10/2012 | Hangauer et al. .......... | 514/235.2 |
| 8,309,549 B2* | 11/2012 | Hangauer et al. .......... | 514/235.5 |
| 2004/0039048 A1 | 2/2004 | Guzman Pastor et al. | |
| 2004/0242572 A1 | 12/2004 | Stenkamp et al. | |
| 2005/0059713 A1 | 3/2005 | Mjalli et al. | |
| 2005/0096337 A1* | 5/2005 | Ackermann et al. .......... | 514/277 |
| 2006/0058553 A1 | 3/2006 | Leahy et al. | |
| 2006/0160800 A1 | 7/2006 | Hangauer | |

(Continued)

FOREIGN PATENT DOCUMENTS

| | | |
|---|---|---|
| EP | 0463638 A1 | 1/1992 |
| JP | 62252755 A | 11/1987 |

(Continued)

OTHER PUBLICATIONS

An et al., "Oxidation of N-Benzylaldimines to N-Benzylamides by MCPBA and $BF_3OEt_2$", *Synlett*, 6:876-878 (2003).
Byrn et al., "Hydrates and Solvates", in *Solid-State Chemistry of Drugs*, 2nd Ed., SSCI, Inc., West Lafayette, IN, Ch. 11, pp. 233-247 (1999).
Cain et al., "Potential Antitumor Agents. IX. Bisquaternary Salts", *J. Med. Chem.*, 11(5):963-966 (1968).
Davidson et al., "Discovery and Characterization of a Substrate Selective p38α Inhibitor", *Biochemistry*, 43:11658-11671 (2004).
Duong et al., "Inhibition of Osteoclast Function by Adenovirus Expressing Antisense Protein-tyrosine Kinase 2", *J. Biol. Chem.*, 276(10):7484-7492 (2001).

(Continued)

*Primary Examiner* — Alicia L Otton
(74) *Attorney, Agent, or Firm* — Cooley LLP; Ivor R. Elrifi; Heidi A. Erlacher

(57) ABSTRACT

The invention relates to compounds and methods for treating cell proliferation disorders.

16 Claims, No Drawings

(56) References Cited

U.S. PATENT DOCUMENTS

| | | |
|---|---|---|
| 2007/0015752 A1 | 1/2007 | Hangauer, Jr. |
| 2010/0210649 A1 | 8/2010 | Djaballah et al. |
| 2010/0249130 A1 | 9/2010 | Hangauer, Jr. |
| 2011/0281872 A1* | 11/2011 | Hangauer et al. .......... 514/235.8 |

FOREIGN PATENT DOCUMENTS

| | | |
|---|---|---|
| JP | 2002020362 A | 1/2002 |
| JP | 2003231633 A | 8/2003 |
| JP | 2006510737 A | 3/2006 |
| WO | WO-9204315 A1 | 3/1992 |
| WO | WO-9219208 A1 | 11/1992 |
| WO | WO-9220645 A1 | 11/1992 |
| WO | WO 94/10105 | 5/1994 |
| WO | WO-9427949 A1 | 12/1994 |
| WO | WO-9612473 A1 | 5/1996 |
| WO | WO 98/21185 * | 5/1998 |
| WO | WO-9901127 A1 | 1/1999 |
| WO | WO-0119788 A2 | 3/2001 |
| WO | WO-0156974 A2 | 8/2001 |
| WO | WO-0185726 A1 | 11/2001 |
| WO | WO-0196307 A2 | 12/2001 |
| WO | WO-0198245 A2 | 12/2001 |
| WO | WO-02079197 A1 | 10/2002 |
| WO | WO-03059903 A2 | 7/2003 |
| WO | WO-03066579 A2 | 8/2003 |
| WO | WO-03076406 A1 | 9/2003 |
| WO | WO-03078404 A1 | 9/2003 |
| WO | WO-03087057 A1 | 10/2003 |
| WO | WO-03093248 A1 | 11/2003 |
| WO | WO-03093297 A2 | 11/2003 |
| WO | WO-03099771 A2 | 12/2003 |
| WO | WO-04000295 A1 | 12/2003 |
| WO | WO-2004/011456 A1 | 2/2004 |
| WO | WO-2004011427 A2 | 2/2004 |
| WO | WO-2004014279 A2 | 2/2004 |
| WO | WO-2004024702 A2 | 3/2004 |
| WO | WO-2004041789 A1 | 5/2004 |
| WO | WO-2004043925 A2 | 5/2004 |
| WO | WO-2004056774 A2 | 7/2004 |
| WO | WO-2005013914 A2 | 2/2005 |
| WO | WO-2005032493 A2 | 4/2005 |
| WO | WO-2005097750 A1 | 10/2005 |
| WO | WO-2006071960 A2 | 7/2006 |
| WO | WO-207026920 A2 | 3/2007 |
| WO | WO-2007095383 A2 | 8/2007 |
| WO | WO-2007136790 A2 | 11/2007 |
| WO | WO-2008/002676 A2 | 1/2008 |
| WO | WO-2008127727 A1 | 10/2008 |
| WO | WO-2008127728 A1 | 10/2008 |

OTHER PUBLICATIONS

Frame, M.C., "Src in cancer: deregulation and consequences for cell behaviour", Biochem. Biophys. Acta, 1602:114-130 (2002).
Garrido et al., "Synthesis of N,N'-Diacyl-1,2-di-(4-pyridyl)ethylenediamines", J. Het. Chem., 18:1305-1308 (1981).
Golub et al., "Molecular Classification of Cancer: Class Discovery and Class Prediction by Gene Expression Monitoring", Science, 286:531-537 (1999).
Guo et al., "Tyrosine Phosphorylation of the NR2B Subunit of the NMDA Receptor in the Spinal Cord during the Development and Maintenance of Inflammatory Hyperalgesia", J. Neurosci., 22(14):6208-6217 (2002).
Hadjeri et al., "Antimitotic Activity of 5-Hydroxy-7-methoxy-2-phenyl-4-quinolones", J. Med. Chem., 47:4964-4970 (2004).
Honma et al., "Antiallergic Agents. 2.[1] N-(1H-Tetrazol-5-yl)-6-phenyl-2-pyridinecarboxamides", J. Med. Chem., 26:1499-1504 (1983).
Huff, J.R., "HIV Protease: A Novel Chemotherapeutic Target for AIDS", J. Med. Chem., 34(8):2305-2314 (1991).
Lala et al., "Role of nitric oxide in tumor progression: Lessons from experimental tumors", Cancer Metastasis Rev., 17(1):91-106 (1998).

Liechti et al., "Salicylanilides as inhibitors of the protein tyrosine kinase epidermal growth factor receptor", Eur. J. Med. Chem., 39(1):11-26 (2004).
Million et al., "Inhibition of the EGF-Stimulated Cellular Proliferation of ER 22 Cells by Hydroxybiphenyl Derivatives", J. Med. Chem., 38(23):4693-4703 (1995).
Miyazaki et al., "Src Kinase Activity is Essential for Osteoclast Function", J. Biol. Chem., 279(17):17660-17666 (2004).
Parang et al., "Recent advances in the discovery of Src kinase inhibitors", Expert Opin. Ther. Patents, 15(9):1183-1207 (2005).
Paul et al., "Src deficiency or blockade of Src activity in mice provides cerebral protection following stroke", Nat. Med., 7(2):222-227 (2001).
Rouhi, A.M., "The Right Stuff: From research and development to the clinic, getting drug crystals right is full of pitfalls", Chem. Eng. News, pp. 32-35 (2003).
U.S. Pharmacopia #23, National Formulary #18, pp. 1843-1844 (1995).
Yu et al., "Src, a molecular switch governing gain control of synaptic transmission mediated by N-methyl-D-aspartate receptors", Proc. Natl. Acad. Sci. USA, 96:7697-7704 (1999).
Zhang et al., "Design, synthesis, and SAR of anthranilamide-based factor Xa inhibitors incorporating substituted biphenyl P4 motifs", Bioorg. Med. Chem. Lett., 14(4):983-987 (2004).
Croteau et al., "Adults with Newly Diagnosed High-Grade Gliomas", Current Treatment Options in Oncology, 2:507-515 (2001).
Han, J., "Advances in Characterization of Pharmaceutical Hydrates", Trends in Bio/Pharmaceutical Industry, 3:25-29 (2006).
Planas-Silva et al., "Targeting c-Src Kinase Enhances Tamoxifen's Inhibitory Effect on Cell Growth by Modulating Expression of Cell Cycle and Survival Proteins", Cancer Chemotherapy Pharmacol., 60(4):535-543 (2006).
Stella et al., "Prodrugs: Challenges and Rewards, Part 1", Biotechnology: Pharmaceutical Aspects, p. 24 (2007).
Vippagunta et al., "Crystalline Solids", Advances Drug Delivery Reviews, 48:3-26 (2001).
Backes et al. "Carbon-Carbon Bond-Forming Methods on Solid Support." J. Am. Chem. Soc. 116.24(1994):11171-11172.
Blessington et al. "Chromatographic Approaches to the Quality Control of Chiral Propionate Anti-Inflammatory Drugs and Herbicides." J. Chromatog. A 469(1989):183-190.
Satoh et al. "An Efficient Synthesis of 4-Aryl-2,6-di-tert-butylphenols by a Palladium-Catalyzed Cross-Coupling Reaction." Synthesis. 11(1994):1146-1148.
Satoh et al. "Comparison of the Inhibitory Action of Synthetic Capsaicin Analogues with Various NADH-ubiquinone Oxidoreductases." Biochim. Biophys. Acta. 1273.1(1996):21-30.
Van Overbeke et al. "Comparative Study on the Enantiomeric Separation of Several Non-Steroidal Anti-Inflammatory Drugs on Two Cellulose-Based Chiral Stationary Phases." J. Liquid Chromatog. 18.12(1995):2427-2443.
Masood et al. "A Convenient Synthesis of Sendaverine." Synth. Commun. 10.7(1980):541-544.
Boschelli et al. "Optimization of 4-Phenylamino-3-quinolinecarbonitriles as Potent Inhibitors of Src Kinase Activity." J. Med. Chem. 44.23(2001):3965-3977.
Cassinelli et al. "Inhibition of c-Met and Prevention of Spontaneous Metastatic Spreading by the 2-indolinone RPI-1." Mol. Cancer Ther. 5.9(2006):2388-2397.
Maeda et al. CAS: 141:199479, 2004.
Pevarello et al. CAS: 141:81703, 2004.
Priego et al. "Natural Polyphenols Facilitate Elimination of HT-29 Colorectal Cancer Xenografts by Chemoradiotherapy: A Bcl-2- and Superoxide Dismutase 2-Dependent Mechanism." Mol. Cancer Ther. 7.10(2008):3330-3342.
Salehi et al. "Facile Conversion of Alcohols into N-Substituted Amides by Magnesium Hydrogensulfate under Hetergenous Conditions." Synth. Commun. 31.13(2001):1947-1951.
Smith et al. CAS: 146:229329, 2007.

* cited by examiner

COMPOSITIONS AND METHODS OF TREATING CELL PROLIFERATION DISORDERS

RELATED APPLICATIONS

This application is a continuation of U.S. Ser. No. 11/796,200, filed Apr. 26, 2007, allowed, which is a continuation of U.S. Ser. No. 11/321,419, now U.S. Pat. No. 7,300,931, filed on Dec. 28, 2005, which claims priority to provisional patent applications U.S. Ser. No. 60/693,834, filed on Dec. 28, 2004, U.S. Ser. No. 60/704,551, filed on Aug. 1, 2005, and U.S. Ser. No. 60/727,341, filed on Oct. 17, 2005, each of which is incorporated herein by reference in its entirety.

BACKGROUND OF THE INVENTION

With more than 563,000 deaths in the United States annually, cancer is the second leading cause of death behind heart disease (UBS Warburg "Disease Dynamics: The Cancer Market," Nov. 8, 2000). Surgery and radiotherapy may be curative if the disease is found early, but current drug therapies for metastatic disease are mostly palliative and seldom offer a long-term cure. Even with the new chemotherapies entering the market, improvement in patient survival is measured in months rather than in years, and the need continues for new drugs effective both in combination with existing agents as first line therapy and as second and third line therapies in treatment of resistant tumors.

A need remains in the art for improved cell proliferation disorder and cancer treatments.

SUMMARY OF THE INVENTION

The invention relates to compounds and methods of using the compounds to treat cell proliferation disorders.

The compounds of the present invention are useful as pharmaceutical agents. For example the compounds may be useful as anti-proliferative agents, for treating mammals, such as for treating humans and animals. The compounds may be used without limitation, for example, as anti-cancer, anti-angiogenesis, anti-metastatic, anti-microbial, anti-bacterial, anti-fungal, anti-parasitic and/or anti-viral agents. The compounds of the invention are useful, for example, in treating lung cancer. The compounds of the invention are also useful, for example, in treating colon cancer. The compounds of the invention are also useful, for example, in treating breast cancer.

The compounds of the invention are useful in treating diseases and disorders that are modulated by tyrosine kinase inhibition. For example, the compounds of the invention are useful in treating diseases and disorders that are modulated by Src kinase. The compounds of the invention may also be useful in treating diseases and disorders that are modulated by focal adhesion kinase (FAK).

Compounds of the invention include compounds of Formula I, and salts, solvates, hydrates, or prodrugs thereof:

Formula I

T is absent (i.e., the rings are connected by a bond), $CR_{12}R_{13}$, $C(O)$, $O$, $S$, $S(O)$, $S(O)_2$, $NR_{14}$, $C(R_{15}R_{16})C(R_{17}R_{18})$, $CH_2O$, or $OCH_2$;

$X_y$ is CZ, CY, N, or N—O;
$X_z$ is CZ, CY, N, or N—O;
at least one of $X_y$ and $X_z$ is CZ;

Y is selected from hydrogen, hydroxyl, halogen, lower ($C_1$, $C_2$, $C_3$, $C_4$, $C_5$, or $C_6$) alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, and O-benzyl;

$X_a$ is $CR_a$, N, or N—O;
$X_b$ is $CR_b$, N, or N—O;
$X_c$ is $CR_c$, N, or N—O;
$X_d$ is $CR_d$, N, or N—O;
$X_e$ is $CR_e$, N, or N—O;

$R_a$, $R_b$, $R_c$, $R_d$, $R_e$, $R_4$, $R_5$, and $R_6$ are, independently, hydrogen, hydroxyl, halogen, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, $C_1$, $C_2$, $C_3$, $C_4$, $C_5$, or $C_6$ alkyl-O-lower ($C_1$, $C_2$, $C_3$, $C_4$, $C_5$, or $C_6$) alkyl, COOH, COO-lower ($C_1$, $C_2$, $C_3$, $C_4$, $C_5$, or $C_6$) alkyl, $SO_2H$, $SO_2$-lower ($C_1$, $C_2$, $C_3$, $C_4$, $C_5$, or $C_6$) alkyl, or where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl;

V is a bond, —$CH_2$—, —$CH_2CH_2$—, —$CH_2CH_2CH_2$—, —O—$CH_2$—, —$OCH_2CH_2$— or —$OCH_2CH_2CH_2$—;

$R_{12}$, $R_{13}$, $R_{14}$, $R_{15}$, $R_{16}$, $R_{17}$, and $R_{18}$, are, independently, H or $C_1$, $C_2$, $C_3$, $C_4$, $C_5$, or $C_6$ alkyl;

Z is: $(CHR_1)_n$—$C(O)$—$NR_2(CHR_3)_m$—Ar, where Ar is a substituted or unsubstituted aryl or nitrogen-containing heteroaryl group, such as benzene, pyridine, or pyrimidine. For example, Z is;

-continued

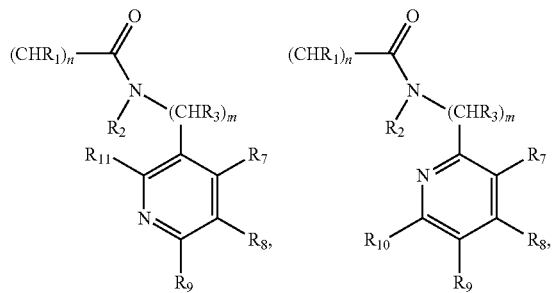

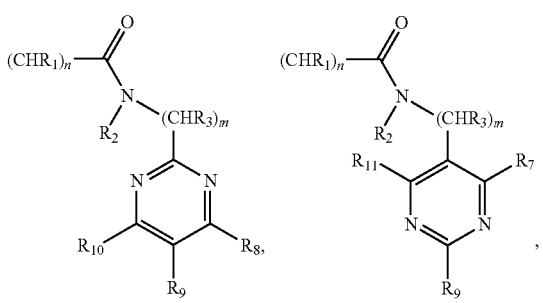

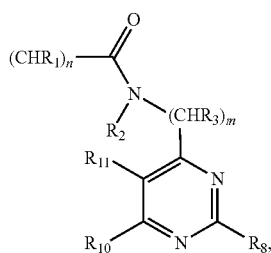

where

R$_1$, R$_2$, and R$_3$ are independently H or C$_1$, C$_2$, C$_3$, C$_4$, C$_5$, or C$_6$ alkyl;

n and m are, independently 0, 1, or 2;

R$_7$, R$_8$, R$_9$, R$_{10}$, and R$_{11}$ are, independently, hydrogen, hydroxyl, halogen, C$_1$, C$_2$, C$_3$, C$_4$, C$_5$, or C$_6$ alkyl, C$_1$, C$_2$, C$_3$, C$_4$, C$_5$, or C$_6$ alkoxy, O-lower (C$_1$, C$_2$, C$_3$, C$_4$, C$_5$, or C$_6$) alkyl-aryl, O-benzyl, C$_1$, C$_2$, C$_3$, C$_4$, C$_5$, or C$_6$ alkyl-OH, C$_1$, C$_2$, C$_3$, C$_4$, C$_5$, or C$_6$ alkyl-O—C$_1$, C$_2$, C$_3$, C$_4$, C$_5$, or C$_6$ alkyl,

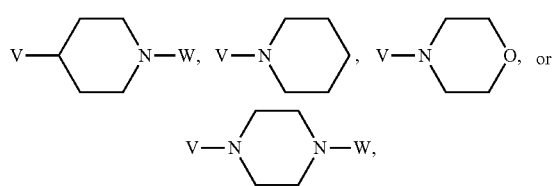

where W is H, or C$_1$, C$_2$, C$_3$, C$_4$, C$_5$, or C$_6$ alkyl, C$_1$, C$_2$, C$_3$, C$_4$, C$_5$, or C$_6$ alkyl-aryl;

V is a bond, —CH$_2$—, —CH$_2$CH$_2$—, —CH$_2$CH$_2$CH$_2$—, —O—CH$_2$—, —OCH$_2$CH$_2$—, or —OCH$_2$CH$_2$CH$_2$—.

In certain compounds of the invention, Z is

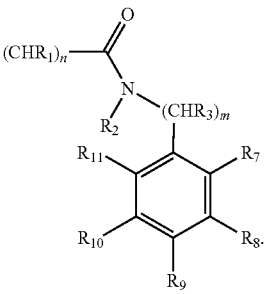

Certain compounds of the invention are selected from Compounds 1-136 and 137. For example, the compound of the invention is Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, or 137.

Compounds of the invention include Compounds 33, 38, 40, 76, 133, 134, 136 and 137.

In certain Compounds of Formula I, at least one of X$_a$, X$_b$, X$_c$, X$_d$ and X$_e$ is N.

For example, in the compound of Formula I, X$_a$ is N and each of X$_b$, X$_c$, X$_d$ and X$_e$ is CR.

In certain compounds of Formula I, X$_y$ is CY, and X$_z$ is CZ.

For example, in certain compounds of Formula I, Y is hydrogen.

In certain compounds of Formula I, R$_b$ is C$_1$, C$_2$, C$_3$, C$_4$, C$_5$, or C$_6$ alkoxy. For example, R$_b$ is methoxy or ethoxy. In certain compounds of Formula I, R$_b$ is hydrogen. In other compounds of Formula I, R$_b$ is selected from F, Cl, Br, and I.

In other compounds of Formula I, R$_b$ is

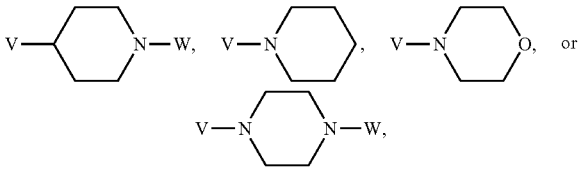

where W is H, or C$_1$, C$_2$, C$_3$, C$_4$, C$_5$, or C$_6$ alkyl, C$_1$, C$_2$, C$_3$, C$_4$, C$_5$, or C$_6$ alkyl-aryl; and V is a bond, —CH$_2$—, —CH$_2$CH$_2$—, —CH$_2$CH$_2$CH$_2$—, —O—CH$_2$—, —OCH$_2$CH$_2$— or —OCH$_2$CH$_2$CH$_2$—. For example, V is a bond. In certain compounds of Formula I, W is hydrogen. In other compounds of Formula I, W is C$_1$, C$_2$, C$_3$, C$_4$, C$_5$, or C$_6$ alkyl.

In certain compounds of Formula I, R$_c$ is C$_1$, C$_2$, C$_3$, C$_4$, C$_5$, or C$_6$ alkoxy. For example, R$_c$ is methoxy or ethoxy. In other compounds of Formula I, R$_c$ is hydrogen, F, Cl, Br, or I.

In other compounds of Formula I, R$_c$ is

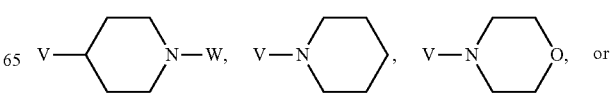

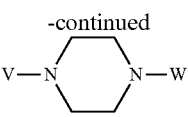

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl; and V is a bond, —$CH_2$—, —$CH_2CH_2$—, —$CH_2CH_2CH_2$—, —O—$CH_2$—, —$OCH_2CH_2$— or —$OCH_2CH_2CH_2$—.

For example, V is a bond. In certain compounds of Formula I, W is hydrogen. In other compounds of Formula I, W is $C_1$, $C_2$, $C_3$, $C_4$, $C_5$, or $C_6$ alkyl.

In certain compounds of Formula I, $R_d$ is $C_1$, $C_2$, $C_3$, $C_4$, $C_5$, or $C_6$ alkoxy. For example, $R_d$ is methoxy or ethoxy. In other compounds of Formula I, $R_d$ is hydrogen, F, Cl, Br, or I.

In other compounds of Formula I, $R_d$ is

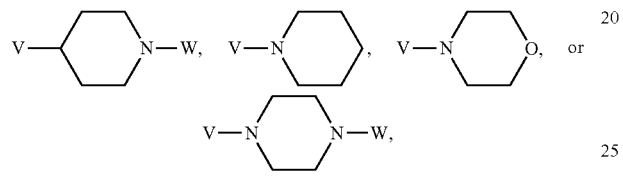

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl; and V is a bond, —$CH_2$—, —$CH_2CH_2$—, —$CH_2CH_2CH_2$—, —O—$CH_2$—, —$OCH_2CH_2$— or —$OCH_2CH_2CH_2$—.

For example, V is a bond. In certain compounds of Formula I, W is hydrogen. In other compounds of Formula I, W is $C_1$, $C_2$, $C_3$, $C_4$, $C_5$, or $C_6$ alkyl.

The invention includes a solvate of a compound according to Formula I.

The invention also includes a hydrate of a compound according to Formula I.

The invention also includes an acid addition salt of a compound according to Formula I. For example, a hydrochloride salt.

The invention also includes a prodrug of a compound according to Formula I.

The invention also includes a pharmaceutically acceptable salt of a compound of Formula I.

The invention also includes a composition of a compound according to Formula I and at least one pharmaceutically acceptable excipient.

The invention relates to a compound of Formula I, having a structure according to one of Formulae II-XIII:

Formula II:

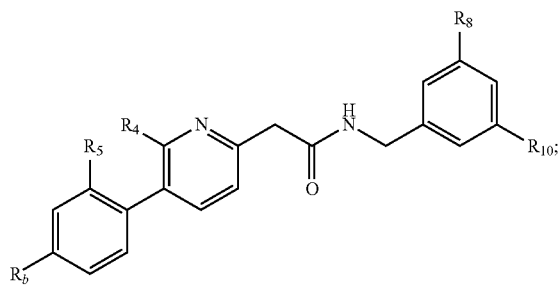

Formula III:

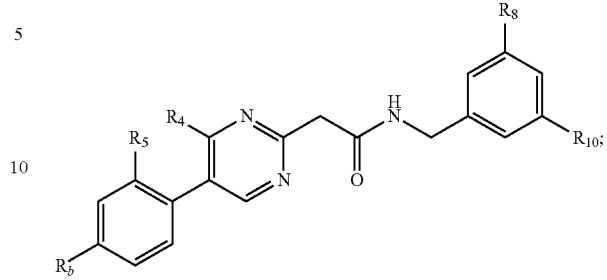

Formula IV:

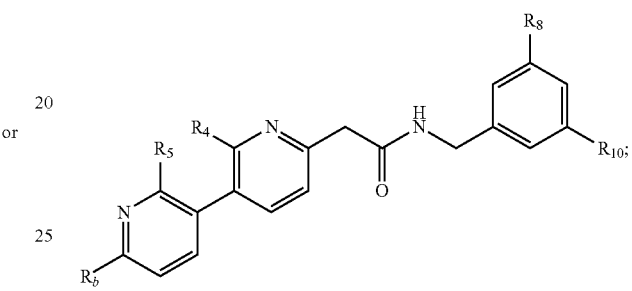

Formula V:

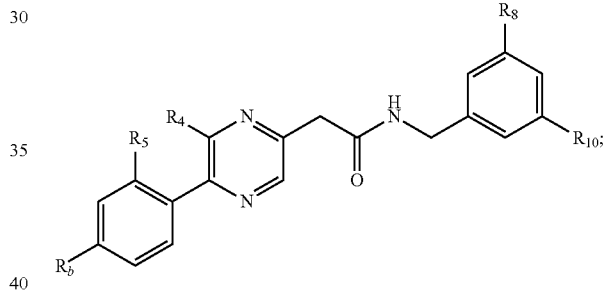

Formula VI:

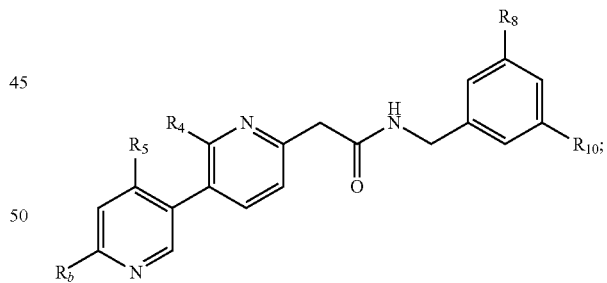

Formula VII:

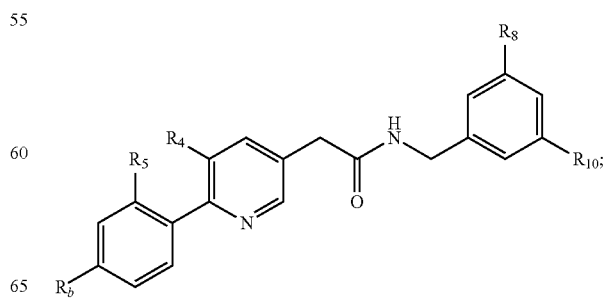

Formula VIII:

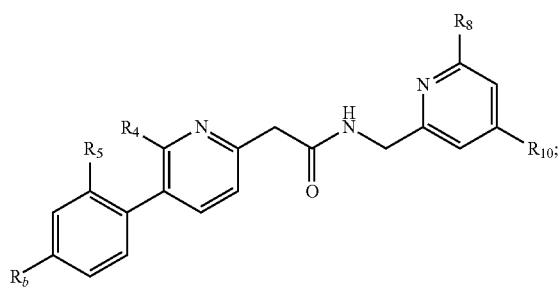

Formula IX:

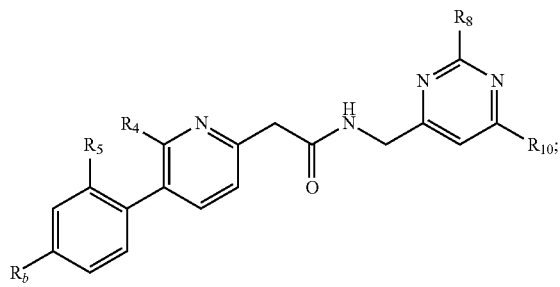

Formula X:

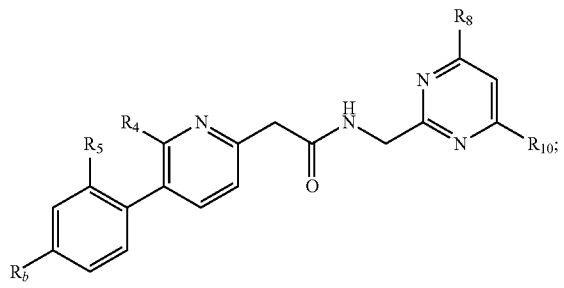

Formula XI:

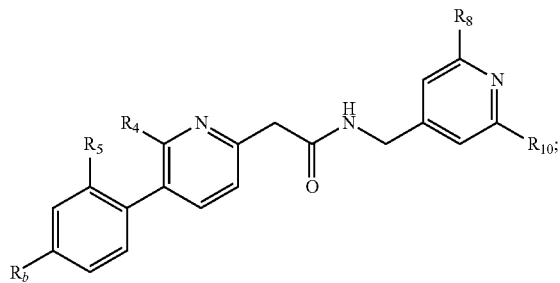

Formula XII:

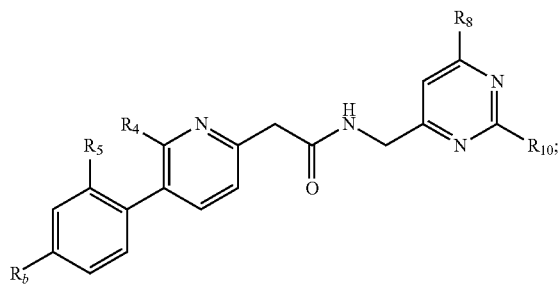

Formula XIII:

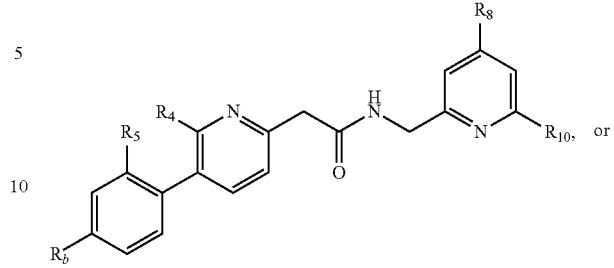

a salt, solvate, hydrate, or prodrug thereof, where: $R_b$, $R_4$, $R_5$, $R_9$, and $R_{10}$ are, independently, hydrogen, hydroxyl, halogen, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, $C_1$, $C_2$, $C_3$, $C_4$, $C_5$, or $C_6$ alkyl-O-lower ($C_1$, $C_2$, $C_3$, $C_4$, $C_5$, or $C_6$) alkyl, COOH, COO-lower ($C_1$, $C_2$, $C_3$, $C_4$, $C_5$, or $C_6$) alkyl, $SO_2H$, $SO_2$-lower ($C_1$, $C_2$, $C_3$, $C_4$, $C_5$, or $C_6$) alkyl,

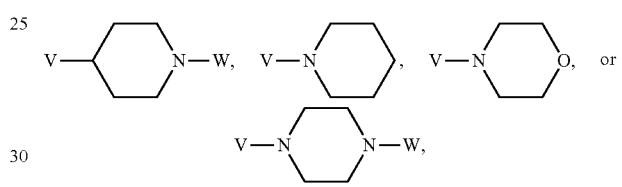

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl, and V is a bond, —$CH_2$—, —$CH_2CH_2$—, —$CH_2CH_2CH_2$—, —O—$CH_2$—, —$OCH_2CH_2$— or —$OCH_2CH_2CH_2$—.

For example, in the compound of Formula II-XIII, $R_8$ is hydrogen, F, Cl, Br, or I. For example, $R_8$ is F. In certain compounds, $R_8$ is H.

In certain compounds of Formula II-XIII, $R_b$ is $C_1$, $C_2$, $C_3$, $C_4$, $C_5$, or $C_6$ alkoxy. For example, $R_b$ is methoxy or ethoxy.

In certain compounds of Formula II-XIII, $R_b$ is hydrogen, Cl, Br, or I. In other compounds, in the compound of Formula II-XIII, $R_b$ is

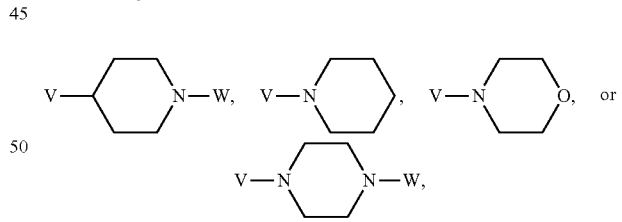

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl, and V is a bond, —$CH_2$—, —$CH_2CH_2$—, —$CH_2CH_2CH_2$—, —O—$CH_2$—, —$OCH_2CH_2$— or —$OCH_2CH_2CH_2$—.

In certain compounds of Formula II-XIII, $R_4$ is hydrogen, $C_1$, $C_2$, $C_3$, $C_4$, $C_5$, or $C_6$ alkoxy, F, Cl, Br, or I. In other compounds, in the compound of Formula II-XIII, $R_4$ is

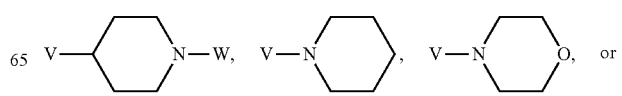

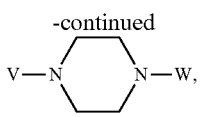

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl; and V is a bond, $-CH_2-$, $-CH_2CH_2-$, $-CH_2CH_2CH_2-$, $-O-CH_2-$, $-OCH_2CH_2-$ or $-OCH_2CH_2CH_2-$.

In certain compounds of Formula II-XIII, $R_5$ is hydrogen, $C_1$, $C_2$, $C_3$, $C_4$, $C_5$, or $C_6$ alkoxy, F, Cl, Br, or I. In other compounds, in the compound of Formula II-XIII, $R_5$ is

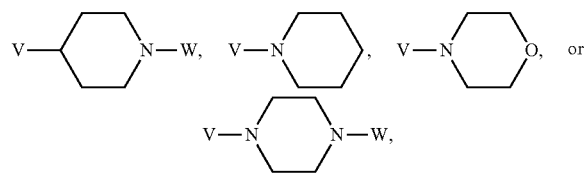

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl; and V is a bond, $-CH_2-$, $-CH_2CH_2-$, $-CH_2CH_2CH_2-$, $-O-CH_2-$, $-OCH_2CH_2-$ or $-OCH_2CH_2CH_2-$.

In certain compounds of Formula II-XIII, $R_{10}$ is hydrogen, $C_1$, $C_2$, $C_3$, $C_4$, $C_5$, or $C_6$ alkoxy, F, Cl, Br, or I. For example, $R_{10}$ is methoxy, ethoxy or isobutoxy.

In other compounds of Formula II-XIII, $R_{10}$ is

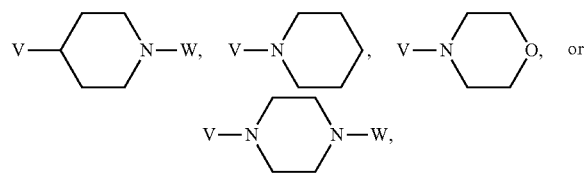

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl; and V is a bond, $-CH_2-$, $-CH_2CH_2-$, $-CH_2CH_2CH_2-$, $-O-CH_2-$, $-OCH_2CH_2-$ or $-OCH_2CH_2CH_2-$.

For example, in the compound of Formula II-XIII, W is hydrogen, or $C_1$, $C_2$, $C_3$, $C_4$, $C_5$, or $C_6$ alkyl.

Certain compounds of the invention include compounds according to Formula II.

The invention relates to a solvate of a compound according to one of Formulae II-XIII. The invention also relates to a hydrate of a compound according to one of Formulae II-XIII.

The invention also relates to an acid addition salt of a compound according to one of Formulae II-XIII. For example, a hydrochloride salt.

Further, the invention relates to a prodrug of a compound according to one of Formulae II-XIII.

The invention also relates to a pharmaceutically acceptable salt of a compound of one of Formulae II-XIII.

The invention includes compositions comprising a compound according to one of Formulae I-XIII and at least one pharmaceutically acceptable excipient.

Certain compounds of the invention are non-ATP competitive kinase inhibitors.

The invention also includes a method of preventing or treating a cell proliferation disorder by administering a pharmaceutical composition that includes a compound according to one of Formulae I-XIII, or a salt, solvate, hydrate, or prodrug thereof, and at least one pharmaceutically acceptable excipient to a subject in need thereof.

For example, the cell proliferation disorder is pre-cancer or cancer. The cell proliferation disorder treated or prevented by the compounds of the invention may be a cancer, such as, for example, colon cancer or lung cancer.

The cell proliferation disorder treated or prevented by the compounds of the invention may be a hyperproliferative disorder The cell proliferation disorder treated or prevented by the compounds of the invention may be psoriases.

For example, the treatment or prevention of the proliferative disorder may occur through the inhibition of a tyrosine kinase. For example, the tyrosine kinase can be a Src kinase or focal adhesion kinase (FAK).

The invention relates to a method of treating or preventing a disease or disorder that is modulated by tyrosine kinase inhibition, by administering a pharmaceutical composition that includes a compound according to Formula I or one of Formulae II-XIII, or a salt, solvate, hydrate, or prodrug thereof, and at least one pharmaceutically acceptable excipient. For example, the disease or disorder that is modulated by tyrosine kinase inhibition is cancer, pre-cancer, a hyperproliferative disorder, or a microbial infection. For example, the compound is a compound according to Formula I or II.

The pharmaceutical composition of the invention may modulate a kinase pathway. For example, the kinase pathway is a Src kinase pathway, or a focal adhesion kinase pathway.

The pharmaceutical composition of the invention may modulate a kinase directly. For example, the kinase is Src kinase, or focal adhesion kinase.

Certain pharmaceutical compositions of the invention are non-ATP competitive kinase inhibitors.

The compounds of the invention are also useful to treat or prevent a microbial infection, such as a bacterial, fungal, parasitic or viral infection.

Certain pharmaceutical compositions of the invention include a compound selected from Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, and 137. For example, the pharmaceutical composition includes Compound 33, 38, 40, 76, 133, 134, 136 or 137.

Certain pharmaceutical compositions of the invention include a compound selected from the compounds listed in Table 2.

A compound of the invention may be used as a pharmaceutical agent. For example, a compound of the invention is used as an anti-proliferative agent, for treating humans and/or animals, such as for treating humans and/or other mammals. The compounds may be used without limitation, for example, as anti-cancer, anti-angiogenesis, anti-microbial, anti-bacterial, anti-fungal, anti-parasitic and/or anti-viral agents. Additionally, the compounds may be used for other cell proliferation-related disorders such as diabetic retinopathy, macular degeneration and psoriases. Anti-cancer agents include anti-metastatic agents.

The compound of the invention used as a pharmaceutical agent may be selected from Compounds 1-136 and 137. For example, the compound of the invention used as a pharmaceutical agent is Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, or 137. For example, the compound of the invention used as a pharmaceutical agent is selected from Compounds 33, 38, 40, 76, 133, 134, 136 and 137.

Certain pharmaceutical agents include a compound selected from the compounds listed in Table 2.

In one aspect of the invention, a compound of the invention, for example, a compound of Formula I or one of Formulae II-XIII, is used to treat or prevent a cell proliferation disorder in an subject. In one aspect of the embodiment, the cell proliferation disorder is pre-cancer or cancer. In another aspect of the embodiment, the cell proliferation disorder is a hyperproliferative disorder. In another embodiment, prevention or treatment of the cell proliferation disorder, cancer or hyperproliferative disorder occurs through the inhibition of a kinase. In another embodiment, prevention or treatment of the cell proliferation disorder, cancer or hyperproliferative disorder occurs through the inhibition of a tyrosine kinase. In another embodiment, prevention or treatment of the cell proliferation disorder, cancer or hyperproliferative disorder occurs through the inhibition of Src kinase or focal adhesion kinase (FAK). In another embodiment, the subject is a mammal. Preferably, the subject is human.

The invention is also drawn to a method of treating or preventing cancer or a proliferation disorder in a subject, comprising administering an effective amount of a compound of the invention, for example, a compound of Formula I or one of Formulae II-XIII. For example, the compound of the invention may be a kinase inhibitor. The compound of the invention may be a non-ATP competitive kinase inhibitor. The compound of the invention may inhibit a kinase directly, or it may affect the kinase pathway.

The above description sets forth rather broadly the more important features of the present invention in order that the detailed description thereof that follows may be understood, and in order that the present contributions to the art may be better appreciated. Other objects and features of the present invention will become apparent from the following detailed description considered in conjunction with the examples.

DETAILED DESCRIPTION OF THE INVENTION

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description. In the specification, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present specification will control.

The invention relates to compounds and methods of using compounds to treat cell proliferation disorders.

The compounds of the present invention are useful as pharmaceutical agents, particularly as anti-proliferative agents, for treating humans and animals, particularly for treating humans and other mammals. The compounds may be used without limitation, for example, as anti-cancer, anti-angiogenesis, anti-metastatic, anti-microbial, anti-bacterial, anti-fungal, anti-parasitic and/or anti-viral agents. The compounds may be used for other cell proliferation-related disorders such as psoriases.

Compounds of the invention include compounds of formula I, and salts thereof:

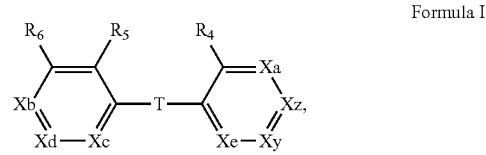

Formula I where:

T is absent (i.e., the rings are connected by a bond), $CR_{12}R_{13}$, $C(O)$, $O$, $S$, $S(O)$, $S(O)_2$, $NR_{14}$, $C(R_{15}R_{16})C(R_{17}R_{18})$, $CH_2O$, or $OCH_2$;

$X_y$ is CZ, CY, N, or N—O;

$X_z$ is CZ, CY, N, or N—O;

at least one of $X_y$ and $X_z$ is CZ;

Y is selected from hydrogen, hydroxyl, halogen, lower ($C_1$, $C_2$, $C_3$, $C_4$, $C_5$, or $C_6$) alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, and O-benzyl;

$X_a$ is $CR_a$ or N, or N—O;

$X_b$ is $CR_b$, N, or N—O;

$X_c$ is $CR_c$ or N, or N—O;

$X_d$ is $CR_d$ or N, or N—O;

$X_e$ is $CR_e$, N, or N—O;

$R_a$, $R_b$, $R_c$, $R_d$, $R_e$, $R_4$, $R_5$, and $R_6$ are, independently, hydrogen, hydroxyl, halogen, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, $C_1$, $C_2$, $C_3$, $C_4$, $C_5$, or $C_6$ alkyl-O-lower ($C_1$, $C_2$, $C_3$, $C_4$, $C_5$, or $C_6$) alkyl, COOH, COO-lower ($C_1$, $C_2$, $C_3$, $C_4$, $C_5$, or $C_6$) alkyl, $SO_2H$, $SO_2$-lower ($C_1$, $C_2$, $C_3$, $C_4$, $C_5$, or $C_6$) alkyl,

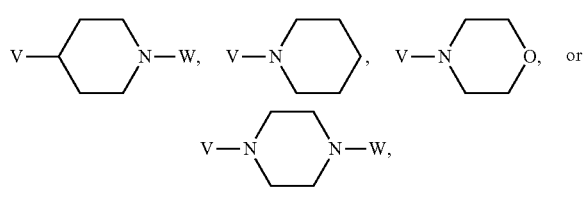

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl;

V is a bond, —$CH_2$—, —$CH_2CH_2$—, —$CH_2CH_2CH_2$—, —O—$CH_2$—, —$OCH_2CH_2$— or —$OCH_2CH_2CH_2$—;

$R_{12}$, $R_{13}$, $R_{14}$, $R_{15}$, $R_{16}$, $R_{17}$, and $R_{18}$, are, independently, H or $C_1$, $C_2$, $C_3$, $C_4$, $C_5$, or $C_6$ alkyl;

Z is $(CHR_1)_n$—$C(O)$—$NR_2(CHR_3)_m$—Ar, where Ar is a substituted or unsubstituted aryl or nitrogen-containing heteroaryl group, such as benzene, pyridine, or pyrimidine. For example, Z is:

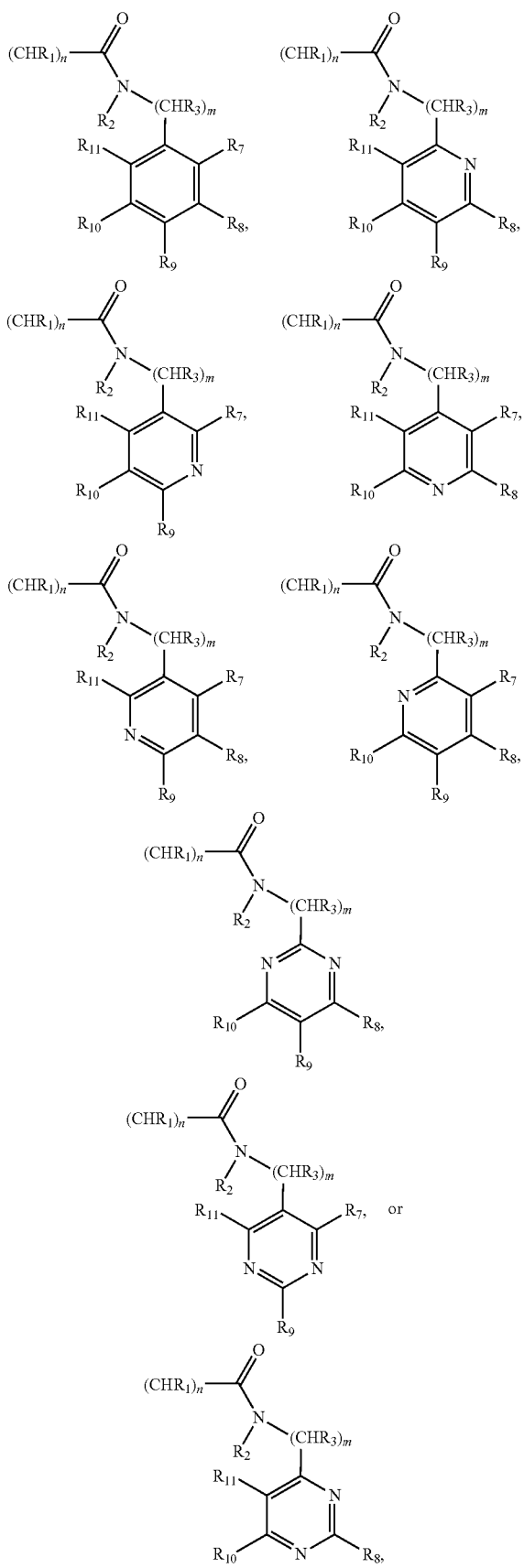

where $R_1$, $R_2$, and $R_3$ are independently H or $C_1$, $C_2$, $C_3$, $C_4$, $C_5$, or $C_6$ alkyl;

n and m are, independently 0, 1, or 2; $R_7$, $R_8$, $R_9$, $R_{10}$, and $R_{11}$ are, independently, hydrogen, hydroxyl, halogen, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, $C_1$, $C_2$, $C_3$, $C_4$, $C_5$, or $C_6$ alkyl-O—$C_1$, $C_2$, $C_3$, $C_4$, $C_5$, or $C_6$ alkyl,

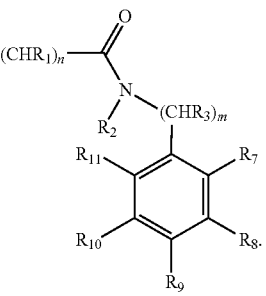

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl;

V is a bond, —$CH_2$—, —$CH_2CH_2$—, —$CH_2CH_2CH_2$—, —O—$CH_2$—, —$OCH_2CH_2$—, or —$OCH_2CH_2CH_2$—.

In certain compounds of the invention, Z is

Certain compounds of the invention are selected from Compounds 1-136 and 137. For example, the compound of the invention is Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, or 137.

Compounds of the invention include Compounds 33, 38, 40, 76, 133, 134, 136 and 137.

In certain Compounds of Formula I, at least one of $X_a$, $X_b$, $X_c$, $X_d$ and $X_e$ is N.

For example, in the compound of Formula I, $X_a$ is N and each of $X_b$, $X_c$, $X_d$ and $X_e$ is CR.

In certain compounds of Formula I, $X_y$ is CY, and $X_z$ is CZ.

For example, in certain compounds of Formula I, Y is hydrogen.

The compounds of the invention can tolerate a wide variety of functional groups, so various substituted starting materials can be used to synthesize them. The syntheses described herein generally provide the desired final bi-aryl compound at or near the end of the overall process, although it may be desirable in certain instances to further convert the compound to a pharmaceutically acceptable salt, ester, or prodrug thereof.

In certain compounds of Formula I, $R_b$ is $C_1$, $C_2$, $C_3$, $C_4$, $C_5$, or $C_6$ alkoxy. For example, $R_b$ is methoxy or ethoxy. In certain compounds of Formula I, $R_b$ is hydrogen. In other compounds of Formula I, $R_b$ is selected from F, Cl, Br, and I. For example, $R_b$ is F.

In other compounds of Formula I, $R_b$ is

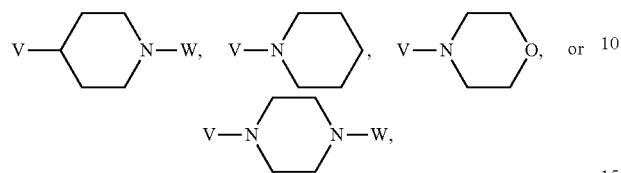

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl; and V is a bond, —$CH_2$—, —$CH_2CH_2$—, —$CH_2CH_2CH_2$—, —O—$CH_2$—, —$OCH_2CH_2$— or —$OCH_2CH_2CH_2$—. For example, V is a bond. In certain compounds of Formula I, V is —$CH_2$—, —$CH_2CH_2$— or —$CH_2CH_2CH_2$—. In other compounds, V is —O—$CH_2$—, —$OCH_2CH_2$— or —$OCH_2CH_2CH_2$—.

In certain compounds of Formula I, W is hydrogen. In other compounds, W is $C_1$, $C_2$, $C_3$, $C_4$, $C_5$, or $C_6$ alkyl. In some compounds, W is methyl.

In certain compounds of Formula I, $R_c$ is halogen, for example, $R_c$ is F, Cl, Br, or I. In some compounds, $R_c$ is F. In other compounds, $R_c$ is Cl.

In some compounds, $R_c$ is $C_1$, $C_2$, $C_3$, $C_4$, $C_5$, or $C_6$ alkoxy. In some compounds, $R_c$ is methoxy or ethoxy. In some embodiments, $R_c$ is ethoxy.

In other compounds of Formula I, $R_c$ is hydrogen.

In other compounds of Formula I, $R_c$ is

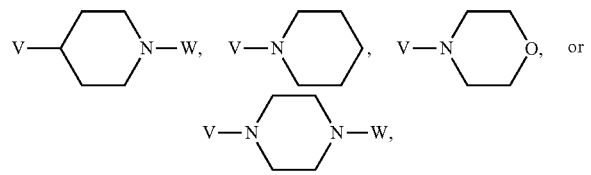

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl; V is a bond, —$CH_2$—, —$CH_2CH_2$—, —$CH_2CH_2CH_2$—, —O—$CH_2$—, —$OCH_2CH_2$— or —$OCH_2CH_2CH_2$—. In some compounds, V is a bond. In other compounds, V is —$CH_2$—, —$CH_2CH_2$— or —$CH_2CH_2CH_2$—. In other compounds, V is —O—$CH_2$—, —$OCH_2CH_2$— or —$OCH_2CH_2CH_2$—.

In some compounds of Formula I, W is hydrogen. In other compounds, W is $C_1$, $C_2$, $C_3$, $C_4$, $C_5$, or $C_6$ alkyl. In certain compounds, W is methyl.

In certain compounds of Formula I, $R_b$ is $C_1$, $C_2$, $C_3$, $C_4$, $C_5$, or $C_6$ alkoxy. For example, $R_b$ is methoxy or ethoxy. In certain compounds of Formula I, $R_b$ is hydrogen. In other compounds of Formula I, $R_b$ is selected from F, Cl, Br, and I. For example, $R_b$ is F.

In other compounds of Formula I, $R_b$ is

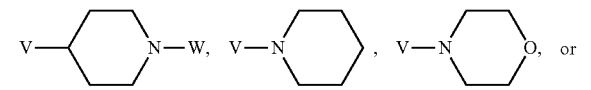

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl; and V is a bond, —$CH_2$—, —$CH_2CH_2$—, —$CH_2CH_2CH_2$—, —O—$CH_2$—, —$OCH_2CH_2$— or —$OCH_2CH_2CH_2$—. For example, V is a bond. In certain compounds of Formula I, V is —$CH_2$—, —$CH_2CH_2$— or —$CH_2CH_2CH_2$—. In other compounds, V is —O—$CH_2$—, —$OCH_2CH_2$— or —$OCH_2CH_2CH_2$—.

In certain compounds of Formula I, W is hydrogen. In other compounds, W is $C_1$, $C_2$, $C_3$, $C_4$, $C_5$, or $C_6$ alkyl. In some compounds, W is methyl.

In certain compounds of Formula I, $R_d$ is halogen, for example, $R_d$ is F, Cl, Br, or I. In some compounds, $R_d$ is F. In other compounds, $R_d$ is Cl.

In some compounds, $R_d$ is $C_1$, $C_2$, $C_3$, $C_4$, $C_5$, or $C_6$ alkoxy. In some compounds, $R_d$ is methoxy or ethoxy. In some embodiments, $R_d$ is ethoxy.

In other compounds of Formula I, $R_d$ is hydrogen.

In other compounds of Formula I, $R_d$ is

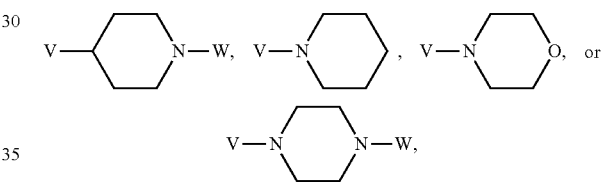

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl; V is a bond, —$CH_2$—, —$CH_2CH_2$—, —$CH_2CH_2CH_2$—, —O—$CH_2$—, —$OCH_2CH_2$— or —$OCH_2CH_2CH_2$—. In some compounds, V is a bond. In other compounds, V is —$CH_2$—, —$CH_2CH_2$— or —$CH_2CH_2CH_2$—. In other compounds, V is —O—$CH_2$—, —$OCH_2CH_2$— or —$OCH_2CH_2CH_2$—.

In some compounds of Formula I, W is hydrogen. In other compounds, W is $C_1$, $C_2$, $C_3$, $C_4$, $C_5$, or $C_6$ alkyl. In certain compounds, W is methyl.

The invention relates to a compound of Formula I, having a structure according to one of Formulae II-XIII:

Formula II:

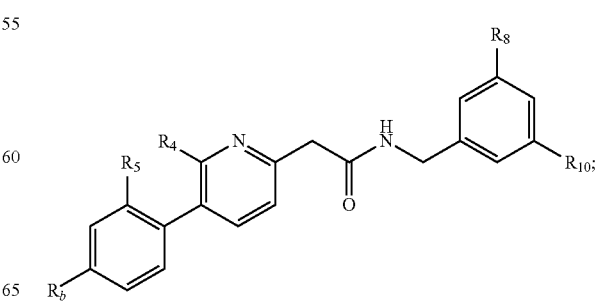

Formula III:
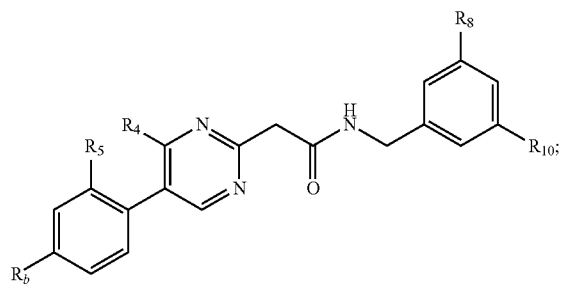
Formula IV:
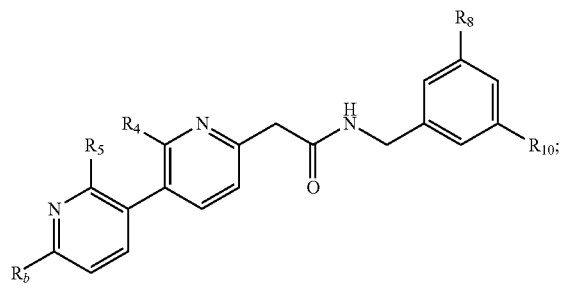
Formula V:
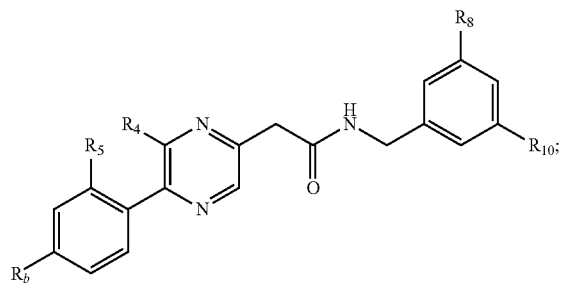
Formula VI:
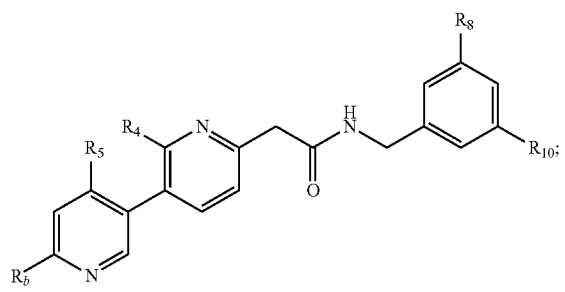
Formula VII:
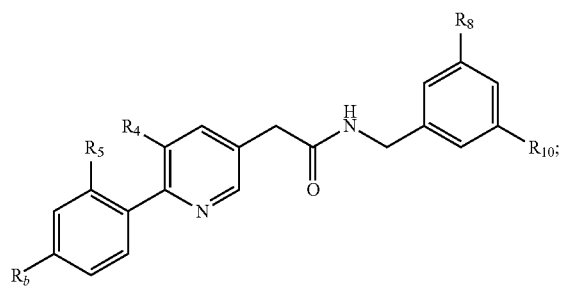
Formula VIII:
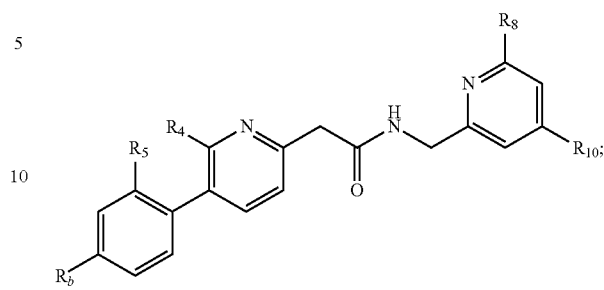
Formula IX:
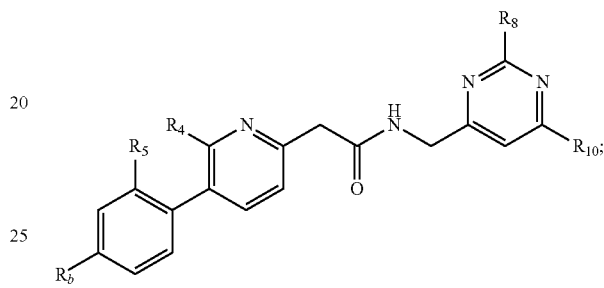
Formula X:
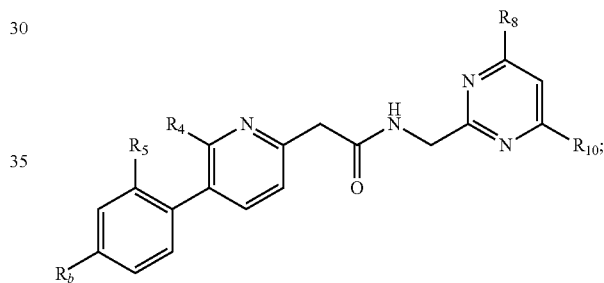
Formula XI:
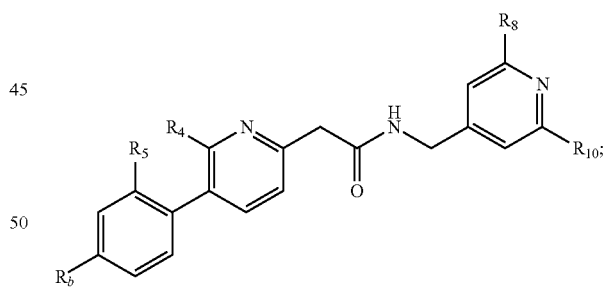
Formula XII:
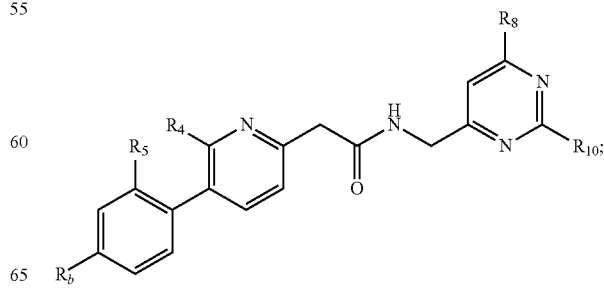

-continued

Formula XIII:

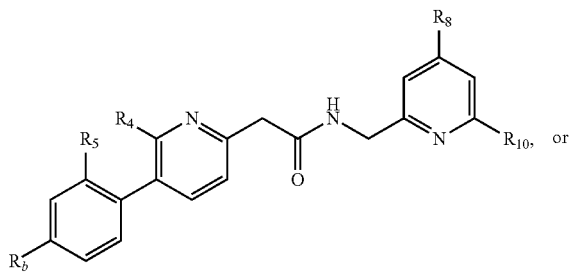

a salt, solvate, hydrate, or prodrug thereof, where:

$R_b$, $R_4$, $R_5$, $R_8$, and $R_{10}$ are, independently, hydrogen, hydroxyl, halogen, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, $C_1$, $C_2$, $C_3$, $C_4$, $C_5$, or $C_6$ alkyl-O-lower ($C_1$, $C_2$, $C_3$, $C_4$, $C_5$, or $C_6$) alkyl, COOH, COO-lower ($C_1$, $C_2$, $C_3$, $C_4$, $C_5$, or $C_6$) alkyl, $SO_2H$, $SO_2$-lower ($C_1$, $C_2$, $C_3$, $C_4$, $C_5$, or $C_6$) alkyl,

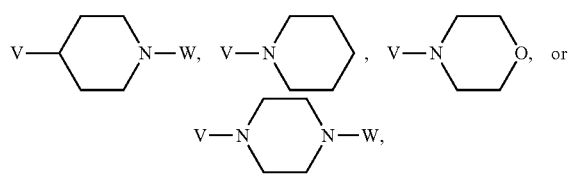

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl, and V is a bond, $—CH_2—$, $—CH_2CH_2—$, $—CH_2CH_2CH_2—$, $—O—CH_2—$, $—OCH_2CH_2—$ or $—OCH_2CH_2CH_2—$.

For example, in the compound of Formula II-XIII, $R_8$ is hydrogen, F, Cl, Br, or I. For example, $R_8$ is F. In certain compounds, $R_8$ is H.

In certain compounds of Formula II-XIII, $R_b$ is $C_1$, $C_2$, $C_3$, $C_4$, $C_5$, or $C_6$ alkoxy. For example, $R_b$ is methoxy or ethoxy. In certain compounds, $R_b$ is ethoxy. In certain compounds, $R_b$ is hydrogen.

In certain compounds of Formula II-XIII, $R_b$ is Cl, Br, or I. For example, $R_b$ is F or Cl. In other compounds, in the compound of Formula II-XIII, $R_b$ is

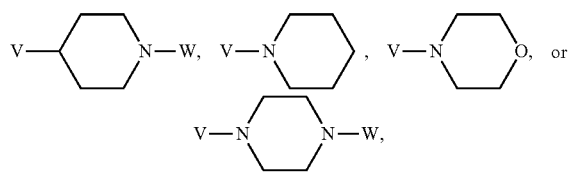

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl, and V is a bond, $—CH_2—$, $—CH_2CH_2—$, $—CH_2CH_2CH_2—$, $—O—CH_2—$, $—OCH_2CH_2—$ or $—OCH_2CH_2CH_2—$. In some compounds, V is $—O—CH_2—$, $—OCH_2CH_2—$ or $—OCH_2CH_2CH_2—$. In certain compounds W is H. In other compounds, W is $C_1$, $C_2$, $C_3$, $C_4$, $C_5$, or $C_6$ alkyl. For example, W is methyl.

In certain compounds of Formula II-XIII, $R_4$ is hydrogen, $C_1$, $C_2$, $C_3$, $C_4$, $C_5$, or $C_6$ alkoxy, F, Cl, Br, or I. In some compounds, $R_4$ is $C_1$, $C_2$, $C_3$, $C_4$, $C_5$, or $C_6$ alkoxy. For example, $R_4$ is methoxy or ethoxy. In certain compounds, $R_4$ is ethoxy. In other compounds, in the compound of Formula II-XIII, $R_4$ is

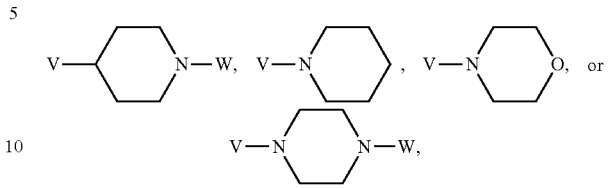

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl; and V is a bond, $—CH_2—$, $—CH_2CH_2—$, $—CH_2CH_2CH_2—$, $—O—CH_2—$, $—OCH_2CH_2—$ or $—OCH_2CH_2CH_2—$. In certain compounds, V is a bond. In other compounds, V is $—CH_2—$, $—CH_2CH_2—$ or $—CH_2CH_2CH_2—$. In other compounds, V is $—O—CH_2—$, $—OCH_2CH_2—$ or $—OCH_2CH_2CH_2—$.

In certain compounds of Formula II-XIII, $R_5$ is hydrogen, $C_1$, $C_2$, $C_3$, $C_4$, $C_5$, or $C_6$ alkoxy, F, Cl, Br, or I. For example, $R_5$ is hydrogen. In some compounds, $R_5$ is ethoxy. In certain compounds $R_5$ is F. In other compounds, in the compound of Formula II-XIII, $R_5$ is

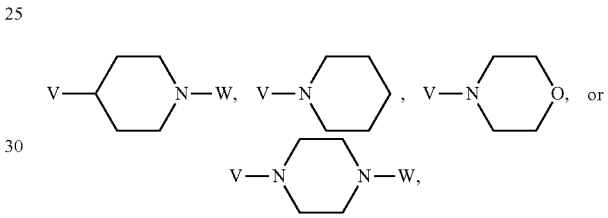

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl; and V is a bond, $—CH_2—$, $—CH_2CH_2—$, $—CH_2CH_2CH_2—$, $—O—CH_2—$, $—OCH_2CH_2—$ or $—OCH_2CH_2CH_2—$. In certain compounds, V is a bond. In other compounds, V is $—CH_2—$, $—CH_2CH_2—$ or $—CH_2CH_2CH_2—$. In other compounds, V is $—O—CH_2—$, $—OCH_2CH_2—$ or $—OCH_2CH_2CH_2—$.

In certain compounds of Formula III, $R_{10}$ is hydrogen, $C_1$, $C_2$, $C_3$, $C_4$, $C_5$, or $C_6$ alkoxy, F, Cl, Br, or I. In some compounds $R_{10}$ is $C_1$, $C_2$, $C_3$, $C_4$, $C_5$, or $C_6$ alkoxy. For example, $R_{10}$ is methoxy or ethoxy. In some compounds, $R_{10}$ is isobutoxy. In some compounds, $R_{10}$ is hydrogen. In certain compounds, $R_{10}$ is halogen. For example, $R_{10}$ is F or Cl.

In other compounds of Formula III, $R_{10}$ is

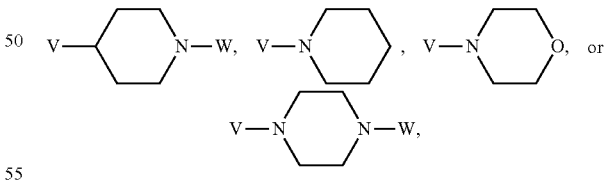

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl; and V is a bond, $—CH_2—$, $—CH_2CH_2—$, $—CH_2CH_2CH_2—$, $—O—CH_2—$, $—OCH_2CH_2—$ or $—OCH_2CH_2CH_2—$. In certain compounds, V is a bond. In other compounds, V is $—CH_2—$, $—CH_2CH_2—$ or $—CH_2CH_2CH_2—$. In other compounds, V is $—O—CH_2—$, $—OCH_2CH_2—$ or $—OCH_2CH_2CH_2—$.

For example, in the compound of Formula II-XIII, W is hydrogen, or $C_1$, $C_2$, $C_3$, $C_4$, $C_5$, or $C_6$ alkyl. In some compounds, W is methyl.

Certain compounds of the invention include compounds according to Formula II.

Compounds of the invention include those listed in Table 1:

TABLE 1

| Compound # | KX # | Compound |
|---|---|---|
| 1 | 1-136 | |
| 2 | 1-305 | |
| 3 | 1-306 | |
| 4 | 1-307 | |
| 5 | 1-308 | |
| 6 | 1-309 | |

TABLE 1-continued
| Compound # | KX # | Compound |
|---|---|---|
| 7 | 1-310 | 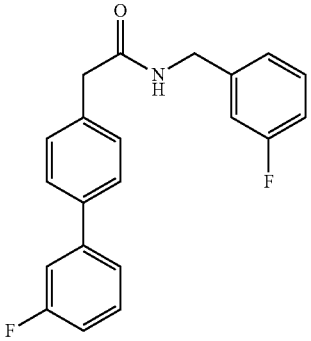 [SMILES: O=C(Cc1ccc(-c2cccc(F)c2)cc1)NCc1cccc(F)c1] |
| 8 | 1-311 | 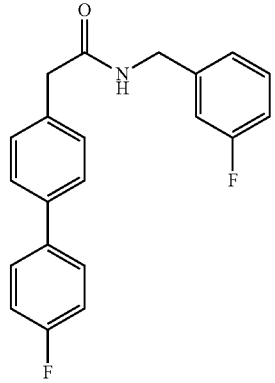 [SMILES: O=C(Cc1ccc(-c2ccc(F)cc2)cc1)NCc1cccc(F)c1] |
| 9 | 1-312 | 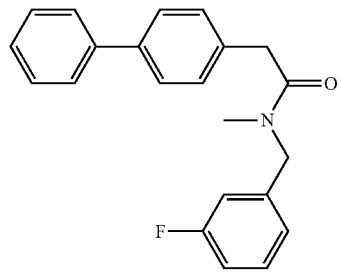 [SMILES: CN(Cc1cccc(F)c1)C(=O)Cc1ccc(-c2ccccc2)cc1] |
| 10 | 1-313 | 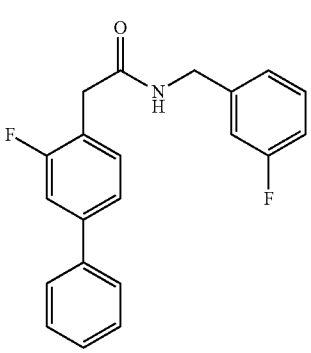 [SMILES: O=C(Cc1ccc(-c2ccccc2)cc1F)NCc1cccc(F)c1] |

TABLE 1-continued
| Compound # | KX # | Compound |
|---|---|---|
| 11 | 1-314 | 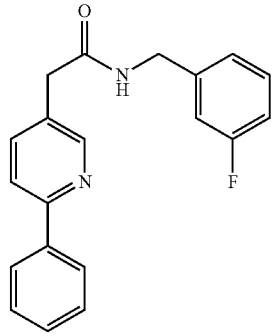 [SMILES: O=C(Cc1ccc(-c2ccccc2)nc1)NCc1cccc(F)c1] |
| 12 | 1-315 | 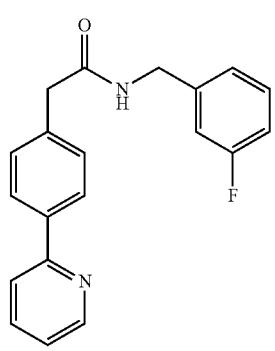 [SMILES: O=C(Cc1ccc(-c2ccccn2)cc1)NCc1cccc(F)c1] |
| 13 | 1-316 | 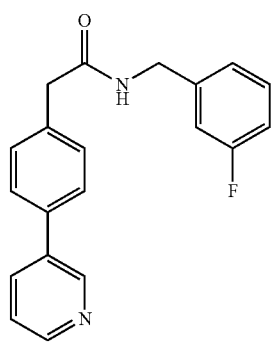 [SMILES: O=C(Cc1ccc(-c2cccnc2)cc1)NCc1cccc(F)c1] |
| 14 | 1-317 | 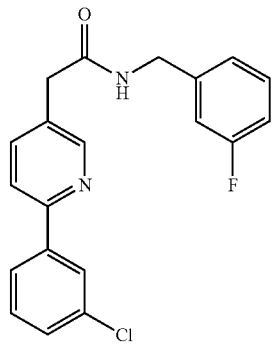 [SMILES: O=C(Cc1ccc(-c2cccc(Cl)c2)nc1)NCc1cccc(F)c1] |

TABLE 1-continued
| Compound # | KX # | Compound |
|---|---|---|
| 15 | 1-318 | 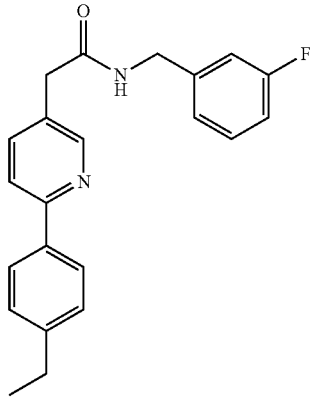 [SMILES: CCc1ccc(-c2ccc(CC(=O)NCc3cccc(F)c3)cn2)cc1] |
| 16 | 1-319 | 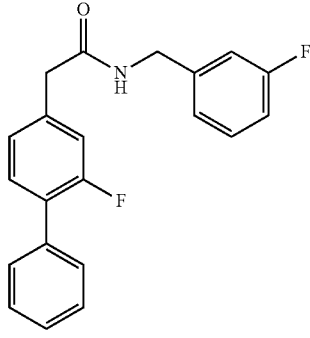 [SMILES: O=C(Cc1ccc(-c2ccccc2)c(F)c1)NCc1cccc(F)c1] |
| 17 | 1-320 | 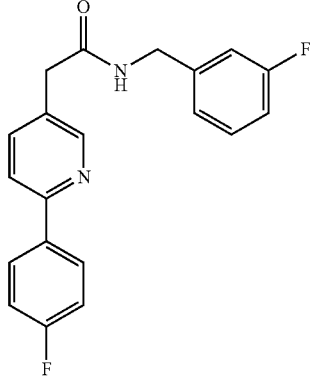 [SMILES: O=C(Cc1ccc(-c2ccc(F)cc2)nc1)NCc1cccc(F)c1] |
| 18 | 1-321 | 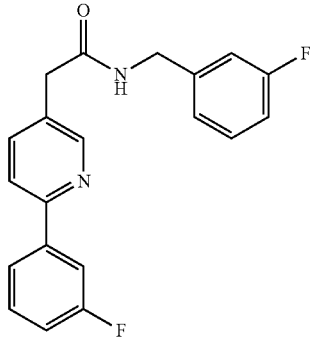 [SMILES: O=C(Cc1ccc(-c2cccc(F)c2)nc1)NCc1cccc(F)c1] |

TABLE 1-continued

| Compound # | KX # | Compound |
|---|---|---|
| 19 | 1-322 | 2-[6-(3-ethoxyphenyl)pyridin-3-yl]-N-(3-fluorobenzyl)acetamide |
| 20 | 1-323 | 4-{5-[2-(3-fluorobenzylamino)-2-oxoethyl]pyridin-2-yl}benzoic acid |
| 21 | 1-324 | 2-[6-(2-ethoxyphenyl)pyridin-3-yl]-N-(3-fluorobenzyl)acetamide |
| 22 | 1-325 | 2-[6-(4-ethoxyphenyl)pyridin-3-yl]-N-(3-fluorobenzyl)acetamide |

TABLE 1-continued
| Compound # | KX # | Compound |
|---|---|---|
| 23 | 1-326 | 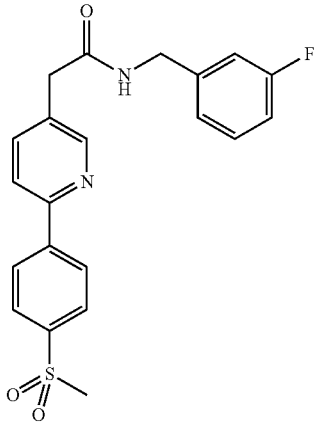 [SMILES: CS(=O)(=O)c1ccc(-c2ccc(CC(=O)NCc3cccc(F)c3)cn2)cc1] |
| 24 | 1-327 | 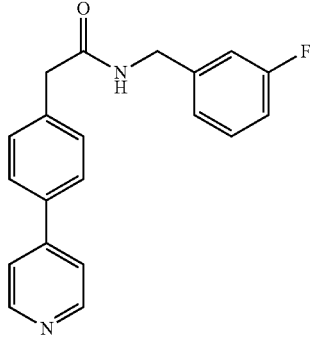 [SMILES: O=C(Cc1ccc(-c2ccncc2)cc1)NCc1cccc(F)c1] |
| 25 | 1-329 | 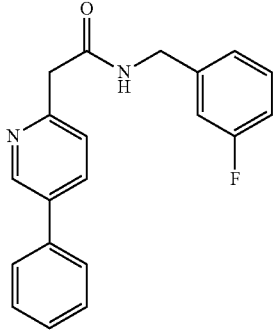 [SMILES: O=C(Cc1ccc(-c2ccccc2)cn1)NCc1cccc(F)c1] |
| 26 | 1-357 | 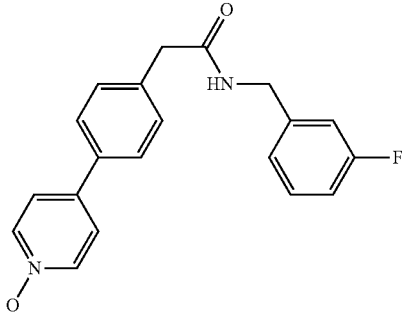 |

TABLE 1-continued
| Compound # | KX # | Compound |
|---|---|---|
| 27 | 1-358 | 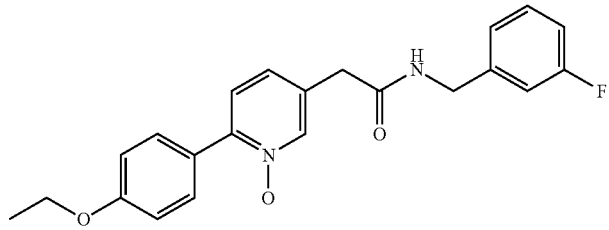 |
| 28 | 2-359 | 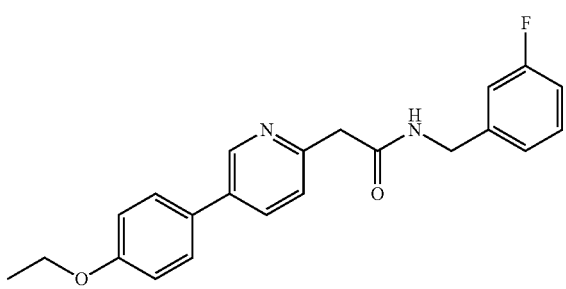 [SMILES: CCOc1ccc(-c2ccc(CC(=O)NCc3cccc(F)c3)nc2)cc1] |
| 29 | 2-368 | 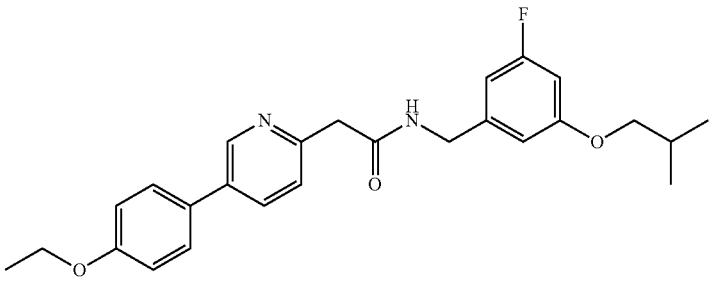 [SMILES: CCOc1ccc(-c2ccc(CC(=O)NCc3cc(F)cc(OCC(C)C)c3)nc2)cc1] |
| 30 | 2-380 | 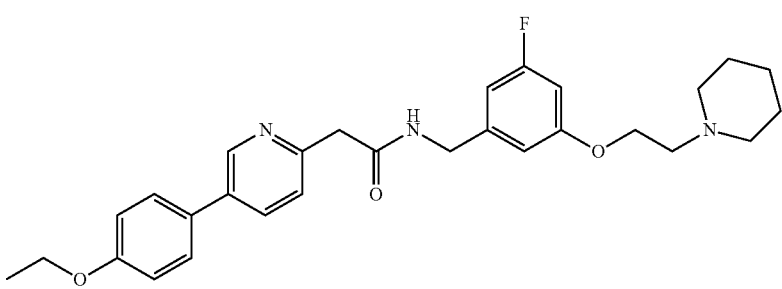 [SMILES: CCOc1ccc(-c2ccc(CC(=O)NCc3cc(F)cc(OCCN4CCCCC4)c3)nc2)cc1] |
| 31 | 2-378 | 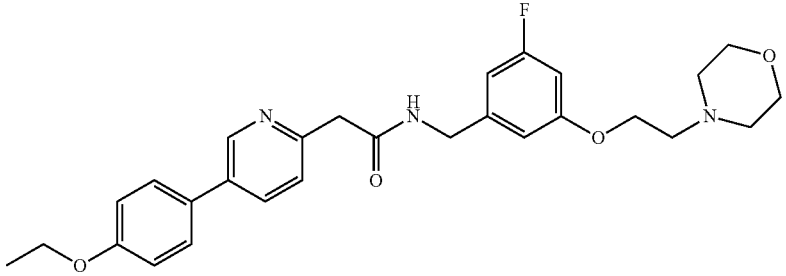 [SMILES: CCOc1ccc(-c2ccc(CC(=O)NCc3cc(F)cc(OCCN4CCOCC4)c3)nc2)cc1] |

TABLE 1-continued
| Compound # | KX # | Compound |
|---|---|---|
| 32 | | 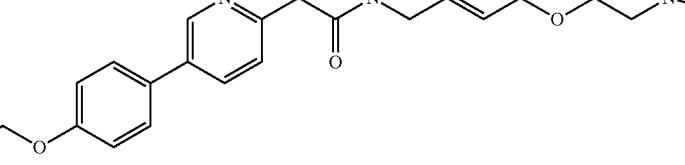 |
| 33 | 2-381 | 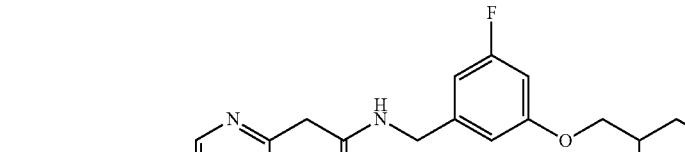 |
| 34 | | 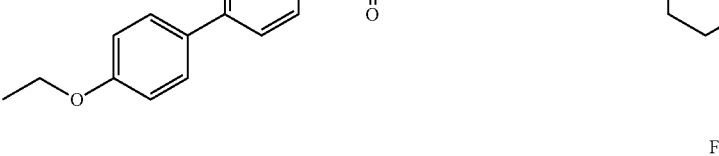 |
| 35 | | 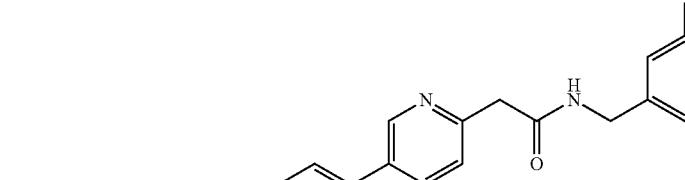 |
| 36 | 2-375 | 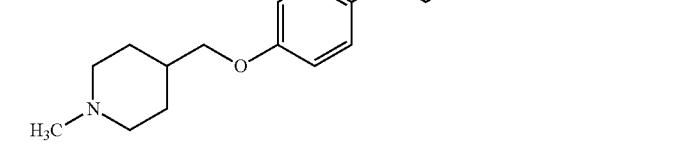 |

TABLE 1-continued
| Compound # | KX # | Compound |
|---|---|---|
| 37 | 2-386 | 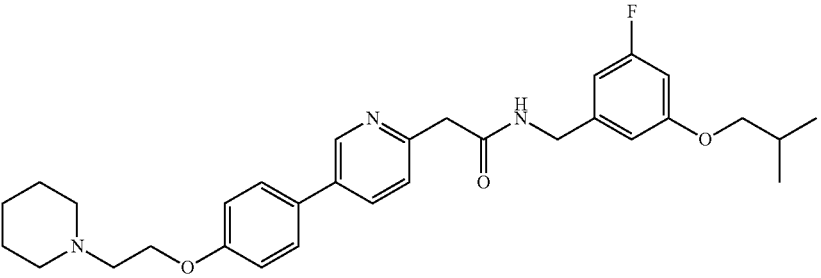 [SMILES: CC(C)COc1cc(F)cc(CNC(=O)Cc2ccc(-c3ccc(OCCN4CCCCC4)cc3)cn2)c1] |
| 38 | 2-377 | 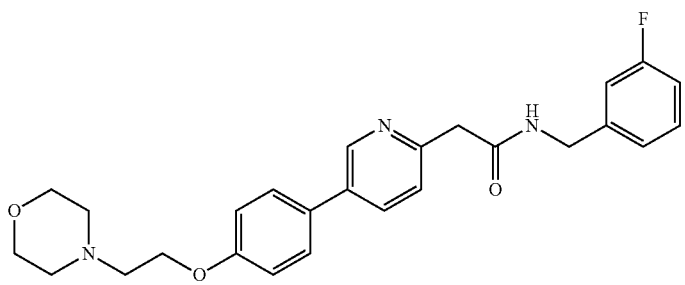 [SMILES: O=C(Cc1ccc(-c2ccc(OCCN3CCOCC3)cc2)cn1)NCc1cccc(F)c1] |
| 39 | 2-387 | 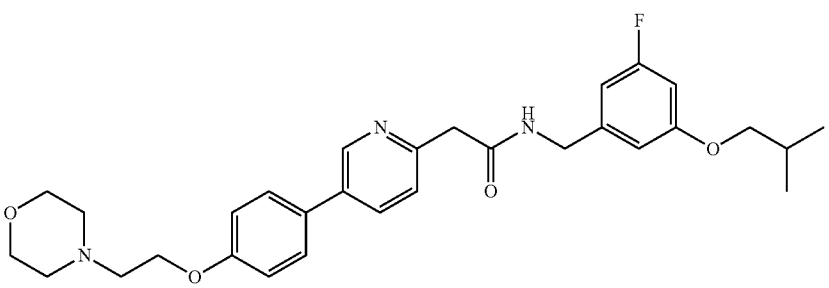 [SMILES: CC(C)COc1cc(F)cc(CNC(=O)Cc2ccc(-c3ccc(OCCN4CCOCC4)cc3)cn2)c1] |
| 40 | 2-365 | 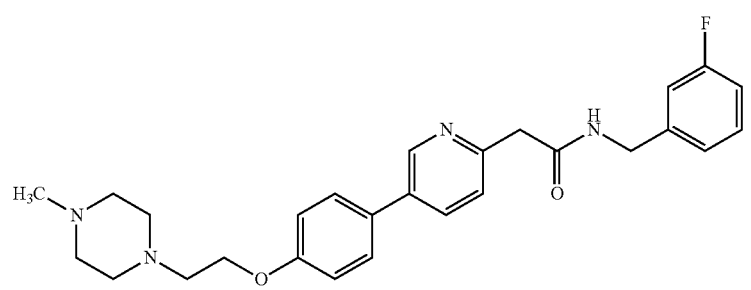 [SMILES: CN1CCN(CCOc2ccc(-c3ccc(CC(=O)NCc4cccc(F)c4)nc3)cc2)CC1] |
| 41 | 2-367 | 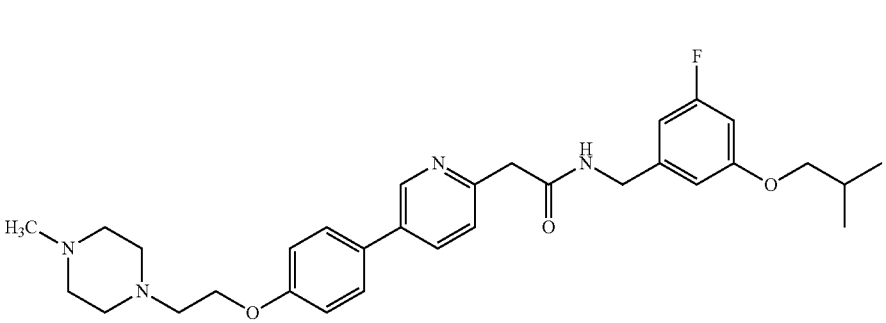 [SMILES: CC(C)COc1cc(F)cc(CNC(=O)Cc2ccc(-c3ccc(OCCN4CCN(C)CC4)cc3)cn2)c1] |

TABLE 1-continued
| Compound # | KX # | Compound |
|---|---|---|
| 42 | | 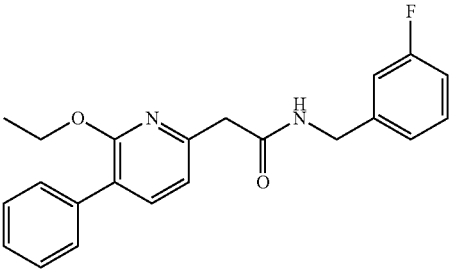 [SMILES: CCOc1nc(CC(=O)NCc2cccc(F)c2)ccc1-c1ccccc1] |
| 43 | | 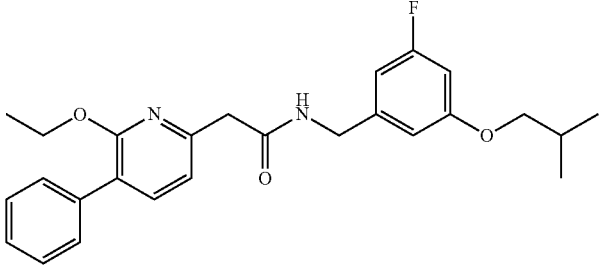 [SMILES: CCOc1nc(CC(=O)NCc2cc(F)cc(OCC(C)C)c2)ccc1-c1ccccc1] |
| 44 | | 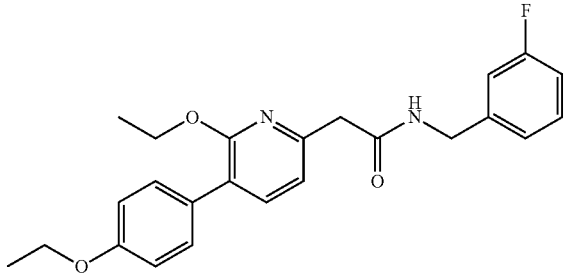 [SMILES: CCOc1ccc(-c2ccc(CC(=O)NCc3cccc(F)c3)nc2OCC)cc1] |
| 45 | | 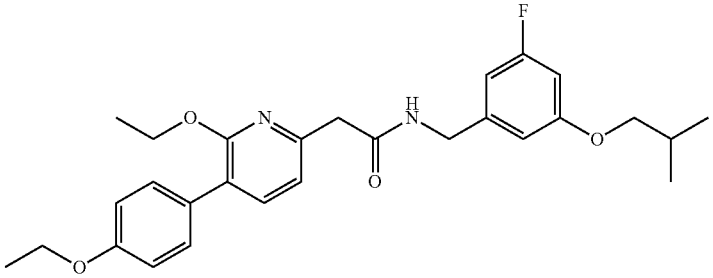 [SMILES: CCOc1ccc(-c2ccc(CC(=O)NCc3cc(F)cc(OCC(C)C)c3)nc2OCC)cc1] |
| 46 | | 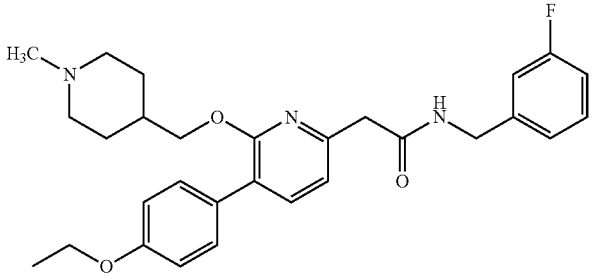 [SMILES: CCOc1ccc(-c2ccc(CC(=O)NCc3cccc(F)c3)nc2OCC2CCN(C)CC2)cc1] |

TABLE 1-continued
| Compound # | KX # | Compound |
|---|---|---|
| 47 | | 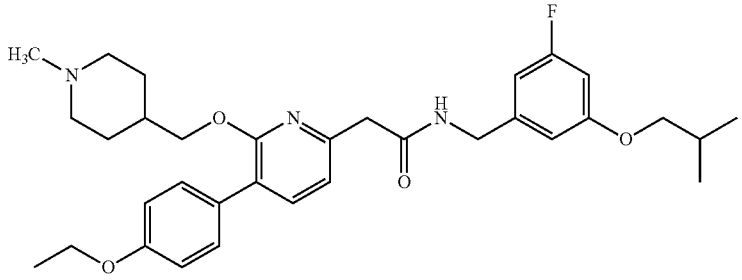 [SMILES: CCOc1ccc(-c2ccc(CC(=O)NCc3cc(F)cc(OCC(C)C)c3)nc2OCC2CCN(C)CC2)cc1] |
| 48 | | 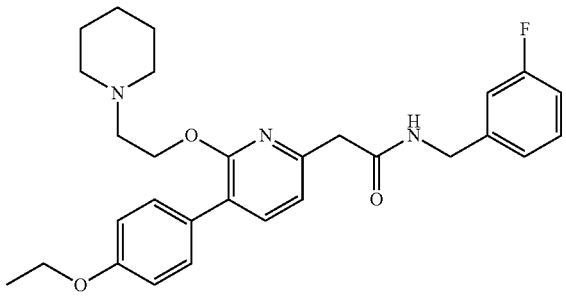 [SMILES: CCOc1ccc(-c2ccc(CC(=O)NCc3cccc(F)c3)nc2OCCN2CCCCC2)cc1] |
| 49 | | 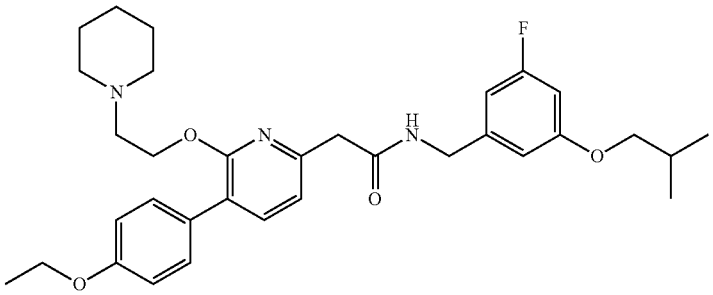 [SMILES: CCOc1ccc(-c2ccc(CC(=O)NCc3cc(F)cc(OCC(C)C)c3)nc2OCCN2CCCCC2)cc1] |
| 50 | | 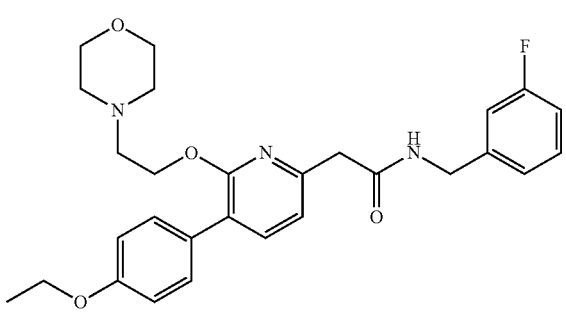 [SMILES: CCOc1ccc(-c2ccc(CC(=O)NCc3cccc(F)c3)nc2OCCN2CCOCC2)cc1] |
| 51 | | 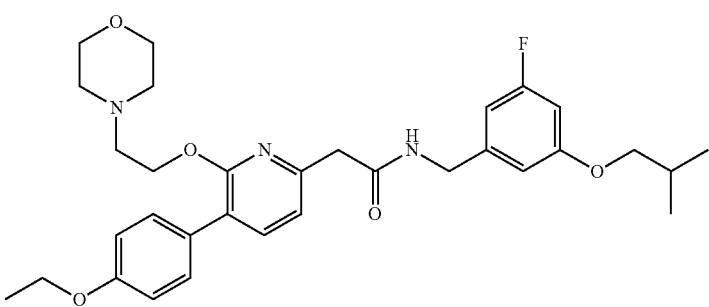 [SMILES: CCOc1ccc(-c2ccc(CC(=O)NCc3cc(F)cc(OCC(C)C)c3)nc2OCCN2CCOCC2)cc1] |

TABLE 1-continued
| Compound # | KX # | Compound |
|---|---|---|
| 52 | | 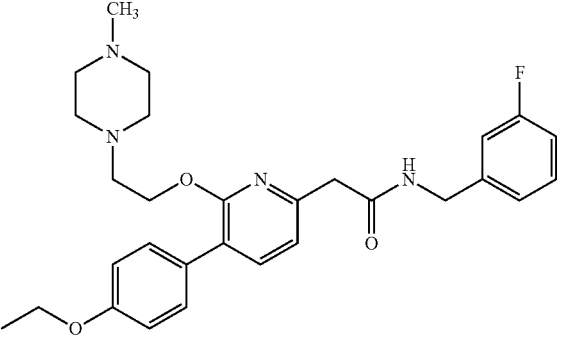 [SMILES: CCOc1ccc(-c2ccc(CC(=O)NCc3cccc(F)c3)nc2OCCN2CCN(C)CC2)cc1] |
| 53 | | 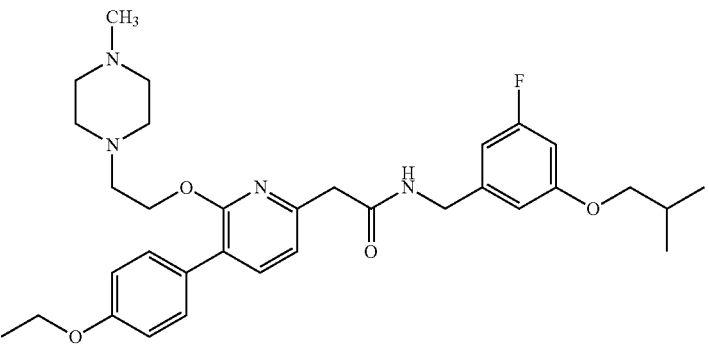 [SMILES: CCOc1ccc(-c2ccc(CC(=O)NCc3cc(F)cc(OCC(C)C)c3)nc2OCCN2CCN(C)CC2)cc1] |
| 54 | 2-360 | 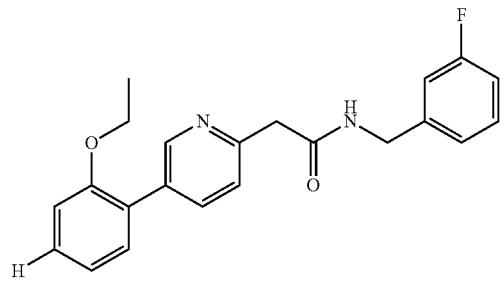 [SMILES: CCOc1ccccc1-c1ccc(CC(=O)NCc2cccc(F)c2)nc1] |
| 55 | 2-369 | 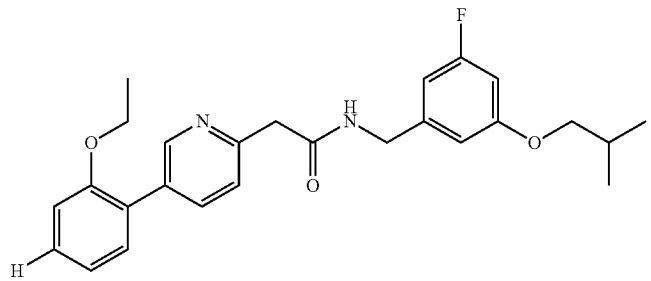 [SMILES: CCOc1ccccc1-c1ccc(CC(=O)NCc2cc(F)cc(OCC(C)C)c2)nc1] |
| 56 | | 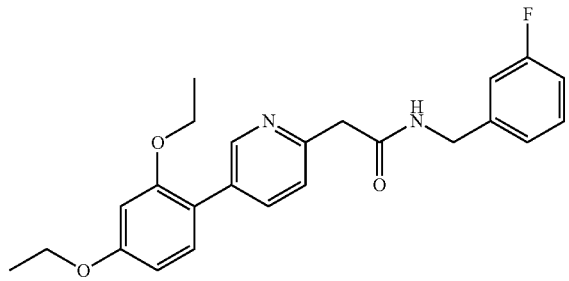 [SMILES: CCOc1ccc(-c2ccc(CC(=O)NCc3cccc(F)c3)nc2)c(OCC)c1] |

TABLE 1-continued
| Compound # | KX # | Compound |
|---|---|---|
| 57 | | 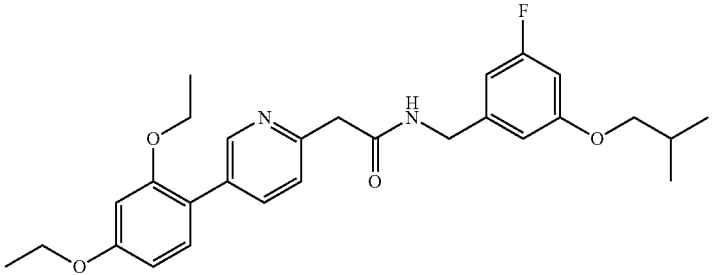 [SMILES: CCOc1ccc(-c2ccc(CC(=O)NCc3cc(F)cc(OCC(C)C)c3)nc2)c(OCC)c1] |
| 58 | | 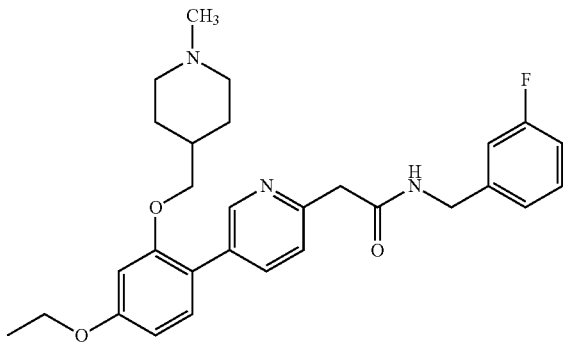 [SMILES: CCOc1ccc(-c2ccc(CC(=O)NCc3cccc(F)c3)nc2)c(OCC2CCN(C)CC2)c1] |
| 59 | | 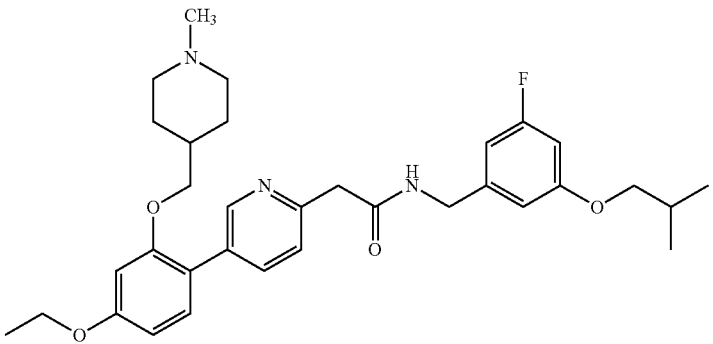 [SMILES: CCOc1ccc(-c2ccc(CC(=O)NCc3cc(F)cc(OCC(C)C)c3)nc2)c(OCC2CCN(C)CC2)c1] |
| 60 | 2-389 | 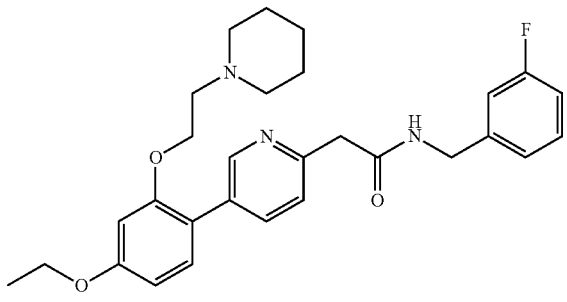 [SMILES: CCOc1ccc(-c2ccc(CC(=O)NCc3cccc(F)c3)nc2)c(OCCN2CCCCC2)c1] |
| 61 | | 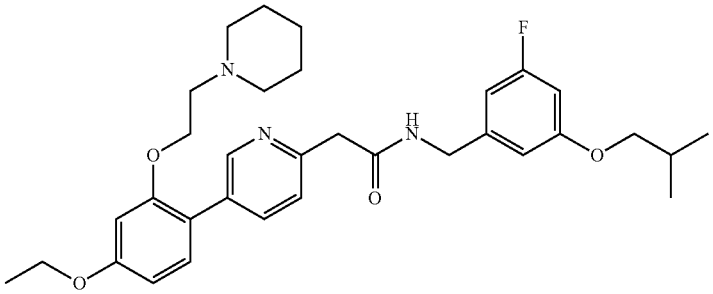 [SMILES: CCOc1ccc(-c2ccc(CC(=O)NCc3cc(F)cc(OCC(C)C)c3)nc2)c(OCCN2CCCCC2)c1] |

TABLE 1-continued
| Compound # | KX # | Compound |
|---|---|---|
| 62 | | 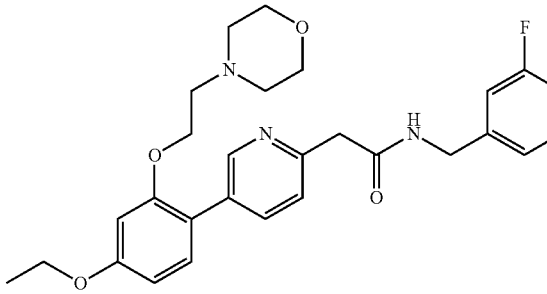 |
| 63 | | 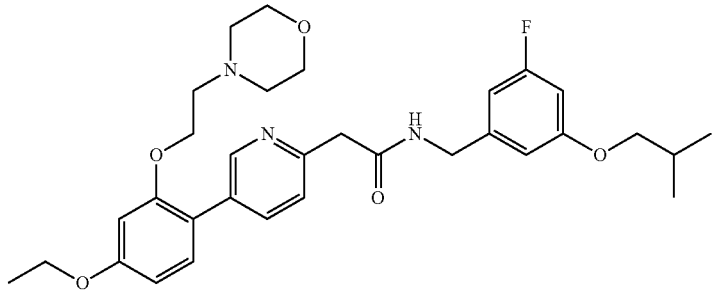 [SMILES: CCOc1ccc(-c2ccc(CC(=O)NCc3cc(F)cc(OCC(C)C)c3)nc2)c(OCCN2CCOCC2)c1] |
| 64 | 2-384 | 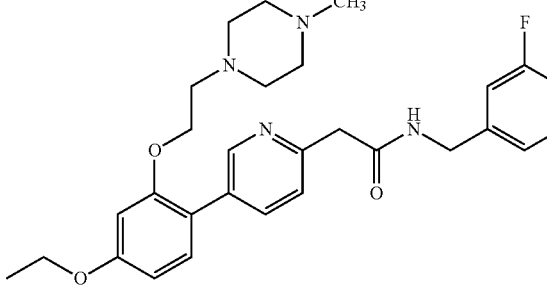 |
| 65 | | 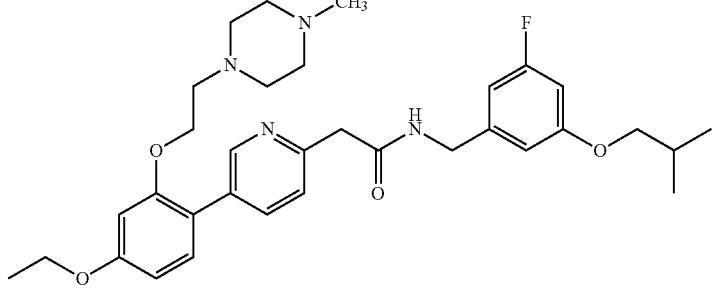 |
| 66 | 2-388 | 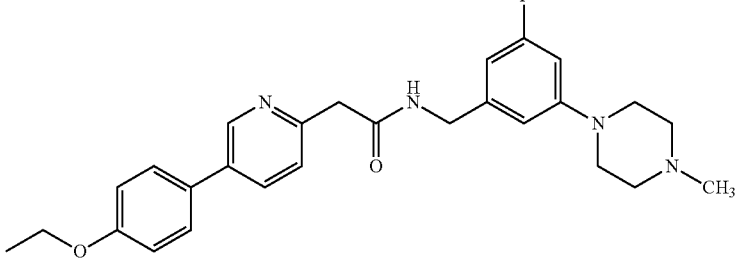 |

TABLE 1-continued

| Compound # | KX # | Compound |
|---|---|---|
| 67 | | (structure) |
| 68 | 2-382 | (structure) |
| 69 | | (structure) |
| 70 | 2-379 | (structure) |
| 71 | | (structure) |

TABLE 1-continued

| Compound # | KX # | Compound |
|---|---|---|
| 72 | 2-373 | |
| 73 | | |
| 74 | 2-376 | |
| 75 | 2-366 | |
| 76 | 2-361 | |

TABLE 1-continued
| Compound # | KX # | Compound |
|---|---|---|
| 77 | 2-370 | 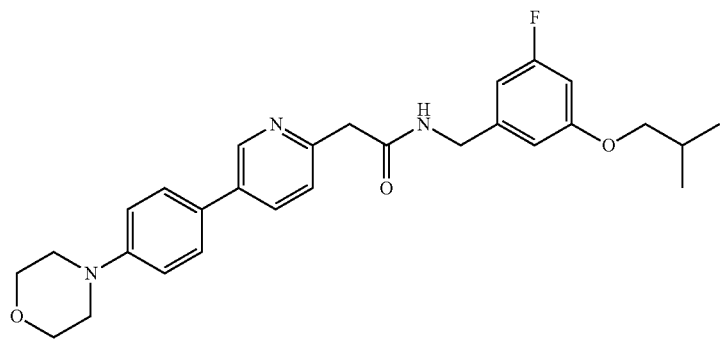 [SMILES: CC(C)COc1cc(F)cc(CNC(=O)Cc2ccc(-c3ccc(N4CCOCC4)cc3)cn2)c1] |
| 78 | 2-362 | 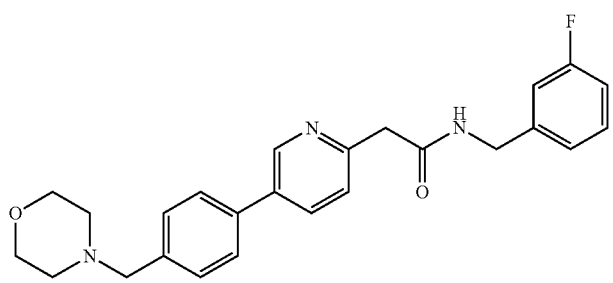 [SMILES: O=C(Cc1ccc(-c2ccc(CN3CCOCC3)cc2)cn1)NCc1cccc(F)c1] |
| 79 | 2-363 | 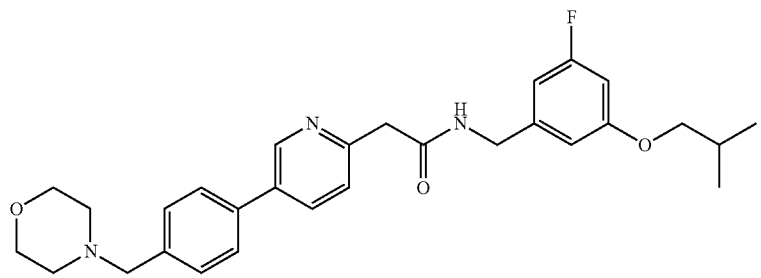 [SMILES: CC(C)COc1cc(F)cc(CNC(=O)Cc2ccc(-c3ccc(CN4CCOCC4)cc3)cn2)c1] |
| 80 | 2-372 | 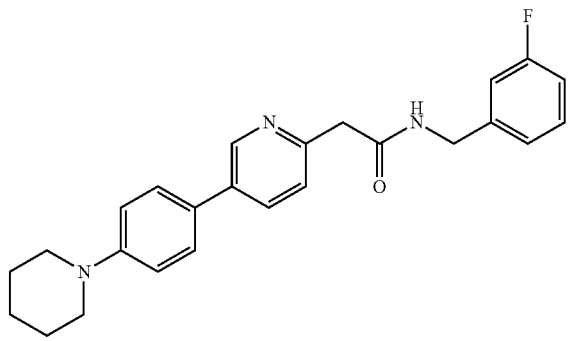 [SMILES: O=C(Cc1ccc(-c2ccc(N3CCCCC3)cc2)cn1)NCc1cccc(F)c1] |
| 81 | 2-371 | 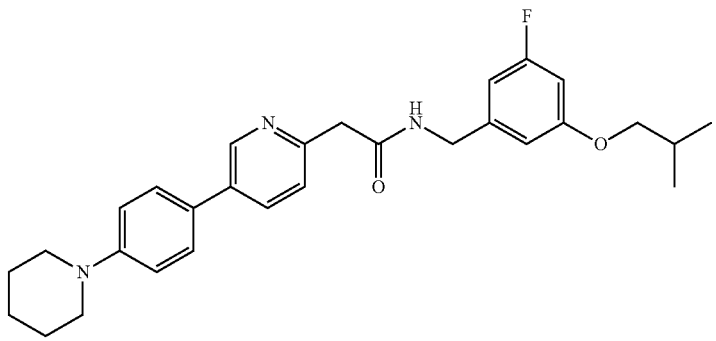 [SMILES: CC(C)COc1cc(F)cc(CNC(=O)Cc2ccc(-c3ccc(N4CCCCC4)cc3)cn2)c1] |

TABLE 1-continued

| Compound # | KX # | Compound |
|---|---|---|
| 82 | 2-364 | |
| 83 | 2-385 | |
| 84 | | |
| 85 | | |
| 86 | | |

TABLE 1-continued
| Compound # | KX # | Compound |
|---|---|---|
| 87 | | 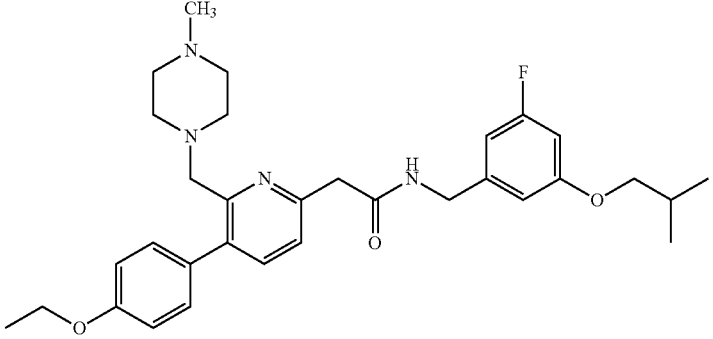 [SMILES: CCOc1ccc(-c2ccc(CC(=O)NCc3cc(F)cc(OCC(C)C)c3)nc2CN2CCN(C)CC2)cc1] |
| 88 | | 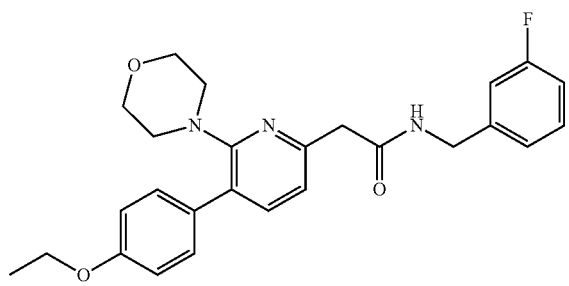 [SMILES: CCOc1ccc(-c2ccc(CC(=O)NCc3cccc(F)c3)nc2N2CCOCC2)cc1] |
| 89 | | 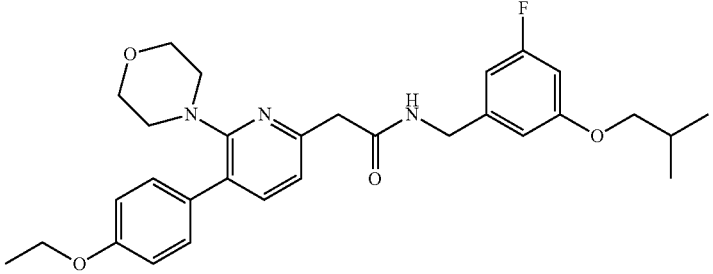 [SMILES: CCOc1ccc(-c2ccc(CC(=O)NCc3cc(F)cc(OCC(C)C)c3)nc2N2CCOCC2)cc1] |
| 90 | | 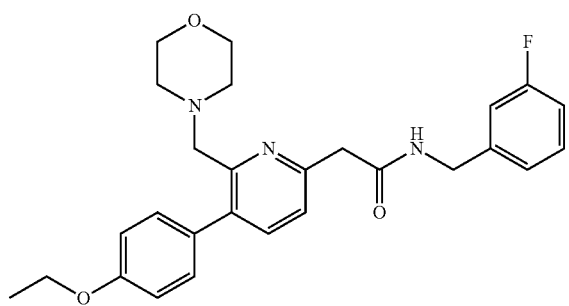 [SMILES: CCOc1ccc(-c2ccc(CC(=O)NCc3cccc(F)c3)nc2CN2CCOCC2)cc1] |
| 91 | | 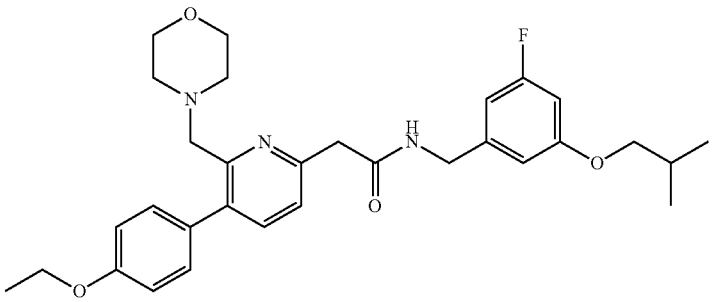 [SMILES: CCOc1ccc(-c2ccc(CC(=O)NCc3cc(F)cc(OCC(C)C)c3)nc2CN2CCOCC2)cc1] |

TABLE 1-continued
| Compound # | KX # | Compound |
|---|---|---|
| 92 | | 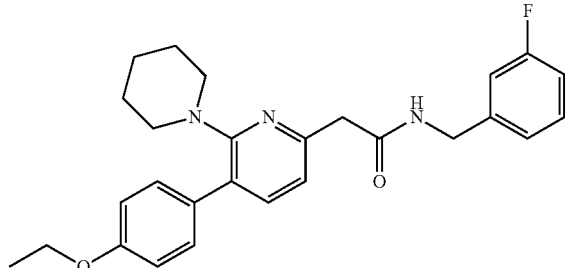 |
| 93 | | 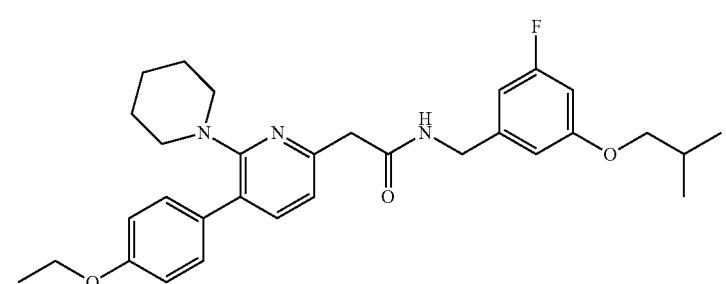 |
| 94 | | 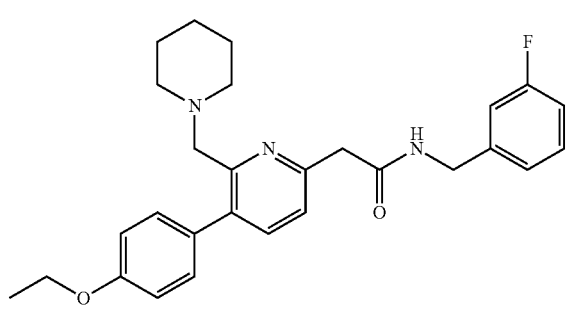 [SMILES: CCOc1ccc(-c2ccc(CC(=O)NCc3cccc(F)c3)nc2CN2CCCCC2)cc1] |
| 95 | | 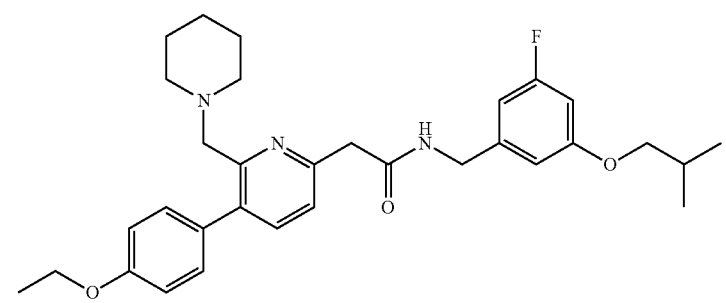 [SMILES: CCOc1ccc(-c2ccc(CC(=O)NCc3cc(F)cc(OCC(C)C)c3)nc2CN2CCCCC2)cc1] |
| 96 | | 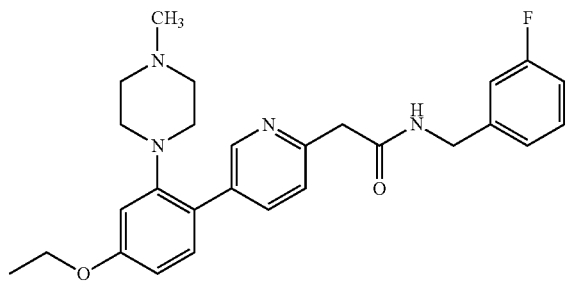 [SMILES: CCOc1ccc(-c2ccc(CC(=O)NCc3cccc(F)c3)nc2)c(N2CCN(C)CC2)c1] |

TABLE 1-continued

| Compound # | KX # | Compound |
|---|---|---|
| 97 | | |
| 98 | | |
| 99 | | |
| 100 | | |
| 101 | | |

TABLE 1-continued
| Compound # | KX # | Compound |
|---|---|---|
| 102 | | 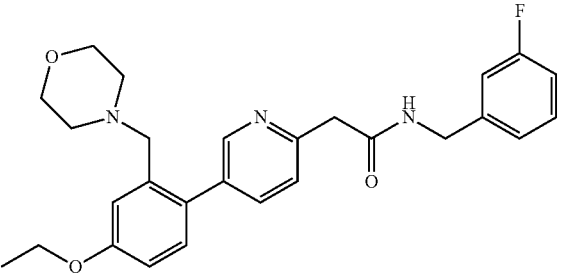 [SMILES: CCOc1ccc(-c2ccc(CC(=O)NCc3cccc(F)c3)nc2)c(CN2CCOCC2)c1] |
| 103 | | 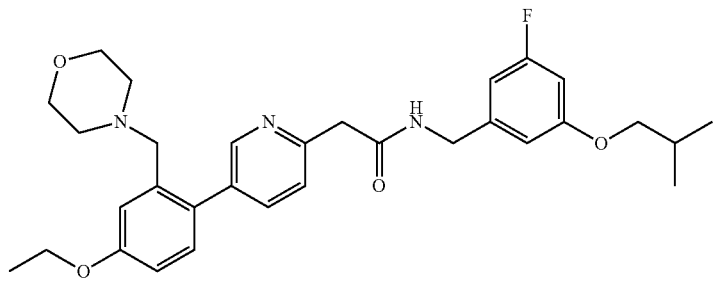 [SMILES: CCOc1ccc(-c2ccc(CC(=O)NCc3cc(F)cc(OCC(C)C)c3)nc2)c(CN2CCOCC2)c1] |
| 104 | | 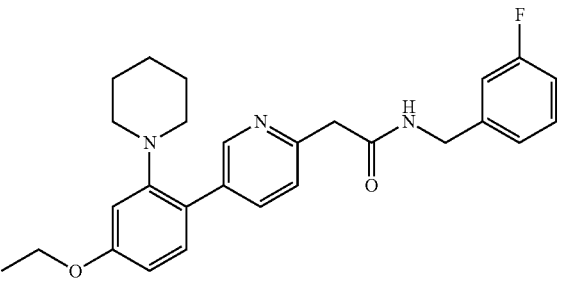 [SMILES: CCOc1ccc(-c2ccc(CC(=O)NCc3cccc(F)c3)nc2)c(N2CCCCC2)c1] |
| 105 | | 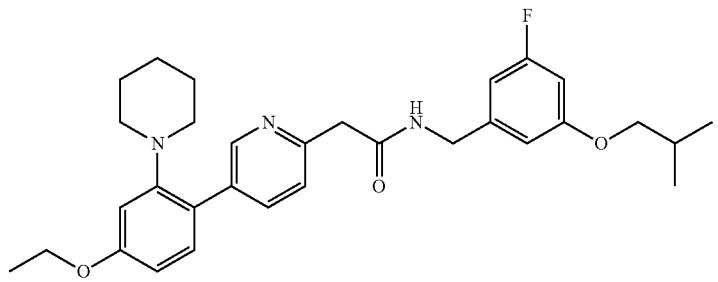 [SMILES: CCOc1ccc(-c2ccc(CC(=O)NCc3cc(F)cc(OCC(C)C)c3)nc2)c(N2CCCCC2)c1] |
| 106 | | 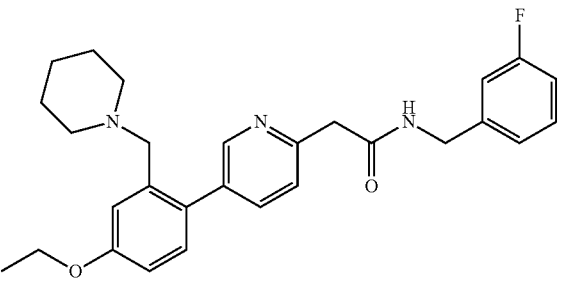 [SMILES: CCOc1ccc(-c2ccc(CC(=O)NCc3cccc(F)c3)nc2)c(CN2CCCCC2)c1] |

TABLE 1-continued

| Compound # | KX # | Compound |
|---|---|---|
| 107 | | |
| 108A | 1-072 (Chiral Center) | |
| 108B | 1-121 (Opposite Enantiomer Of 108A) | |
| 109 | 1-75 | |
| 110 | 1-62 | |
| 111 | 1-64 | |

TABLE 1-continued

| Compound # | KX # | Compound |
|---|---|---|
| 112 | 1-117 | |
| 113 | | |
| 114 | 2-390 | |
| 115 | 2-374 | |
| 116 | 2-383 | |

TABLE 1-continued
| Compound # | KX # | Compound |
|---|---|---|
| 117 | | 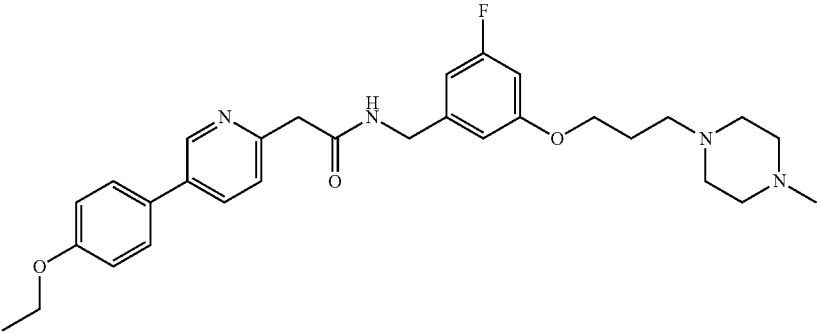 [SMILES: CCOc1ccc(-c2ccc(CC(=O)NCc3cc(F)cc(OCCCN4CCN(C)CC4)c3)nc2)cc1] |
| 118 | | 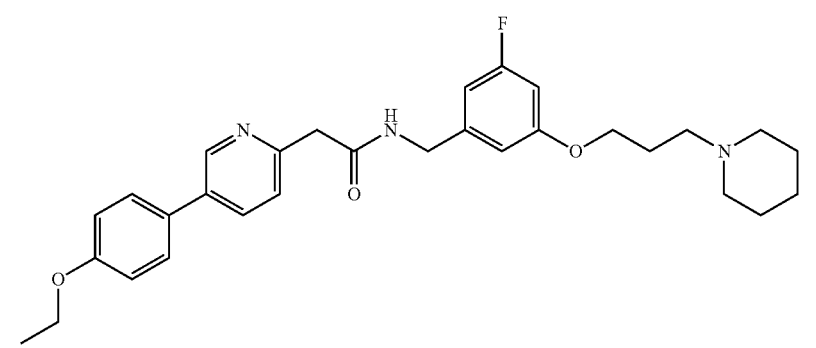 [SMILES: CCOc1ccc(-c2ccc(CC(=O)NCc3cc(F)cc(OCCCN4CCCCC4)c3)nc2)cc1] |
| 119 | | 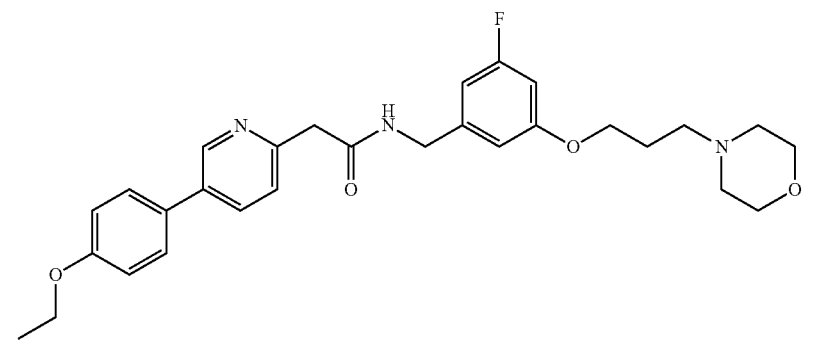 [SMILES: CCOc1ccc(-c2ccc(CC(=O)NCc3cc(F)cc(OCCCN4CCOCC4)c3)nc2)cc1] |
| 120 | | 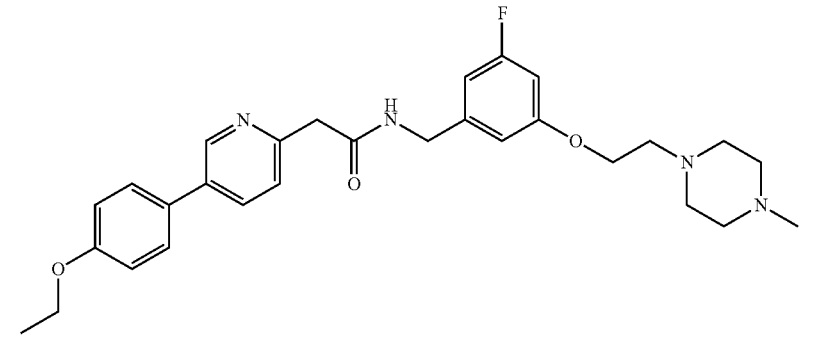 [SMILES: CCOc1ccc(-c2ccc(CC(=O)NCc3cc(F)cc(OCCN4CCN(C)CC4)c3)nc2)cc1] |

TABLE 1-continued

| Compound # | KX # | Compound |
|---|---|---|
| 121 | | |
| 122 | | |
| 123 | | |
| 124 | | |
| 125 | | |

TABLE 1-continued

| Compound # | KX # | Compound |
|---|---|---|
| 126 | | |
| 127 | | |
| 128 | | |
| 129 | | |
| 130 | | |

TABLE 1-continued
| Compound # | KX # | Compound |
|---|---|---|
| 131 | | 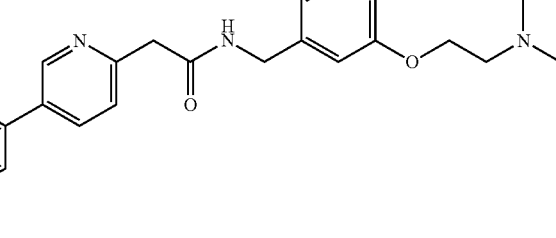 |
| 132 | | 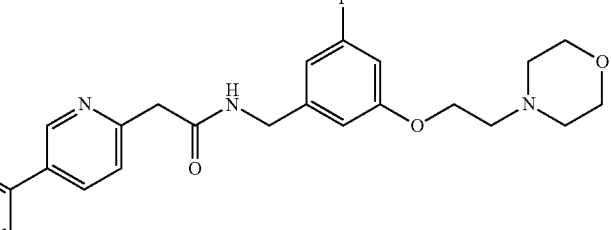 |
| 133 | 2-392 | 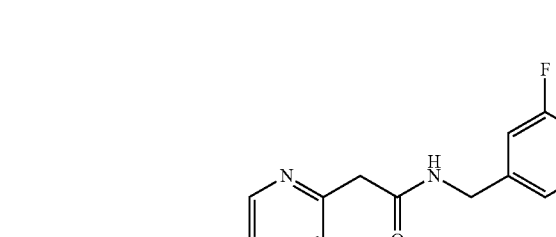 |
| 134 | 2-391 | 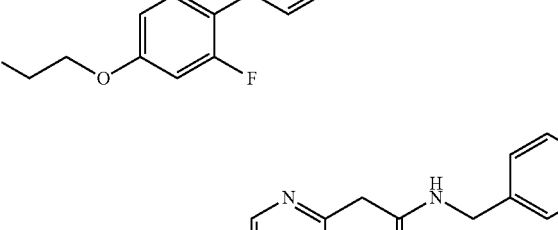 |
| 135 | 329-N oxide | 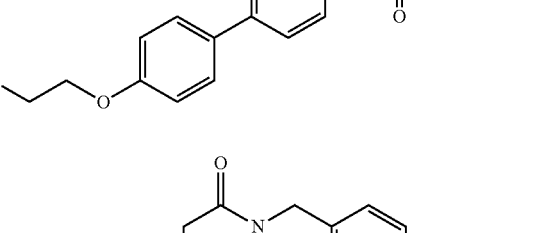 |

TABLE 1-continued
| Compound # | KX # | Compound |
|---|---|---|
| 136 | 2-393 | |
| 137 | 2-394 | |
Other Compounds are listed in Table 2.
TABLE 2
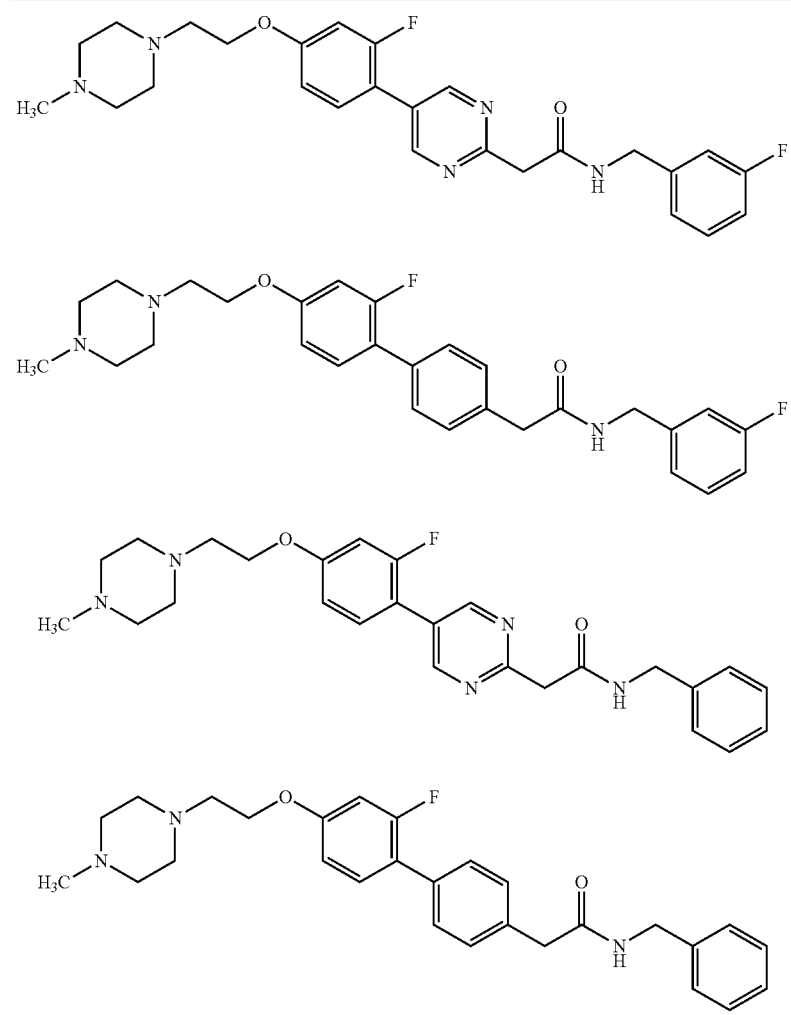

TABLE 2-continued
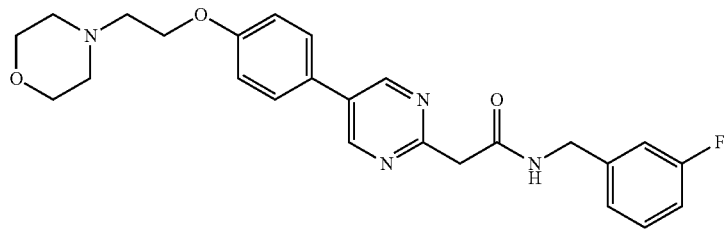 [SMILES: O=C(Cc1ncc(-c2ccc(OCCN3CCOCC3)cc2)cn1)NCc1cccc(F)c1]
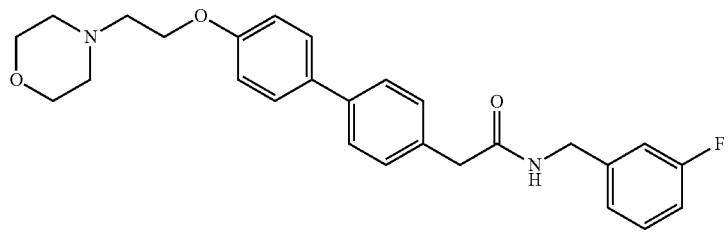 [SMILES: O=C(Cc1ccc(-c2ccc(OCCN3CCOCC3)cc2)cc1)NCc1cccc(F)c1]
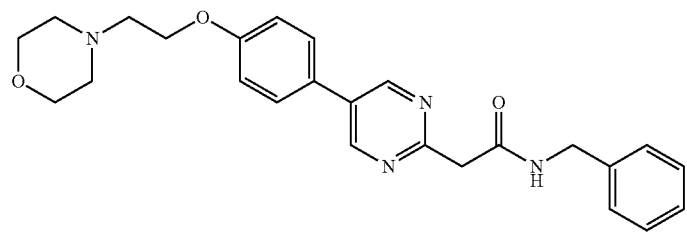 [SMILES: O=C(Cc1ncc(-c2ccc(OCCN3CCOCC3)cc2)cn1)NCc1ccccc1]
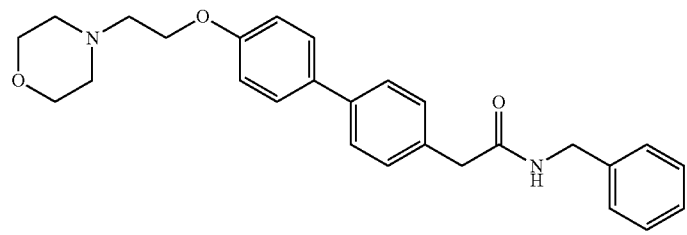 [SMILES: O=C(Cc1ccc(-c2ccc(OCCN3CCOCC3)cc2)cc1)NCc1ccccc1]
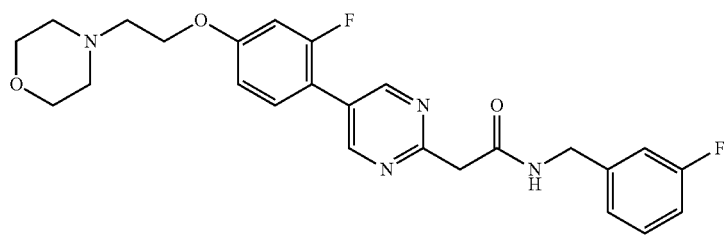 [SMILES: O=C(Cc1ncc(-c2ccc(OCCN3CCOCC3)cc2F)cn1)NCc1cccc(F)c1]
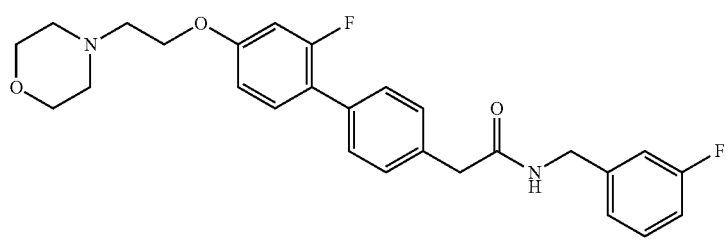 [SMILES: O=C(Cc1ccc(-c2ccc(OCCN3CCOCC3)cc2F)cc1)NCc1cccc(F)c1]

TABLE 2-continued
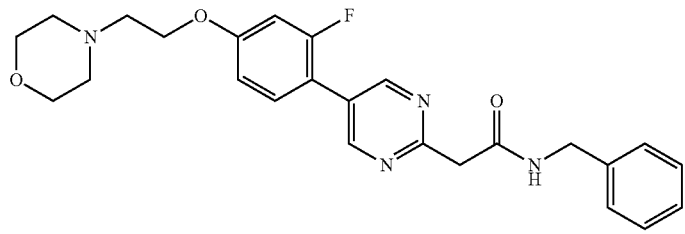 [SMILES: O=C(Cc1ncc(-c2ccc(OCCN3CCOCC3)cc2F)cn1)NCc1ccccc1]
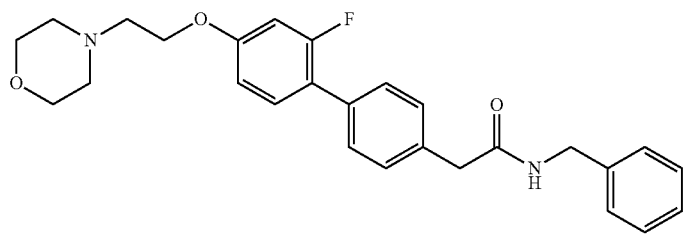 [SMILES: O=C(Cc1ccc(-c2ccc(OCCN3CCOCC3)cc2F)cc1)NCc1ccccc1]
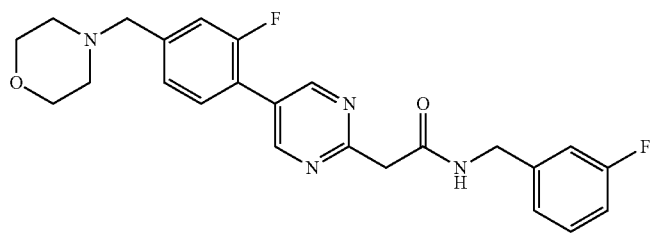 [SMILES: O=C(Cc1ncc(-c2ccc(CN3CCOCC3)cc2F)cn1)NCc1cccc(F)c1]
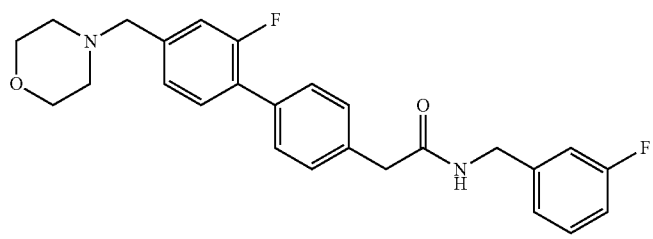 [SMILES: O=C(Cc1ccc(-c2ccc(CN3CCOCC3)cc2F)cc1)NCc1cccc(F)c1]
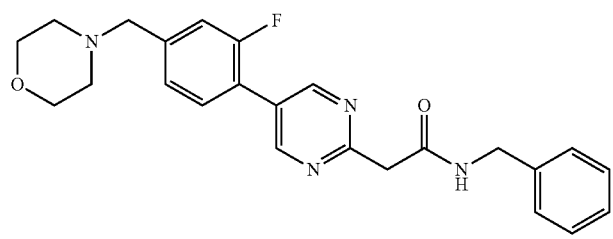 [SMILES: O=C(Cc1ncc(-c2ccc(CN3CCOCC3)cc2F)cn1)NCc1ccccc1]
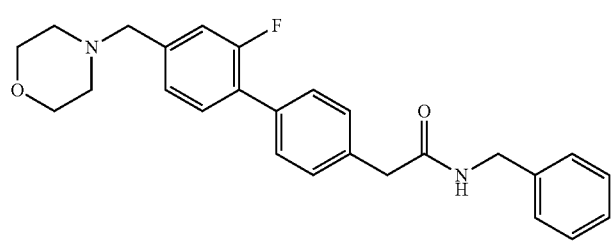 [SMILES: O=C(Cc1ccc(-c2ccc(CN3CCOCC3)cc2F)cc1)NCc1ccccc1]

TABLE 2-continued
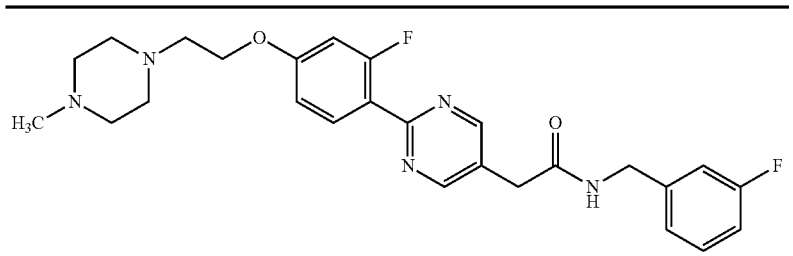
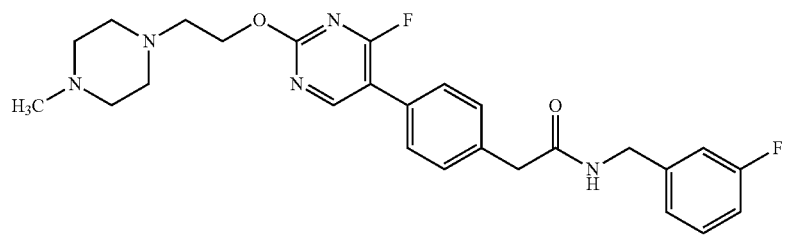 [SMILES: CN1CCN(CCOc2ncc(-c3ccc(CC(=O)NCc4cccc(F)c4)cc3)c(F)n2)CC1]
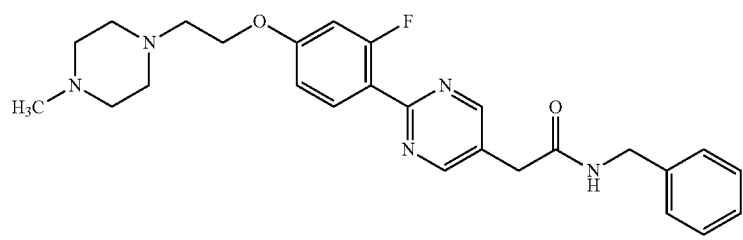 [SMILES: CN1CCN(CCOc2ccc(-c3ncc(CC(=O)NCc4ccccc4)cn3)c(F)c2)CC1]
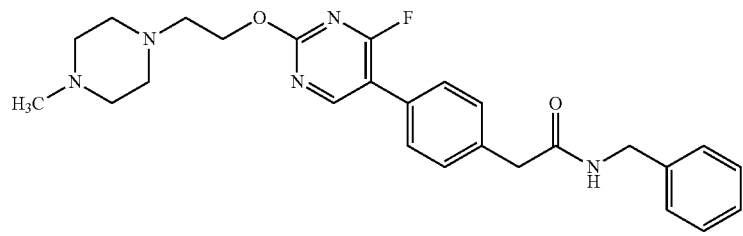 [SMILES: CN1CCN(CCOc2ncc(-c3ccc(CC(=O)NCc4ccccc4)cc3)c(F)n2)CC1]
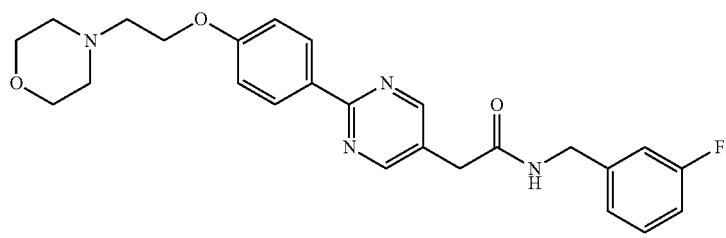 [SMILES: O=C(Cc1cnc(-c2ccc(OCCN3CCOCC3)cc2)nc1)NCc1cccc(F)c1]
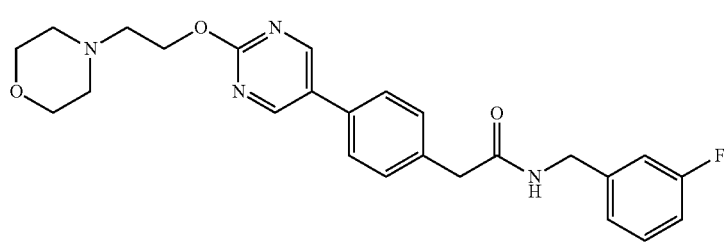

TABLE 2-continued
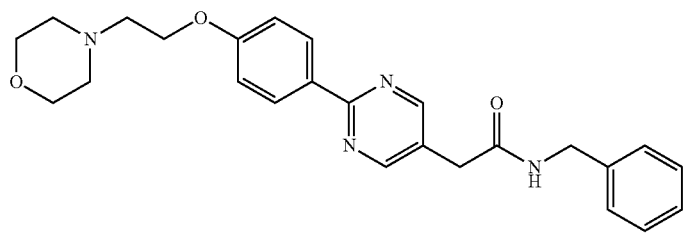 [SMILES: O=C(Cc1cnc(-c2ccc(OCCN3CCOCC3)cc2)nc1)NCc1ccccc1]
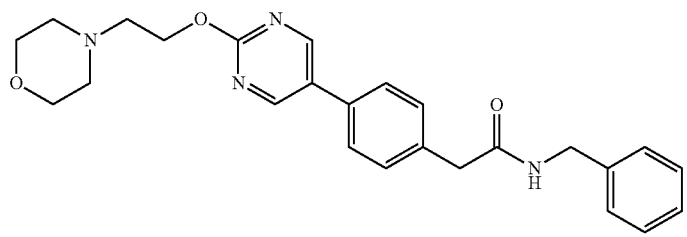 [SMILES: O=C(Cc1ccc(-c2cnc(OCCN3CCOCC3)nc2)cc1)NCc1ccccc1]
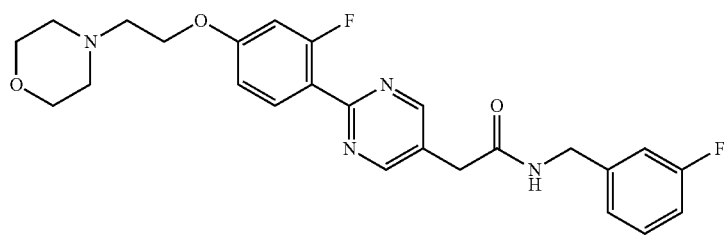
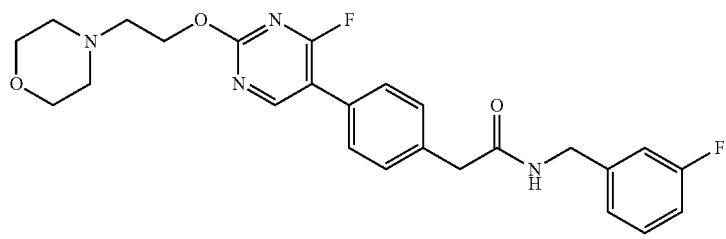 [SMILES: O=C(Cc1ccc(-c2cnc(OCCN3CCOCC3)nc2F)cc1)NCc1cccc(F)c1]
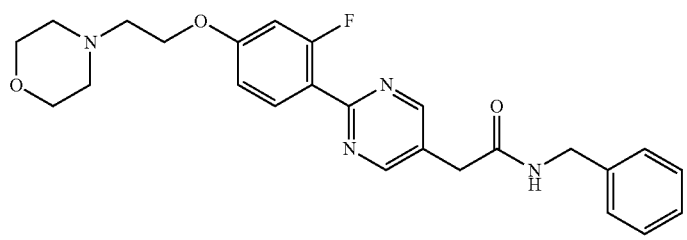 [SMILES: O=C(Cc1cnc(-c2ccc(OCCN3CCOCC3)cc2F)nc1)NCc1ccccc1]
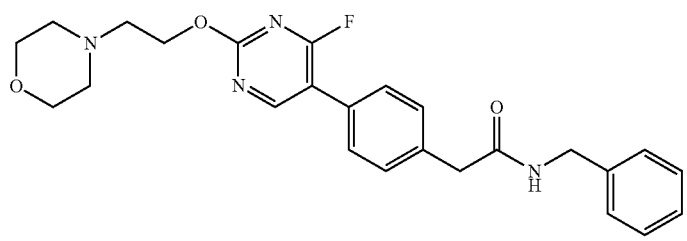 [SMILES: O=C(Cc1ccc(-c2cnc(OCCN3CCOCC3)nc2F)cc1)NCc1ccccc1]

TABLE 2-continued
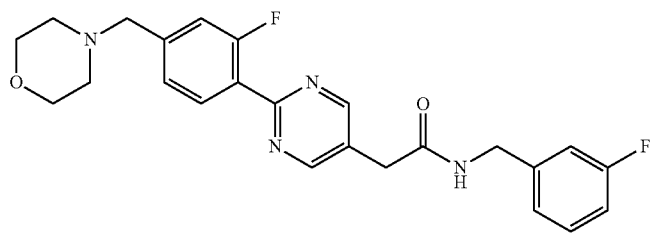 [SMILES: O=C(Cc1cnc(-c2ccc(CN3CCOCC3)cc2F)nc1)NCc1cccc(F)c1]
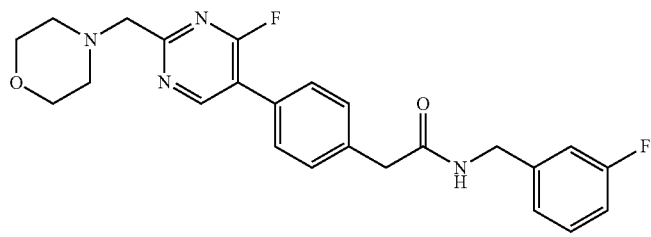 [SMILES: O=C(Cc1ccc(-c2cnc(CN3CCOCC3)nc2F)cc1)NCc1cccc(F)c1]
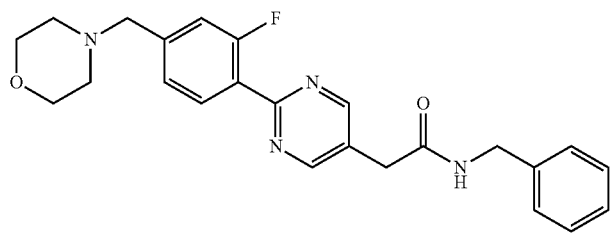 [SMILES: O=C(Cc1cnc(-c2ccc(CN3CCOCC3)cc2F)nc1)NCc1ccccc1]
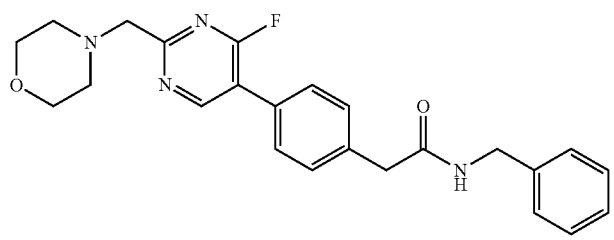 [SMILES: O=C(Cc1ccc(-c2cnc(CN3CCOCC3)nc2F)cc1)NCc1ccccc1]
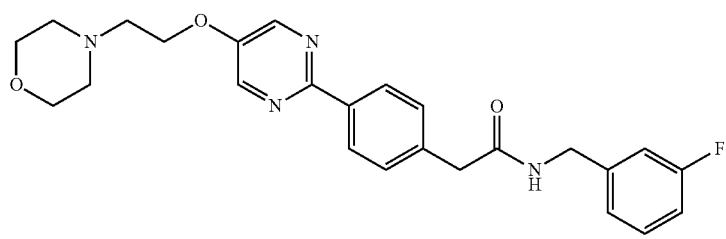 [SMILES: O=C(Cc1ccc(-c2ncc(OCCN3CCOCC3)cn2)cc1)NCc1cccc(F)c1]
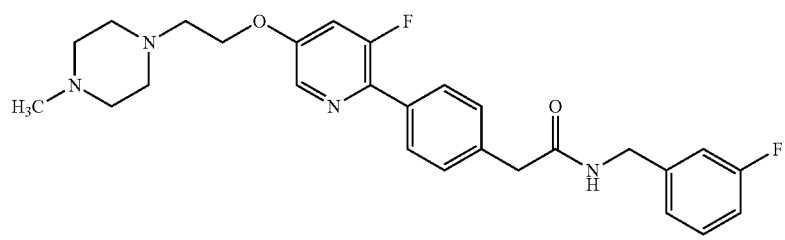 [SMILES: CN1CCN(CCOc2cnc(-c3ccc(CC(=O)NCc4cccc(F)c4)cc3)c(F)c2)CC1]

TABLE 2-continued
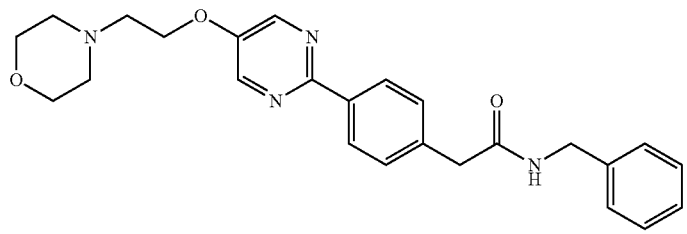 [SMILES: O=C(Cc1ccc(-c2ncc(OCCN3CCOCC3)cn2)cc1)NCc1ccccc1]
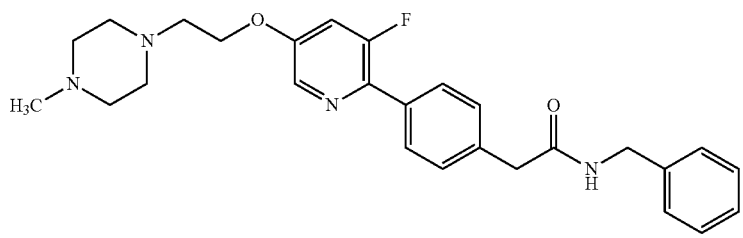 [SMILES: CN1CCN(CCOc2cnc(-c3ccc(CC(=O)NCc4ccccc4)cc3)c(F)c2)CC1]
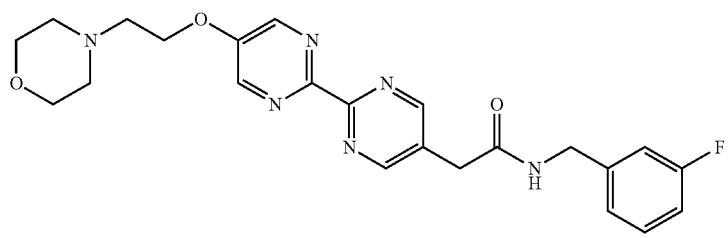
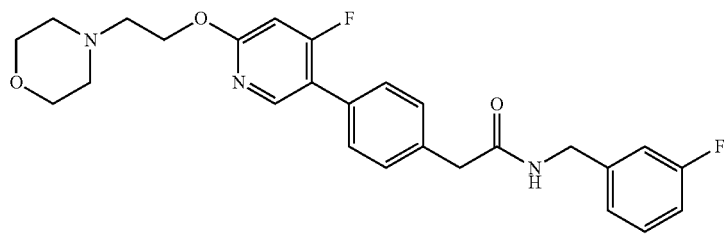 [SMILES: O=C(Cc1ccc(-c2cnc(OCCN3CCOCC3)cc2F)cc1)NCc1cccc(F)c1]
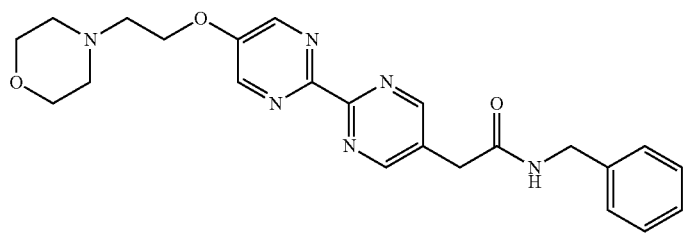 [SMILES: O=C(Cc1cnc(-c2ncc(OCCN3CCOCC3)cn2)nc1)NCc1ccccc1]
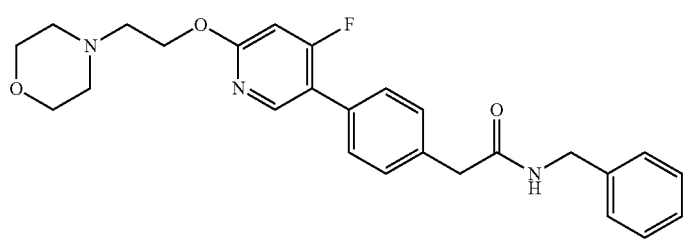 [SMILES: O=C(Cc1ccc(-c2cnc(OCCN3CCOCC3)cc2F)cc1)NCc1ccccc1]

TABLE 2-continued
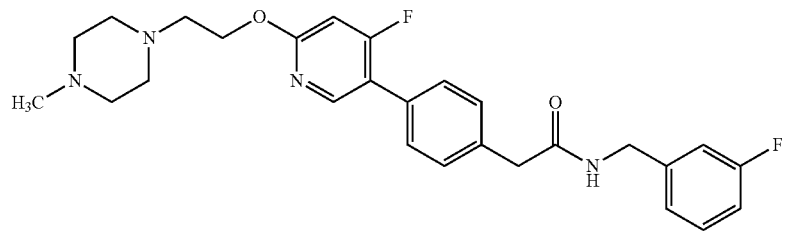 [SMILES: CN1CCN(CCOc2cc(F)c(-c3ccc(CC(=O)NCc4cccc(F)c4)cc3)cn2)CC1]
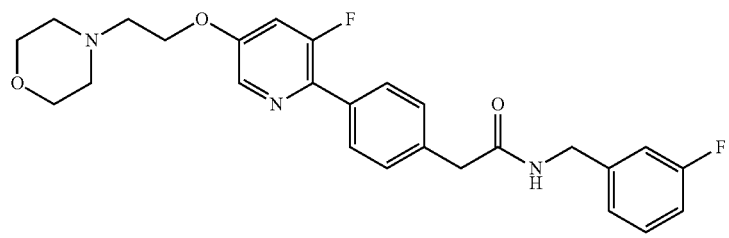 [SMILES: O=C(Cc1ccc(-c2ncc(OCCN3CCOCC3)cc2F)cc1)NCc1cccc(F)c1]
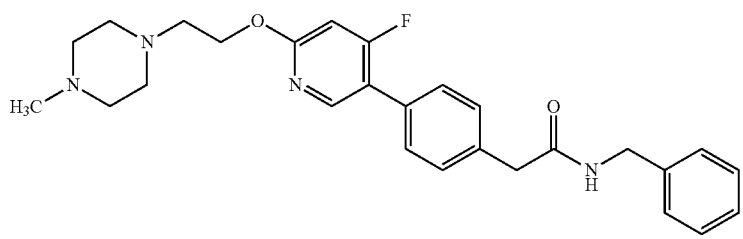 [SMILES: CN1CCN(CCOc2cc(F)c(-c3ccc(CC(=O)NCc4ccccc4)cc3)cn2)CC1]
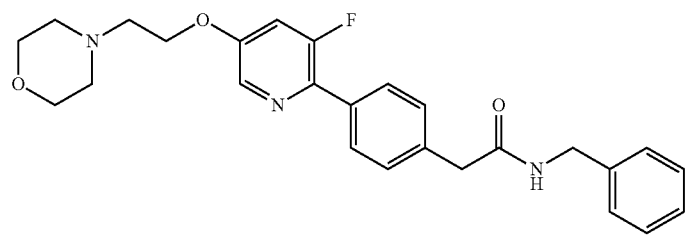 [SMILES: O=C(Cc1ccc(-c2ncc(OCCN3CCOCC3)cc2F)cc1)NCc1ccccc1]
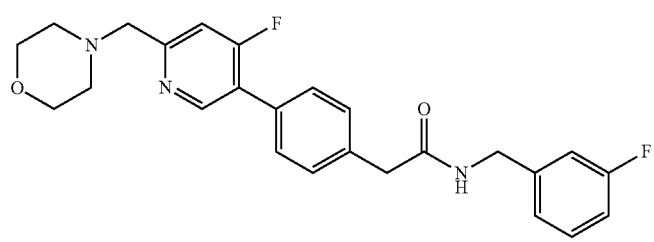 [SMILES: O=C(Cc1ccc(-c2cnc(CN3CCOCC3)cc2F)cc1)NCc1cccc(F)c1]
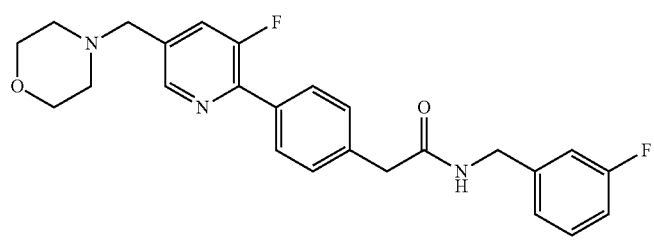 [SMILES: O=C(Cc1ccc(-c2ncc(CN3CCOCC3)cc2F)cc1)NCc1cccc(F)c1]

TABLE 2-continued
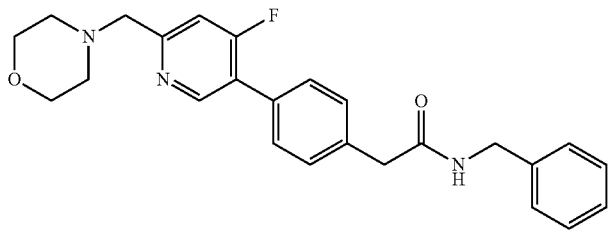 [SMILES: O=C(Cc1ccc(-c2cnc(CN3CCOCC3)cc2F)cc1)NCc1ccccc1]
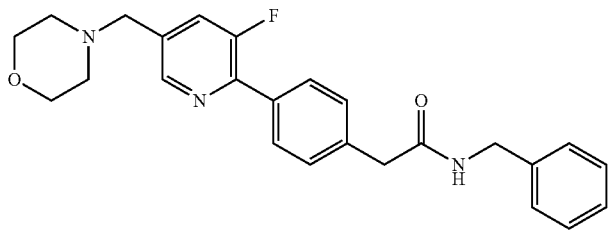 [SMILES: O=C(Cc1ccc(-c2ncc(CN3CCOCC3)cc2F)cc1)NCc1ccccc1]
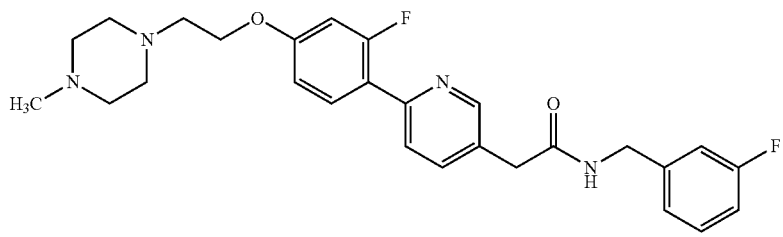 [SMILES: CN1CCN(CCOc2ccc(-c3ccc(CC(=O)NCc4cccc(F)c4)cn3)c(F)c2)CC1]
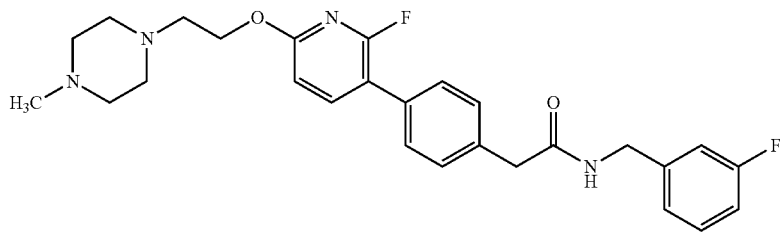 [SMILES: CN1CCN(CCOc2ccc(-c3ccc(CC(=O)NCc4cccc(F)c4)cc3)c(F)n2)CC1]
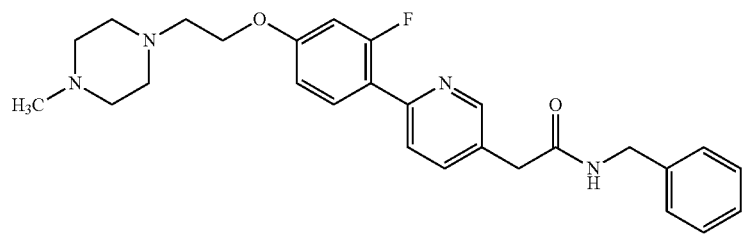 [SMILES: CN1CCN(CCOc2ccc(-c3ccc(CC(=O)NCc4ccccc4)cn3)c(F)c2)CC1]
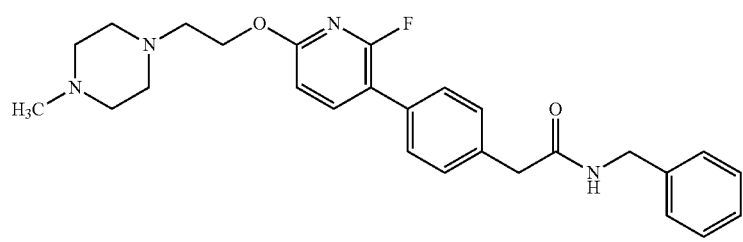

TABLE 2-continued
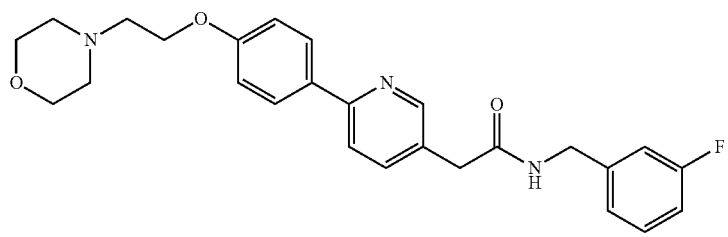
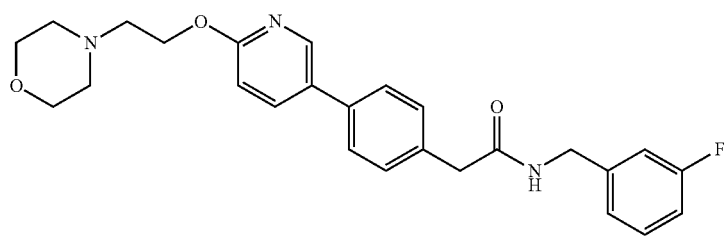 [SMILES: O=C(Cc1ccc(-c2ccc(OCCN3CCOCC3)nc2)cc1)NCc1cccc(F)c1]
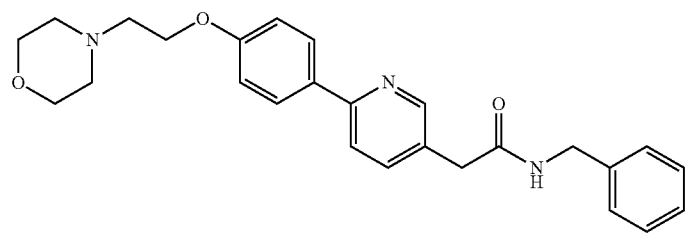 [SMILES: O=C(Cc1ccc(-c2ccc(OCCN3CCOCC3)cc2)nc1)NCc1ccccc1]
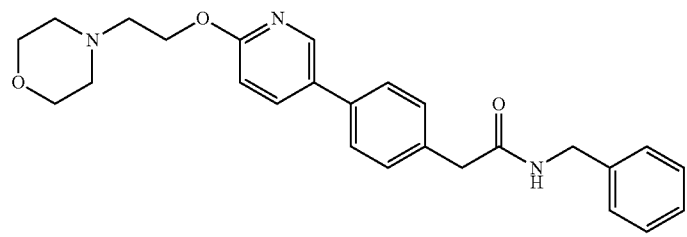 [SMILES: O=C(Cc1ccc(-c2ccc(OCCN3CCOCC3)nc2)cc1)NCc1ccccc1]
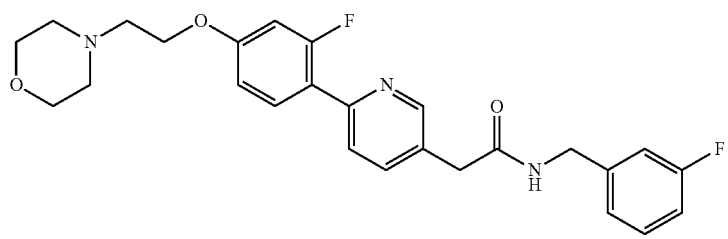 [SMILES: O=C(Cc1ccc(-c2ccc(OCCN3CCOCC3)cc2F)nc1)NCc1cccc(F)c1]
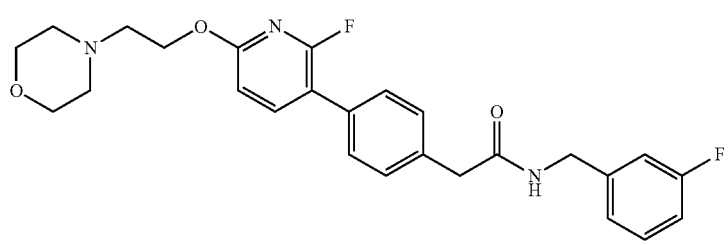 [SMILES: O=C(Cc1ccc(-c2ccc(OCCN3CCOCC3)nc2F)cc1)NCc1cccc(F)c1]

TABLE 2-continued
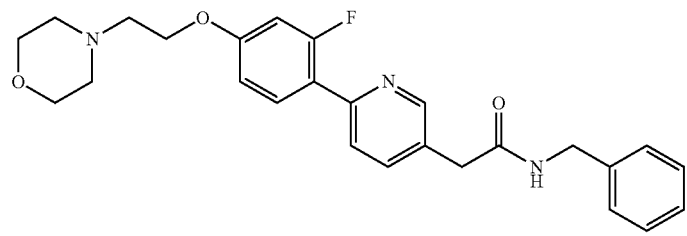 [SMILES: O=C(Cc1ccc(-c2ccc(OCCN3CCOCC3)cc2F)nc1)NCc1ccccc1]
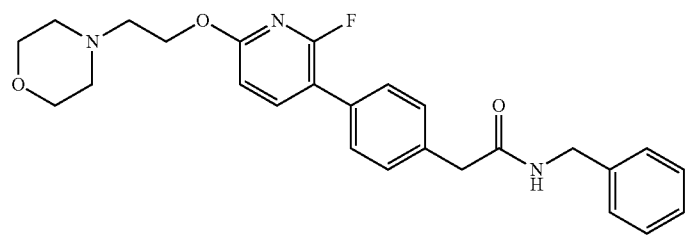 [SMILES: O=C(Cc1ccc(-c2ccc(OCCN3CCOCC3)nc2F)cc1)NCc1ccccc1]
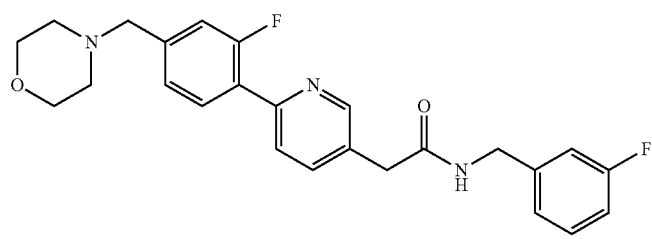 [SMILES: O=C(Cc1ccc(-c2ccc(CN3CCOCC3)cc2F)nc1)NCc1cccc(F)c1]
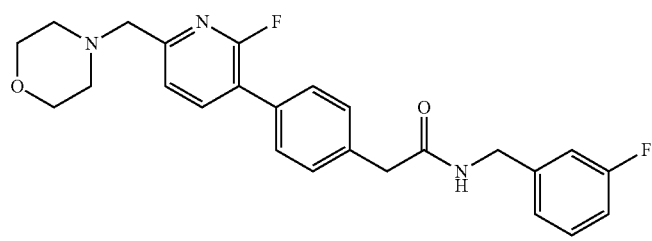 [SMILES: O=C(Cc1ccc(-c2ccc(CN3CCOCC3)nc2F)cc1)NCc1cccc(F)c1]
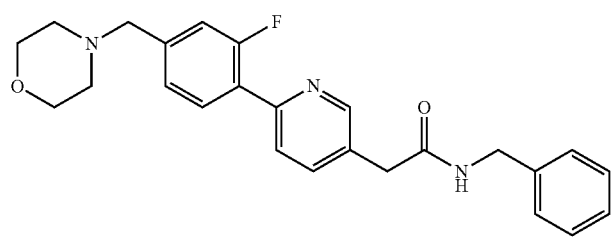 [SMILES: O=C(Cc1ccc(-c2ccc(CN3CCOCC3)cc2F)nc1)NCc1ccccc1]
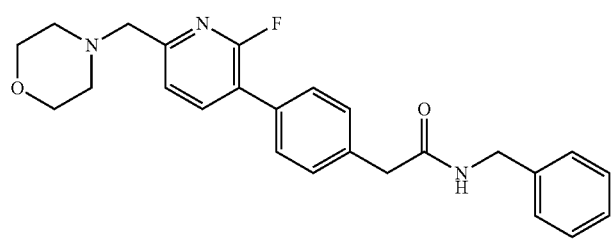 [SMILES: O=C(Cc1ccc(-c2ccc(CN3CCOCC3)nc2F)cc1)NCc1ccccc1]

TABLE 2-continued
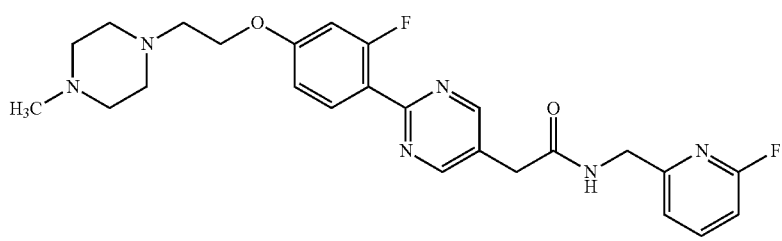 [SMILES: CN1CCN(CCOc2ccc(-c3ncc(CC(=O)NCc4cccc(F)n4)cn3)c(F)c2)CC1]
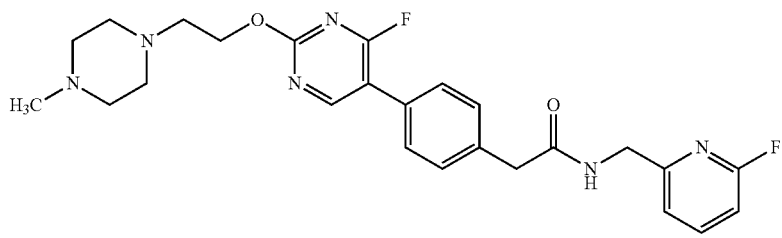 [SMILES: CN1CCN(CCOc2ncc(-c3ccc(CC(=O)NCc4cccc(F)n4)cc3)c(F)n2)CC1]
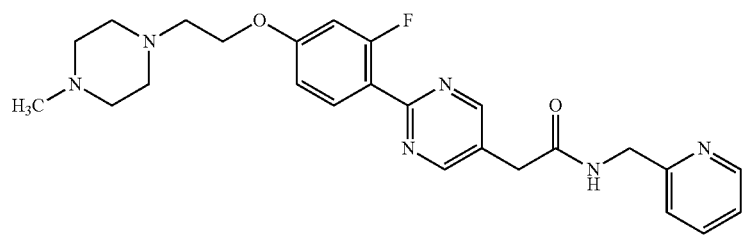
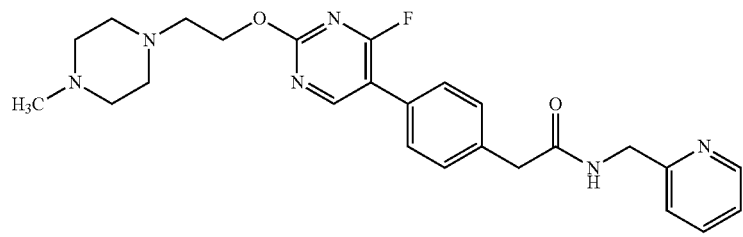 [SMILES: CN1CCN(CCOc2ncc(-c3ccc(CC(=O)NCc4ccccn4)cc3)c(F)n2)CC1]
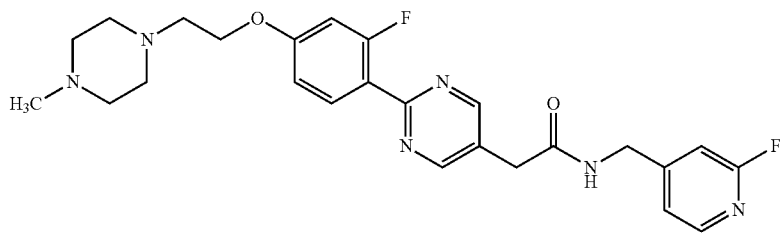 [SMILES: CN1CCN(CCOc2ccc(-c3ncc(CC(=O)NCc4ccnc(F)c4)cn3)c(F)c2)CC1]
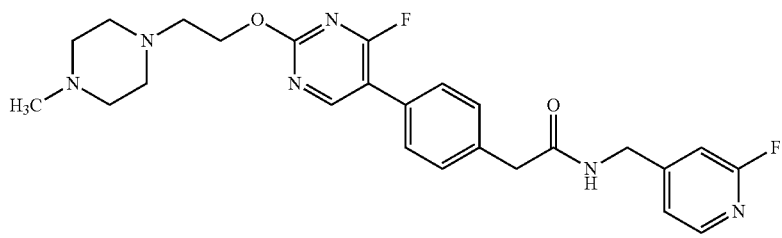 [SMILES: CN1CCN(CCOc2ncc(-c3ccc(CC(=O)NCc4ccnc(F)c4)cc3)c(F)n2)CC1]

TABLE 2-continued
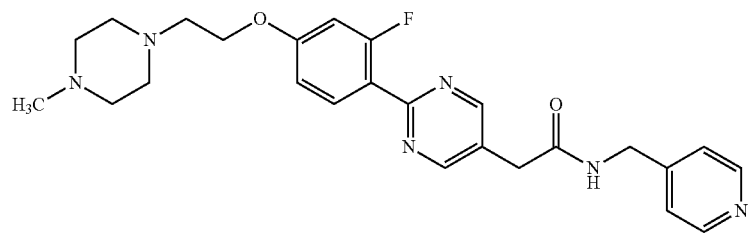 [SMILES: CN1CCN(CCOc2ccc(-c3ncc(CC(=O)NCc4ccncc4)cn3)c(F)c2)CC1]
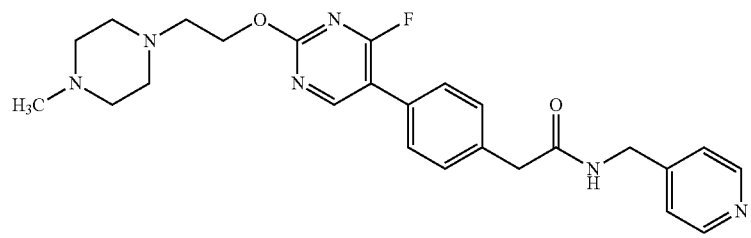 [SMILES: CN1CCN(CCOc2ncc(-c3ccc(CC(=O)NCc4ccncc4)cc3)c(F)n2)CC1]
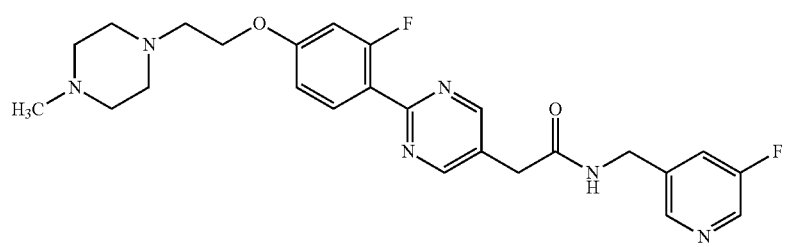 [SMILES: CN1CCN(CCOc2ccc(-c3ncc(CC(=O)NCc4cncc(F)c4)cn3)c(F)c2)CC1]
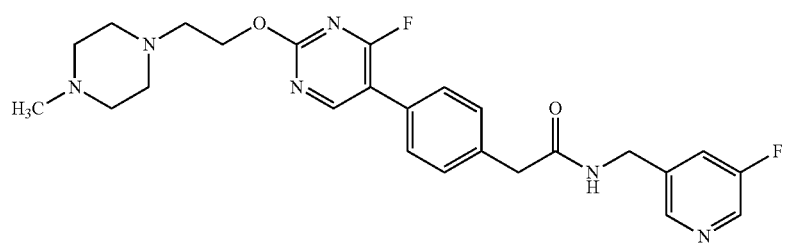 [SMILES: CN1CCN(CCOc2ncc(-c3ccc(CC(=O)NCc4cncc(F)c4)cc3)c(F)n2)CC1]
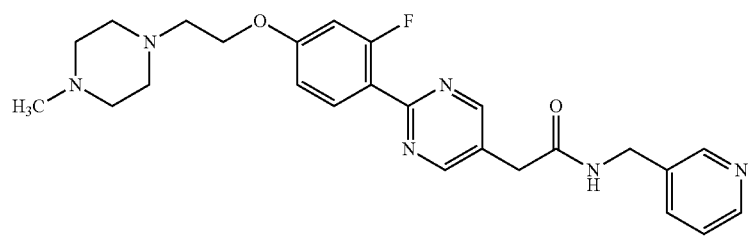 [SMILES: CN1CCN(CCOc2ccc(-c3ncc(CC(=O)NCc4cccnc4)cn3)c(F)c2)CC1]
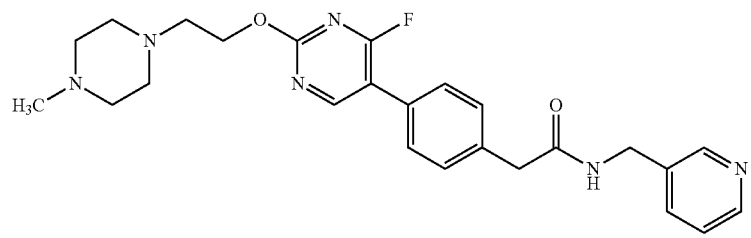 [SMILES: CN1CCN(CCOc2ncc(-c3ccc(CC(=O)NCc4cccnc4)cc3)c(F)n2)CC1]

TABLE 2-continued
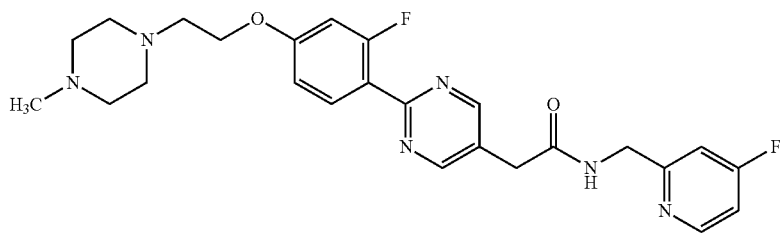
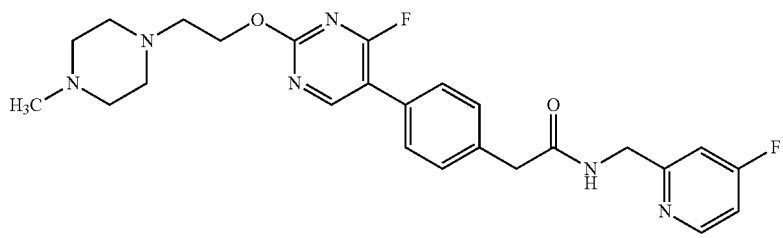 [SMILES: CN1CCN(CCOc2ncc(-c3ccc(CC(=O)NCc4cc(F)ccn4)cc3)c(F)n2)CC1]
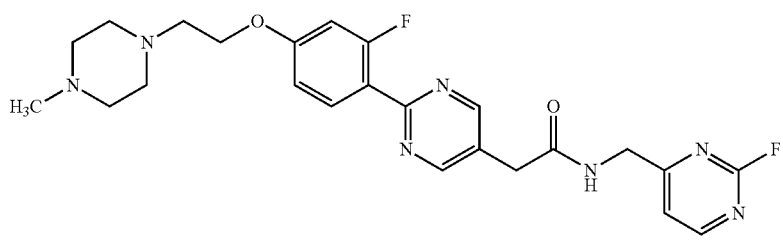
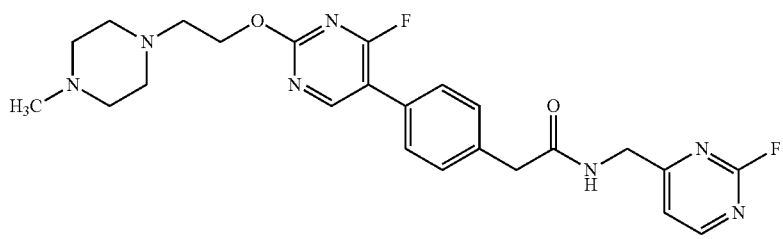 [SMILES: CN1CCN(CCOc2ncc(-c3ccc(CC(=O)NCc4ccnc(F)n4)cc3)c(F)n2)CC1]
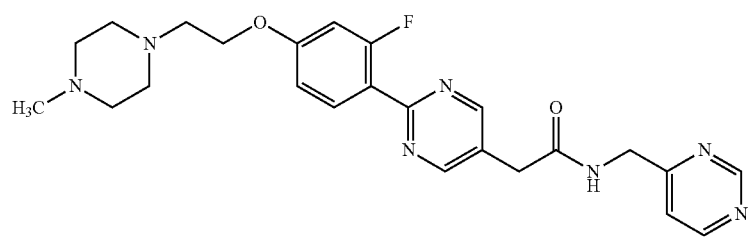 [SMILES: CN1CCN(CCOc2ccc(-c3ncc(CC(=O)NCc4ccncn4)cn3)c(F)c2)CC1]
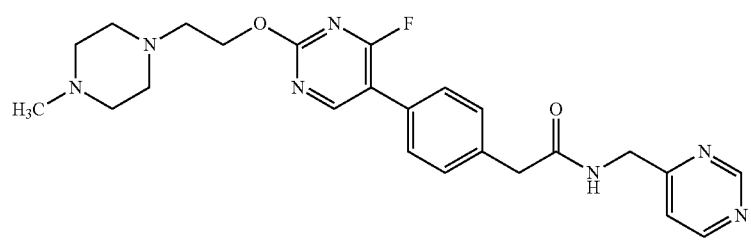 [SMILES: CN1CCN(CCOc2ncc(-c3ccc(CC(=O)NCc4ccncn4)cc3)c(F)n2)CC1]

TABLE 2-continued
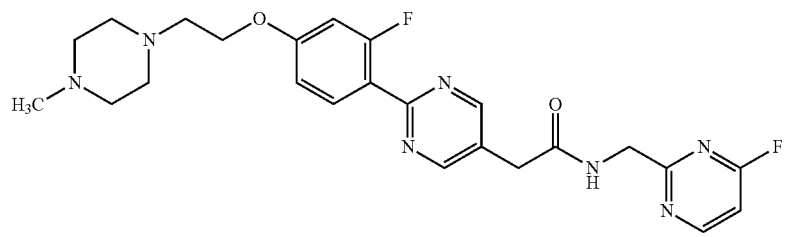 [SMILES: CN1CCN(CCOc2ccc(-c3ncc(CC(=O)NCc4nccc(F)n4)cn3)c(F)c2)CC1]
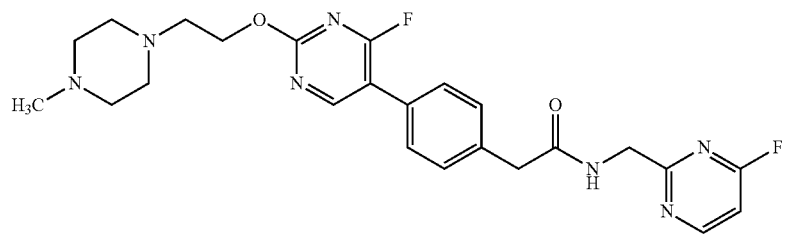
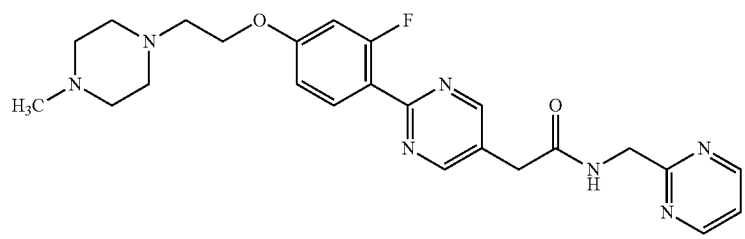
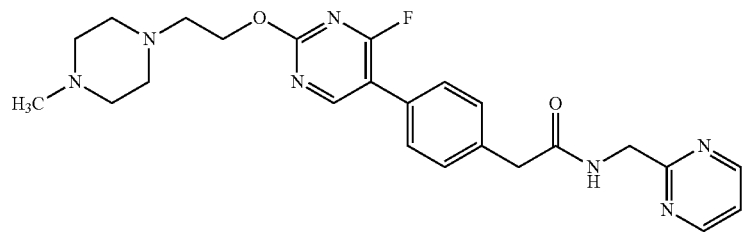 [SMILES: CN1CCN(CCOc2ncc(-c3ccc(CC(=O)NCc4ncccn4)cc3)c(F)n2)CC1]
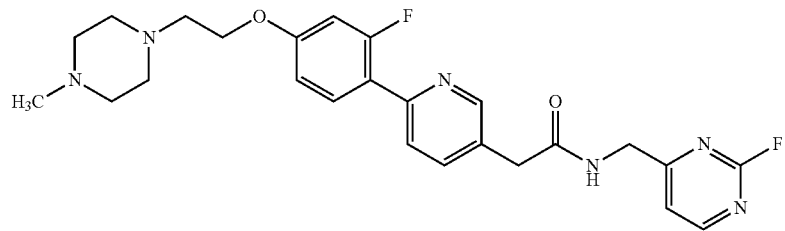 [SMILES: CN1CCN(CCOc2ccc(-c3ccc(CC(=O)NCc4ccnc(F)n4)cn3)c(F)c2)CC1]
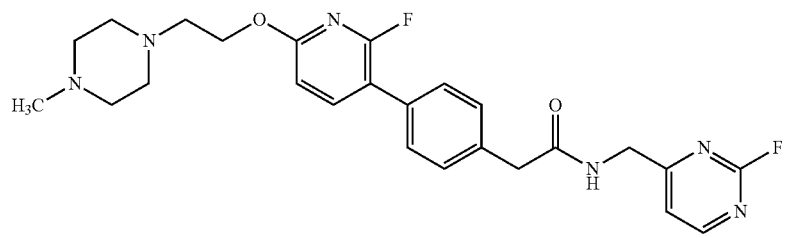 [SMILES: CN1CCN(CCOc2ccc(-c3ccc(CC(=O)NCc4ccnc(F)n4)cc3)c(F)n2)CC1]

TABLE 2-continued
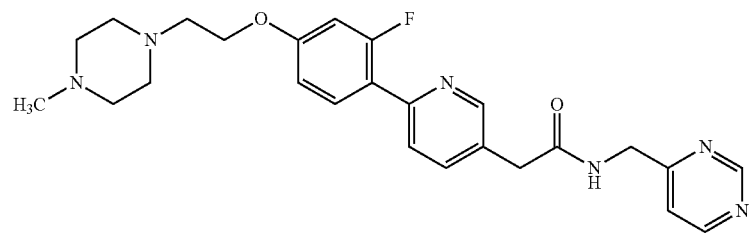 [SMILES: CN1CCN(CCOc2ccc(-c3ccc(CC(=O)NCc4ccncn4)cn3)c(F)c2)CC1]
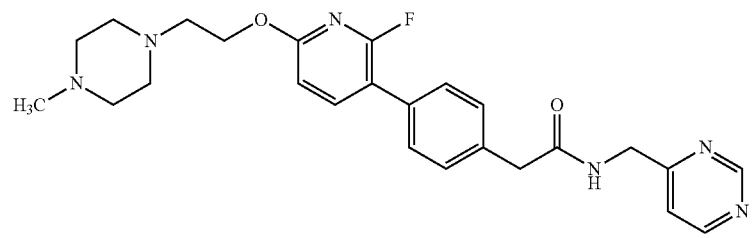 [SMILES: CN1CCN(CCOc2ccc(-c3ccc(CC(=O)NCc4ccncn4)cc3)c(F)n2)CC1]
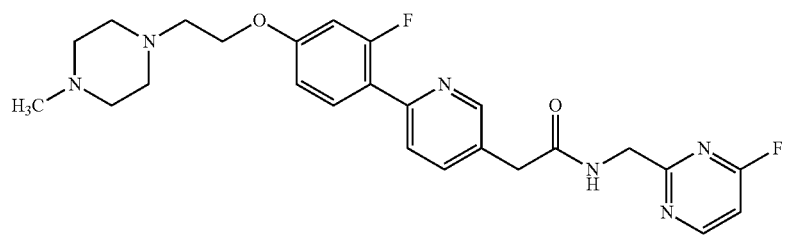 [SMILES: CN1CCN(CCOc2ccc(-c3ccc(CC(=O)NCc4nccc(F)n4)cn3)c(F)c2)CC1]
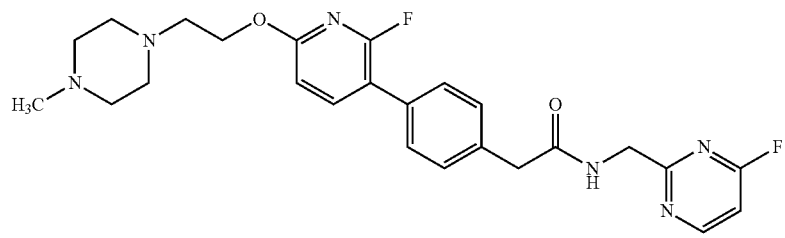 [SMILES: CN1CCN(CCOc2ccc(-c3ccc(CC(=O)NCc4nccc(F)n4)cc3)c(F)n2)CC1]
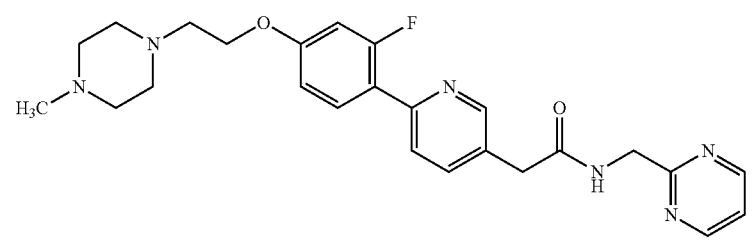 [SMILES: CN1CCN(CCOc2ccc(-c3ccc(CC(=O)NCc4ncccn4)cn3)c(F)c2)CC1]
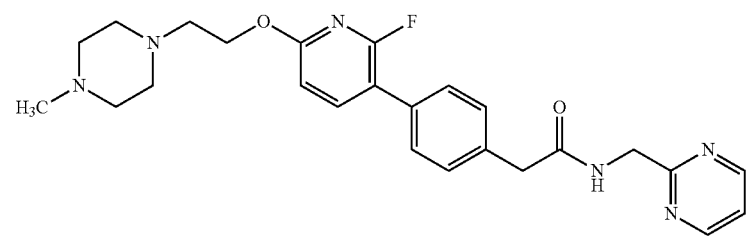 [SMILES: CN1CCN(CCOc2ccc(-c3ccc(CC(=O)NCc4ncccn4)cc3)c(F)n2)CC1]

TABLE 2-continued
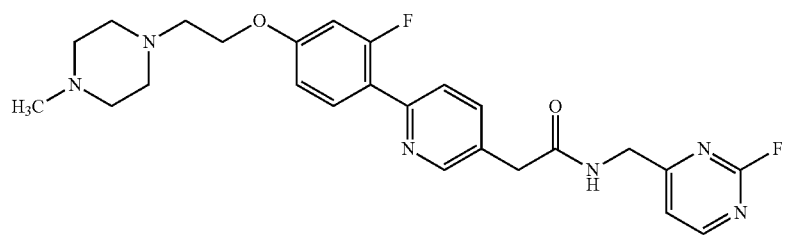 [SMILES: CN1CCN(CCOc2ccc(-c3ccc(CC(=O)NCc4ccnc(F)n4)cn3)c(F)c2)CC1]
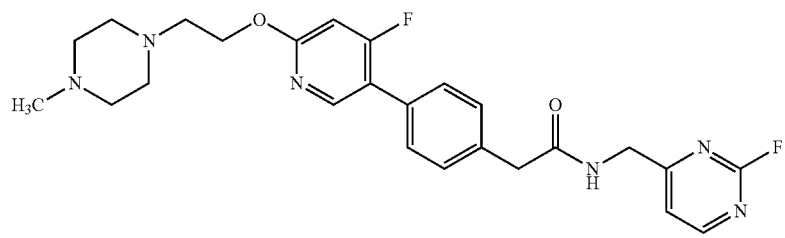 [SMILES: CN1CCN(CCOc2cc(F)c(-c3ccc(CC(=O)NCc4ccnc(F)n4)cc3)cn2)CC1]
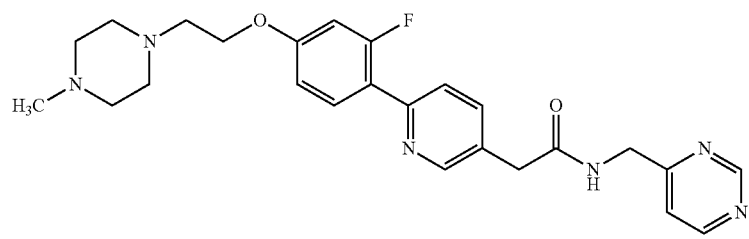 [SMILES: CN1CCN(CCOc2ccc(-c3ccc(CC(=O)NCc4ccncn4)cn3)c(F)c2)CC1]
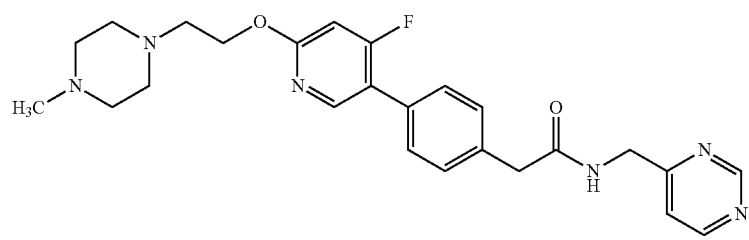 [SMILES: CN1CCN(CCOc2cc(F)c(-c3ccc(CC(=O)NCc4ccncn4)cc3)cn2)CC1]
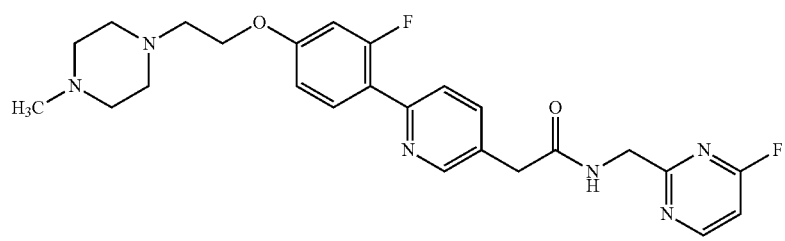 [SMILES: CN1CCN(CCOc2ccc(-c3ccc(CC(=O)NCc4nccc(F)n4)cn3)c(F)c2)CC1]
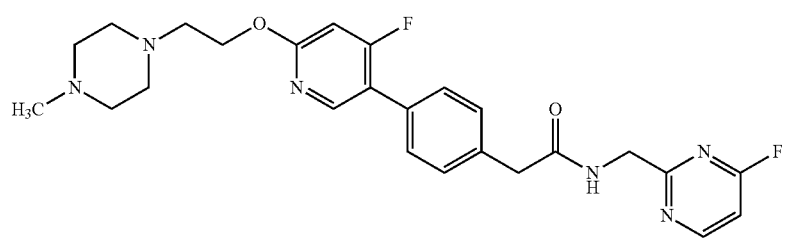 [SMILES: CN1CCN(CCOc2cc(F)c(-c3ccc(CC(=O)NCc4nccc(F)n4)cc3)cn2)CC1]

TABLE 2-continued
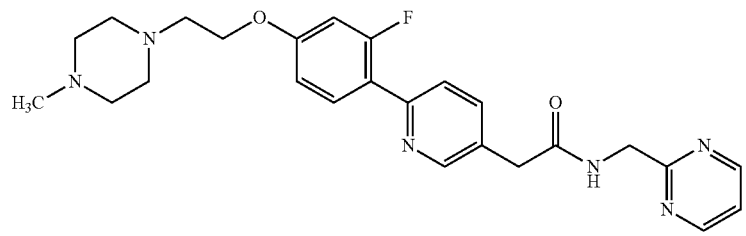
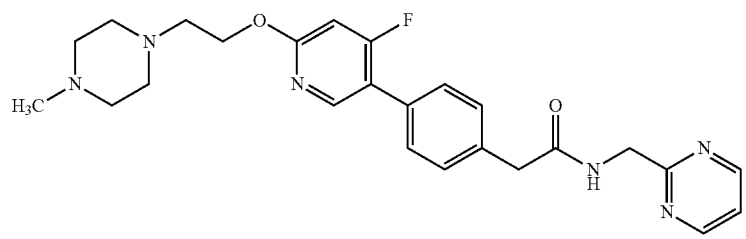 [SMILES: CN1CCN(CCOc2cc(F)c(-c3ccc(CC(=O)NCc4ncccn4)cc3)cn2)CC1]
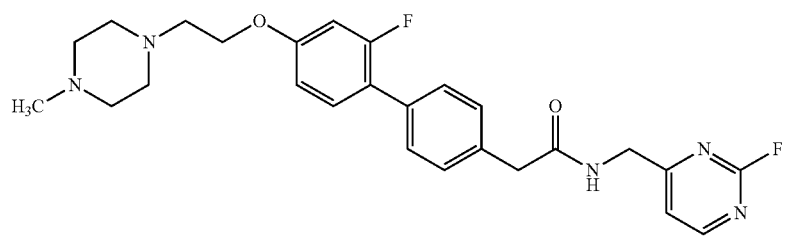 [SMILES: CN1CCN(CCOc2ccc(-c3ccc(CC(=O)NCc4ccnc(F)n4)cc3)c(F)c2)CC1]
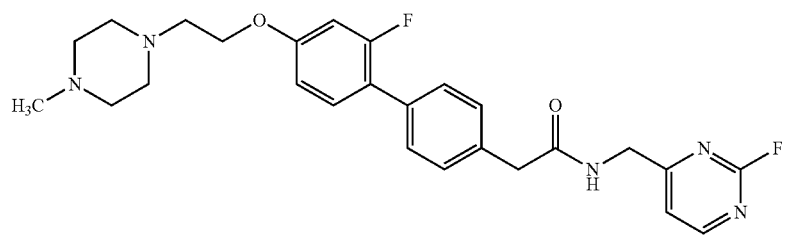 [SMILES: CN1CCN(CCOc2ccc(-c3ccc(CC(=O)NCc4ccnc(F)n4)cc3)c(F)c2)CC1]
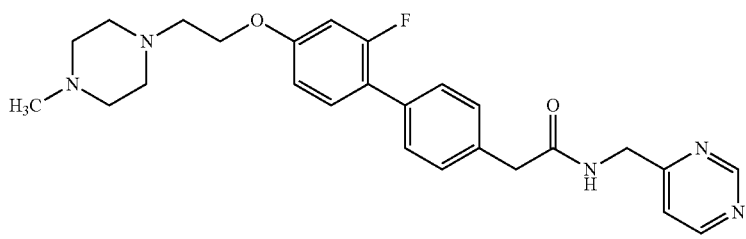 [SMILES: CN1CCN(CCOc2ccc(-c3ccc(CC(=O)NCc4ccncn4)cc3)c(F)c2)CC1]
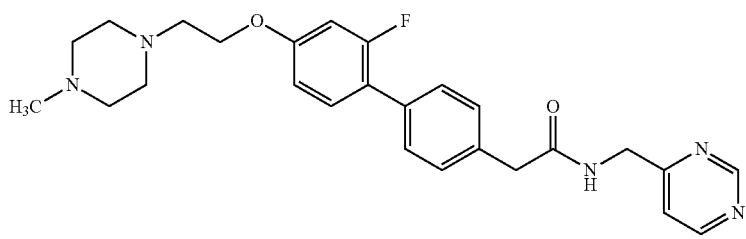 [SMILES: CN1CCN(CCOc2ccc(-c3ccc(CC(=O)NCc4ccncn4)cc3)c(F)c2)CC1]

TABLE 2-continued

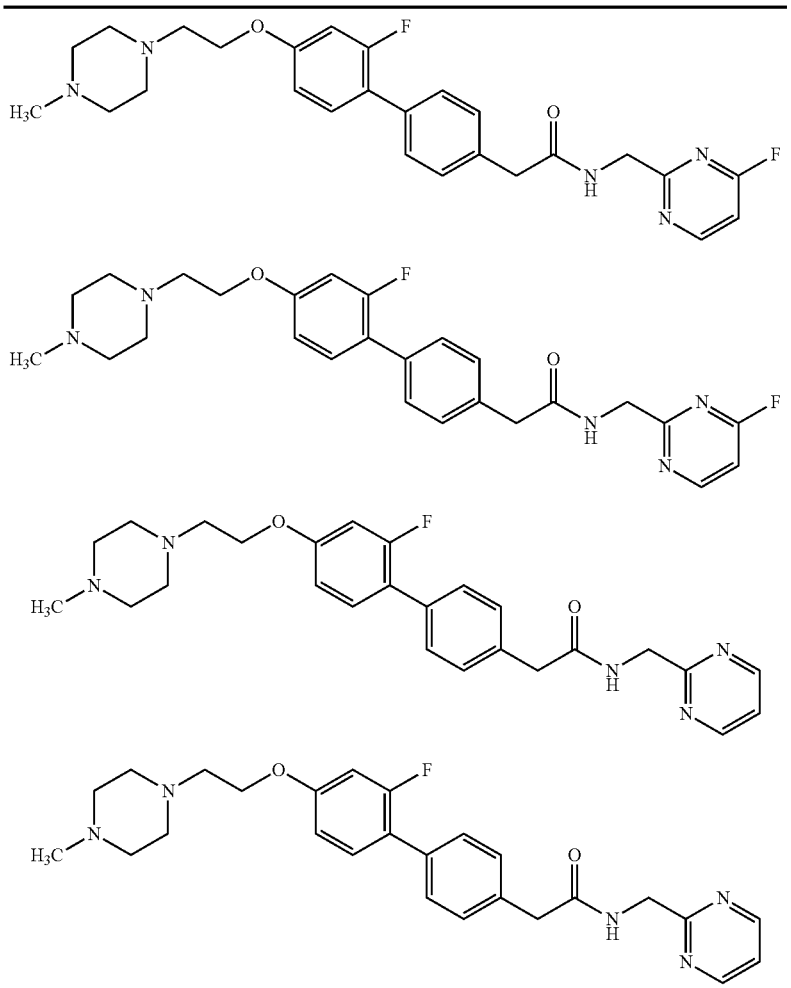

The invention relates to a solvate of a compound according to one of Formulae I-XIII. The invention also relates to a hydrate of a compound according to one of Formulae I-XIII.

The invention also relates to an acid addition salt of a compound according to one of Formulae I-XIII. For example, a hydrochloride salt.

Further, the invention relates to a prodrug of a compound according to one of Formulae I-XIII.

The invention also relates to a pharmaceutically acceptable salt of a compound of one of Formulae I-XIII.

The invention includes compositions comprising a compound according to one of Formulae I-XIII and at least one pharmaceutically acceptable excipient.

Certain compounds of the invention are non-ATP competitive kinase inhibitors.

The invention also includes a method of preventing or treating a cell proliferation disorder by administering a pharmaceutical composition that includes a compound according to one of Formulae I-XIII, or a salt, solvate, hydrate, or prodrug thereof, and at least one pharmaceutically acceptable excipient to a subject in need thereof.

For example, the cell proliferation disorder is pre-cancer or cancer. The cell proliferation disorder treated or prevented by the compounds of the invention may be a cancer, such as, for example, colon cancer or lung cancer.

The cell proliferation disorder treated or prevented by the compounds of the invention may be a hyperproliferative disorder The cell proliferation disorder treated or prevented by the compounds of the invention may be psoriases.

For example, the treatment or prevention of the proliferative disorder may occur through the inhibition of a tyrosine kinase. For example, the tyrosine kinase can be a Src kinase or focal adhesion kinase (FAK).

The invention relates to a method of treating or preventing a disease or disorder that is modulated by tyrosine kinase inhibition, by administering a pharmaceutical composition that includes a compound according to Formula I or one of Formulae II-XIII, or a salt, solvate, hydrate, or prodrug thereof, and at least one pharmaceutically acceptable excipient. For example, the disease or disorder that is modulated by tyrosine kinase inhibition is cancer, pre-cancer, a hyperproliferative disorder, or a microbial infection. For example, the compound is a compound according to Formula I or II.

The pharmaceutical composition of the invention may modulate a kinase pathway. For example, the kinase pathway is a Src kinase pathway, or focal adhesion kinase pathway.

The pharmaceutical composition of the invention may modulate a kinase directly. For example, the kinase is Src kinase, or focal adhesion kinase.

Certain pharmaceutical compositions of the invention are non-ATP competitive kinase inhibitors.

For example, the compounds of the invention are useful to treat or prevent a microbial infection, such as a bacterial, fungal, parasitic or viral infection.

Certain pharmaceutical compositions of the invention include a compound selected from Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, and 137. For example, the pharmaceutical composition includes Compound 33, 38, 40, 76, 133, 134, 136 or 137.

Certain pharmaceutical compositions of the invention include a compound selected from the compounds listed in Table 2.

A compound of the invention may be used as a pharmaceutical agent. For example, a compound of the invention is used as an anti-proliferative agent, for treating humans and/or animals, such as for treating humans and/or other mammals. The compounds may be used without limitation, for example, as anti-cancer, anti-angiogenesis, anti-microbial, anti-bacterial, anti-fungal, anti-parasitic and/or anti-viral agents. Additionally, the compounds may be used for other cell proliferation-related disorders such as diabetic retinopathy, macular degeneration and psoriases. Anti-cancer agents include anti-metastatic agents.

The compound of the invention used as a pharmaceutical agent may be selected from Compounds 1-136 and 137. For example, the compound of the invention used as a pharmaceutical agent is Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, or 137. For example, the compound of the invention used as a pharmaceutical agent is selected from Compounds 33, 38, 40, 76, 133, 134, 136 and 137.

Certain pharmaceutical agents include a compound selected from the compounds listed in Table 2.

In one aspect of the invention, a compound of the invention, for example, a compound of Formula I or one of Formulae II-XIII, is used to treat or prevent a cell proliferation disorder in an subject. In one aspect of the embodiment, the cell proliferation disorder is pre-cancer or cancer. In another aspect of the embodiment, the cell proliferation disorder is a hyperproliferative disorder. In another embodiment, prevention or treatment of the cell proliferation disorder, cancer or hyperproliferative disorder occurs through the inhibition of a kinase. In another embodiment, prevention or treatment of the cell proliferation disorder, cancer or hyperproliferative disorder occurs through the inhibition of a tyrosine kinase. In another embodiment, prevention or treatment of the cell proliferation disorder, cancer or hyperproliferative disorder occurs through the inhibition of Src kinase or focal adhesion kinase (FAK). In another embodiment, the subject is a mammal. Preferably, the subject is human.

The invention is also drawn to a method of treating or preventing cancer or a proliferation disorder in a subject, comprising administering an effective amount of a compound of the invention, for example, a compound of Formula I or one of Formulae II-XIII. For example, the compound of the invention may be a kinase inhibitor. The compound of the invention may be a non-ATP competitive kinase inhibitor. The compound of the invention may inhibit a kinase directly, or it may affect the kinase pathway.

DEFINITIONS

For convenience, certain terms used in the specification, examples and appended claims are collected here.

Protein kinases are a large class of enzymes which catalyze the transfer of the γ-phosphate from ATP to the hydroxyl group on the side chain of Ser/Thr or Tyr in proteins and peptides and are intimately involved in the control of various important cell functions, perhaps most notably: signal transduction, differentiation, and proliferation. There are estimated to be about 2,000 distinct protein kinases in the human body, and although each of these phosphorylate particular protein/peptide substrates, they all bind the same second substrate ATP in a highly conserved pocket. About 50% of the known oncogene products are protein tyrosine kinases (PTKs), and their kinase activity has been shown to lead to cell transformation.

The PTKs can be classified into two categories, the membrane receptor PTKs (e.g. growth factor receptor PTKs) and the non-receptor PTKs (e.g. the Src family of proto-oncogene products and focal adhesion kinase (FAK)). The hyperactivation of Src has been reported in a number of human cancers, including those of the colon, breast, lung, bladder, and skin, as well as in gastric cancer, hairy cell leukemia, and neuroblastoma.

"Treating", includes any effect, e.g., lessening, reducing, modulating, or eliminating, that results in the improvement of the condition, disease, disorder, etc. "Treating" or "treatment" of a disease state includes: (1) preventing the disease state, i.e. causing the clinical symptoms of the disease state not to develop in a subject that may be exposed to or predisposed to the disease state, but does not yet experience or display symptoms of the disease state; (2) inhibiting the disease state, i.e., arresting the development of the disease state or its clinical symptoms; or (3) relieving the disease state, i.e., causing temporary or permanent regression of the disease state or its clinical symptoms.

"Disease state" means any disease, disorder, condition, symptom, or indication.

As used herein, the term "cell proliferative disorder" refers to conditions in which the unregulated and/or abnormal growth of cells can lead to the development of an unwanted condition or disease, which can be cancerous or non-cancerous, for example a psoriatic condition. As used herein, the terms "psoriatic condition" or "psoriasis" refers to disorders involving keratinocyte hyperproliferation, inflammatory cell infiltration, and cytokine alteration.

In a preferred embodiment, the cell proliferation disorder is cancer. As used herein, the term "cancer" includes solid tumors, such as lung, breast, colon, ovarian, brain, liver, pancreas, prostate, malignant melanoma, non-melanoma skin cancers, as well as hematologic tumors and/or malignancies, such as childhood leukemia and lymphomas, multiple myeloma, Hodgkin's disease, lymphomas of lymphocytic and cutaneous origin, acute and chronic leukemia such as acute lymphoblastic, acute myelocytic or chronic myelocytic leukemia, plasma cell neoplasm, lymphoid neoplasm and cancers associated with AIDS.

In addition to psoriatic conditions, the types of proliferative diseases which may be treated using the compositions of the present invention are epidermic and dermoid cysts, lipomas, adenomas, capillary and cutaneous hemangiomas, lymphangiomas, nevi lesions, teratomas, nephromas, myofibromatosis, osteoplastic tumors, and other dysplastic masses and the like. The proliferative diseases can include dysplasias and disorders of the like.

An "effective amount" of a compound of the disclosed invention is the quantity which, when administered to a subject having a disease or disorder, results in regression of the disease or disorder in the subject. Thus, an effective amount of a compound of the disclosed invention is the quantity which, when administered to a subject having a cell proliferation disorder, results in regression of cell growth in the subject. The amount of the disclosed compound to be administered to a subject will depend on the particular disorder, the mode of administration, co-administered compounds, if any, and the characteristics of the subject, such as general health, other diseases, age, sex, genotype, body weight and tolerance to drugs. The skilled artisan will be able to determine appropriate dosages depending on these and other factors.

As used herein, the term "effective amount" refers to an amount of a compound, or a combination of compounds, of the present invention effective when administered alone or in combination as an anti-proliferative agent. For example, an effective amount refers to an amount of the compound present in a formulation or on a medical device given to a recipient patient or subject sufficient to elicit biological activity, for example, anti-proliferative activity, such as e.g., anti-cancer activity or anti-neoplastic activity. The combination of compounds optionally is a synergistic combination. Synergy, as described, for example, by Chou and Talalay, *Adv. Enzyme Regul.* vol. 22, pp. 27-55 (1984), occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, or increased anti-proliferative effect, or some other beneficial effect of the combination compared with the individual components.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

A therapeutically effective amount of one or more of the compounds can be formulated with a pharmaceutically acceptable carrier for administration to a human or an animal. Accordingly, the compounds or the formulations can be administered, for example, via oral, parenteral, or topical routes, to provide an effective amount of the compound. In alternative embodiments, the compounds prepared in accordance with the present invention can be used to coat or impregnate a medical device, e.g., a stent.

The term "prophylactically effective amount" means an effective amount of a compound or compounds, of the present invention that is administered to prevent or reduce the risk of unwanted cellular proliferation.

"Pharmacological effect" as used herein encompasses effects produced in the subject that achieve the intended purpose of a therapy. In one preferred embodiment, a pharmacological effect means that primary indications of the subject being treated are prevented, alleviated, or reduced. For example, a pharmacological effect would be one that results in the prevention, alleviation or reduction of primary indications in a treated subject. In another preferred embodiment, a pharmacological effect means that disorders or symptoms of the primary indications of the subject being treated are prevented, alleviated, or reduced. For example, a pharmacological effect would be one that results in the prevention or reduction of primary indications in a treated subject.

With respect to the chemical compounds useful in the present invention, the following terms can be applicable:

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., $=O$), then 2 hydrogens on the atom are replaced. Keto substituents are not present on aromatic moieties. Ring double bonds, as used herein, are double bonds that are formed between two adjacent ring atoms (e.g., C=C, C=N, or N=N).

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

The compounds described herein may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic, and geometric isomeric forms of a structure are intended, unless the specific stereochemistry or isomeric form is specifically indicated. All tautomers of shown or described compounds are also considered to be part of the present invention.

When any variable (e.g., $R_1$) occurs more than one time in any constituent or formula for a compound, its definition at each occurrence is independent of its definition at every other occurrence. Thus, for example, if a group is shown to be substituted with 0-2 $R_1$ moieties, then the group may optionally be substituted with up to two $R_1$ moieties and $R^1$ at each occurrence is selected independently from the definition of $R_1$. Also, combinations of substituents and/or variables are permissible, but only if such combinations result in stable compounds.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such substituent. Combinations of substituents and/or variables are permissible, but only if such combinations result in stable compounds.

Compounds of the present invention that contain nitrogens can be converted to N-oxides by treatment with an oxidizing agent (e.g., 3-chloroperoxybenzoic acid (m-CPBA) and/or hydrogen peroxides) to afford other compounds of the present invention. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds of the present invention can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_{1-6}$ alkyl, $C_{1-6}$ alkenyl, $C_{1-6}$ alkynyl, $C_{3-14}$ carbocycle, or 3-14-membered heterocycle) derivatives.

When an atom or chemical moiety is followed by a subscripted numeric range (e.g., $C_{1-6}$), the invention is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

As used herein, "alkyl" is intended to include both branched and straight-chain saturated aliphatic hydrocarbon groups having the specified number of carbon atoms. For example, $C_{1-6}$ alkyl is intended to include $C_1$, $C_2$, $C_3$, $C_4$, $C_5$, and $C_6$ alkyl groups. Examples of alkyl include, but are not limited to, methyl, ethyl, n-propyl, i-propyl, n-butyl, s-butyl, t-butyl, n-pentyl, s-pentyl, and n-hexyl. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), and more preferably four or fewer. Likewise, preferred cycloalkyls have from three to eight carbon atoms in their ring structure, and more preferably have five or six carbons in the ring structure.

Unless the number of carbons is otherwise specified, "lower alkyl" includes an alkyl group, as defined above, but having from one to ten, more preferably from one to six, carbon atoms in its backbone structure. "Lower alkenyl" and "lower alkynyl" have chain lengths of, for example, 2-5 carbon atoms.

The term "alkyl" also includes both "unsubstituted alkyls" and "substituted alkyls", the latter of which refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)).

"Alkenyl" includes unsaturated aliphatic groups analogous in length and possible substitution to the alkyls described above, but that contain at least one double bond. For example, the term "alkenyl" includes straight-chain alkenyl groups (e.g., ethenyl, propenyl, butenyl, pentenyl, hexenyl, heptenyl, octenyl, nonenyl, decenyl), branched-chain alkenyl groups, cycloalkenyl (e.g., alicyclic) groups (e.g., cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term "alkenyl" further includes alkenyl groups, which include oxygen, nitrogen, sulfur or phosphorous atoms replacing one or more hydrocarbon backbone carbons. In certain embodiments, a straight chain or branched chain alkenyl group has six or fewer carbon atoms in its backbone (e.g., $C_2$-$C_6$ for straight chain, $C_3$-$C_6$ for branched chain). Likewise, cycloalkenyl groups may have from three to eight carbon atoms in their ring structure, and more preferably have five or six carbons in the ring structure. The term "$C_2$-$C_6$" includes alkenyl groups containing two to six carbon atoms. The term "$C_3$-$C_6$" includes alkenyl groups containing three to six carbon atoms.

The term "alkenyl" also includes both "unsubstituted alkenyls" and "substituted alkenyls", the latter of which refers to alkenyl moieties having substituents replacing a hydrogen on one or more hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight-chain alkynyl groups (e.g., ethynyl, propynyl, butynyl, pentynyl, hexynyl, heptynyl, octynyl, nonynyl, decynyl), branched-chain alkynyl groups, and cycloalkyl or cycloalkenyl substituted alkynyl groups. The term "alkynyl" further includes alkynyl groups having oxygen, nitrogen, sulfur or phosphorous atoms replacing one or more hydrocarbon backbone carbons. In certain embodiments, a straight chain or branched chain alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

The term "alkynyl" also includes both "unsubstituted alkynyls" and "substituted alkynyls", the latter of which refers to alkynyl moieties having substituents replacing a hydrogen on one or more hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aryl" includes groups with aromaticity, including 5- and 6-membered "unconjugated", or single-ring, aromatic groups that may include from zero to four heteroatoms, as well as "conjugated", or multicyclic, systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthyridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

As used herein, "halo" or "halogen" refers to fluoro, chloro, bromo, and iodo. The term "perhalogenated" generally refers to a moiety wherein all hydrogens are replaced by halogen atoms.

"Counterion" is used to represent a small, negatively charged species such as chloride, bromide, hydroxide, acetate, and sulfate.

The term "non-hydrogen substituent" refers to substituents other than hydrogen. Non-limiting examples include alkyl groups, alkoxy groups, halogen groups, hydroxyl groups, aryl groups, etc.

As used herein, "carbocycle" or "carbocyclic ring" is intended to mean any stable monocyclic, bicyclic, or tricyclic ring having the specified number of carbons, any of which may be saturated, unsaturated, or aromatic. For example a $C_{3-14}$ carbocycle is intended to mean a mono-, bi-, or tricyclic ring having 3, 4, 5, 6, 7, 8, 9, 10, 11, 12, 13, or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl, and tetrahydronaphthyl. Bridged rings are also included in the definition of carbocycle, including, for example, [3.3.0]bicyclooctane, [4.3.0]bicyclononane, [4.4.0]bicyclodecane, and [2.2.2]bicyclooctane. A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge. Fused (e.g., naphthyl and tetrahydronaphthyl) and spiro rings are also included.

As used herein, the term "heterocycle" or "heterocyclic" is intended to mean any stable monocyclic, bicyclic, or tricyclic ring which is saturated, unsaturated, or aromatic and comprises carbon atoms and one or more ring heteroatoms, e.g., 1 or 1-2 or 1-3 or 1-4 or 1-5 or 1-6 heteroatoms, independently selected from the group consisting of nitrogen, oxygen, and sulfur. A bicyclic or tricyclic heterocycle may have one or more heteroatoms located in one ring, or the heteroatoms may be located in more than one ring. The nitrogen and sulfur heteroatoms may optionally be oxidized (i.e., N→O and $S(O)_p$, where p=1 or 2). When a nitrogen atom is included in the ring it is either N or NH, depending on whether or not it is attached to a double bond in the ring (i.e., a hydrogen is present if needed to maintain the tri-valency of the nitrogen atom). The nitrogen atom may be substituted or unsubstituted (i.e., N or NR wherein R is H or another substituent, as defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge. Spiro and fused rings are also included.

As used herein, the term "aromatic heterocycle" or "heteroaryl" is intended to mean a stable 5, 6, or 7-membered monocyclic or bicyclic aromatic heterocyclic ring or 7, 8, 9, 10, 11, or 12-membered bicyclic aromatic heterocyclic ring which consists of carbon atoms and one or more heteroatoms, e.g., 1 or 1-2 or 1-3 or 1-4 or 1-5 or 1-6 heteroatoms, independently selected from the group consisting of nitrogen, oxygen, and sulfur. In the case of bicyclic heterocyclic aromatic rings, only one of the two rings needs to be aromatic (e.g., 2,3-dihydroindole), though both may be (e.g., quinoline). The second ring can also be fused or bridged as defined above for heterocycles. The nitrogen atom may be substituted or unsubstituted (i.e., N or NR wherein R is H or another substituent, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

"Acyl" includes compounds and moieties that contain the acyl radical (CH$_3$CO—) or a carbonyl group. "Substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Acylamino" includes moieties wherein an acyl moiety is bonded to an amino group. For example, the term includes alkylcarbonylamino, arylcarbonylamino, carbamoyl and ureido groups.

"Aroyl" includes compounds and moieties with an aryl or heteroaromatic moiety bound to a carbonyl group. Examples of aroyl groups include phenylcarboxy, naphthyl carboxy, etc.

"Alkoxyalkyl", "alkylaminoalkyl" and "thioalkoxyalkyl" include alkyl groups, as described above, which further include oxygen, nitrogen or sulfur atoms replacing one or more hydrocarbon backbone carbon atoms, e.g., oxygen, nitrogen or sulfur atoms.

The term "alkoxy" or "alkoxyl" includes substituted and unsubstituted alkyl, alkenyl, and alkynyl groups covalently linked to an oxygen atom. Examples of alkoxy groups (or alkoxyl radicals) include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, and trichloromethoxy.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or heteroatoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O$^-$.

"Polycyclyl" or "polycyclic radical" refers to two or more cyclic rings (e.g., cycloalkyls, cycloalkenyls, cycloalkynyls, aryls and/or heterocyclyls) in which two or more carbons are common to two adjoining rings. Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminocarbonyl, aralkylaminocarbonyl, alkenylaminocarbonyl, alkylcarbonyl, arylcarbonyl, aralkylcarbonyl, alkenylcarbonyl, aminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

An "anionic group," as used herein, refers to a group that is negatively charged at physiological pH. Preferred anionic groups include carboxylate, sulfate, sulfonate, sulfinate, sulfamate, tetrazolyl, phosphate, phosphonate, phosphinate, or phosphorothioate or functional equivalents thereof. "Functional equivalents" of anionic groups are intended to include bioisosteres, e.g., bioisosteres of a carboxylate group. Bioisosteres encompass both classical bioisosteric equivalents and non-classical bioisosteric equivalents. Classical and non-classical bioisosteres are known in the art (see, e.g., Silverman, R. B. The Organic Chemistry of Drug Design and Drug Action, Academic Press, Inc.: San Diego, Calif., 1992, pp. 19-23). A particularly preferred anionic group is a carboxylate.

In the present specification, the structural formula of the compound represents a certain isomer for convenience in some cases, but the present invention includes all isomers such as geometrical isomer, optical isomer based on an asymmetrical carbon, stereoisomer, tautomer and the like which occur structurally and an isomer mixture and is not limited to the description of the formula for convenience, and may be any one of isomer or a mixture. Therefore, an asymmetrical carbon atom may be present in the molecule and an optically active compound and a racemic compound may be present in the present compound, but the present invention is not limited to them and includes any one. In addition, a crystal polymorphism may be present but is not limiting, but any crystal form may be single or a crystal form mixture, or an anhydride or hydrate. Further, so-called metabolite which is produced by degradation of the present compound in vivo is included in the scope of the present invention.

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

"Chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Calm, Ingold and Prelog. (Cahn et al, *Angew. Chem. Inter. Edit.* 1966, 5, 385; errata 511; Cahn et al., *Angew. Chem.* 1966, 78, 413; Calm and Ingold, *J. Chem. Soc.* 1951 (London), 612; Cahn et al., *Experientia* 1956, 12, 81; Cahn, J., *Chem. Educ.* 1964, 41, 116).

"Geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Further, the structures and other compounds discussed in this application include all atropic isomers thereof "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Tautomers" refers to compounds whose structures differ markedly in arrangement of atoms, but which exist in easy and rapid equilibrium. It is to be understood that compounds of Formula I may be depicted as different tautomers. It should also be understood that when compounds have tautomeric forms, all tautomeric forms are intended to be within the scope of the invention, and the naming of the compounds does not exclude any tautomer form.

Some compounds of the present invention can exist in a tautomeric form which are also intended to be encompassed within the scope of the present invention.

The compounds, salts and prodrugs of the present invention can exist in several tautomeric forms, including the enol and imine form, and the keto and enamine form and geometric isomers and mixtures thereof. All such tautomeric forms are included within the scope of the present invention. Tautomers exist as mixtures of a tautomeric set in solution. In solid form, usually one tautomer predominates. Even though one tautomer may be described, the present invention includes all tautomers of the present compounds A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertible by tautomerizations is called tautomerism.

Of the various types of tautomerism that are possible, two are commonly observed. In keto-enol tautomerism a simultaneous shift of electrons and a hydrogen atom occurs. Ring-chain tautomerism, is exhibited by glucose. It arises as a result of the aldehyde group (—CHO) in a sugar chain molecule reacting with one of the hydroxy groups (—OH) in the same molecule to give it a cyclic (ring-shaped) form.

Tautomerizations are catalyzed by: Base: 1. deprotonation; 2. formation of a delocalized anion (e.g. an enolate); 3. protonation at a different position of the anion; Acid: 1. protonation; 2. formation of a delocalized cation; 3. deprotonation at a different position adjacent to the cation.

Common tautomeric pairs are: ketone-enol, amide-nitrile, lactam-lactim, amide-imidic acid tautomerism in heterocyclic rings (e.g. in the nucleobases guanine, thymine, and cytosine), amine-enamine and enamine-enamine. Examples include:

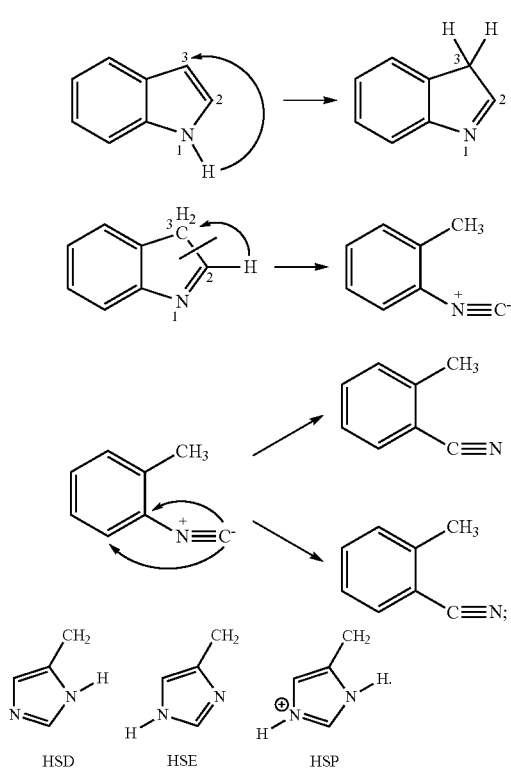

It will be noted that the structure of some of the compounds of the invention include asymmetric carbon atoms. It is to be understood accordingly that the isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate. The compounds of this invention may exist in stereoisomeric form, therefore can be produced as individual stereoisomers or as mixtures.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative", refers to compounds that have a common core structure, and are substituted with various groups as described herein. For example, all of the compounds represented by formula I are indole derivatives, and have formula I as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996).

A "pharmaceutical composition" is a formulation containing the disclosed compounds in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salt, hydrate, solvate, or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalation, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In a preferred embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

A "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). Most preferably, the subject is human.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

The compounds of the invention are capable of further forming salts. All of these forms are also contemplated within the scope of the claimed invention.

"Pharmaceutically acceptable salt" of a compound means a salt that is pharmaceutically acceptable and that possesses the desired pharmacological activity of the parent compound.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same salt.

The pharmaceutically acceptable salts of the present invention can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th ed. (Mack Publishing Company, 1990). For example, salts can include, but are not limited to, the hydrochloride and acetate salts of the aliphatic amine-containing, hydroxylamine-containing, and imine-containing compounds of the present invention.

The compounds of the present invention can also be prepared as esters, for example pharmaceutically acceptable esters. For example a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds of the present invention can also be prepared as prodrugs, for example pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.) the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl, carboxy, or carbonyl group is bonded to any group that, may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, esters groups (e.g. ethyl esters, morpholinoethanol esters) of carboxyl functional groups, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, See Bundegaard, H. "Design of Prodrugs" p1-92, Elesevier, New York-Oxford (1985).

"Protecting group" refers to a grouping of atoms that when attached to a reactive group in a molecule masks, reduces or prevents that reactivity. Examples of protecting groups can be found in Green and Wuts, *Protective Groups in Organic Chemistry*, (Wiley, $2^{nd}$ ed. 1991); Harrison and Harrison et al., *Compendium of Synthetic Organic Methods*, Vols. 1-8 (John Wiley and Sons, 1971-1996); and Kocienski, *Protecting Groups*, (Verlag, $3^{rd}$ ed. 2003).

The term "amine protecting group" is intended to mean a functional group that converts an amine, amide, or other nitrogen-containing moiety into a different chemical group that is substantially inert to the conditions of a particular chemical reaction. Amine protecting groups are preferably removed easily and selectively in good yield under conditions that do not affect other functional groups of the molecule. Examples of amine protecting groups include, but are not limited to, formyl, acetyl, benzyl, t-butyldimethylsilyl, t-butyldiphenylsilyl, t-butyloxycarbonyl (Boc), p-methoxybenzyl, methoxymethyl, tosyl, trifluoroacetyl, trimethylsilyl (TMS), fluorenylmethyloxycarbonyl, 2-trimethylsilyl-ethyoxycarbonyl, 1-methyl-1-(4-biphenylyl)ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarbonyl (FMOC), nitro-veratryloxycarbonyl (NVOC), and the like. Other suitable amine protecting groups are straightforwardly identified by those of skill in the art.

Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

"Stable compound" and "stable structure" are meant to indicate a compound that is sufficiently robust to survive isolation to a useful degree of purity from a reaction mixture, and formulation into an efficacious therapeutic agent.

In the specification, the singular forms also include the plural, unless the context clearly dictates otherwise. Unless defined otherwise, all technical and scientific terms used herein have the same meaning as commonly understood by one of ordinary skill in the art to which this invention belongs. In the case of conflict, the present specification will control.

All percentages and ratios used herein, unless otherwise indicated, are by weight.

"Combination therapy" (or "co-therapy") includes the administration of a compound of the invention and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present invention.

"Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Throughout the description, where compositions are described as having, including, or comprising specific components, it is contemplated that compositions also consist essentially of, or consist of the recited components. Similarly, where processes are described as having, including, or comprising specific process steps, the processes also consist essentially of, or consist of, the recited processing steps. Further, it should be understood that the order of steps or order for performing certain actions are immaterial so long as the invention remains operable. Moreover, two or more steps or actions may be conducted simultaneously.

The compounds, or pharmaceutically acceptable salts thereof, is administered orally, nasally, transdermally, pulmonary, inhalationally, buccally, sublingually, intraperitoneally, subcutaneously, intramuscularly, intravenously, rectally, intrapleurally, intrathecally and parenterally. In a preferred embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Techniques for formulation and administration of the disclosed compounds of the invention can be found in *Remington: the Science and Practice of Pharmacy*, $19^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

In one embodiment, the compound is prepared for oral administration, wherein the disclosed compounds or salts thereof are combined with a suitable solid or liquid carrier or diluent to form capsules, tablets, pills, powders, syrups, solutions, suspensions and the like.

The tablets, pills, capsules, and the like contain from about 1 to about 99 weight percent of the active ingredient and a binder such as gum tragacanth, acacias, corn starch or gelatin; excipients such as dicalcium phosphate; a disintegrating agent such as corn starch, potato starch or alginic acid; a lubricant such as magnesium stearate; and/or a sweetening agent such as sucrose, lactose, saccharin, xylitol, and the like. When a dosage unit form is a capsule, it often contains, in addition to materials of the above type, a liquid carrier such as a fatty oil.

In some embodiments, various other materials are present as coatings or to modify the physical form of the dosage unit. For instance, in some embodiments, tablets are coated with shellac, sugar or both. In some embodiments, a syrup or elixir contains, in addition to the active ingredient, sucrose as a sweetening agent, methyl and propylparabens as preservatives, a dye and a flavoring such as cherry or orange flavor, and the like.

For some embodiments relating to parental administration, the disclosed compounds, or salts, solvates, tautomers or polymorphs thereof, can be combined with sterile aqueous or organic media to form injectable solutions or suspensions. Injectable compositions are preferably aqueous isotonic solutions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, preferably about 1 to 50%, of the active ingredient.

For example, injectable solutions are produced using solvents such as sesame or peanut oil or aqueous propylene glycol, as well as aqueous solutions of water-soluble pharmaceutically-acceptable salts of the compounds. In some embodiments, dispersions are prepared in glycerol, liquid polyethylene glycols and mixtures thereof in oils. Under ordinary conditions of storage and use, these preparations contain a preservative to prevent the growth of microorganisms. The terms "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

For rectal administration, suitable pharmaceutical compositions are, for example, topical preparations, suppositories or enemas. Suppositories are advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, preferably about 1 to 50%, of the active ingredient.

In some embodiments, the compounds are formulated to deliver the active agent by pulmonary administration, e.g., administration of an aerosol formulation containing the active agent from, for example, a manual pump spray, nebulizer or pressurized metered-dose inhaler. In some embodiments, suitable formulations of this type also include other agents, such as antistatic agents, to maintain the disclosed compounds as effective aerosols.

A drug delivery device for delivering aerosols comprises a suitable aerosol canister with a metering valve containing a pharmaceutical aerosol formulation as described and an actuator housing adapted to hold the canister and allow for drug delivery. The canister in the drug delivery device has a headspace representing greater than about 15% of the total volume of the canister. Often, the polymer intended for pulmonary administration is dissolved, suspended or emulsified in a mixture of a solvent, surfactant and propellant. The mixture is maintained under pressure in a canister that has been sealed with a metering valve.

For nasal administration, either a solid or a liquid carrier can be used. The solid carrier includes a coarse powder having particle size in the range of, for example, from about 20 to about 500 microns and such formulation is administered by rapid inhalation through the nasal passages. In some embodiments where the liquid carrier is used, the formulation is administered as a nasal spray or drops and includes oil or aqueous solutions of the active ingredients.

Also contemplated are formulations that are rapidly dispersing dosage forms, also known as "flash dose" forms. In particular, some embodiments of the present invention are formulated as compositions that release their active ingredients within a short period of time, e.g., typically less than about five minutes, preferably less than about ninety seconds, more preferably in less than about thirty seconds and most preferably in less than about ten or fifteen seconds. Such formulations are suitable for administration to a subject via a variety of routes, for example by insertion into a body cavity or application to a moist body surface or open wound.

Typically, a "flash dosage" is a solid dosage form that is administered orally, which rapidly disperses in the mouth, and hence does not require great effort in swallowing and allows the compound to be rapidly ingested or absorbed through the oral mucosal membranes. In some embodiments, suitable rapidly dispersing dosage forms are also used in other applications, including the treatment of wounds and other bodily insults and diseased states in which release of the medicament by externally supplied moisture is not possible.

"Flash dose" forms are known in the art; see for example, effervescent dosage forms and quick release coatings of insoluble microparticles in U.S. Pat. Nos. 5,578,322 and 5,607,697; freeze dried foams and liquids in U.S. Pat. Nos. 4,642,903 and 5,631,023; melt spinning of dosage forms in U.S. Pat. Nos. 4,855,326, 5,380,473 and 5,518,730; solid, free-form fabrication in U.S. Pat. No. 6,471,992; saccharide-based carrier matrix and a liquid binder in U.S. Pat. Nos. 5,587,172, 5,616,344, 6,277,406, and 5,622,719; and other forms known to the art.

The compounds of the invention are also formulated as "pulsed release" formulations, in which the compound is released from the pharmaceutical compositions in a series of releases (i.e., pulses). The compounds are also formulated as "sustained release" formulations in which the compound is continuously released from the pharmaceutical composition over a prolonged period.

Also contemplated are formulations, e.g., liquid formulations, including cyclic or acyclic encapsulating or solvating agents, e.g., cyclodextrins, polyethers, or polysaccharides (e.g., methylcellulose), or more preferably, polyanionic β-cyclodextrin derivatives with a sodium sulfonate salt group separate from the lipophilic cavity by an alkyl ether spacer group or polysaccharides. In a preferred embodiment, the agent is methylcellulose. In another preferred embodiment, the agent is a polyanionic β-cyclodextrin derivative with a sodium sulfonate salt separated from the lipophilic cavity by a butyl ether spacer group, e.g., CAPTISOL® (CyDex, Overland, Kans.). One skilled in the art can evaluate suitable agent/disclosed compound formulation ratios by preparing a solution of the agent in water, e.g., a 40% by weight solution; preparing serial dilutions, e.g. to make solutions of 20%, 10, 5%, 2.5%, 0% (control), and the like; adding an excess (compared to the amount that can be solubilized by the agent) of the disclosed compound; mixing under appropriate conditions, e.g., heating, agitation, sonication, and the like; centrifuging or filtering the resulting mixtures to obtain clear solutions; and analyzing the solutions for concentration of the disclosed compound.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

Example 1

Syntheses

Representative syntheses of compounds of the invention are described herein.

Synthesis of Compounds 1 and 2 (KX1-136 and KX1-305)

3-benzyloxybenzonitrile

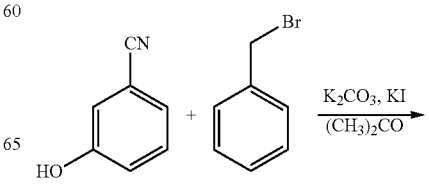

135

-continued

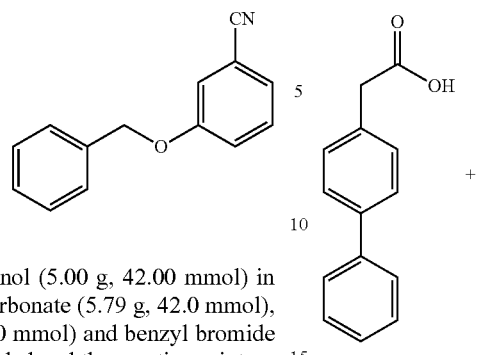

To a solution of 3-cyanophenol (5.00 g, 42.00 mmol) in acetone (100 ml), potassium carbonate (5.79 g, 42.0 mmol), potassium iodide (335 mg, 21.0 mmol) and benzyl bromide (4.20 ml, 42.00 mmol) were added and the reaction mixture refluxed for 12 hrs (TLC, ethyl acetate:hexane 1:1, $R_f$=0.6), then the solvent removed under vacuum and the residue portioned between water (50 ml) and ethyl acetate (50 ml), the organic layer was washed with water twice and dried over anhydrous sodium sulfate and evaporated under reduced pressure to give the target ether as a yellow oil (8.46 g) 96% yield; $^1$H NMR (DMSO (dimethylsulfoxide), 400 MHz): δ 7.51-7.33 (m, 9H), 5.16 (s, 2H).

3-benzyloxybenzylaminehydrochloride

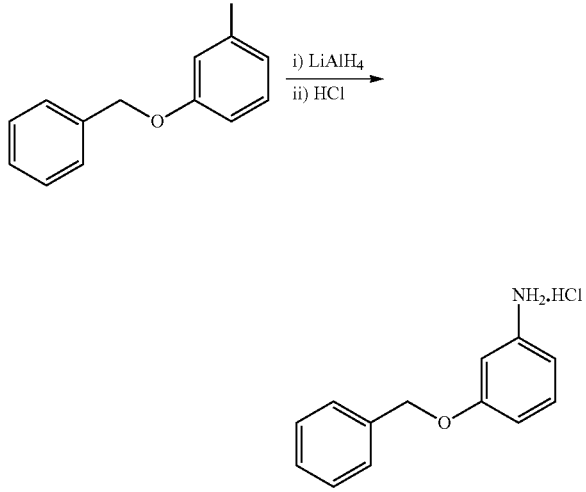

To a suspension of lithium aluminum hydride, LAH (4.314 g, 113.684 mmol) in dry ether (200 ml) a solution of the 3-benzyloxybenzonitrile in ether (7.92 g, 37.894 mmol) was added drop-wise during 10 min at room temperature, and allowed to stir for 4 hrs (TLC, ethyl acetate:hexane 1:3, $R_f$=0.5), the reaction was quenched with 10 ml ethyl acetate and 10 ml water and filtered. The organic layer was washed with water, dried over $Na_2SO_4$ and treated with 10 ml conc. HCl to form instant white precipitate (6 g) 68% yield. $^1$H NMR (DMSO, 400 MHz): δ 8.33 (s, 3H), 7.45-7.37 (m, 4H), 7.34-7.30 (m, 2H), 7.19 (s, 1H), 7.02 (t, J=10 Hz, 2H), 5.10 (s, 2H), 3.97 (s, 2H).

136

N(3-benzyloxy-benzyl)-4-biphenylacetamide

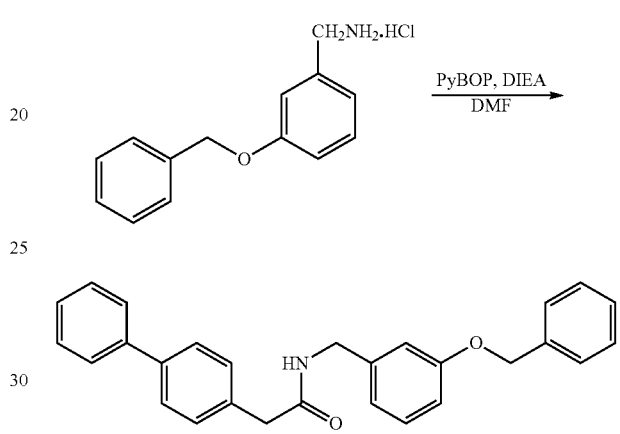

To a solution of 4-biphenyl acetic acid (2.29 g, 10.45 mmol) in dimethylformamide, DMF, (30 ml) was added diisopropylethylamine, DIEA, (5.47 ml, 31.35 mmol) and stirred at room temperature for 15 min, then benzotriazolyloxy-tris[pyrrolidino]-phosphonium hexafluorophosphate, PyBOP™, (5.43 g, 10.45 mmol) was added and the stirring was continued for further 30 min, then 3-benzyloxybenzylaminehydrochloride (2.6 g, 10.45 mmol) was added and the stirring continued for 24 hrs. The reaction mixture was then poured on to ice cooled water acidified with (10 ml) 1 N HCl and extracted with ethyl acetate (100 ml) and the organic layer washed with saturated solution of $NaHCO_3$, water and brine, dried over $Na_2SO_4$ and the solvent removed under vacuum to give a yellowish-white powder of the desired compound (2.65 g) 62% yield.

Another procedure involves use amide formation using the acid chloride as shown in the following reaction.

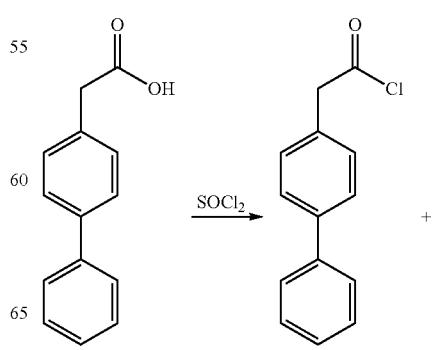

-continued

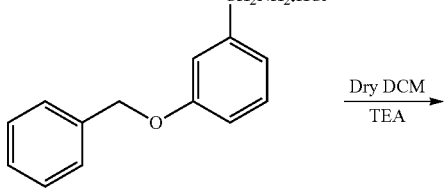

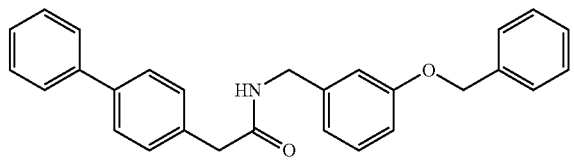

To 4-biphenylacetic acid (2.5 g) in a flask, thionylchloride (20 ml) was added and heated to reflux for 1 h, cooled, and the excess thionylchloride removed under vacuum to dryness, then the produced crude acid chloride 2.8 g, dissolved in dry DCM (dichloromethane) (30 ml), and added drop wise at 0° C. to equimolar amount of the 3-benzyloxybenzylamine solution in DCM (10 ml) with (1.5 mol) of triethylamine (TEA) and stirred for 5 hrs, then poured onto acidified cold water, the organic layer washed with water, brine and the solvent removed under reduced pressure to give the target amide in 80% yield. $^1$H NMR (DMSO, 500 MHz): δ 8.58 (t, J=12 Hz 1H), 7.60-7.57 (m, 4H), 7.44-7.29 (m, 10H), δ 7.21 (t, J=16.5 Hz, 2H), 6.85 (d, J=6.5 Hz, 2H), 6.81 (d, J=8.0 Hz, 1H), 5.00 (s, 2H), 4.24 (d, J=6 Hz, 2H), 3.51 (s, 2H).

Compound 1:
N(3-hydroxy-benzyl)-4-biphenylacetamide

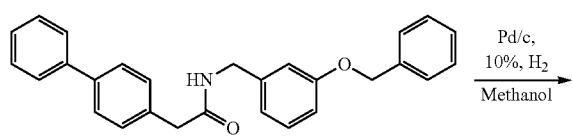

To remove the benzyl group of this ether (5.00 g, 13.35 mmol) was dissolved in methanol (20 ml), to this solution was added a catalytic amount of 10% Pd/C (355 mg, 2.21 mmol) in a Parr hydrogenator (55 psi) for 5 hrs, filtered through celite and the solvent removed under vacuum to give the target phenol as yellowish powder (3.20 g) 84% yield, which crystallized from methanol to give (1.5 g) of white crystalline material, mp=169-170° C. $^1$HNMR (DMSO, 400 MHz): δ 9.34 (s, 1H), 8.53 (s, 1H), 7.63 (d, J=8 Hz, 2H), 7.58 (d, J=8.4 Hz, 2H), 7.44 (t, J=7.6 Hz, 2H), 7.35 (d, J=8 Hz, 3H), 7.07 (t, J=8 Hz, 1H), 6.65-6.60 (m, 3H), 4.17 (d, J=5.6 Hz, 2H), 3.5 (s, 2H). FAB (fast atom bombardment) HRMS m/e calcd. For (M+H) $C_{21}H_{20}NO_2$: 318.1449. found: 318.1484.

Compound 2:
N(3-fluoro-benzyl)-4-biphenylacetamide

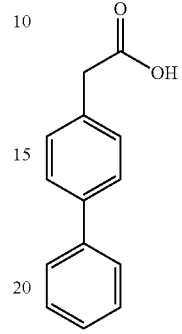 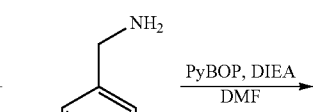

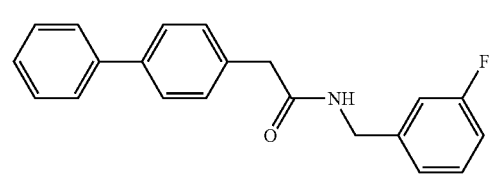

To a solution of 4-biphenyl acetic acid (2.00 g, 9.42 mmol) in DMF (20 ml) was added DIEA (3.29 ml, 18.84 mmol) and stirred at room temperature for 15 min, then PyBOP (4.90 g, 9.42 mmol) added and the stirring continued for further 30 min, then 3-fluorobenzylamine (1.18 g, 9.42 mmol) added and the stirring continued for 24 hrs, then the reaction mixture poured on to ice cooled water acidified with (10 ml) 1 N HCl and extracted with ethyl acetate (100 ml) and the organic layer washed with saturated solution of $NaHCO_3$, water and brine, dried over $Na_2SO_4$ and the solvent removed under vacuum to give a white powder of the desired compound (1.00 g) 33% yield. Another method involves the acid chloride coupling method described below.

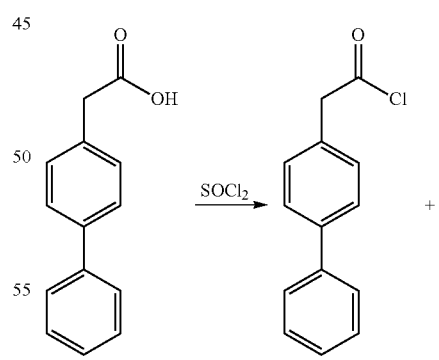

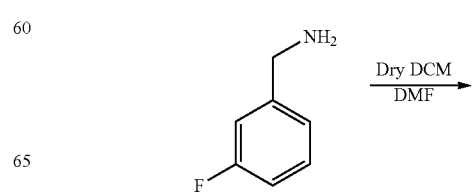

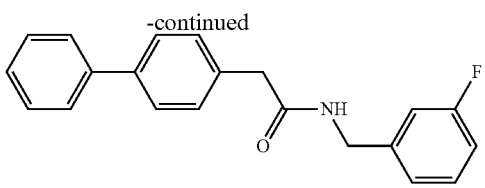

4-biphenylacetic acid (2.5 g, 11.78 mmol) charged in a flask then thionylchloride (15 ml) was added and heated to reflux for 1 h, cooled, and the excess thionylchloride removed under vacuum to dryness, then the produced crude acid chloride (2.8 g, 12.13 mmol) dissolved in dry DCM (30 ml), and added drop wise at 0° C. to (1.38 ml, 12.13 mmol) of the 3-fluorobenzylamine solution in DCM (10 ml) along with (1.69 ml, 12.13 mmol) of TEA and stirred for 5 hrs, then poured onto acidified cold water, the organic layer washed with water, brine and the solvent removed under reduced pressure to give the target amide (3.1 g) 80% yield. Recrystallized from methanol, mp=170-172° C. NMR (DMSO, 500 MHz): δ 8.62 (t, J=11 Hz, 1H), 7.63 (d, J=8 Hz, 2H), 7.59 (d, J=8.5 Hz, 2H), 7.44 (t, J=7.5 Hz, 2H), 7.37-7.31 (m, 4H), 7.08-7.01 (m, 3H), 4.28 (d, J=5.5 Hz, 2H), 3.52 (s, 2H). FAB HRMS m/e calcd. For (M+H) $C_{21}H_{18}FNO$: 320.1406. found: 320.2, and the base peak found: 342.1262 for (M+Na). calcd. 342.1372.

Synthesis of Compound 3, KX1-306

The synthesis, outlined in Scheme 1, began with acid chloride formation of biphenylacetic acid followed by amide coupling with 3,5-dibenzyloxybenzylamine. A large number of impurities were introduced by acid chloride formation. However, other amide coupling procedures such as, for example, PyBOP or carbodiimides, can also be used in this reaction.

Cleavage of one of the benzyl groups was accomplished under high pressure hydrogen (50-60 psi) for 15 hours. The reaction was monitored by TLC. Silica gel chromatography was used to separate the product from the starting material as well as the dihydroxy side-product.

Biphenyl acetic acid (220 mg, 1.00 mmol) was dissolved in DCM, 5 eq (0.38 mL) of thionyl chloride were added and the reaction was refluxed for 4 hours. Solvents were removed in vacuo and the residue was dissolved in DCM. 3,5-Dibenzyloxybenzylamine (1.1 eq) was added followed by TEA (1 eq). The reaction was then stirred at room temperature overnight. The reaction was diluted to 45 mL (with DCM) and washed with 1 N HCl (3×20 L), saturated sodium bicarbonate (3×20 mL), and brine (3×20 mL). The Reaction was then dried with sodium sulfate and removed in vacuo to give 330 mg of crude product. Silica gel chromatography (1:1 DCM:EtOAc (ethyl acetate)) gave 220 mg pure product. TLC Rf=0.2 (single spot, 7:3 hexanes:EtOAc). LCMS 514.2 (m+H) 536.2 (m+Na). $^1$HNMR (300 MHz, $CDCl_3$) δ (ppm) 3.65 (s, 2H), 4.50 (d, 5.7 Hz, 2H), 4.96 (s, 4H), 5.71 (s, 1H), 6.43 (s, 2H), 6.49 (s, 1H), 7.58-7.26 (m, 19H).

The dibenzyloxyamide (1) was dissolved in 15 ml EtOAc (ethyl acetate) with gentle heating in a Parr bottle. This was put on the hydrogenator at 50 psi hydrogen for 15 hr. The reaction was filtered through celite and the solvent was removed in vacuo to give a crude mixture of starting material and product. Silica gel chromatography gave 50 mg 1 and 41 mg desired product KX1-306; LCMS 424.1 (m+H), 446.2 (m+Na), 847.0 (2m+H), 868.9 (2m+Na). $^1$HNMR (400 MHz, $CDCl_3$) δ (ppm) 3.66 (s, 2H), 4.38 (d, 5.6 Hz, 2H), 4.98 (s, 2H), 5.71 (s, 1H), 6.43 (s, 2H), 6.49 (s, 1H), 7.30-7.45 (m, 10H), 7.54-7.57 (m, 4H).

Scheme 1

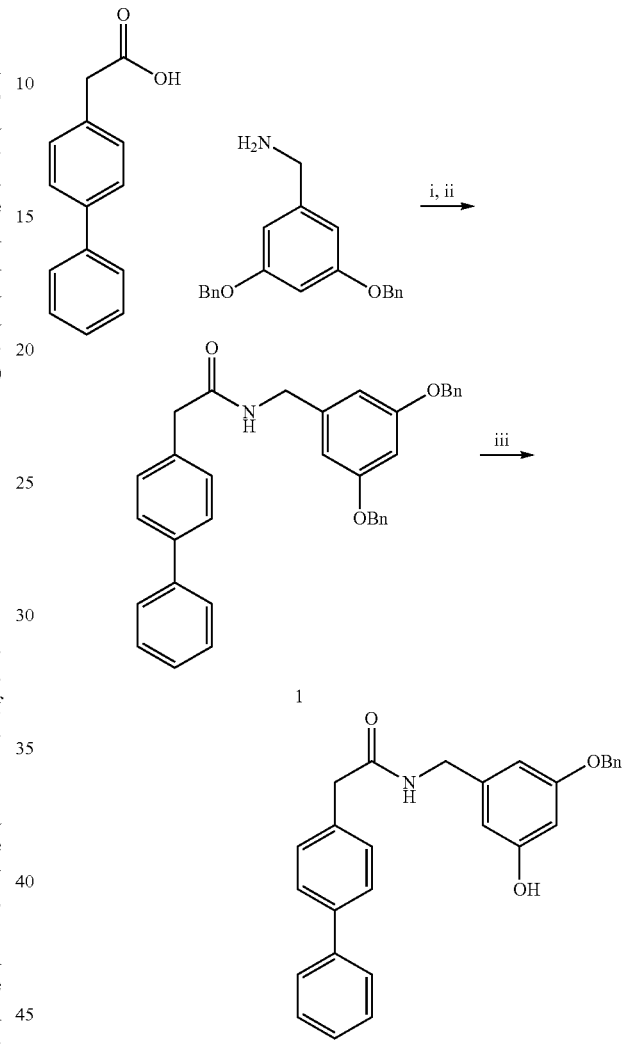

KX1-306

Reagents:
i) $SOCl_2$, DCM.
ii) 3,5dibenzyloxybenzylamine (1.0 eq), TEA (2.0 eq) 20% yield (two steps, with chromatography).
iii) 10% Pd/C (10 mol %), $H_2$, 55 psi, EtOAc 24 hr (53%, after chromatography, BORMS.

Synthesis of Compound 4, KX1-307

The synthesis is outlined in Scheme 2. In one synthesis, the reaction commenced with amide bond formation to give 2, followed by a Suzuki coupling with phenylboronic acid to give the meta-biphenyl product Compound 4, KX1-307. In the Suzuki reaction, the biphenyl product was formed but the reaction did not go to completion (by NMR and LCMS) despite additional, time, heat, and extra catalyst. Using silica gel chromatography, the product could not be separated from the bromo starting material 2. Reversing the Suzuki and amide coupling solved the separation problem and successfully produced the metabiphenyl amide KX1-307 as well as 2'-Fluorobiphenyl-4-acetamide KX1-309 (compound 6, Scheme 3).

3-Bromophenylacetic acid (250 mg, 1.163 mmol) and 156 mg (1.1 eq) of phenylboronic acid were dissolved in 6 mL water:isopropanol (6:1). Sodium carbonate (160 mg, 1.3 eq) was dissolved in 0.5 mL distilled water and added to the reaction followed by Pd(OH)$_2$/C (74 mg, 3 mol %). This was rotated in a 65° C. water bath for 5 hours. The reaction was filtered through filter paper. Filter paper was washed with 25 mL isopropanol:water:1 N NaOH (35:5:1). Washes were combined and acidified to pH 2 with 1 N sulfuric acid. Isopropanol was removed in vacuo and water (10 mL) was added. This aqueous layer was washed with dichloromethane (3×20 mL). Organic washes were combined, dried with sodium sulfate, and removed in vacuo to give 215 mg (87% yield) of the biphenyl product 3. TLC Rf=0.7 (long streak, 1:1 EtOAc:DCM). $^1$HNMR (300 MHz, CDCl$_3$) δ (ppm) 3.72 (s, 2H), 7.26-7.60 (m, 9H).

3-Biphenylacetic acid (3) (100 mg, 0.472 mmol), 3-Fluorobenzylamine (1.1 eq), 1-(3-dimethylaminopropyl)-3-ethyl-carbodiimide hydrochloride, EDCI, (1.1 eq), and HOBT (1-hydroxyenzotriazole, 1.0 eq) were all dissolved in 10 mL anhydrous DCM. After 10 min DIEA (1.1 eq) was added and the reaction was allowed to go overnight. The reaction was diluted to 25 mL and washed with 1N HCl (3×10 L), saturated sodium bicarbonate (3×10 mL), and brine (2×20 mL). The reaction was dried with sodium sulfate and removed in vacuo to give 124 mg pure KX1-307 (83% yield). TLC Rf=0.7 (single spot, 1:1 EtOAc:DCM). $^1$HNMR (300 MHz, CDCl$_3$) δ (ppm) 3.69 (s, 2H) 4.40 (d, 6.0 Hz) 5.77 (s, 1H) 6.86-6.96 (m, 3H) 7.10-7.26 (m, 2H) 7.32 (m, 8H).

Scheme 2

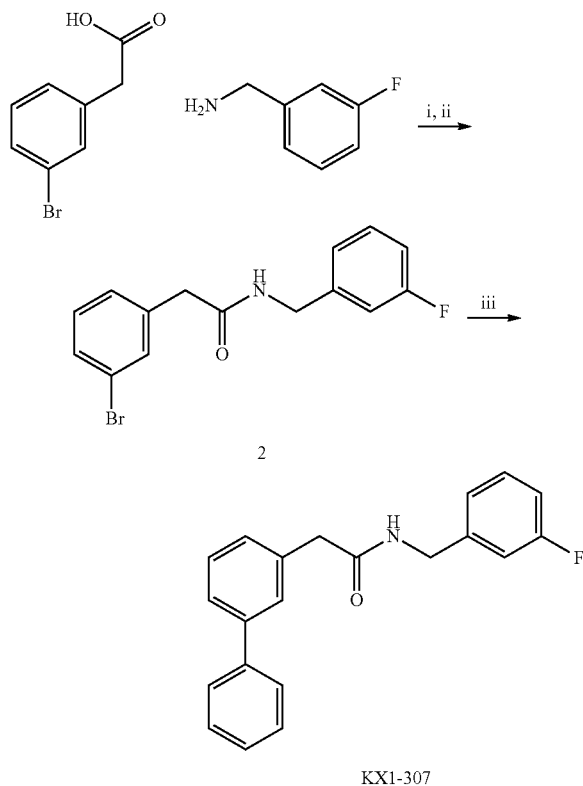

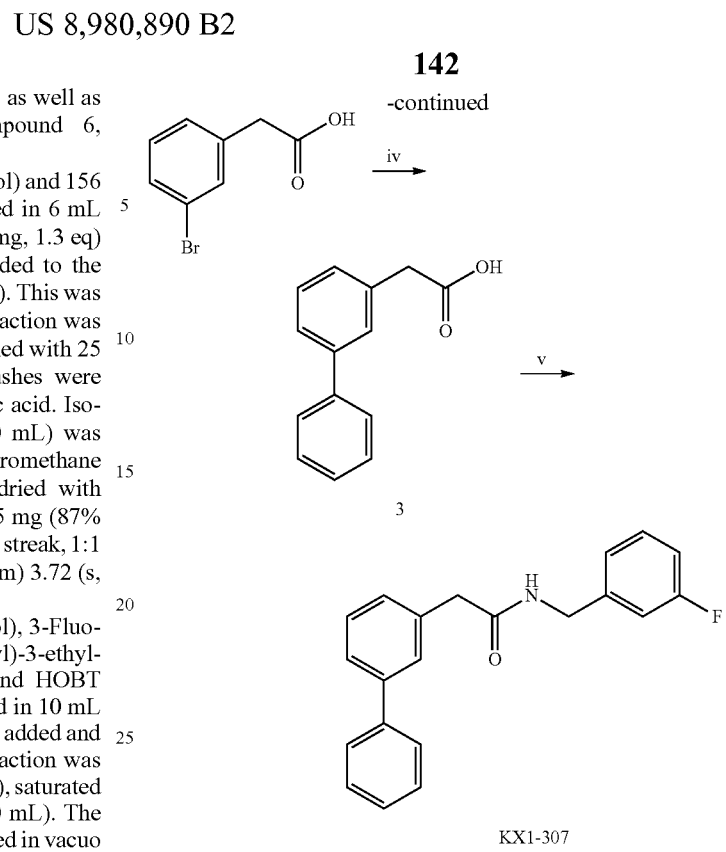

Reagents:
i) SOCl$_2$, DCM.
ii) 3-Fluorobenzylamine(1.1 eq), DIEA (2.2 eq) (20% after chromatography).
iii) Phenylboronic acid(1.2 eq), 2 M sodium carbonate, Pd(PPh$_3$)$_4$ (3 mol %), Toluene (inseparable miture).
iv) Phenylboronic acid (1.1 eq), Na$_2$CO$_3$ (1.3 eq), Pd(OH)$_2$/C (3 mol %), 1:6 isopropanol:water (87% yield).
v) 3-Fluorobenzylamine(1.1 eq), EDCI(1.1 eq), HOBT(1.0 eq), DIEA (1.1 eq) (83% yield).

Synthesis of Compound 6, KX-309

The synthesis is outlined in Scheme 3. 4-Bromophenylacetic acid (500 mg, 2.33 mmol) and 358 mg of 2-fluorophenylboronic acid (1.1 eq) were dissolved in 12 mL, 6:1 water:isopropanol. Sodium carbonate (320 mg, 1.3 eq) was dissolved in 1 mL distilled water and added to the reaction followed by Pd(OH)$_2$/C (148 mg, 3 mol %). This was rotated in a 65° C. water bath for 5 hours. The reaction was filtered through filter paper. Filter paper was washed with 50 mL isopropanol:water:1 N NaOH (35:5:1). Washes were combined and acidified to pH 2 with 1 N sulfuric acid. Isopropanol was removed in vacuo, water (20 mL) was added and washed with dichloromethane (3×30 mL). Organic washes were combined, dried with sodium sulfate, and removed in vacuo to give 177 mg (35% yield) of the biphenyl product 4. TLC Rf=0.7 (long streak, 1:1 EtOAc:DCM). $^1$HNMR (500 MHz, CDCl$_3$) δ (ppm) 3.73 (s, 2H), 7.16 (t, 10.5 Hz, 1H), 7.22 (t, 7.5 Hz, 1H), 7.32 (qd, 1.5 Hz, 7.5 Hz, 1H), 7.38 (d, 8.0 Hz, 2H), 7.44 (td, 1.5 Hz, 7.5 Hz, 1H), 7.54 (d, 8.0 Hz, 2H).

2'-Fluorobiphenylacetic acid (4) (103 mg, 0.448 mmol), 3-Fluorobenzylamine (1.1 eq), EDCI (1.1 eq), and HOBT (1.0 eq) were all dissolved in 6 mL anhydrous DCM. After 10 min DIEA (1.1 eq) was added and the reaction was allowed to go overnight. Reaction was diluted to 25 mL and washed with 1 N HCl (3×10 L), saturated sodium bicarbonate (3×10 mL), and brine (2×20 mL). The reaction was dried with sodium sulfate and removed in vacuo to give 126 mg pure Compound 6, KX1-309 (83% yield). LCMS 360.1 (m+Na) 696.8 (2m+Na). ¹HNMR (300 MHz, CDCl₃) δ (ppm) 3.67 (s, 2H) 4.21 (d, 6.0 Hz, 2H) 5.79 (s, 1H) 6.87-6.98 (m, 3H) 7.10-7.44 (m, 7H) 7.53 (dd, 1.5 Hz, 7.5 Hz, 2H).

Scheme 3

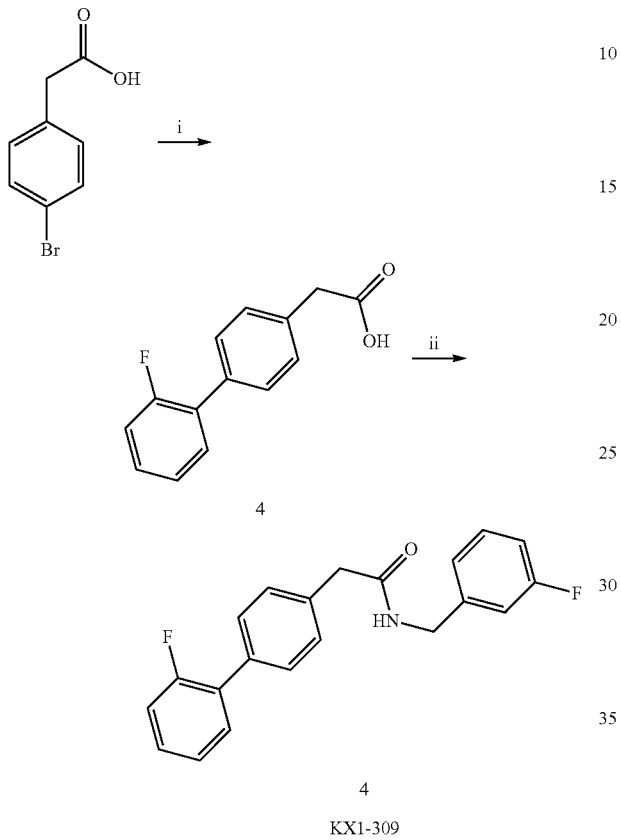

KX1-309

Reagents:
i) Phenylboronic acid(1.1 eq), Na₂CO₃(1.3 eq), Pd(OH)₂/C (3 mol %), 1:6 isopropanol: water (35% yield).
ii) 3-Fluorobenzylamine (1.1 eq), EDCI (1.1 eq), HOBT(1.0 eq), DIEA (1.1 eq), 83% yield.

Synthesis of Compound 5: N-(3-fluorophenyl)-4-biphenylacetamide, KX1-308

Thionyl chloride (0.38 ml, 5.0 mmole) was added to an ice water cooled solution of 4-Biphenylacetic acid (0.2 g, 0.9 mmole) in 5 ml dichloromethane, solution allowed to warm to room temperature then heated under reflux for 1 hr, the solvent and excess thionyl chloride was evaporated under vacuum, the oil formed was redissolved in 5 ml dichloromethane followed by addition of 4-Dimethylaminopyridine (0.12 gm, 1.0 mmole) and 3-Fluoroaniline (0.11 gm, 1.0 mmole), stirred at room temperature over night, then the reaction mixture was diluted with 10 ml dichloromethane and 20 ml water, the organic layer washed with 1 N HCl, saturated NaHCO₃ solution, and saturated NaCl solution, dried using Na₂SO₄ and evaporated dryness (0.2 gm, 72%), H₁-NMR INOVA-500 (CDCl₃) δ 3.805 (s, 2H), 6.815 (t, J=8.5 Hz, 1H), 7.068 (d, J=8.0 Hz, 1H), 7.218-7.284 (m, 2H), 7.380-7.499 (m, 6H) 7.620-7.664 (m, 4H). MS (m/z) 306.2 (M+H)⁺.

Synthesis of Compound 7: N-(3-fluorobenzyl)-4-(3-fluorophenyl)phenylacetamide, KX1-310

Synthesis of (4'-Fluoro-biphenyl-4-yl)-acetic acid: 4-Bromo-phenylacetic acid (0.5 gm, 2.3 mmole), 3-fluorophenylboronic acid (0.36 gm, 2.4 mmole) and 50% water wet 10% Palladium carbon (0.16 gm, 0.075 mmole Pd) were added to 10 ml of 5:1 water isopropanol mixture, then Na₂CO₃ (0.32 gm, 3 mmole) dissolved in 3 ml of water was added to the above mixture, the reaction was heated at 65-70° C. overnight, the reaction was cooled to room temperature, diluted with 20 ml of 70:15:1 i-PrOH/H₂O/10% NaOH, filtered, the catalyst was washed with 20 ml×3 using the above mixture, the filtrate was acidified using 20% H₂SO₄, filtered and dried (3'-Fluoro-biphenyl-4-yl)-acetic acid: (0.4 gm, 75%) H¹-NMR INOVA-500 (DMSO d₆) δ 3.623 (s, 2H), 7.192 (m, 1H), 7.358 (d, J=8.0 Hz, 2H), 7.474-7.515 (m, 3H), 7.652 (d, J=8.0 Hz, 2H), 12.316 (s, 1H).

3-fluorobenzylamine (0.14 ml, 1.1 mmole), PyBOP (0.57 gm, 1.1 mmole), and DIEA (0.36 ml, 2.2 mmole) was dissolved in DMF stirred overnight, the reaction mixture was then poured into water, solid was collected by filtration, re-crystallized using water-methanol. (0.22 gm, 76%); H¹-NMR INOVA-500 (DMSO d₆) δ 3.550 (s, 2H), 4.303 (d, J=6.5 Hz, 2H), 7.027-7.097 (m, 3H), 7.197 (m, 1H), 7.350 (m, 1H), 7.389 (d, J=8.0 Hz, 2H), 7.477-7.518 (m, 3H), 7.657 (d, J=8.0 Hz, 2H), 8.652 (t, J=5.5 Hz, 1H). MS (m/z) 338.1 (M+H)⁺.

Synthesis of Compound 8, N-(3-fluorobenzyl)-4-(4-fluorophenyl)phenylacetamide, KX1-311

Synthesis of (4'-Fluoro-biphenyl-4-yl)-acetic acid: 4-Bromo-phenylacetic acid (0.5 gm, 2.3 mmole), 4-fluorophenylboronic acid (0.36 gm, 2.4 mmole) and 50% water wet 10% Palladium carbon (0.16 gm, 0.075 mmole Pd) were added to 10 ml of 5:1 water isopropanol mixture, then Na₂CO₃ (0.32 gm, 3 mmole) dissolved in 3 ml of water was added to the above mixture, the reaction was heated at 65-70° C. overnight, the reaction was cooled to room temperature, diluted with 20 ml of 70:15:1 i-PrOH/H₂O/10% NaOH, filtered, the catalyst was washed with 20 ml×3 using the above mixture, the filtrate was acidified using 20% H₂SO₄, filtered and dried (0.4 gm, 75%) H¹-NMR INOVA-500 (DMSO d₆) δ 3.621 (s, 2H), 7.290 (t, J=8.5 Hz, 2H), 7.351 (d, J=7.5 Hz, 2H), 7.593 (d, J=7.5 Hz, 2H), 7.695 (t, J=7 Hz, 2H), 12.386 (s, 1H).

(4'-Fluoro-biphenyl-4-yl)-acetic acid (0.2 gm, 0.9 mmole), 3-fluorobenzylamine (0.14 ml, 1.1 mmole), PyBOP (0.57 gm, 1.1 mmole), and DIEA (0.36 ml, 2.2 mmole) was dissolved in DMF stirred overnight, the reaction mixture was then poured into water, solid was collected by filtration, re-crystallized using water-methanol. (0.26 gm, 90%); H¹-NMR INOVA-500 (DMSO d₆) δ 3.541 (s, 2H), 4.304 (d, J=5.5 Hz, 2H), 7.027-7.098 (m, 3H), 7.273-7.382 (m, 5H), 7.582 (d, J=8.0, 2H), 7.694 (m, 2H), 8.641 (t, J=5.5 Hz, 2H) MS (m/z) 338.1 (M+H)⁺.

Synthesis of Compound 9, N-(3-fluorobenzyl)-N-methyl-4-biphenylacetamide, KX1-312

4-biphenylacetic acid (0.25 gm, 1.2 mmole), N-methyl-3-fluorobenzylamine (0.16 gm, 1.2 mmole), EDCI (0.23 gm, 1.2 mmole), and DIEA (0.42 ml, 2.4 mmole) was dissolved in 10 ml DCM and stirred overnight. The reaction mixture was diluted with 10 ml of DCM washed with 10% HCl, saturated NaHCO₃ solution, and saturated NaCl solution, dried using Na$_2$SO$_4$ and evaporated to produce viscous clear oil (160 mg, 43%), H$^1$-NMR INOVA-500 (DMSO d$_6$) indicated the presence of a mixture of cis and trans isomers in a ratio of 1:2, running the NMR experiment was run at 50° C. slightly change the value for the chemical shift, but had almost no effect on the ratio. Protons are labeled H$_a$ or H$_b$ to indicate it belongs to one isomer or the other. H$^1$-NMR INOVA-500 (DMSO d$_6$) 2.813 (s, 3H$_a$), 3.000 (s, 3H$_b$), 3.784 (s, 2H$_a$), 3.841 (s, 2H$_b$), 4.543 (s, 2H$_b$), 4.681 (s, 2H$_a$), 6.931-7.649 (m, 13H$_a$+13H$_b$). MS (m/z) 334.2 (M+H)$^+$.

Synthesis of Compound 10, N-(3-fluorobenzyl)-4-phenyl-2-fluorophenylacetamide, KX1-313

Synthesis of 4-Bromo-2-fluoro-phenylacetamide: 4-Bromo-2-fluorobenzylbromide (5 gm, 18.7 mmole) was dissolved in 30 ml ethanol, to which water solution (10 ml) of KCN (2.43 gm, 37.4 mmole) was added, refluxed overnight, then it was cooled to room temperature, poured into 200 ml of crushed ice, filtered, chromatographed using 1:1 ethyl acetate followed by ethyl acetate (the cyano compound was hydrolyzed on the silica gel to produce the carboxamide), which was evaporated to produce white solid, (1.3 gm, 32%) H$^1$-NMR INOVA-500 (DMSO d$_6$) δ 3.436 (s, 2H), 7.005 (s, 1H), 7.289 (t, J=8.0 Hz, 1H), 7.361 (d, J=8.0 Hz, 1H), 7.478 (m, 1H), 7.517 (s, 1H).

Synthesis of 4-Bromo-2-fluoro-phenylacetic acid: 4-Bromo-2-fluoro-phenylacetamide (1.3 gm) was suspended in 100 ml of 30% NaOH, heating at reflux temperature for 24 hrs, cooled to room temperature, washed with DCM, and ethyl acetate. The aqueous layer was acidified with conc. HCl, extracted with ethyl acetate, evaporated; the residue was crystallized from isopropanol-water to give needle crystals (0.5 gm, 38%) H$^1$-NMR INOVA-500 (DMSO d$_6$) δ 3.619 (s, 2H), 7.316 (t, J=8.0 Hz, 1H), 7.379 (dd, J=8.0, 1.5 Hz, 1H), 7.516 (dd, J=8.0, 1.5 Hz, 1H), 12.555 (s, 1H).

Synthesis of 4-phenyl-2-fluorophenylacetic acid: 4-Bromo-2-fluoro-phenylacetic acid (0.25 gm, 1.1 mmole), phenylboronic acid (0.15 gm, 1.2 mmole) and 50% water wet 10% Palladium carbon (0.07 gm, 0.033 mmole Pd) were added to 10 ml of 5:1 water isopropanol mixture, then Na$_2$CO$_3$ (0.14 gm, 1.3 mmole) dissolved in 3 ml of water was added to the above mixture, the reaction was heated at 65-70° C. overnight, the reaction was cooled to room temperature, diluted with 20 ml of 70:15:1 i-PrOH/H$_2$O/10% NaOH, filtered, the catalyst was washed with 20 ml×3 using the above mixture, the filtrate was acidified using 20% H$_2$SO$_4$, filtered and dried (0.2 gm, 83%) H$^1$-NMR INOVA-500 (DMSO d$_6$) δ 3.675 (s, 2H), 7.382-7.518 (m, 6H), 7.707 (d, J=7.5 Hz, 2H), 12.498 (s, 1H).

Synthesis of N-(3-fluorobenzyl)-4-phenyl-2-fluorophenylacetamide: 4-phenyl-2-fluorophenylacetic acid (0.2 gm, 0.9 mmole), 3-fluorobenzylamine (0.14 ml, 1.1 mmole), PyBOP (0.57 gm, 1.1 mmole), and DIEA (0.36 ml, 2.2 mmole) was dissolved in DMF stirred overnight, the reaction mixture was then poured into water, solid was collected by filtration, re-crystallized using water-methanol. (0.20 gm, 70%); H$^1$-NMR INOVA-500 (DMSO d$_6$) δ 3.612 (s, 2H), 4.318 (d, J=6 Hz, 2H), 7.064-7.117 (m, 3H), 7.345-7.503 (m, 7H), 7.695 (d, J=7.5 Hz, 2H), 8.660 (t, J=6 Hz, 1H). MS (m/z) 338.1 (M+H)$^+$.

Synthesis of Compound 11, N (3-fluorobenzyl)-2-phenylpyridine-5-acetamide, KX1-314

Synthesis of 2-phenylpyridine-5-acetic acid: 2-chloropyridine-5-acetic acid (0.2 gm, 1.21 mmole), phenylboronic acid (0.16 gm, 1.3 mmole) and 50% water wet 10% Palladium carbon (0.08 gm, 0.036 mmole Pd) were added to 10 ml of 5:1 water isopropanol mixture, then Na$_2$CO$_3$ (0.15 gm, 1.4 mmole) dissolved in 3 ml of water was added to the above mixture, the reaction was heated at 65-70° C. overnight, the reaction was cooled to room temperature, diluted with 20 ml of 70:15:1 i-PrOH/H$_2$O/10% NaOH, filtered, the catalyst was washed with 20 ml×3 using the above mixture, the filtrate was dried under vacuum and crude mixture was used without any purification in the next step.

Synthesis of N(3-fluorobenzyl)-2-phenylpyridine-5-acetamide: To the crude from the above reaction, 3-fluorobenzylamine (0.15 gm, 1.2 mmole), PyBOP(0.67 gm, 1.3 mmole), and DIEA (0.32 gm, 2.6 mmole) and was stirred in DMF overnight. The reaction mixture was then poured into water; solid was collected by filtration, re-crystallized using water-methanol (0.06 gm, 18% in two steps). H$^1$-NMR INOVA-500 (CDCl$_3$) δ3.645 (s, 2H), 4.438 (d, J=5.5 Hz, 2H), 5.867 (s, 1H), 6.925-7.009 (m, 3H), 7.268 (m, 1H), 7.408-7.493 (m, 3H), 7.735 (m, 2H), 7.965-7.982 (m, 2H), 8.582 (s, 1H). MS (m/z) 321.2 (M+H)$^+$.

Synthesis of Compound 12, N-(3-Fluoro-benzyl)-2-(4-pyridin-2-yl-phenyl)-acetamide, KX1-315

Synthesis of 4-(2-Pyridinyl)benzylalcohol: 4-(2-Pyridinyl)benzaldehyde (2 gm, 11 mmole), and NaBH$_4$ (0.42 gm, 11 mmole) were stirred at room temperature for 2 hr, ethanol was evaporated, residue dissolved in ethyl acetate washed with saturated NaHCO$_3$ solution, and saturated NaCl solution, dried using Na$_2$SO$_4$ and evaporated to produce white solid (1.5 gm, 75%).

Synthesis of (4-Pyridin-2-yl-phenyl)-acetic acid: The crude of 4-(2-Pyridinyl)benzylalcohol was dissolved in 20 ml DCM, cooled using ice/methanol, triethylamine (1.25 ml, 8.9 mmole) was added followed by methanesulfonylchloride (0.7 ml, 8.9 mmole) added drop wise over 5 minutes. The reaction was allowed to stir at room temperature till the TLC indicated consumption of the starting material (3 hrs), after completion of the reaction, the reaction mixture was washed with water, saturated NaHCO$_3$ solution, and saturated NaCl solution, dried using Na$_2$SO$_4$ and evaporated to produce yellow oil, the oil produced was dissolved in 25 ml of 90% ethanol, KCN (1.05 gm, 16.2 mmole) was then added and it was heated under reflux overnight. Ethanol was evaporated; solid was washed with 50 ml water and filtered. The solid was dissolved in 30 ml of conc. HCl, refluxed for 48 hr; charcoal was added refluxed for 1 hr, filtered. The HCl was evaporated, the solid formed was dissolved in 5 ml of water, NaOH 1 N was added drop wise while extracting with ethyl acetate, the ethyl acetate extract was dried with Na$_2$SO$_4$ and evaporated to produce white solid (0.6 gm, 35% in 3 steps) H$^1$-NMR INOVA-500 (DMSO d$_6$) δ 3.641 (s, 2H), 7.345 (t, J=6.0 Hz, 1H), 7.381 (d, J=8.5 Hz, 2H), 7.879 (t, J=8.0 Hz, 1H), 7.951 (d, J=8.0 Hz, 1H), 8.034 (d, J=8.0 Hz, 2H), 8.662 (d, J=4.0 Hz, 1H), 12.390 (s, 1H).

Synthesis of N-(3-Fluoro-benzyl)-2-(4-pyridin-2-yl-phenyl)-acetamide: (4-Pyridin-2-yl-phenyl)-acetic acid (0.2 gm, 0.9 mmole), 3-fluorobenzylamine (0.14 ml, 1.1 mmole), PyBOP (0.57 gm, 1.1 mmole), and DIEA (0.36 ml, 2.2 mmole) was dissolved in DMF stirred overnight, the reaction mixture was then poured into water, solid was collected by filtration, re-crystallized using water-methanol. (0.13 gm, 45%); H$^1$-NMR INOVA-500 (DMSO d$_6$) δ 3.563 (s, 2H), 4.305 (d, J=6.0 Hz, 2H), 7.032-7.095 (m, 3H), 7.332-7.360 (m, 2H), 7.404 (d, J=8.0 Hz, 2H), 7.874 (t, J=7.0 Hz, 1H), 7.948 (d, J=8.0 Hz, 1H), 8.034 (d, J=8.0 Hz, 2H), 8.659 (d, J=4 Hz, 2H). MS (m/z) 321.2 (M+H)+.

Synthesis of Compounds 13 and 24

Syntheses of the pyridyl derivatives, Compound 13, KX1-316, and Compound 24, KX1-327, are shown in Scheme 4. The amide was made first with an EDCI coupling to give amide 5. The Suzuki with 3- or 4-pyridylboronic acids was then performed. The basic nature of the pyridine ring was exploited to purify the product from and remaining starting material. The product was pulled into the aqueous phase away from the starting material using 1 N HCl. After several organic washes the aqueous layer was basified and the product extracted with ethyl acetate. This purification procedure worked well and eliminated the need for chromatography. KX1-316 (Compound 13)

A flame dried 50 mL round bottom flask with two condensers was charged with argon. Dimethoxyethane, 15 mL and 1 mL 2 M potassium carbonate was heated to 45° C. while argon was bubbled through the solution. After 1 hour the bromo amide (240 mg, 0.7475 mmol) and 3-pyridylboronic acid (92 mg, 1.1 eq) were added. After one hour, Pd(PPh$_3$)$_4$ (43 mg, 5 mol %) was added neat. Reaction was heated at 65-75° C. for 48 hours. The solvent was poured into a round bottom flask, the remaining residue was washed with ethyl acetate. Solvents were combined and removed in vacuo. The residue was taken up in 20 mL 1 N HCl and washed with ethyl acetate (3×10 mL). The acid layer was then basified with a combination of 2 N NaOH and saturated sodium bicarbonate to pH 8-9. The aqueous layer was then washed with ethyl acetate (3×20 mL). Solvent extracts were combined, dried with sodium sulfate and removed in vacuo. Residue was purified on silica gel column (1:1 DCM: EtOAc) to give 90 mg of the desired product (38% yield). TLC, Rf 0.2 (1:1 DCM:EtOAc). LCMS 321.3 (m+H) 640.8 (2 m+Na) 662.9 (2M+Na). $^1$HNMR (500 MHz, DMSO) 3.54 (s, 2H) 4.29 (d, 6.0 Hz, 2H) 7.00-7.08 (m, 3H) 7.34 (q, 8.0 Hz, 1H) 7.40 (d, 10.0 Hz, 2H) 7.47 (dd, 6.0 Hz, 10.0 Hz, 1H) 7.66 (d, 10.0 Hz, 2H) 8.05 (dt, 2.5 Hz, 10.0 Hz, 1H) 8.55 (dd, 2.0 Hz, 6.0 Hz, 1H) 6.40 (t, 7.0 Hz, 1H) 8.78 (d, 2.5 Hz, 1H).

KX1-327 (Compound 24)

A flame dried 50 mL round bottom flask with two condensers was charged with argon. Dimethoxyethane, 15 mL and 1 mL 2 M potassium carbonate was heated to 45° C. while argon was bubbled through the solution. After 1 hour the bromo amide (150 mg, 0.4672 mmol) and 4-pyridylboronic acid (57 mg, 1 eq) were added. After one hour Pd(PPh$_3$)$_4$ (27 mg, 5 mol %) was added neat. Reaction was heated at 65-75° C. for 72 hours. The solvent was poured into a round bottom flask, the remaining residue was washed with ethyl acetate. Solvents were combined and removed in vacuo. The residue was taken up in 20 mL 1 N HCl and washed with ethyl acetate (3×10 mL). The acid layer was then basified with a combination of 2 N NaOH and saturated sodium bicarbonate to pH 8-9. The aqueous layer was then washed with ethyl acetate (3×20 mL). Solvent extracts were combined, dried with sodium sulfate and removed in vacuo to give 71 mg of the desired product (48% yield). TLC, Rf 0.2 (1:1 DCM:EtOAc). LCMS 321.3 (m+H). $^1$HNMR (500 MHz, DMSO) 3.56 (s, 2H) 4.29 (d, 6.0 Hz, 2H) 7.04 (m, 3H) 7.34 (q, 6.5 Hz, 1H) 7.42 (d, 8.0 Hz, 2H) 7.69 (d, 6.0 Hz, 2H) 7.75 (d, 8.5 Hz, 2H) 8.61 (d, 6.0 Hz, 2H) 8.64 (t, 5.5 Hz, 1H).

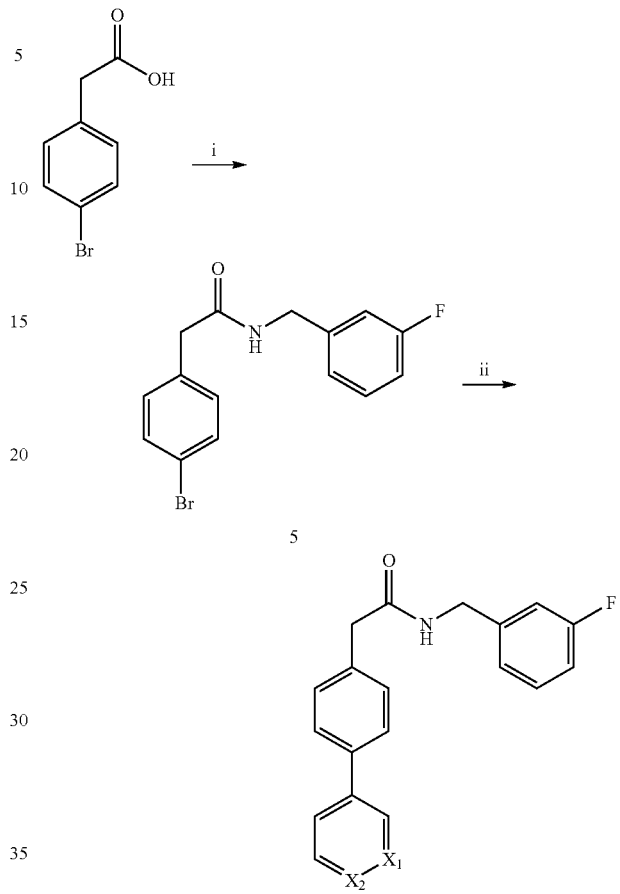

Scheme 4

Reagents:
i) 3-Fluorobenzylamine (1.1 eq), EDCl (1.1 eq), HOBT(1.0 eq), DIEA (1.1 eq), 88% yield.
ii) 3(or 4)-Pyridylboronic acid(1.1 eq), Na$_2$CO$_3$(1.3 eq), Pd(PPh$_3$)$_4$ (5 mol %), Dimethoxyethane, 2 M Na$_2$CO$_3$ (2 eq).
KX1-316 (X$_1$═N, X$_2$═C) 38%, KX1-327(X$_1$═C, X$_2$═N) 47%.

Synthesis of Compound 14, 2-[6-(3-Chloro-phenyl)-pyridin-3-yl]-N-(3-fluoro-benzyl)-acetamide, KX1-317

Synthesis of 2-(3-Chloro-phenyl)-pyridine-5-acetic acid: 2-chloropyridine-5-acetic acid (0.2 gm, 1.21 mmole), 3-chlorophenylboronic acid (0.2 gm, 1.3 mmole) and 50% water wet 10% Palladium carbon (0.08 gm, 0.036 mmole Pd) were added to 10 ml of 5:1 water isopropanol mixture, then Na$_2$CO$_3$ (0.15 gm, 1.4 mmole) dissolved in 3 ml of water was added to the above mixture, the reaction was heated at 65-70° C. overnight, the reaction was cooled to room temperature, diluted with 20 ml of 70:15:1 i-PrOH/H$_2$O/10% NaOH, filtered, the catalyst was washed with 20 ml×3 using the above mixture, the filtrate was dried under vacuum and crude mixture was used without any purification in the next step.

Synthesis of 2-[6-(3-Chloro-phenyl)-pyridin-3-yl]-N-(3-fluoro-benzyl)-acetamide: To the crude from the above reaction, 3-fluorobenzylamine (0.15 gm, 1.2 mmole), PyBOP (0.67 gm, 1.3 mmole), and DIEA (0.32 gm, 2.6 mmole) and was stirred in DMF overnight. The reaction mixture was then poured into water; solid was collected by filtration, re-crystallized using water-methanol (0.02 gm, 6% in two steps).

H$^1$-NMR INOVA-500 (DMSO d$_6$) δ 3.611 (s, 2H), 4.314 (d, J=6.0 Hz, 2H), 7.048-7.106 (m, 3H), 7.364 (m, 1H), 7.500-7.545 (m, 2H), 7.808 (dd, J=8.0, 2.0 Hz, 1H), 7.997 (d, J=8.0 Hz, 1H), 8.046 (d, J=8.0 Hz, 1H), 8.126 (d, J=2.0 Hz, 1H), 8.578 (s, 1H), 8.699 (bs, 1H). MS (m/z) 355.2 (M+H)$^+$.

Synthesis of Compound 14, 2-[6-(4-Ethyl-phenyl)-pyridin-3-yl]-N-(3-fluoro-benzyl)-acetamide, KX1-318

Synthesis of 2-(6-Chloro-pyridin-3-yl)-N-(3-fluoro-benzyl)-acetamide: 2-chloropyridine-5-acetic acid (0.2 gm, 1.21 mmole), 3-fluorobenzylamine (0.15 ml, 1.2 mmole), PyBOP (0.67 gm, 1.3 mmole), and DIEA (0.43 ml, 2.6 mmole) was dissolved in DMF stirred overnight, the reaction mixture was then poured into water, solid was collected by filtration, re-crystallized using water-methanol. (0.3 gm, 85%); H$^1$-NMR INOVA-500 (CDCl$_3$) δ 3.562 (s, 2H), 4.429 (d, J=6.5 Hz, 2H), 5.868 (s, 1H), 6.929-7.015 (m, 3H), 7.300-7.333 (m, 2H), 7.668 (dd, J=8, 2.5 Hz, 1H), 8.280 (d, J=2.5 Hz, 1H).

Synthesis of 2-[6-(4-ethyl-phenyl)-pyridin-3-yl]-N-(3-fluoro-benzyl)-acetamide: 2-(6-Chloro-pyridin-3-yl)-N-(3-fluoro-benzyl)-acetamide and (0.125 gm, 0.5 mmole), 4-ethylbenzeneboronic acid (0.083 gm, 0.55 mmole) was dissolved in dimethoxymethane (DME), Na$_2$CO$_3$ (0.11 gm, 1 mmole) in 5 ml of water was added to the DME solution, the solution was then degassed for 30 min (Ar through the solution and vacuum applied for the first 5 min), Palladiumtetrakistriphenylphosphine (0.029 gm, 0.025 mmole) was added, degassed for additional 15 min, refluxed for 24 hr. The reaction was allowed to cool to room temperature, filtered, solid washed with ethyl acetate; the organic layer was dried, evaporated. The residue was chromatographed using ethyl acetate/hexane 3:2. The product is white solid (0.08 gm, 47%). H$^1$-NMR INOVA-500 (DMSO d$_6$) δ 1.228 (t, J=7.5 Hz, 3H), 2.669 (q, J=7.5 Hz, 2H), 3.590 (s, 2H), 4.321 (d, J=6 Hz, 2H), 7.053-7.113 (m, 3H), 7.324-7.375 (m, 3H), 7.766 (dd, J=9.0, 2.0 Hz, 1H), 7.887 (d, J=8.5 Hz, 1H), 7.994 (d, J=8.0 Hz, 2H), 8.548 (s, 1H), 8.696 (t, J=5.5 Hz, 1H). MS (m/z) 349.3 (M+H)$^+$.

Synthesis of Compound 16, N-(3-Fluoro-benzyl)-2-(2-fluoro-biphenyl-4-yl)-acetamide, KX1-319

Synthesis of 2-Fluoro-biphenyl-4-carbaldehyde: 4-Bromo-2-fluoro-biphenyl (2 gm, 8 mmole) was dissolved in 20 ml of anhydrous tetrahydrofuran, THF, cooled to −78° C. under argon (Ar), n-Butyl lithium 2.5 M (3.5 ml, 8.8 mmole) was added drop wise over 10 min, and was stirred for additional 1 hr, DMF anhydrous (0.68 ml, 8.8 mmole) was then added, stirred for additional 1 hr, then warmed to room temperature over 4 hr, It was then quenched with water, extracted with ether, ether was dried, evaporated, the produced compound was purified using 9:1 hexane/ethyl acetate, to produce white solid (1 gm, 62.5%); H$^1$-NMR INOVA-500 (CDCl$_3$) δ 7.416-7.495 (m, 3H), 7.581-7.661 (m, 4H), 7.723 (d, J=8.0 Hz, 1H), 9.991 (s, 1H).

Synthesis of (2-Fluoro-biphenyl-4-yl)-methanol: 2-Fluoro-biphenyl-4-carbaldehyde (1 gm, 5 mmole), NaBH$_4$ were dissolved in ethanol stirred for 2 hrs, NaOH 10% was added, ethanol was evaporated, the reaction mixture was extracted with ethyl acetate, the ethyl acetate extract was dried with Na$_2$SO$_4$ and evaporated to produce white solid (0.8 gm, 80%). H$^1$-NMR INOVA-500 (CDCl$_3$) δ 2.266 (s, 1H), 4.683 (s, 2H), 7.142-7.168 (m, 2H), 7.339-7.442 (m, 4H), 7.519-7.535 (m, 2H).

Synthesis of (2-Fluoro-biphenyl-4-yl)-acetic acid: (2-Fluoro-biphenyl-4-yl)-methanol (0.75 gm, 3.7 mmole) was dissolved in 20 ml DCM, cooled using ice/methanol, triethylamine (0.55 ml, 4.0 mmole) was added followed by methanesulfonylchloride (0.3 ml, 4.0 mmole) added drop wise over 5 minutes. The reaction was allowed to stir at room temperature till the TLC indicated consumption of the starting material (2 hrs), after completion of the reaction, the reaction mixture was washed with water, saturated NaHCO$_3$ solution, and saturated NaCl solution, dried using Na$_2$SO$_4$ and evaporated to produce yellow oil, the oil produced was dissolved in 25 ml of 70% ethanol, KCN (0.4 gm, 6 mmole) was then added and it was heated under reflux overnight. Ethanol was evaporated; solid was washed with 50 ml water and filtered. The solid was dissolved in 20 ml of ethanol, then 20 ml of conc. H$_2$SO$_4$ was added, and was refluxed overnight; the solution was allowed to cool to room temperature, poured to 200 ml of crushed ice, the solid was collected by vacuum filtration, suspended in 25 ml of NaOH 30%, heated at reflux temperature for 24 hrs, cooled to room temperature, washed with DCM and ethyl acetate. The aqueous layer was acidified with conc. HCl, extracted with ethyl acetate, evaporated; the residue was crystallized from isopropanol-water to give white solid (0.15 gm, 18% in 3 steps) H$^1$-NMR INOVA-500 (DMSO d$_6$) δ 3.672 (s, 2H), 7.191-7.254 (m, 2H), 7.389-7.560 (m, 6H), 12.494 (s, 1H).

Synthesis of N-(3-Fluoro-benzyl)-2-(2-fluoro-biphenyl-4-yl)-acetamide: (2-Fluoro-biphenyl-4-yl)-acetic acid (0.12 gm, 0.5 mmole), 3-fluorobenzylamine (0.0.8 ml, 0.6 mmole), PyBOP (0.34 gm, 0.6 mmole), and DIEA (0.22 ml, 1.3 mmole) was dissolved in DMF stirred overnight, the reaction mixture was then poured into water, solid was collected by filtration, re-crystallized using water-methanol. (0.140 gm, 83%); H$^1$-NMR INOVA-500 (DMSO d$_6$) δ 3.580 (s, 2H), 4.316 (d, J=5.5 Hz, 2H), 7.037-7.110 (m, 3H), 7.210-7.247 (m, 2H), 7.343-7.372 (m, 2H), 7.457-7.501 (m, 3H), 7.544 (d, J=8.0 Hz, 2H), 8.660 (t, J=6.0 Hz, 1H). MS (m/z) 338.1 (M+H)$^+$.

Synthesis of Compound 17, N-(3-Fluoro-benzyl)-2-[6-(4-fluoro-phenyl)-pyridin-3-yl]-acetamide, KX1-320

Synthesis of 2-(6-Chloro-pyridin-3-yl)-N-(3-fluoro-benzyl)-acetamide: 2-chloropyridine-5-acetic acid (0.2 gm, 1.21 mmole), 3-fluorobenzylamine (0.15 ml, 1.2 mmole), PyBOP (0.67 gm, 1.3 mmole), and DIEA (0.43 ml, 2.6 mmole) was dissolved in DMF stirred overnight, the reaction mixture was then poured into water, solid was collected by filtration, re-crystallized using water-methanol. (0.3 gm, 85%); H$^1$-NMR INOVA-500 (CDCl$_3$) δ 3.562 (s, 2H), 4.429 (d, J=6.5 Hz, 2H), 5.868 (s, 1H), 6.929-7.015 (m, 3H), 7.300-7.333 (m, 2H), 7.668 (dd, J=8, 2.5 Hz, 1H), 8.280 (d, J=2.5 Hz, 1H).

Synthesis of N-(3-Fluoro-benzyl)-2-[6-(4-fluoro-phenyl)-pyridin-3-yl]-acetamide: 2-(6-Chloro-pyridin-3-yl)-N-(3-fluoro-benzyl)-acetamide and (0.093 gm, 0.33 mmole), 4-fluorobenzeneboronic acid (0.052 gm, 0.37 mmole) was dissolved in DME, Na$_2$CO$_3$ (0.07 gm, 0.66 mmole) in 5 ml of water was added to the DME solution, the solution was then degassed for 30 min (Ar through the solution and vacuum applied for the first 5 min), Palladiumtetrakistriphenylphosphine (0.016 gm, 0.015 mmole) was added, degassed for additional 15 min, refluxed for 24 hr. The reaction was allowed to cool to room temperature, filtered, solid washed with ethyl acetate; the organic layer was dried, evaporated. The residue was chromatographed using ethyl acetate/hexane 3:2. then it crystallized from methanol-water to produce white solid (0.013 gm, 12%). H$^1$-NMR INOVA-500 (DMSO d$_6$) δ 3.587 (s, 2H), 4.306 (d, J=5.0 Hz, 2H), 7.041-7.099 (m, 3H), 7.295-7.363 (m, 3H), 7.777 (d, J=7.5, 1H), 7.913 (d, J=8.0 Hz, 1H), 8.119 (s, 2H), 8.546 (s, 1H), 8.702 (s, 1H). MS (m/z) 339.2 (M+H)$^+$.

Synthesis of Compound 18, N-(3-Fluoro-benzyl)-2-[6-(3-fluoro-phenyl)-pyridin-3-yl]-acetamide, KX1-321

Synthesis of 2-(6-Chloro-pyridin-3-yl)-N-(3-fluoro-benzyl)-acetamide: 2-chloropyridine-5-acetic acid (0.2 gm, 1.21 mmole), 3-fluorobenzylamine (0.15 ml, 1.2 mmole), PyBOP (0.67 gm, 1.3 mmole), and DIEA (0.43 ml, 2.6 mmole) was dissolved in DMF stirred overnight, the reaction mixture was then poured into water, solid was collected by filtration, re-crystallized using water-methanol. (0.3 gm, 85%); H$^1$-NMR INOVA-500 (CDCl$_3$) δ 3.562 (s, 2H), 4.429 (d, J=6.5 Hz, 2H), 5.868 (s, 1H), 6.929-7.015 (m, 3H), 7.300-7.333 (m, 2H), 7.668 (dd, J=8, 2.5 Hz, 1H), 8.280 (d, J=2.5 Hz, 1H).

Synthesis of N-(3-Fluoro-benzyl)-2-[6-(3-fluoro-phenyl)-pyridin-3-yl]-acetamide: 2-(6-Chloro-pyridin-3-yl)-N-(3-fluoro-benzyl)-acetamide and (0.125 gm, 0.5 mmole), 3-fluorobenzeneboronic acid (0.08 gm, 0.55 mmole) was dissolved in DME, Na$_2$CO$_3$ (0.11 gm, 1.0 mmole) in 5 ml of water was added to the DME solution, the solution was then degassed for 30 min (Ar through the solution and vacuum applied for the first 5 min), Palladiumtetrakistriphenylphosphine (0.029 gm, 0.025 mmole) was added, degassed for additional 15 min, refluxed for 24 hr. The reaction was allowed to cool to room temperature, filtered, solid washed with ethyl acetate; the organic layer was dried, evaporated. The residue was chromatographed using ethyl acetate/hexane 3:2, then it crystallized from methanol-water to produce white solid (0.075 gm, 45%). H$^1$-NMR INOVA-500 (DMSO d$_6$) δ 3.614 (s, 2H), 4.318 (d, J=6.0 Hz, 2H), 7.053-7.099 (m, 3H), 7.273 (t, J=9.0 Hz, 1H), 7.367 (q, J=7.0 Hz, 1H), 7.542 (q, J=7.0 Hz, 1H), 7.812 (d, J=8.0 Hz, 1H), 7.891 (d, J=10.0 Hz, 1H), 7.942 (d, J=7.5 Hz, 1H), 7.992 (d, J=8.0 Hz, 1H), 8.583 (s, 1H), 8.717 (s, 1H). MS 339.2 (M+H)$^+$.

Synthesis of Compound 19, 2-[6-(3-Ethoxy-phenyl)-pyridin-3-yl]-N-(3-fluoro-benzyl)-acetamide, KX1-322

Synthesis of 2-(6-Chloro-pyridin-3-yl)-N-(3-fluoro-benzyl)-acetamide: 2-chloropyridine-5-acetic acid (0.2 gm, 1.21 mmole), 3-fluorobenzylamine (0.15 ml, 1.2 mmole), PyBOP (0.67 gm, 1.3 mmole), and DIEA (0.43 ml, 2.6 mmole) was dissolved in DMF stirred overnight, the reaction mixture was then poured into water, solid was collected by filtration, re-crystallized using water-methanol. (0.3 gm, 85%); H$^1$-NMR INOVA-500 (CDCl$_3$) δ 3.562 (s, 2H), 4.429 (d, J=6.5 Hz, 2H), 5.868 (s, 1H), 6.929-7.015 (m, 3H), 7.300-7.333 (m, 2H), 7.668 (dd, J=8, 2.5 Hz, 1H), 8.280 (d, J=2.5 Hz, 1H).

Synthesis of N-(3-Fluoro-benzyl)-2-[6-(3-fluoro-phenyl)-pyridin-3-yl]-acetamide: 2-(6-Chloro-pyridin-3-yl)-N-(3-fluoro-benzyl)-acetamide and (0.15 gm, 0.54 mmole), 3-ethoxybenzeneboronic acid (0.096 gm, 0.6 mmole) was dissolved in DME, Na$_2$CO$_3$ (0.11 gm, 1.08 mmole) in 5 ml of water was added to the DME solution, the solution was then degassed for 30 min (Ar through the solution and vacuum applied for the first 5 min), Palladiumtetrakistriphenylphosphine (0.031 gm, 0.027 mmole) was added, degassed for additional 15 min, refluxed for 24 hr. The reaction was allowed to cool to room temperature, filtered, solid washed with ethyl acetate; the organic layer was dried, evaporated. The residue was chromatographed using ethyl acetate/hexane 3:2. then it crystallized from methanol-water to produce white solid (0.03 gm, 17%). H$^1$-NMR INOVA-500 (DMSO d$_6$) δ 1.366 (t, J=7.0 Hz, 3H), 3.591 (s, 2H), 4.110 (q, J=7.0 Hz, 2H), 4.312 (d, J=5.5 Hz, 2H), 6.985 (d, J=7.5 Hz, 1H), 7.048-7.105 (m, 3H), 7.342-7.402 (m, 2H), 7.621 (m, 2H), 7.770 (d, J=7.0 Hz, 1H), 7.826 (d, J=8.0 Hz, 1H), 7.942 (d, J=7.5 Hz, 1H), 8.550 (s, 1H), 8.701 (s, 1H). MS (m/z) 365.2 (M+H)$^+$.

Synthesis of Compound 20, 4-{5-[3-Fluoro-benzyl-carbamoyl)-methyl]-pyridin-2-yl}-benzoic acid, KX1-323

Synthesis of 2-(6-Chloro-pyridin-3-yl)-N-(3-fluoro-benzyl)-acetamide: 2-chloropyridine-5-acetic acid (0.2 gm, 1.21 mmole), 3-fluorobenzylamine (0.15 ml, 1.2 mmole), PyBOP (0.67 gm, 1.3 mmole), and DIEA (0.43 ml, 2.6 mmole) was dissolved in DMF stirred overnight, the reaction mixture was then poured into water, solid was collected by filtration, re-crystallized using water-methanol. (0.3 gm, 85%); H$^1$-NMR INOVA-500 (CDCl$_3$) δ 3.562 (s, 2H), 4.429 (d, J=6.5 Hz, 2H), 5.868 (s, 1H), 6.929-7.015 (m, 3H), 7.300-7.333 (m, 2H), 7.668 (dd, J=8, 2.5 Hz, 1H), 8.280 (d, J=2.5 Hz, 1H).

Synthesis of N-(3-Fluoro-benzyl)-2-[6-(3-fluoro-phenyl)-pyridin-3-yl]-acetamide: 2-(6-Chloro-pyridin-3-yl)-N-(3-fluoro-benzyl)-acetamide and (0.15 gm, 0.54 mmole), 4-carboxybenzeneboronic acid (0.096 gm, 0.6 mmole) was dissolved in DME, Na$_2$CO$_3$ (0.11 gm, 1.08 mmole) in 5 ml of water was added to the DME solution, the solution was then degassed for 30 min (Ar through the solution and vacuum applied for the first 5 min), Palladiumtetrakistriphenylphosphine (0.031 gm, 0.027 mmole) was added, degassed for additional 15 min, refluxed for 24 hr. The reaction was allowed to cool to room temperature, filtered, solid washed with ethyl acetate, NaOH 10%, the aqueous layer was washed several times with ethyl acetate, neutralized by drop wise addition of HCl 1% having ethyl acetate in the medium with shaking after each addition of the HCl, ethyl acetate was evaporated and the solid formed was crystallized from methanol-water to produce a white solid (0.07 gm, 40%). H$^1$-NMR INOVA-500 (DMSO d$_6$) δ 3.625 (s, 2H), 4.318 (d, J=5.5 Hz, 2H), 7.053-7.111 (m, 3H), 7.376 (q, J=7.0 Hz, 1H), 7.8341 (d, J=8.0, 1H), 8.015-8.063 (m, 3H), 8.206 (d, J=8.0 Hz, 1H), 8.613 (s, 1H), 8.724 (t, J=5.5, 1H). MS (m/z) 365.3 (M+H)$^+$.

Synthesis of Compound 21, 2-[6-(2-Ethoxy-phenyl)-pyridin-3-yl]-N-(3-fluoro-benzyl)-acetamide, KX1-324

Synthesis of 2-(6-Chloro-pyridin-3-yl)-N-(3-fluoro-benzyl)-acetamide: 2-chloropyridine-5-acetic acid (0.2 gm, 1.21 mmole), 3-fluorobenzylamine (0.15 ml, 1.2 mmole), PyBOP (0.67 gm, 1.3 mmole), and DIEA (0.43 ml, 2.6 mmole) was dissolved in DMF stirred overnight, the reaction mixture was then poured into water, solid was collected by filtration, re-crystallized using water-methanol. (0.3 gm, 85%); H$^1$-NMR INOVA-500 (CDCl$_3$) δ 3.562 (s, 2H), 4.429 (d, J=6.5 Hz, 2H), 5.868 (s, 1H), 6.929-7.015 (m, 3H), 7.300-7.333 (m, 2H), 7.668 (dd, J=8, 2.5 Hz, 1H), 8.280 (d, J=2.5 Hz, 1H).

Synthesis of 2-[6-(2-Ethoxy-phenyl)-pyridin-3-yl]-N-(3-fluoro-benzyl)-acetamide: 2-(6-Chloro-pyridin-3-yl)-N-(3-fluoro-benzyl)-acetamide and (0.15 gm, 0.54 mmole), 2-ethoxybenzeneboronic acid (0.096 gm, 0.6 mmole) was dissolved in DME, Na$_2$CO$_3$ (0.11 gm, 1.08 mmole) in 5 ml of water was added to the DME solution, the solution was then degassed for 30 min (Ar through the solution and vacuum applied for the first 5 min), Palladiumtetrakistriphenylphosphine (0.031 gm, 0.027 mmole) was added, degassed for additional 15 min, refluxed for 24 hr. The reaction was allowed to cool to room temperature, filtered, solid washed with ethyl acetate; the organic layer was dried, evaporated. The residue was chromatographed using ethyl acetate/hexane 2:1, then it crystallized from methanol-water to produce a white solid (0.075 gm, 40%). $H^1$-NMR INOVA-500 (DMSO $d_6$) δ 1.339 (t, J=7.0 Hz, 3H), 3.581 (s, 2H), 4.112 (q, J=7.0 Hz, 2H), 4.322 (d, J=5.5 Hz, 2H), 7.032-7.135 (m, 5H), 7.358-7.387 (m, 2H), 7.703 (d, J=7.0, 1H), 7.748 (d, J=7.0 Hz, 1H), 7.871 (d, J=7.0 Hz, 1H), 8.548 (s, 1H), 8.725 (s, 1H). MS (m/z) 365.2 $(M+H)^+$.

Synthesis of Compound 22, 2-[6-(4-Ethoxy-phenyl)-pyridin-3-yl]-N-(3-fluoro-benzyl)-acetamide, KX1-325

Synthesis of 2-(6-Chloro-pyridin-3-yl)-N-(3-fluoro-benzyl)-acetamide: 2-chloropyridine-5-acetic acid (0.2 gm, 1.21 mmole), 3-fluorobenzylamine (0.15 ml, 1.2 mmole), PyBOP (0.67 gm, 1.3 mmole), and DIEA (0.43 ml, 2.6 mmole) was dissolved in DMF stirred overnight, the reaction mixture was then poured into water, solid was collected by filtration, recrystallized using water-methanol. (0.3 gm, 85%); $H^1$-NMR INOVA-500 (CDCl$_3$) δ 3.562 (s, 2H), 4.429 (d, J=6.5 Hz, 2H), 5.868 (s, 1H), 6.929-7.015 (m, 3H), 7.300-7.333 (m, 2H), 7.668 (dd, J=8, 2.5 Hz, 1H), 8.280 (d, J=2.5 Hz, 1H).

Synthesis of 2-[6-(4-Ethoxy-phenyl)-pyridin-3-yl]-N-(3-fluoro-benzyl)-acetamide: 2-(6-Chloro-pyridin-3-yl)-N-(3-fluoro-benzyl)-acetamide and (0.15 gm, 0.54 mmole), 4-ethoxybenzeneboronic acid (0.096 gm, 0.6 mmole) was dissolved in DME, Na$_2$CO$_3$ (0.11 gm, 1.08 mmole) in 5 ml of water was added to the DME solution, the solution was then degassed for 30 min (Ar through the solution and vacuum applied for the first 5 min), Palladiumtetrakistriphenylphosphine (0.031 gm, 0.027 mmole) was added, degassed for additional 15 min, refluxed for 24 hr. The reaction was allowed to cool to room temperature, filtered, solid washed with ethyl acetate; the organic layer was dried, evaporated. The residue was chromatographed using ethyl acetate/hexane 2:1, then it crystallized from methanol-water to produce a white solid (0.08 gm, 42%). $H^1$-NMR INOVA-500 (DMSO $d_6$) δ 1.357 (t, J=7.0 Hz, 3H), 3.564 (s, 2H), 4.090 (q, J=7.0 Hz, 2H), 4.309 (d, J=6.0 Hz, 2H), 7.012-7.103 (m, 5H), 7.361 (q, J=7.0 Hz, 1H), 7.726 (d, J=8.0 Hz, 1H), 7.842 (d, J=8.0 Hz, 1H), 8.012 (d, J=8.5 Hz, 2H), 8.503 (s, 1H), 8.686 (s, 1H). MS (m/z) 365.2 $(M+H)^+$.

Scale-up synthesis of Compound 22HCl, 2-[6-(4-Ethoxy-phenyl)-pyridin-3-yl]-N-(3-fluoro-benzyl)-acetamide HCl, KX1-325 HCl Synthesis of 2-(6-Chloro-pyridin-3-yl)-N-(3-fluoro-benzyl)-acetamide HCl: 2-chloropyridine-5-acetic acid (6.0 gm, 34 mmole), 3-fluorobenzylamine (4.5 ml, 34 mmole), PyBOP (18 gm, 36 mmole), and DIEA (12.5 ml, 75 mmole) was dissolved in DMF stirred overnight, the reaction mixture was then poured into water, solid was collected by filtration, recrystallized using water-methanol (6.3 gm, 70%); $H^1$-NMR INOVA-500 (CDCl$_3$) δ 3.562 (s, 2H), 4.429 (d, J=6.5 Hz, 2H), 5.868 (s, 1H), 6.929-7.015 (m, 3H), 7.300-7.333 (m, 2H), 7.668 (dd, J=8, 2.5 Hz, 1H), 8.280 (d, J=2.5 Hz, 1H).

Synthesis of 2-[6-(4-Ethoxy-phenyl)-pyridin-3-yl]-N-(3-fluoro-benzyl)-acetamide: 2-(6-Chloro-pyridin-3-yl)-N-(3-fluoro-benzyl)-acetamide and (4.8 gm, 17.2 mmole), 4-ethoxybenzeneboronic acid (3.14 gm, 18.9 mmole) was suspended in DME (100 ml), Na$_2$CO$_3$ (3.6 gm, 34.4 mmole) in 15 ml of water was added to the DME solution, the solution was then degassed for 30 min (Ar through the solution and vacuum applied for the first 5 min), Palladiumtetrakistriphenylphosphine (0.99 gm, 0.86 mmole) was added, degassed for additional 15 min, refluxed overnight. The reaction was allowed to cool to room temperature, filtered, the solid washed with cold ethyl acetate and saturated NaHCO$_3$ solution, the solid was then recrystallized from methanol to produce white solid (4.8 gm).

4.6 gm of the free amine was dissolved in 50 ml ethanol with gentle heating, then 25 ml of 4 N HCl in ethyl acetate was added, the solution was concentrated to 20 ml, then diluted with 100 ml of cold ethyl acetate, the solid formed was filtered washed with more ethyl acetate (50×2) and dried (4.3 gm, 65%); $H^1$-NMR INOVA-500 (DMSO $d_6$) δ 1.386 (t, J=7.0 Hz, 3H), 3.822 (s, 2H), 4.179 (q, J=7.0 Hz, 2H), 4.339 (d, J=6.0 Hz, 2H), 7.074-7.182 (m, 5H), 7.374 (m, 1H), 8.106 (d, J=8.0 Hz, 1H), 8.263 (d, J=8.0 Hz, 1H), 8.312 (s, 2H), 8.718 (s, 1H), 8.981 (s, 1H). MS (m/z) 365.2 $(M+H)^+$.

Melting Point of the free base: 0.1 gm of the HCl salt was stirred in 10 ml of 20% NaOH for 10 min, filtered; the solid was crystallized from ethanol water, dried in the oven at 100° C. for 2 hrs. Melting point was found to be 173-176° C.

Synthesis of Compound 23, N-(3-Fluoro-benzyl)-2-[6-(4-methanesulfonyl-phenyl)-pyridin-3-yl]-acetamide, KX1-326

Synthesis of 2-(6-Chloro-pyridin-3-yl)-N-(3-fluoro-benzyl)-acetamide: 2-chloropyridine-5-acetic acid (0.2 gm, 1.21 mmole), 3-fluorobenzylamine (0.15 ml, 1.2 mmole), PyBOP (0.67 gm, 1.3 mmole), and DIEA (0.43 ml, 2.6 mmole) was dissolved in DMF stirred overnight, the reaction mixture was then poured into water, solid was collected by filtration, recrystallized using water-methanol (0.3 gm, 85%); $H^1$-NMR INOVA-500 (CDCl$_3$) δ 3.562 (s, 2H), 4.429 (d, J=6.5 Hz, 2H), 5.868 (s, 1H), 6.929-7.015 (m, 3H), 7.300-7.333 (m, 2H), 7.668 (dd, J=8, 2.5 Hz, 1H), 8.280 (d, J=2.5 Hz, 1H).

Synthesis of N-(3-Fluoro-benzyl)-2-[6-(4-methanesulfonyl-phenyl)-pyridin-3-yl]-acetamide: 2-(6-Chloro-pyridin-3-yl)-N-(3-fluoro-benzyl)-acetamide and (0.15 gm, 0.54 mmole), 4-methanesulfonyl benzeneboronic acid (0.12 gm, 0.6 mmole) was dissolved in DME, Na$_2$CO$_3$ (0.11 gm, 1.08 mmole) in 5 ml of water was added to the DME solution, the solution was then degassed for 30 min (Ar through the solution and vacuum applied for the first 5 min), Palladiumtetrakistriphenylphosphine (0.031 gm, 0.027 mmole) was added, degassed for additional 15 min, refluxed for 24 hr. The reaction was allowed to cool to room temperature, filtered, solid washed with ethyl acetate; the organic layer was dried, evaporated. The residue was chromatographed using ethyl acetate/hexane 2:1, then it crystallized from methanol-water to produce a white solid (0.02 gm, 10%); $H^1$-NMR INOVA-500 (DMSO $d_6$) δ 3.341 (s, 3H), 3.635 (s, 2H), 4.315 (d, J=7.0 Hz, 2H), 7.047-7.110 (m, 3H), 7.366 (q, J=9.0 Hz, 1H), 7.857 (d, J=8.5 Hz, 1H), 8.027-8.081 (m, 3H), 8.343 (d, J=10.5 Hz, 2H), 8.631 (s, 1H), 8.731 (s, 1H). MS (m/z) 399.2 $(M+H)^+$.

Synthesis of Compound 24, KX1-327, and Compound 26, KX1-357

The syntheses are shown in Scheme 5.

Compound 24, KX1-327 HCl

A solution of 75 mL 1,2-Dimethoxyethane and 16 mL 2 M sodium carbonate was thoroughly degassed by heating at 50°

C. with an argon stream through the solvent. 5.00 g of the 4-bromophenyl acetamide (5, 15.6 mmol) and 1.95 grams of 4-pyridylboronic acid (1.00 eq) were added to and degassing continued for 1 hour. Tetrakis(triphenylphosphine) palladium (5 mol %) was added neat and the reaction was refluxed for 24 hours. The reaction was cooled and poured into 300 mL distilled water and filtered to give 5.014 g crude product. This crude product was taken up in 1 L of a 1 to 1 mix of 1 N HCl and ethyl acetate. The organic layer was discarded and the aqueous layer was washed two more times with EtOAc. The aqueous layer was the basified with solid sodium bicarbonate to pH 7.5. This was then extracted 3×300 mL EtOAc to give about 3.25 g of semi-pure product. Pure crystals of the free base were made by dissolving 200 mg in a minimum amount of ethyl acetate with gentle heating and sonication. Hexanes was added to this solution until it became cloudy. This was heated until clear. Addition of more hexanes followed by heating was repeated two more times. This clear solution was allowed to stand overnight in a sealed vessel. White crystals formed which were washed with hexanes and dried to give about 50 mg (mp 145-146° C.). The rest of the product was dissolved in ethanol and two equivalents of hydrochloric acid (1.1 M in EtOAc) were added. After 1 hour the ethanol was removed and redissolved in the least amount of ethanol at 40° C. EtOAc was added until the solution became cloudy. The solution was allowed to stand and the desired product crystallized as pure white crystals. The crystals were filtered off, washed with EtOAc and dried to give 2.4 grams (48% overall yield); LCMS 321.3 (m+H). $^1$HNMR (500 MHz, DMSO) 3.61 (s, 2H) 4.29 (d, 7.5 Hz, 2H) 7.04 (m, 3H) 7.34 (q, 9.5 Hz, 1H) 7.50 (d, 10.5 Hz, 2H) 7.95 (d, 10.5 Hz, 2H) 8.24 (d, 8.0 Hz, 2H) 8.70 (s, 1H) 8.87 (d, 8.0 Hz, 2H).

Compound 26, KX1-357

47.0 mg of KX1-327 were dissolved in 5 mL DCM. Metachloroperoxybenzoic acid (35.0 mg, 1.4 eq) were added and the reaction was allowed to stir for 13 hours. The reaction was washed 3×5 mL saturated sodium bicarbonate, dried with sodium sulfate and concentrated to give 45 mg of a yellow solid. NMR revealed the product contained about 15% impurity, which may have been m-chlorobenzoic acid (or the peroxide). The solid was redissolved in 5 mL DCM and washed 3× 5 mL saturated sodium bicarbonate, dried with sodium sulfate and concentrated to give 26 mg of the desired product as a yellow solid; LCMS 337.2 (M+H), 672.9 (2M+H), 694.8 (2M+Na). $^1$HNMR (400 MHz, DMSO) 3.54 (s, 2H), 4.28 (d, 6.0 Hz, 2H), 7.00-7.08 (m, 3H), 7.34 (q, 8.0 Hz, 1H), 7.40 (d, 8.4 Hz, 2H), 7.72 (d, 8.4 Hz, 2H), 7.75 (d, 7.2 Hz, 2H), 8.24 (d, 8.4 Hz, 2H), 8.63 (t, 5.6 Hz, 1H).

Scheme 5

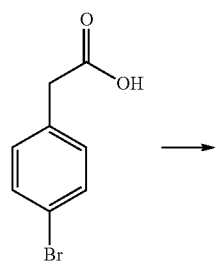

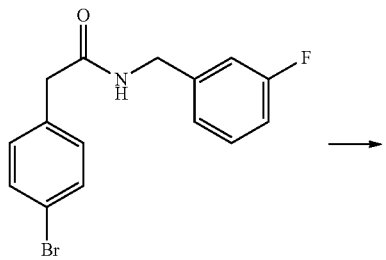

5

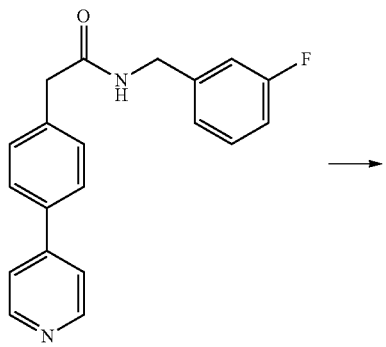

KX1-327

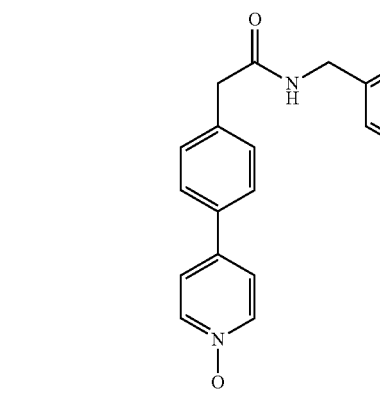

KX1-357

4-Bromophenylacetic acid (6.00 g, 47.9 mmol) was dissolved in 40 mL of anhydrous dichloromethane under an argon atmosphere and cooled in an ice bath. 3-Fluorobenzylamine (1.00 eq) was added and unintended precipitation of the acetic acid/benzylamine salt occurred. More dichloromethane (20 mL) was added followed by DIEA (2.2 eq), HOBT (1.0 eq), and EDCI (1.1 eq). After about 2 hours the solid broke up, 4 hours after that the reaction was finished by TLC. The reaction was diluted with 200 mL of dichloromethane and 200 mL of 1 N hydrochloric acid. Upon shaking in a separatory funnel an emulsion formed. This emulsion was divided in half and dichloromethane was removed. 500 mL ethyl acetate and another 300 mL 1 N HCl was added to each half. The organic layer was washed 2 more times with 1 N HCl, 3×300 mL saturated sodium bicarbonate, and 3×200 mL with saturated sodium chloride. Organic layers from each extraction were combined and dried with sodium sulfate, and solvent was removed to give 13.12 g (85% yield) desired product; $^1$HNMR (500 MHz, CDCl$_3$) δ (ppm) 3.58 (s, 2H), 4.45 (d, 6.0 Hz, 2H), 5.70 (bs, 1H) 6.93 (m, 3H), 7.16 (d, 8.1 Hz, 2H), 7.26 (m, 1H) 7.48 (d, 8.1 Hz, 2H).

Synthesis of Compound 25, KX1-329

As shown in Scheme 6, 5-Hydroxy-2-methylpyridine was converted to the triflate, 6, followed by Suzuki reaction to give the 5-phenyl-2-methylpyridine. The methylpyridine, 7, was deprotonated with n-butyllithium and added to a solution of ethyl carbonate. Saponification followed by amide coupling with PyBOP gave the desired product.

5-Hydroxy-2-methylpyridine (3.00 g, 27.5 mmol) was dissolved in 15 mL anhydrous pyridine and cooled to 0° C. Triflic anhydride (7.76 g, 1.1 eq) was added drop wise over 3 minutes. Following the addition the reaction was removed from the ice bath and allowed to stir for 6 hr. The volume was then reduced to 8 mL in vacuo, diluted with 50 mL distilled water, and then extracted with 75 mL EtOAc. The organic layer was then washed with 1 N HCl (3×50 mL), dried with sodium sulfate, and removed in vacuo to give 2.78 g (42%) of an amber oil (6); LCMS 242.1 (m+H). $^1$HNMR (400 MHz, CDCl$_3$) 2.58 (s, 3H) 7.26 (d, 8.4 Hz, 1H) 7.52 (dd, 2.8 Hz, 8.4 Hz, 1H) 8.47 (d, 2.8 Hz, 1H).

A flame dried 50 mL round bottom flask with two condensers was charged with argon. Dimethoxyethane, 25 mL and 6 mL 2 M sodium carbonate was heated to 45° C. while argon was bubbled through the solution. After 1 hour, the pyridyl triflate (6) (1.538 g, 6.382 mmol) and phenylboronic acid (856 mg, 1.1 eq) were added. After one hour Pd(PPh$_3$)$_4$ (370 mg, 5 mol %) was added, the reaction was heated at 65-75° C. for 48 hours. The solvent was poured into a round bottom flask, the remaining residue was washed with ethyl acetate. Solvents were combined and removed in vacuo. The residue was purified by silica gel chromatography (hexanes:EtOAc) to give 702 mg of the desired product 7 (65% yield); LCMS 170.2 (m+H). $^1$HNMR (400 MHz, CDCl$_3$) 3.60 (s, 3H) 7.22 (d, 8.0 Hz, 1H) 7.38 (t, 7.2 Hz, 1H) 7.46 (t, 7.2 Hz, 2H) 7.56 (d, 8.0 Hz, 2H) 7.77 (dd, 2.4 Hz, 8.0 Hz, 1H) 8.73 (d, 2.4 Hz, 1H).

5-Phenyl-2-methylpyridine (7, 205 mg, 1.223 mmol) was dissolved in freshly distilled THF in flame dried glassware under argon. Cooled to −78° C. in a dry ice/acetone bath for 20 minutes. N-Butyllithium (0.485 mL, 1.0 eq) was added drop wise over 5 minutes. This solution was added to a THF solution of ethyl carbonate (1.5 eq) via a cannula. The solution was stirred for 2 hours before being quenched with methanol added drop wise. 1 N sodium hydroxide (1 mL) was added before removing the organic solvents in vacuo. The remaining aqueous solution was extracted with ether (3×15 mL). Organic layers were combined and dried with sodium sulfate and removed in vacuo to give 208 mg 8 (71% yield) $^1$HNMR (500 MHz, CDCl$_3$) 1.30 (m, 3H) 2.61 (s, 2H) 4.20 (m, 3H) 7.22 (d, 8.0 Hz, 1H) 7.38 (t, 7.5 Hz, 1H) 7.48 (t, 7.5 Hz, 2H) 7.58 (m, 2H) 7.78 (dd, 2.5 Hz, 8.0 Hz, 1H) 8.73 (d, 2.5 Hz, 1H).

Ethyl ester 8 (208 mg, 0.86 mmol) was dissolved in 5 mL THF. 1 N NaOH (about 1 mL) was added and the reaction was put in a 35° C. water bath overnight. The volume of the reaction was reduced to about 1 mL and then acidified with 1 N HCl to precipitate the desired product. The precipitate was isolated by decanting and drying in vacuo to give 54 mg (30% yield) of 9; LCMS 214.1 (m+H) 236.0 (m+Na). $^1$HNMR (400 MHz, CD$_3$OD) 3.64 (s, 2H) 7.24-7.28 (m, 4H) 7.25 (t, 8.4 Hz, 2H) 7.52 (d, 8.4 Hz, 2H) 7.87 (dd, 2.0 Hz, 8.0 Hz, 1H) 8.53 (d, 2.0 Hz, 1H).

Carboxylic acid 9 (54 mg, 0.232 mmol), 3-Fluorobenzylamine (1.1 eq), and PyBOP (1.1 eq) were dissolved in 3 ml anhydrous DMF. After 10 minutes DIEA (1.1 eq) was added and the reaction was allowed to stir overnight. The DMF was removed in vacuo and the residue was taken up with methanol and crystallized from methanol/water to give 44 mg Compound 25, KX1-329 (55%) as clear, needle crystals; TLC, Rf 0.2 (1:1 DCM:EtOAc). LCMS 321.2 (m+H), 343.1 (m+Na), 662.9 (2m+Na). $^1$HNMR (400 MHz, CDCl$_3$) 3.82 (s, 2H), 4.46 (d, 8.8 Hz, 2H), 6.91 (t, 9.2 Hz, 2H) 6.99 (d, 7.6 Hz, 1H), 7.25 (t, 8.4 Hz, 2H), 7.34 (d, 8.0 Hz, 2H) 7.40 (tt, 1.2 Hz, 7.2 Hz, 2H) 7.55 (d, 7.6 Hz, 2H) 7.80 (b, 1H) 7.86 (dd, 2.0 Hz, 7.6 Hz, 1H) 8.73 (d, 2.0 Hz, 1H).

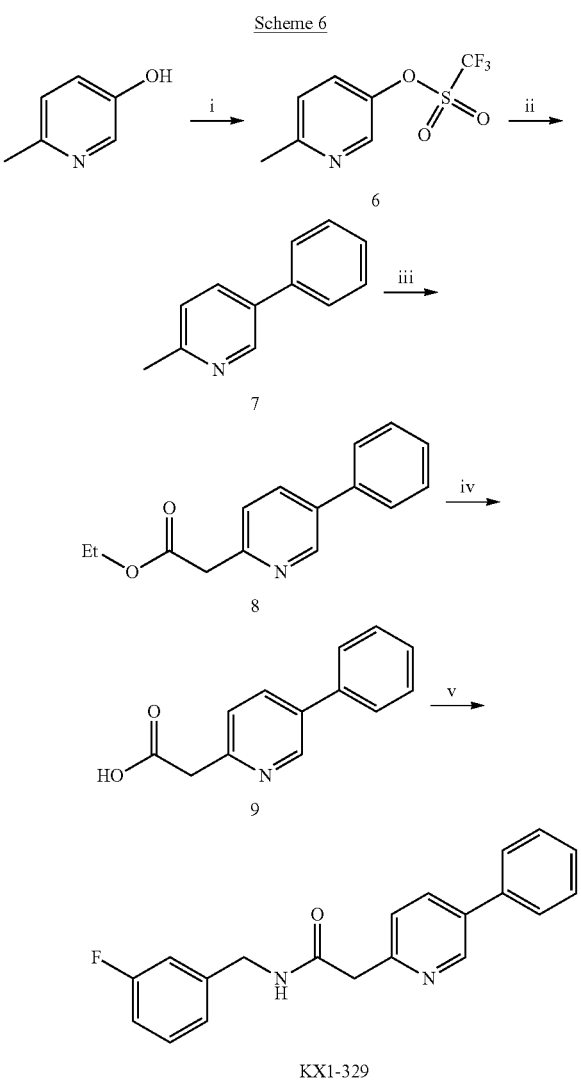

Scheme 6

KX1-329

Reagents:
i) Tf$_2$O, pyridine (43%).
ii) Phenylboronic acid(1.1 eq), Na$_2$CO$_3$(1.3 eq), Pd(PPh$_3$)$_4$ (5 mol %), Dimethoxyethane, 2 M Na$_2$CO$_3$ (2 eq) (65% after chromatography).
iii) n-Butyl lithium (1.0 eq), diethylcarbonate (1.5 eq), anhydrous THF.
iv) LiOH, THF 30° C. (18% after crystallization).
v) 3-fluorobenzylamine(1.1 eq), PyBOP(1.1 eq), DIEA(1.1 eq), DMF (55% yield).

Synthesis of Compound 27, 2-[6-(4-Ethoxy-phenyl)-1-oxo-pyridin-3-yl]-N-(3-fluoro-benzyl)-acetamide, KX1-358

To an ice cooled solution of 0.2 gm of 2-[6-(4-Ethoxy-phenyl)pyridin-3-yl]-N-(3-fluoro-benzyl)-acetamide in 80 ml DCM, 0.13 gm of m-chloroperbenzoic acid was added as solid. After stirring overnight, the reaction was washed with saturated sodium bicarbonate solution, dried with sodium sulfate, evaporated to dryness under vacuum, then chromatographed (silica gel) using ethyl acetate followed by 10% methanol in ethyl acetate to produce 0.16 gm (78%); H¹-NMR INOVA-400 (DMSO d₆) δ 1.357 (t, J=7.0 Hz, 3H), 3.564 (s, 2H), 4.090 (q, J=6.8 Hz, 2H), 4.309 (d, J=5.60 Hz, 2H), 7.012-7.103 (m, 5H), 7.245 (d, J=8.0 Hz, 1H), 7.729 (m, 1H), 7.529 (d, J=8.0 Hz, 1H), 7.800 (d, J=8.5 Hz, 2H), 8.225 (s, 1H), 8.663 (t, J=5.6 Hz, 1H). MS (m/z) 380 (M+H)⁺.

For the following syntheses, unless otherwise noted, reagents and solvents were used as received from commercial suppliers. Proton and carbon nuclear magnetic resonance spectra were obtained on a Bruker AC 300 or a Bruker AV 300 spectrometer at 300 MHz for proton and 75 MHz for carbon. Spectra are given in ppm (δ) and coupling constants, J, are reported in Hertz. Tetramethylsilane was used as an internal standard for proton spectra and the solvent peak was used as the reference peak for carbon spectra. Mass spectra and LC-MS mass data were obtained on a Perkin Elmer Sciex 100 atmospheric pressure ionization (APCI) mass spectrometer. LC-MS analyses were obtained using a Luna C8(2) Column (100×4.6 mm, Phenomenex) with UV detection at 254 nm using a standard solvent gradient program (Method B). Thin-layer chromatography (TLC) was performed using Analtech silica gel plates and visualized by ultraviolet (UV) light, iodine, or 20 wt % phosphomolybdic acid in ethanol. HPLC analyses were obtained using a Prevail C18 column (53×7 mm, Alltech) with UV detection at 254 nm using a standard solvent gradient program (Method A).

Method A:

| Time (min) | Flow (mL/min) | % A | % B |
|---|---|---|---|
| 0.0 | 3.0 | 95.0 | 5.0 |
| 10.0 | 3.0 | 0.0 | 100.0 |
| 11.0 | 3.0 | 0.0 | 100.0 |

A = Water with 0.1 v/v Trifluoroacetic Acid
B = Acetonitrile with 0.1 v/v Trifluoroacetic Acid Method B:

| Time (min) | Flow (mL/min) | % A | % B |
|---|---|---|---|
| 0.0 | 2.0 | 95.0 | 5.0 |
| 4.0 | 2.0 | 5.0 | 95.0 |

A = Water with 0.02 v/v Trifluoroacetic Acid
B = Acetonitrile with 0.02 v/v Trifluoroacetic Acid Synthesis of
N-benzyl-2-(5-bromopyridin-2-yl)acetamide

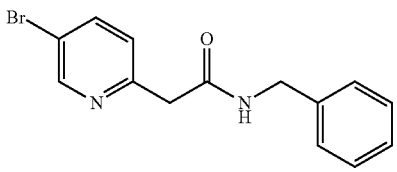 [SMILES: O=C(Cc1ccc(Br)cn1)NCc1ccccc1]

A flask was charged with 5-(5-bromopyridin-2(1H)-ylidene)-2,2-dimethyl-1,3-dioxane-4,6-dione (1.039 g, 3.46 mmol), benzylamine (0.50 mL, 4.58 mmol), and toluene (20 mL). The reaction was brought to reflux under nitrogen for 18 hours, then cooled and placed in a freezer until cold. The product was collected by filtration and washed with hexanes to yield a mass of bright white crystals (1.018 g, 96%).

Synthesis of 4-(2-(4-(4,4,5,5-tetramethyl[1,3,2]dioxaborolan-2-yl)-phenoxy)ethyl)morpholine

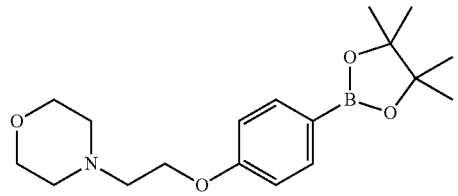 [SMILES: CC1(C)OB(c2ccc(OCCN3CCOCC3)cc2)OC1(C)C]

To a stirring solution of 4-(4,4,5,5-tetramethyl[1,3,2]dioxaborolan-2-yl)-phenol (2.55 g, 11.58 mmol), 2-morpholin-4-ylethanol (1.60 mL, 1.73 g, 13.2 mmol) and triphenyl phosphine (3.64 g, 13.9 mmol) in methylene chloride (60 mL) at 0° C. was added dropwise DIAD (2.82 g, 13.9 mmol). The reaction was allowed to warm to room temperature and stir overnight. After 18 hours, additional portions of triphenyl phosphine (1.51 g, 5.8 mmol), 2-morpholin-4-ylethanol (0.70 mL, 5.8 mmol), and DIAD (1.17 g, 5.8 mmol) were added. After stirring an additional 2 hours at room temperature the reaction was concentrated and the residue purified by flash chromatography (5% to 25% EtOAc in CHCl₃) to provide the product as a white solid (2.855 g, 74%).

Synthesis of Compound 134 KX2-391

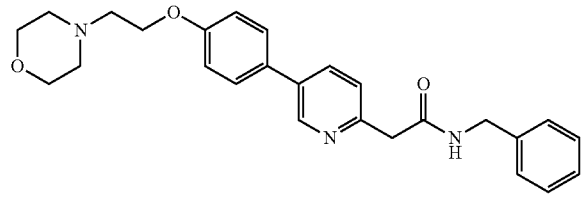 [SMILES: O=C(Cc1ccc(-c2ccc(OCCN3CCOCC3)cc2)cn1)NCc1ccccc1]

A 10 mL reaction tube with a septum closure and stir bar was charged with N-benzyl-2-(5-bromopyridin-2-yl)acetamide (123 mg, 0.403 mmol), 4-(2-(4-(4,4,5,5-tetramethyl[1,3,2]dioxaborolan-2-yl)-phenoxy)ethyl)morpholine (171 mg, 0.513 mmol), and FibreCat 1007¹ (30 mg, 0.015 mmol). Ethanol (3 mL) was added, followed by aqueous potassium carbonate solution (0.60 mL, 1.0 M, 0.60 mmol). The tube was sealed and heated under microwave conditions at 150° C. for 10 minutes. The reaction was cooled and concentrated to remove the majority of the ethanol, and then taken up in 10 mL of ethyl acetate and washed successively with water and saturated sodium chloride solution. The organic layer was dried with MgSO₄, filtered and concentrated to a white solid. This white solid was triturated with ethyl ether to give ALB 30349 as a white solid (137 mg, 79%): mp 135-137° C.; ¹H NMR (300 MHz, CDCl₃) δ 8.70 (d, 1H, J=2.0 Hz), 7.81 (dd, 1H, J=2.4 Hz, J=8.0 Hz), 7.65 (br s, 1H), 7.49 (d, 2H, J=8.8 Hz), 7.37-7.20 (m, 6H), 7.01 (d, 2H, J=8.8 Hz), 4.49 (d, 2H, J=5.8 Hz), 4.16 (t, 2H, J=5.7 Hz, 3.82 (s, 2H), 3.78-3.72 (m, 4H), 2.84 (t, 2H, J=5.7 Hz), 2.62-2.58 (m, 4H); HPLC (Method B) 98.0% (AUC), $t_R$=1.834 min.; APCI MS m/z 432 [M+H]⁺.

[1] Polymer bound di(acetato)dicyclohexylphenylphosphinepalladium(II), manufactured by Johnson Matthey, Inc. and available from Aldrich (catalog #590231).

(4-bromo-3-fluorophenyl)(morpholino)methanone

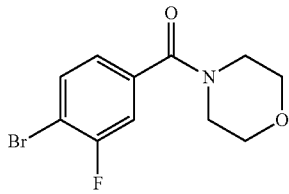 [SMILES: O=C(c1ccc(Br)c(F)c1)N1CCOCC1]

A 500 mL flask was charged with 4-bromo-3-fluorobenzoic acid (5.00 g, 22.83 mmol), 100 mL DMF, morpholine (2.4 ml, 27.5 mmol), and 4-Ethylmorpholine (8.6 ml, 67.9 mmol). HOBt (4.32 g, 32.0 mmol) was added followed by EDC (5.25 g, 27.4 mmol) and the reaction allowed to stir at room temperature for 18 hours. The reaction was concentrated and the resulting orange syrup taken up in 100 mL EtOAc and 100 mL water. The organic layer was washed with 100 mL 2N HCl, 100 mL saturated sodium bicarbonate, and 100 mL saturated sodium chloride. The organic was then dried with MgSO₄, filtered, and concentrated to give 6.476 g (98%) of a viscous yellow oil. This material was used without further purification.

4-(4-bromo-3-fluorobenzyl)morpholine

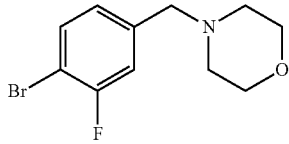 [SMILES: Fc1cc(CN2CCOCC2)ccc1Br]

A 250 ml flask was charged with (4-bromo-3-fluorophenyl)(morpholino)methanone (4.569 g, 15.86 mmol) and dissolved in 16 mL of THF. Diphenylsilane (6.2 ml, 33.4 mmol) was added followed by carbonyltris(triphenylphosphine)rhodium(I)hydride (100 mg, 0.109 mmol) and the reaction stirred at room temperature for 20 hours.

The reaction was diluted with 200 mL of ether and extracted with 1N HCl (2×150 mL). This resulted in the formation of a white precipitate in the separatory funnel. The acid layer and the resulting white precipitate were washed with ether (2×100 mL), and then basified with solid NaOH pellets (23 g). The aqueous layer was then extracted with ether (3×125 mL), dried over MgSO₄, filtered, and concentrated to give 1.35 g (31%) of a colorless oil. This material was used without further purification.

4-(3-fluoro-4-(4,4,5,5-tetramethyl-1,3,2-dioxaborolan-2-yl)benzyl)morpholine

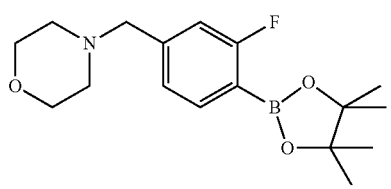 [SMILES: CC1(C)OB(c2ccc(CN3CCOCC3)cc2F)OC1(C)C]

A 10 mL microwave reaction tube with septum closure was charged with 4-(4-bromo-3-fluorobenzyl)morpholine (405 mg, 1.48 mmol), Bis(pinacolato)diboron (516 mg, 2.03 mmol), Pd(dppf)Cl₂·CH₂Cl₂ (62 mg, 0.076 mmol), potassium acetate (659 mg, 6.72 mmol), and DMF (3.6 mL). The vial was placed under nitrogen by evacuation/backfilling (5 cycles) and stirred at 80° C. for 8 hours. The reaction was cooled, diluted with ethyl acetate (25 mL) and filtered. The organics were washed with water (25 mL) and saturated sodium chloride (25 mL). The organic layer was then dried over MgSO₄ and concentrated to a dark oil. The product was purified by silica gel chromatography eluting with 2% MeOH in CHCl₃ to give 310 mg (65%) of an off-white solid.

Synthesis of Compound 136, KX2-393

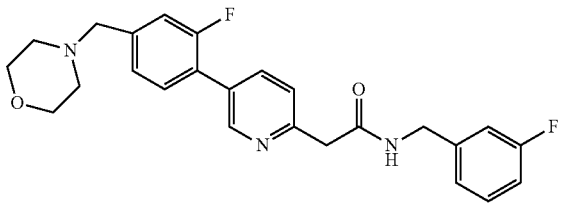 [SMILES: O=C(Cc1ccc(-c2ccc(CN3CCOCC3)cc2F)cn1)NCc1cccc(F)c1]

A 10 mL microwave reaction tube with septum closure was charged with 4-(3-fluoro-4-(4,4,5,5-tetramethyl-1,3,2-dioxaborolan-2-yl)benzyl)morpholine (307 mg, 0.96 mmol), 2-(5-bromopyridin-2-yl)-N-(3-fluorobenzyl)acetamide (247 mg, 0.77 mmol), and FibreCat 1007 (60 mg, 0.03 mmol). Ethanol (3 mL) was added followed by aqueous potassium carbonate solution (1.2 mL, 1.0 M, 1.2 mmol). The tube was sealed and heated under microwave conditions at 150° C. for 10 minutes. The reaction was cooled and concentrated to remove the majority of the ethanol, and then taken up in 10 mL of ethyl acetate and washed successively with water and saturated sodium chloride solution. The organic layer was dried with MgSO₄, filtered, and concentrated. The material was purified by column chromatography (silica gel, 100:0 CHCl₃/MeOH to 95:5 CHCl₃/MeOH) to provide ALB 30351 as a white solid (240 mg, 74%): mp 91-92° C.; ¹H NMR (300 MHz, CDCl₃) δ 8.71 (br s, 1H), 7.86-7.84 (m, 1H), 7.78 (br s, 1H), 7.37 (t, 2H, J=7.5 Hz), 7.28-7.21 (m, 3H), 7.02 (dd, 1H, J=0.6 Hz, J=7.7 Hz), 6.98-6.90 (m, 2H), 4.49 (d, 2H, J=5.9 Hz), 3.84 (s, 2H), 372-3.75 (m, 4H), 3.52 (s, 2H), 2.47-2.50 (m, 4H); HPLC (Method A) 98.7% (AUC), $t_R$=3.866 min.; APCI MS m/z 438 [M+H]⁺.

4-(2-(4-bromo-3-fluorophenoxy)ethyl)morpholine

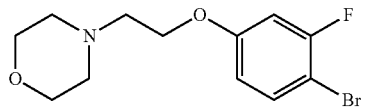 [SMILES: Fc1cc(OCCN2CCOCC2)ccc1Br]

A flask was charged with 4-bromo-3-fluorophenol (4.999 g, 26.2 mmol) and triphenylphosphine (10.298 g, 39.3 mmol). Methylene chloride (120 mL) was added followed by 2-morpholinoethanol (4 mL, 33.0 mmol) and the solution was stirred on an ice water bath to cool. After 5 minutes, diisopropyl azodicarboxylate (7.6 ml, 39.1 mmol) was added over 6 to 8 minutes. The reaction was left stirring on the cold bath to slowly warm to room temperature overnight. The reaction was concentrated and the residue purified by flash chromatography (25% to 100% EtOAc in hexanes) to provide the product as a colorless oil (2.621 g, 33%).

4-(2-(3-fluoro-4-(4,4,5,5-tetramethyl-1,3,2-dioxaborolan-2-yl)phenoxy)ethyl)morpholine

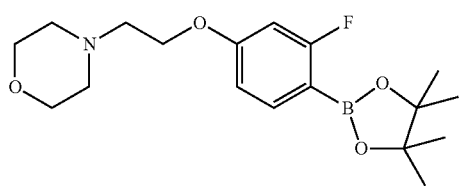 [SMILES: CC1(C)OB(c2ccc(OCCN3CCOCC3)cc2F)OC1(C)C]

A 40 mL microwave reaction tube with a septum closure and stir bar was charged with 4-(2-(4-bromo-3-fluorophenoxy)ethyl)morpholine (307 mg, 1.0 mmol), Bis(pinacolato)diboron (318 mg, 1.25 mmol), Pd(dppf)Cl$_2$—CH$_2$Cl$_2$ (68 mg, 83 μmol), and Potassium acetate (316 mg, 3.22 mmol). DME (20 ml) was added and the tube sealed. The tube was evacuated/backfilled w. N$_2$ (5 cycles) and microwaved at 125° C. for 30 minutes. The reaction was cooled to room temperature, concentrated and the residue purified by column chromatography (silica gel, 2% MeOH in CHCl$_3$) to provide the product as a colorless oil (356 mg, >99%). The $^1$H NMR spectrum shows the product to contain a small amount of pinacol-like impurity. The material was used as-is.

Synthesis of Compound 133, KX2-392

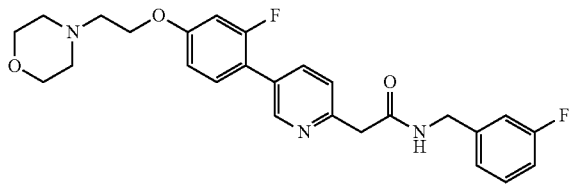 [SMILES: O=C(Cc1ccc(-c2ccc(OCCN3CCOCC3)cc2F)cn1)NCc1cccc(F)c1]

A 10 mL microwave reaction tube with septum closure was charged with 4-(2-(3-fluoro-4-(4,4,5,5-tetramethyl-1,3,2-dioxaborolan-2-yl)phenoxy)ethyl)morpholine (175 mg, 0.50 mmol), 2-(5-bromopyridin-2-yl)-N-(3-fluorobenzyl)acetamide (121 mg, 0.37 mmol), and FibreCat 1007 (30 mg, 0.03 mmol). Ethanol (3 mL) was added followed by aqueous potassium carbonate solution (0.600 mL, 1.0 M, 0.60 mmol). The tube was sealed and heated under microwave conditions at 150° C. for 10 minutes. The reaction was cooled, filtered, and concentrated to remove the majority of the ethanol. The residue was then taken up in 10 mL of ethyl acetate and washed successively with water and saturated sodium chloride solution. The organic layer was dried with MgSO$_4$, filtered, and concentrated. The material was purified by column chromatography (silica gel, 100:0 CHCl$_3$/MeOH to 95:5 CHCl$_3$/MeOH) to provide ALB 30350 as a white solid (70 mg, 40%): mp 126-127° C.; $^1$H NMR (500 MHz, CDCl$_3$) δ 8.67 (br s, 1H), 7.77-7.85 (m, 2H), 7.21-7.37 (m, 3H), 7.02 (d, 1H, J=7.7 Hz), 6.90-6.97 (m, 2H), 6.82 (dd, 1H, J=2.5 Hz, J=8.6 Hz), 6.76 (dd, 1H, J=2.4 Hz, J=12.4 Hz), 4.49 (d, 2H, J=5.9 Hz), 4.15 (t, 2H, J=5.7 Hz), 3.83 (s, 2H), 3.71-3.78 (m, 4H), 2.83 (t, 2H, J=5.7 Hz), 2.56-2.63 (m, 4H); HPLC (Method A)>99% (AUC), t$_R$=4.026 min.; APCI MS m/z 468 [M+H]$^+$.

1-(2-(4-bromo-3-fluorophenoxy)ethyl)-4-methylpiperazine

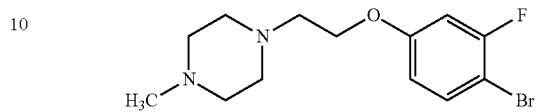

A flask was charged with 4-bromo-3-fluorophenol (5.00 g, 26 mmol) and triphenylphosphine (10.30 g, 39 mmol). Methylene chloride (120 mL) was added followed by 2-(4-methylpiperazin-1-yl)ethanol (4.61 g, 32 mmol) and the solution was stirred on an ice water bath to cool. After 5 minutes, diisopropyl azodicarboxylate (7.6 ml, 39.1 mmol) was added over 6 to 8 minutes. The reaction was left stirring on the cold bath to slowly warm to room temperature overnight. The reaction was concentrated and the residue purified by flash chromatography (25% to 100% EtOAc in hexanes) to provide the product as a colorless oil (2.62 g, 33%).

1-(2-(3-fluoro-4-(4,4,5,5-tetramethyl-1,3,2-dioxaborolan-2-yl)phenoxy)ethyl)-4-methylpiperazine

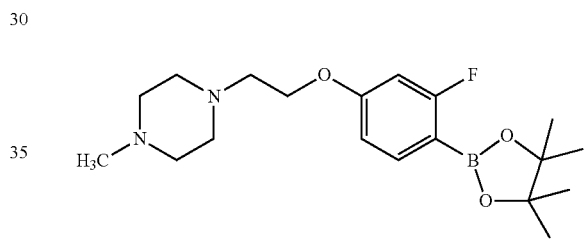

A 40 mL microwave reaction tube with a septum closure and stir bar was charged with 1-(2-(4-bromo-3-fluorophenoxy)ethyl)-4-methylpiperazine (428 mg, 1.35 mmol), Bis(pinacolato)diboron (375 mg, 1.48 mmol), Pd(dppf)Cl$_2$—CH$_2$Cl$_2$ (63 mg, 77 μmol), and Potassium acetate (410 mg, 4.18 mmol). DME (10 ml) was added and the tube sealed. The tube was evacuated/backfilled w. N$_2$ (5 cycles) and microwaved at 100° C. for 30 minutes. Additional Pd(dppf)Cl$_2$—CH$_2$Cl$_2$ (63 mg, 77 μmol) was added and the reaction microwaved at 100° C. for 60 minutes. The reaction was cooled to room temperature, concentrated and the residue purified by column chromatography (silica gel, 1% to 2% MeOH in CHCl$_3$) to provide the product as a dark oil (354 mg, 72%).

Synthesis of Compound 137 KX2-394

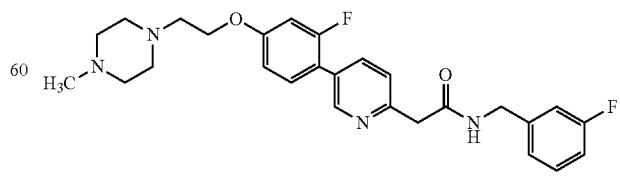

A 10 mL microwave reaction tube with septum closure was charged with 1-(2-(3-fluoro-4-(4,4,5,5-tetramethyl-1,3,2-dioxaborolan-2-yl)phenoxy)ethyl)-4-methylpiperazine (340 mg, 0.93 mmol), 2-(5-bromopyridin-2-yl)-N-(3-fluorobenzyl)acetamide (201 mg, 0.62 mmol), and FibreCat 1007 (125 mg, 0.06 mmol). Ethanol (3 mL) was added followed by aqueous potassium carbonate solution (1.00 mL, 1.0 M, 1.00 mmol). The tube was sealed and heated under microwave conditions at 150° C. for 10 minutes. The reaction was cooled, filtered, and concentrated to remove the majority of the ethanol. The residue was then taken up in 10 mL of ethyl acetate and washed successively with water and saturated sodium chloride solution. The organic layer was dried with $MgSO_4$, filtered, and concentrated. The material was purified by column chromatography (silica gel, 98:2 $CHCl_3$/MeOH to 90:10 $CHCl_3$/MeOH) to provide ALB 30352-2 as a tan gum (28 mg, 9%): $^1$H NMR (300 MHz, $CDCl_3$) δ 8.66 (br s, 1H), 7.78-7.94 (m, 2H), 7.20-7.40 (m, 3H), 6.88-7.06 (m, 3H), 6.70-6.85 (m, 2H), 4.47 (d, 2H, J=5.9 Hz), 4.14 (t, 2H, J=5.7 Hz), 3.83 (s, 2H), 2.85 (t, 2H, J=5.7 Hz), 2.41-2.77 (m, 8H), 2.34 (s, 3H); HPLC (Method A)>99% (AUC), $t_R$=3.778 min.; APCI MS m/z 481 $[M+H]^+$.

Example 2

Cell Growth Inhibition

The drug concentration required to block net cell growth by 50% relative to a control sample is measured as the $GI_{50}$. The $GI_{50}$s for several of the compounds of the invention were assayed as described herein.

The HT29 cell line is a NCI standard human colon carcinoma cell line. HT-29 cells were obtained from ATCC at passage 125 and were used for inhibition studies between passage 126-151. HT29 cells were routinely cultured in McCoy's 5A medium supplemented with Fetal Bovine Serum (1.5% v/v) and L-glutamine (2 mM).

The c-Src 3T3 is a mouse fibroblast NIH 3T3 normal cell line that has been transfected with a point-mutant of human c-Src wherein tyrosine 527 has been converted to a phenylalanine. This mutation results in "constitutively active" c-Src because phosphorylation on tyrosine 527 results in auto-inhibition of Src by having it fold back on its own SH2 domain. With a Phe there, this phosphorylation can't occur and therefore auto-inhibition can't occur. Thus, the always fully active mutant Src then converts the normal mouse fibroblasts into rapidly growing tumor cells. Since the hyperactive Src is the main factor driving growth in these cells (particularly when cultured under low growth serum conditions), compounds active in blocking this growth are thought to work by blocking Src signaling (e.g. as a direct Src kinase inhibitor or as an inhibitor acting somewhere else in the Src signaling cascade). The cells were routinely cultured in DMEM supplemented with Fetal Bovine Serum (2.0% v/V), L-glutamine (2 mM) and Sodium Pyruvate (1 mM).

In the BrdU Assay for cell growth inhibition, quantitation of cell proliferation was based on the measurement of BrdU incorporation during DNA synthesis. The Cell Proliferation ELISA BrdU assay kit (colorimetric) was obtained from Roche Applied Science and performed as per vendor instructions.

Growth inhibition was expressed as a $GI_{50}$ where the $GI_{50}$ is the sample dose that inhibits 50% of cell growth. The growth inhibition (GI) is determined from the formula GI= $(T_0-T_n \times 100/T_0 - CON_n)$ where $T_0$ is the BrdU growth of untreated cells at time "0", is the BrdU growth of treated cells at day "n" and $CON_n$ is the control BrdU growth of control cells at day "n". The $GI_{50}$ was extrapolated and the data plotted using XL-Fit 4.0 software.

Actively growing cultures were trypsinized and cells were resuspended in 190 μL of appropriate culture medium supplemented with 1.05% FBS in each well of a 96-well culture plate (1000 HT-29 cells; 2500 c-Src 3T3 cells). For 96 well culture plate experiments, c-Src 3T3 medium was supplemented with 10 mM HEPES buffer. HT-29 cells were seeded in standard tissue culture 96-well plates and c-Src 3T3 cells were seeded in 96-well plates coated with Poly-D-lysine (BIOCOAT™). To increase $CO_2$ diffusion, c-Src 3T3 96-well plates were incubated with their lids raised by ~2 mm using sterile rubber caps.

Seeded 96 well plates were allowed to attach overnight for 18-24 hours, either at 37° C. and 5% $CO_2$ for HT-29 or at 37° C. and 10% $CO_2$ for c-Src 3T3. Approx 18-24 hours after seeding, the initial growth of cells ($T_o$) was determined for untreated cells using the BrdU assay. Samples were reconstituted in DMSO at 20 mM and intermediate dilutions made using DMEM containing 10% FBS. The final assay concentrations were 1.5% for FBS and 0.05% for DMSO. Samples were added as 10 μL aliquots in triplicate and plates were incubated as above for ~72 hours. Negative (vehicle) and positive controls (e.g., AZ (KX-328)) were included. Plates were assayed for BrdU and the data analyzed as above for $GI_{50}$.

The results are shown in Table 3. In this table, the data is listed as Growth % of Control, such that a lower number at an indicated concentration indicates a greater potency of the compound in blocking growth of that tumor cell line. All compounds were initially prepared as 20 mM DMSO stock solutions and then diluted into buffer for the in vitro tumor growth assays. NG means no cell growth beyond the control and T means the number of cells in the drug treated wells was less than in the control (i.e. net cell loss). NT indicates that the test was not performed. Compound AZ (KX-328) is an ATP-competitive tyrosine kinase inhibitor, as described in Plé et al., J. Med. Chem., 47:871-887 (2004).

As shown in Table 3, $GI_{50}$s were obtained for a number of the compounds in other cell lines. These GI50's were determined using the standard tumor growth inhibition assays, similar to that described in detail for the HT29 cell line above, and the following cell lines: colon tumor cell lines KM12, lung cancer cell line H460 and lung cancer cell line A549 (all are NCI standard tumor cell lines).

TABLE 3

| | | HT-29 Growth, % of Control Mean, n = 3 | | | | | c-Src 3T3 Growth, % of Control Mean, n = 3 | | |
|---|---|---|---|---|---|---|---|---|---|
| KX-# | CMPD | 5 uM | 500 nM | 50 nM | $GI_{50}$ | | 10 uM | 1.0 uM | 100 nM |
| KX2-328 | AZ | T | 10.0 | 73.0 | 99 nM (c-Src 3T3), 794 nM (HT29) | | T | T | 13.0 |
| KX1-136 | 1 | T | T | 83.1 | 53 nM (c-Src 3T3), 484 nM (HT29) 105 nM (KM12) 280 nM (H460) 330 nM (A549) | | T | T | 46.3 |

TABLE 3-continued

| | | HT-29 Growth, % of Control Mean, n = 3 | | | | c-Src 3T3 Growth, % of Control Mean, n = 3 | | |
|---|---|---|---|---|---|---|---|---|
| KX-# | CMPD | 5 uM | 500 nM | 50 nM | GI$_{50}$ | 10 uM | 1.0 uM | 100 nM |
| KX1-305 | 2 | T | T | 107.7 | 349 nM (c-Src 3T3), 877 nM (HT29), 410 nM (KM12) 890 nM (H460) 1.03 uM (A549) | T | T | 35.0 |
| KX1-307 | 4 | 39.4 | 93.8 | 85.9 | | 4.2 | 45.3 | 65.7 |
| KX1-308 | 5 | 32.3 | 76.1 | 87.9 | | 67.1 | 77.7 | 94.5 |
| KX1-312 | 9 | 33.7 | 67.6 | 93.7 | | 12.1 | 94.5 | 98.5 |
| KX1-306 | 3 | T | T | 124.4 | | T | T | 47.0 |
| KX1-313 | 10 | T | T | 80.2 | | T | T | 91.6 |
| KX1-319 | 16 | T | T | 101.2 | | T | T | 88.2 |
| KX1-309 | 6 | T | T | 29.5 | | T | T | T |
| KX1-310 | 7 | T | T | 93.3 | | T | T | 101.8 |
| KX1-311 | 8 | T | T | 60.4 | | T | T | 81.3 |
| KX1-327 | 24 | T | T | 31.6 | >200 nM (c-Src 3T3), 680 nM (HT29) | T | T | 81.3 |
| KX1-316 | 13 | T | 45.1 | 77.8 | >200 nM (c-Src 3T3) | T | T | 88.2 |
| KX1-315 | 12 | T | 50.3 | 66.0 | | T | 88.1 | 89.3 |
| KX1-314 | 11 | 14.4 | 83.7 | 53.21 | | 39.3 | 88.4 | 93.6 |
| KX1-317 | 14 | T | 64.0 | 83.5 | | T | 85.6 | 94.2 |
| KX1-318 | 15 | T | 93.2 | 164.7 | | T | 71.0 | 91.4 |
| KX1-320 | 17 | 86.2 | 132.0 | 111.2 | | 73.1 | 86.5 | 90.4 |
| KX1-321 | 18 | 23.7 | 118.1 | 127.2 | | 55.8 | 96.2 | 95.5 |
| KX1-322 | 19 | T | 87.2 | 114.1 | 3,730 nM (Src 3T3) | T | T | 94.6 |
| KX1-323 | 20 | 60.8 | 106.9 | 105.6 | | 93.2 | 97.3 | 96.6 |
| KX1-324 | 21 | NG | 95.7 | 91.0 | | T | 90.0 | 96.0 |
| KX1-325 | 22 | T | T | 85.0 | 207 nM (c-Src 3T3), 215 nM (HT29) | T | 54.2 | 97.6 |
| KX1-326 | 23 | 43.7 | 73.2 | 65.4 | | 55.7 | 87.3 | 92.2 |
| KX1-329, | 25 | T | T | 101 | 269 nM (c-Src 3T3), 338 nM (HT29) | T | T | 96.0 |
| KX1-357 | 26 | NT | NT | NT | | 9.0 | 95.4 | 101.3 |
| KX1-358 | 27 | NT | NT | NT | | 82.7 | 91.4 | 92.2 |
| KX2-359 | 28 | T | T | T | 34 nM (c-Src 3T3), 45 nM (HT29) | T | T | T |
| KX2-360 | 54 | T | T | 91 | | T | T | 106.0 |
| KX2-361 | 76 | T | T | T | 11 nM (c-Src 3T3), 10 nM (HT29) | T | T | T |
| KX2-362 | 78 | T | T | 86 | 56 nM (c-Src 3T3), 56 nM (HT29) | T | T | 101 |
| KX2-363 | 79 | T | 67 | 92 | | 100 | 70 | 92 |
| KX2-364 | 82 | T | 80 | 105 | | T | 81 | 92 |
| KX2-365 | 40 | T | T | 88 | 133 nM (c-Src 3T3), 93 nM (HT29) | T | T | 88 |
| KX2-366 | 75 | T | 54 | 89 | | T | 83 | 103 |
| KX2-367 | 41 | T | 6 | 64 | | T | T | 102 |
| KX2-368, slightly insoluble | 29 | T | 70 | 107 | | 27 | 101 | 99 |
| KX2-369 | 55 | T | 72 | 87 | | T | 101 | 100 |
| KX2-370 | 77 | 81 | 93 | 112 | | 106 | 105 | 104 |
| KX2-371 | 81 | 16 | 33 | 98 | | 16 | 72 | 75 |
| KX2-372 | 80 | T | T | T | 58 nM (c-Src 3T3); 67 nM (HT-29) | T | T | T |
| KX2-373 | 72 | T | T | 64 | 96 nM (c-Src 3T3); 639 nM (HT-29) | T | T | 97 |
| KX2-374 | 115 | T | 57 | 74 | | T | 84 | 110 |
| KX2-375 | 36 | T | T | 99 | 206 nM (c-Src 3T3); 354 nM (HT-29) | T | T | T |
| KX2-376 | 74 | T | 93 | 96 | >1,600 nM (c-Src 3T3); >400 nM (HT-29) | T | T | T |
| KX2-377 | 38 | T | T | T | 118 nM (c-Src 3T3); 111 nM (HT-29) | T | T | T |
| KX2-378 | 31 | T | 61 | 88 | | 48 | 107 | 122 |
| KX2-379 | 70 | T | 88 | 89 | | T | 104 | 106 |
| KX2-380 | 30 | T | 50 | 100 | | T | 119 | 124 |
| KX2-381 | 33 | T | T | 58 | 914 nM (c-Src 3T3); 375 nM (HT-29) | T | T | 116 |
| KX2-382 | 68 | 50 | 97 | 80 | | 103 | 114 | 117 |
| KX2-383 | 116 | | | | 327 nM (c-Src 3T3); 248 nM (HT-29) | | | |
| KX2-384 | 64 | | | | 1,430 nM (c-Src 3T3); inactive (HT-29) | | | |
| KX2-385 | 83 | | | | 232 nM (c-Src 3T3) | | | |
| KX2-386 | 37 | | | | 897 nM (c-Src 3T3); inactive (HT-29) | | | |
| KX2-387 | 38 | | | | inactive (c-Src 3T3); 1,860 nM (HT-29) | | | |
| KX2-388 | 66 | | | | >1,600 nM (c-Src 3T3); 906 nM (HT-29) | | | |
| KX2-389 | 60 | | | | Inactive (c-Src 3T3); inactive (HT-29) | | | |
| KX1-329 N-oxide | 135 | | | | inactive (c-Src 3T3); inactive (HT-29) | | | |
| KX2-390 | 114 | | | | 797 nM (c-Src 3T3); 868 nM (HT-29) | | | |
| KX2-391 | 133 | | | | 13 nM (c-Src 3T3); 23 nM (HT-29) | | | |
| KX2-392 | 134 | | | | 13 nM (c-Src 3T3); 21 nM (HT-29) | | | |
| KX2-393 | 136 | | | | 24 nM (c-Src 3T3); 52 nM (HT-29) | | | |
| KX2-394 | 137 | | | | 13 nM (c-Src 3T3); 26 nM (HT-29) | | | |

NG = No growth, total growth inhibition;
T = Cytotoxic Effect on Cells, negative growth;
NT = Not tested Other Embodiments While the invention has been described in conjunction with the detailed description thereof, the foregoing description is intended to illustrate and not limit the scope of the invention, which is defined by the scope of the appended claims. Other aspects, advantages, and modifications are within the scope of the following claims. It will be understood by those skilled in the art that various changes in form and details may be made therein without departing from the scope of the invention encompassed by the appended claims.

What is claimed is:

1. A compound according to Formula I:

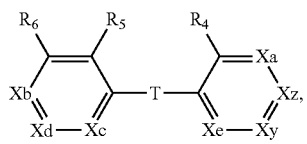

or a pharmaceutically acceptable salt, tautomer, or prodrug thereof, wherein:

T is a bond;

$X_y$ is CY, N, or N—O;

$X_z$ is CZ;

Y is hydrogen, hydroxyl, halogen, lower ($C_1$, $C_2$, $C_3$, $C_4$, $C_5$, or $C_6$) alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, or O-benzyl;

$X_a$ is $CR_a$, N, or N—O;

$X_b$ is $CR_b$, N, or N—O;

$X_c$ is $CR_c$, N, or N—O;

$X_d$ is $CR_d$, N, or N—O;

$X_e$ is $CR_e$, N, or N—O;

$R_a$, $R_b$, $R_c$, $R_d$, $R_e$, $R_4$, $R_5$, and $R_6$ are, independently, hydrogen, hydroxyl, halogen, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, $C_1$, $C_2$, $C_3$, $C_4$, $C_5$, or $C_6$ alkyl-O-lower ($C_1$, $C_2$, $C_3$, $C_4$, $C_5$, or $C_6$) alkyl, COOH, COO-lower ($C_1$, $C_2$, $C_3$, $C_4$, $C_5$, or $C_6$) alkyl, $SO_2H$, $SO_2$-lower ($C_1$, $C_2$, $C_3$, $C_4$, $C_5$, or $C_6$)alkyl,

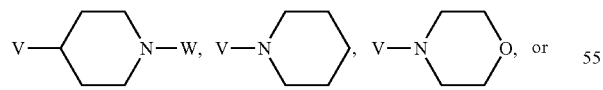

W is H, $C_1$, $C_2$, $C_3$, $C_4$, $C_5$, or $C_6$ alkyl, or $C_1$, $C_2$, $C_3$, $C_4$, $C_5$, or $C_6$ alkyl-aryl;

V is a bond, —$CH_2$—, —$CH_2CH_2$—, —$CH_2CH_2CH_2$—, —O—$CH_2$—, —$OCH_2CH_2$—, or —$OCH_2CH_2CH_2$—;

Z is:

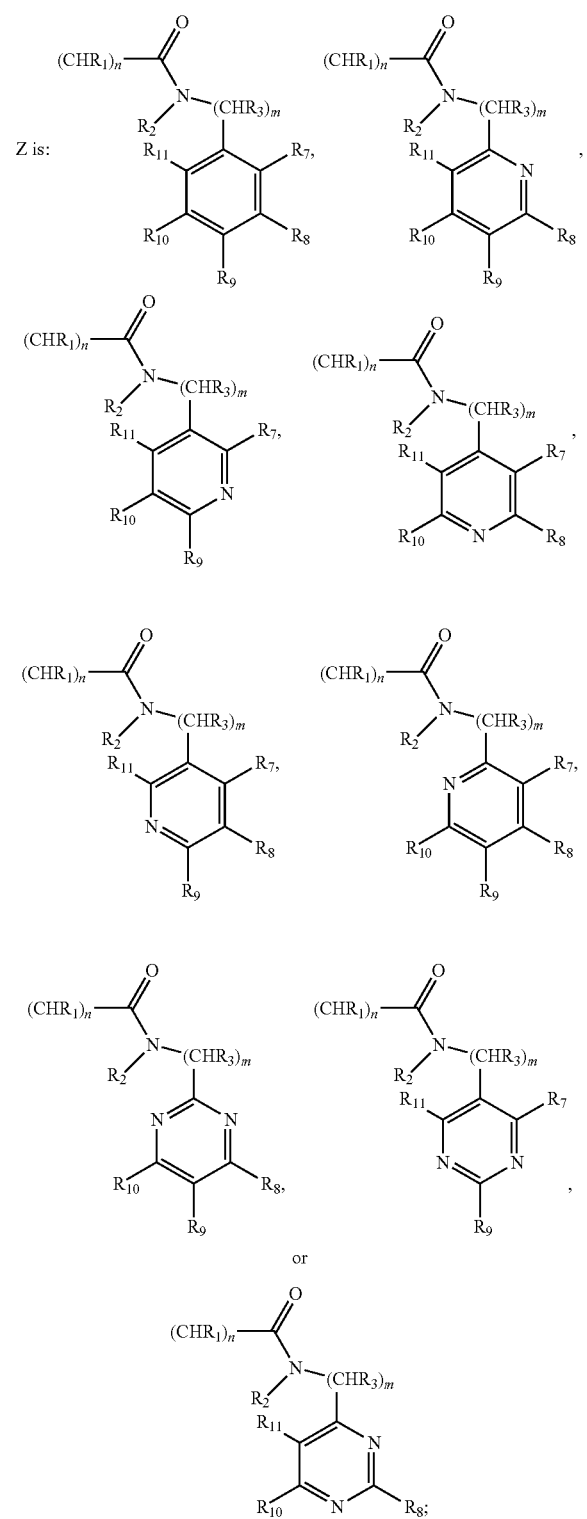

$R_7$, $R_8$, $R_9$, $R_{10}$, and $R_{11}$ are, independently, hydrogen, hydroxyl, halogen, unsubstituted $C_1$, $C_2$, $C_3$, $C_4$, $C_5$, or $C_6$ alkyl, unsubstituted $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, unsubstituted $C_1$, $C_2$, $C_3$, $C_4$, $C_5$, or $C_6$ alkyl-OH, $C_1$, $C_2$, $C_3$, $C_4$, $C_5$, or $C_6$ alkyl-O—$C_1$, $C_2$, $C_3$, $C_4$, $C_5$, or $C_6$ alkyl,

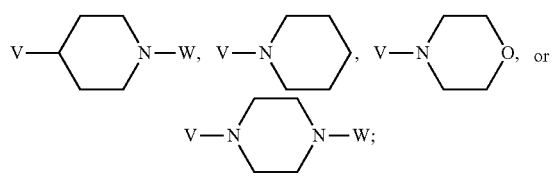

$R_1$, $R_2$, and $R_3$ are independently H or $C_1$, $C_2$, $C_3$, $C_4$, $C_5$, or $C_6$ alkyl;
n is 1, or 2; and
m is 1,
wherein at least one of $X_a$, $X_b$, $X_c$, $X_d$ and $X_e$ is N; provided that when $X_a$ is N, $X_e$ is not N.

2. The compound of claim 1, wherein $X_y$ is CY.
3. The compound of claim 1, wherein Y is hydrogen.
4. The compound of claim 1, wherein Z is

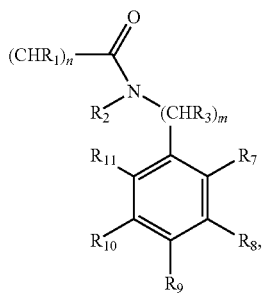

5. The compound of claim 1, wherein $R_b$ is $C_1$, $C_2$, $C_3$, $C_4$, $C_5$, or $C_6$ alkoxy.

6. The compound of claim 1, wherein $R_b$ is

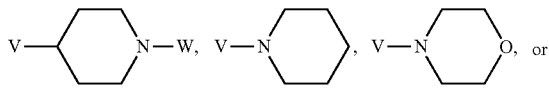

wherein W is H, $C_1$, $C_2$, $C_3$, $C_4$, $C_5$, or $C_6$ alkyl, or $C_1$, $C_2$, $C_3$, $C_4$, $C_5$, or $C_6$ alkyl-aryl; and V is a bond, —$CH_2$—, —$CH_2CH_2$—, —$CH_2CH_2CH_2$—, —O—$CH_2$—, —$OCH_2CH_2$—, or —$OCH_2CH_2CH_2$—.

7. The compound of claim 6, wherein V is a bond.

8. The compound of claim 1, wherein $X_a$ is N, $X_b$ is $CR_b$, $X_c$ is $CR_c$, $X_d$ is $CR_d$ and $X_e$ is $CR_e$.

9. The compound of claim 1, wherein said compound is a pharmaceutically acceptable salt.

10. A composition comprising a compound according to claim 1 and at least one pharmaceutically acceptable excipient.

11. A compound, selected from:

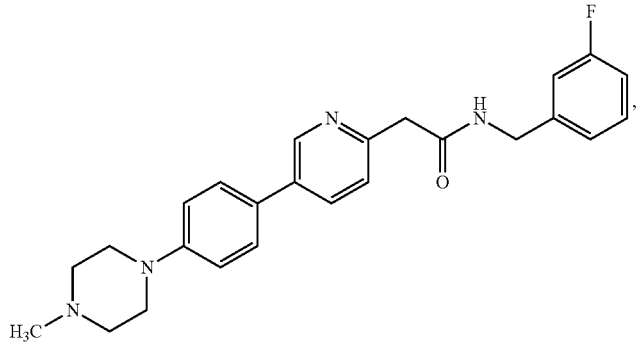

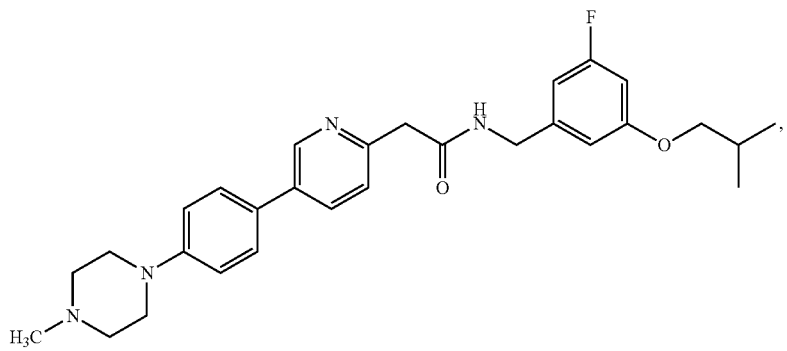

-continued
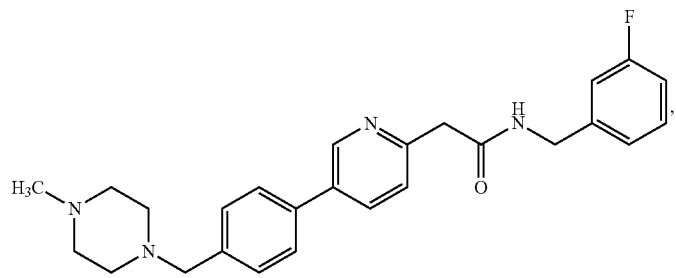
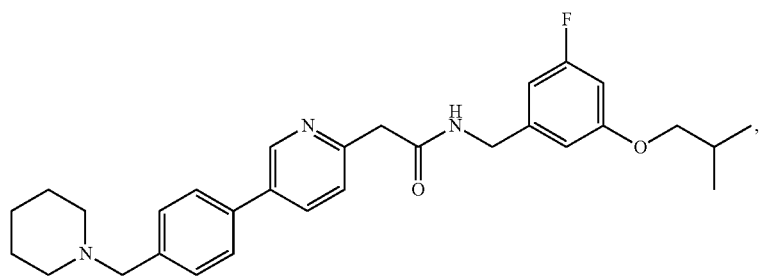
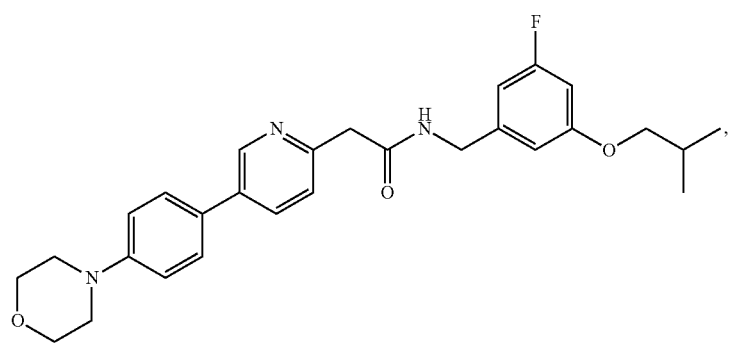
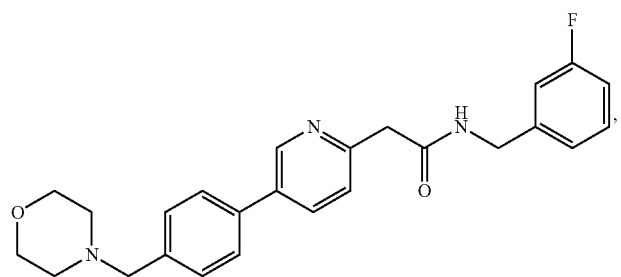
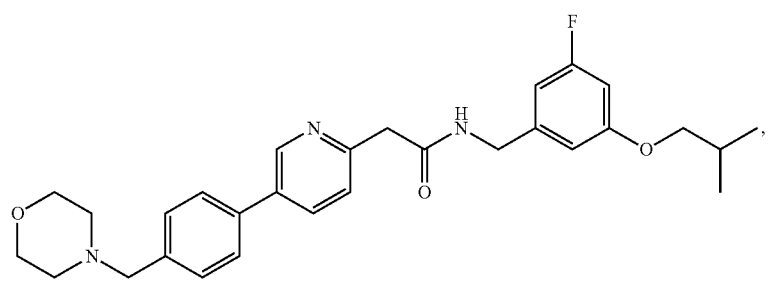

-continued
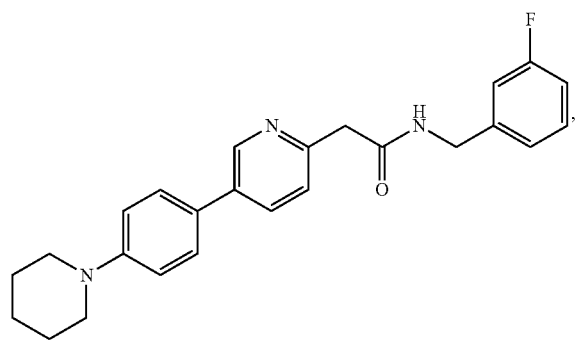
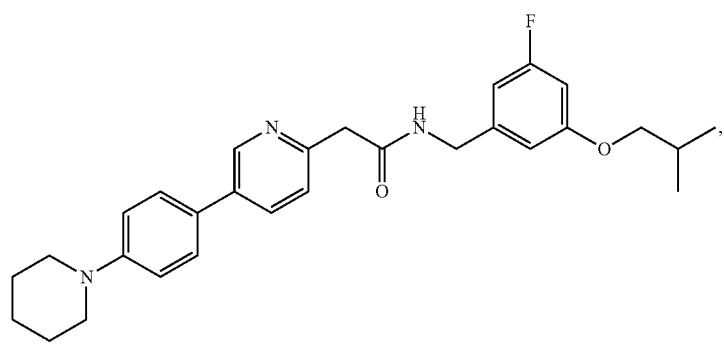
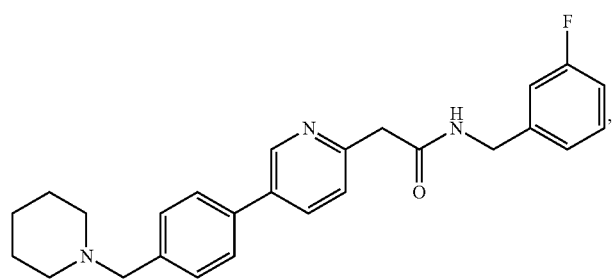
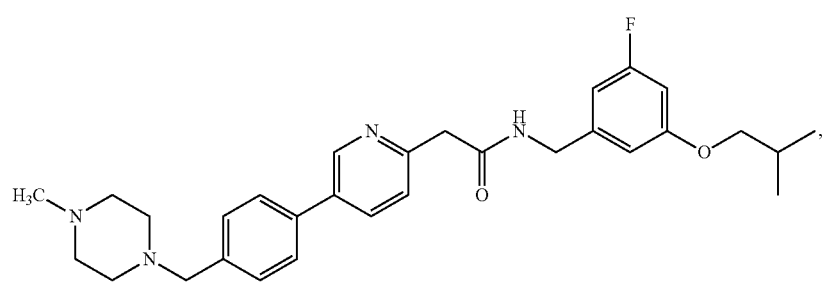
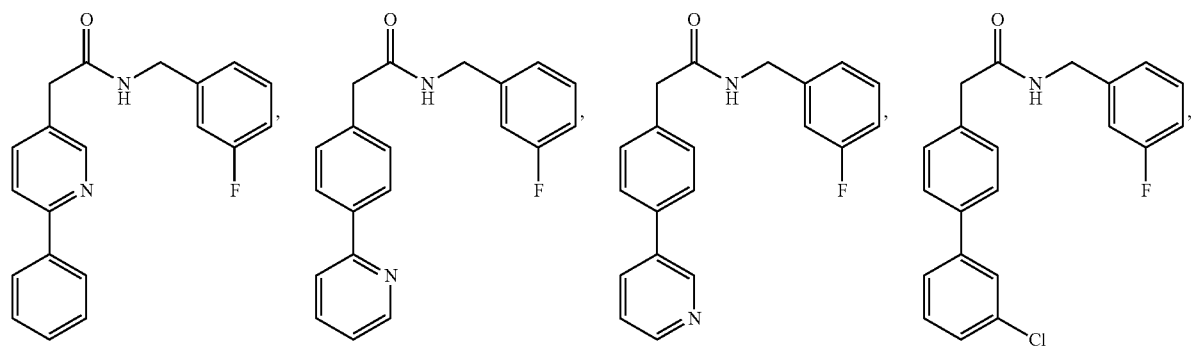

-continued
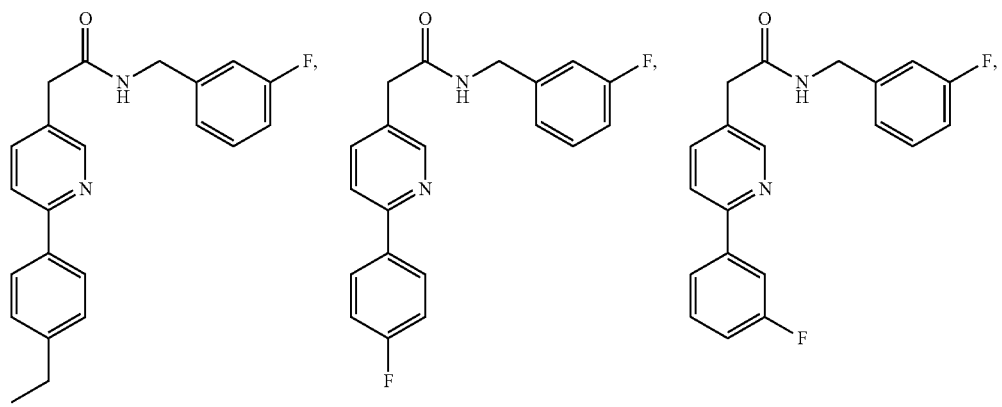
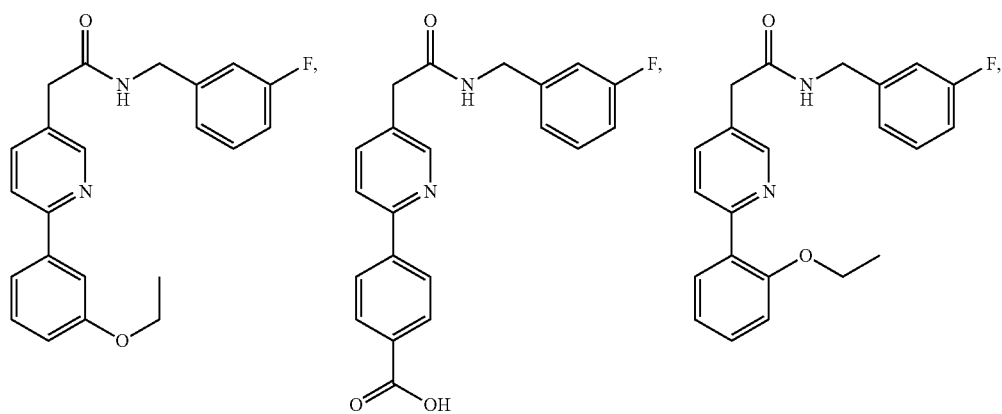
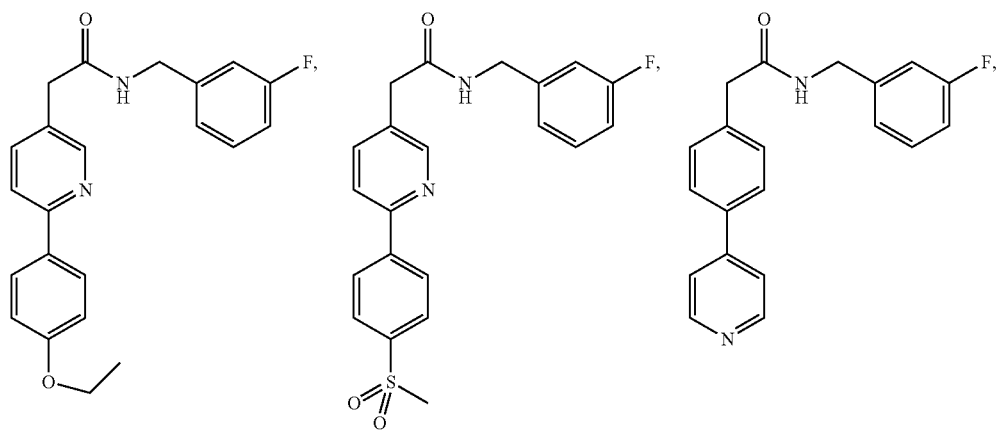
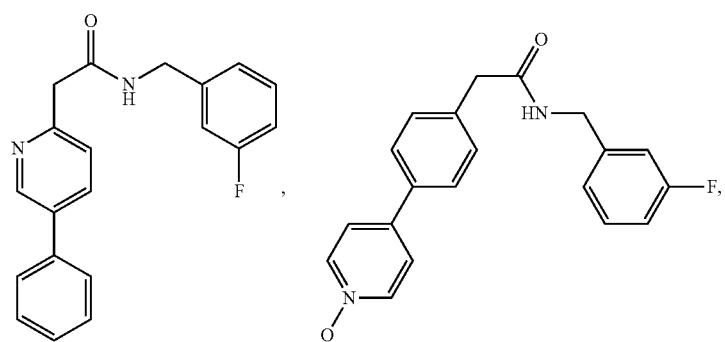

179 180
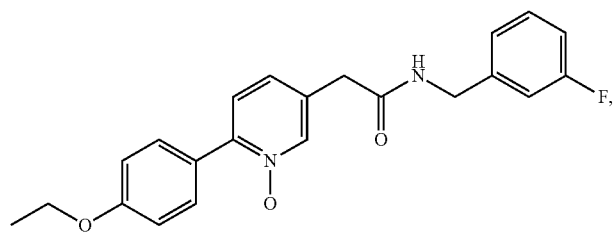
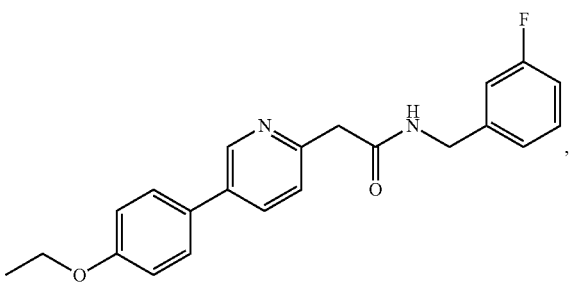
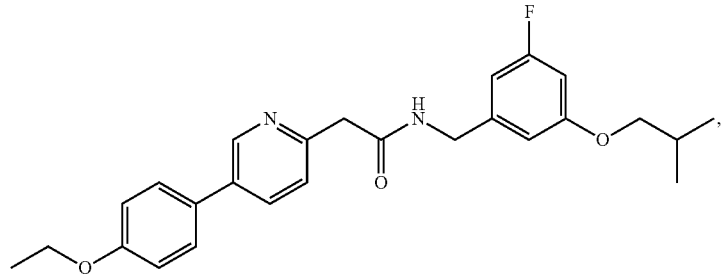
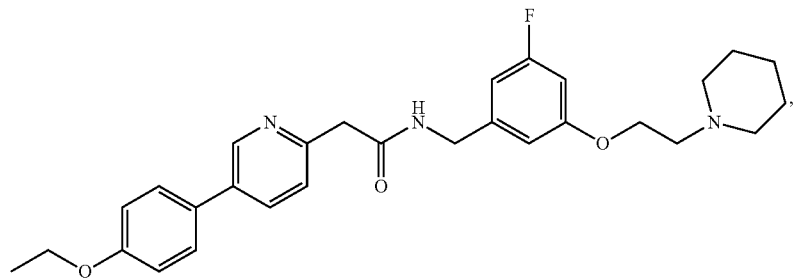
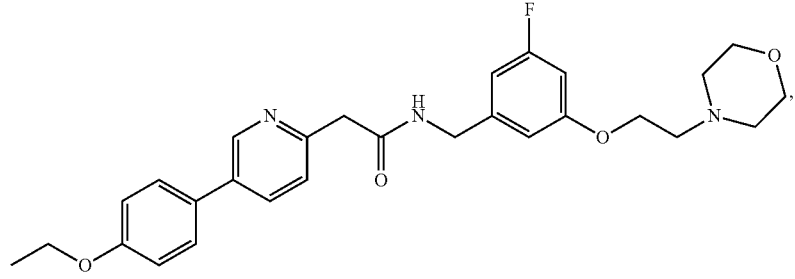
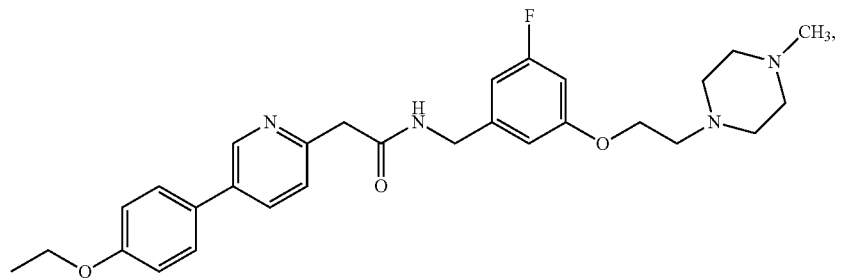
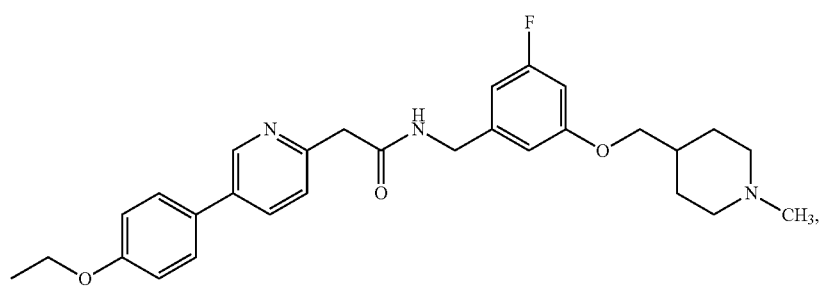

-continued
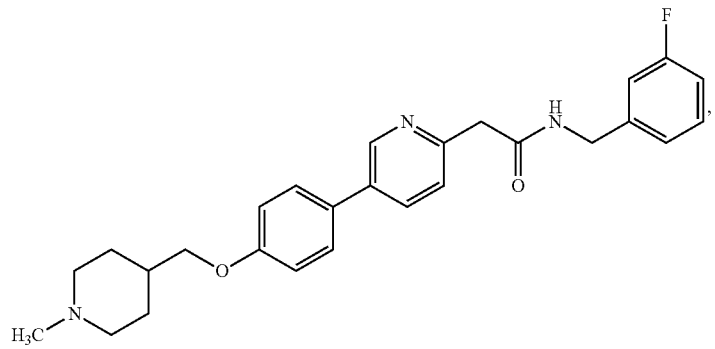
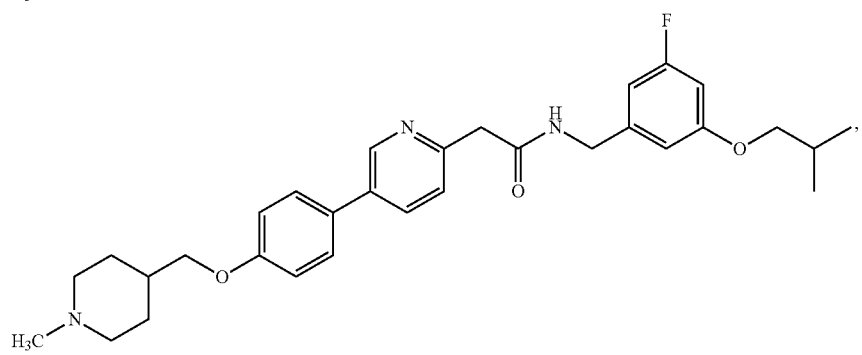
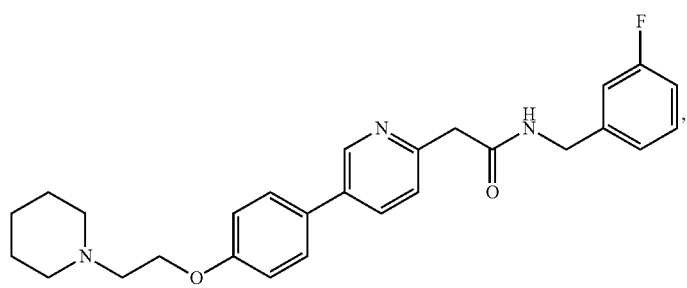
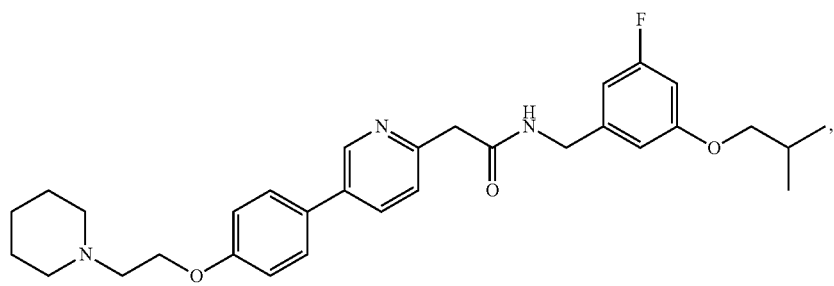
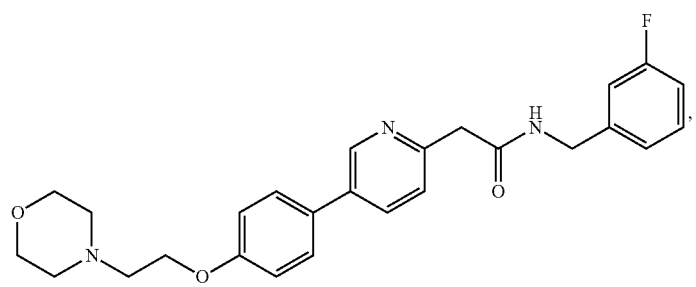

-continued
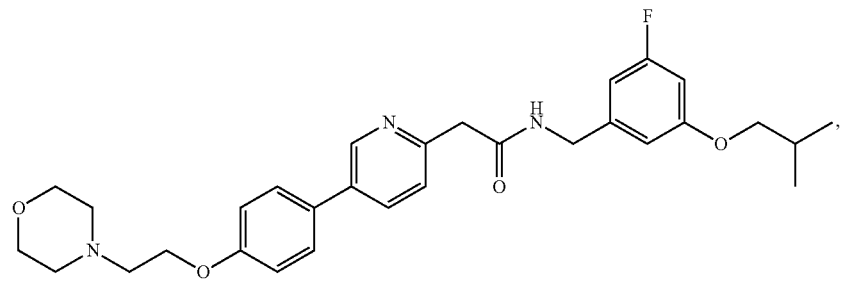
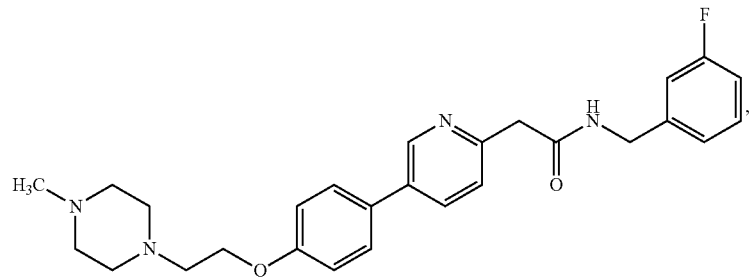
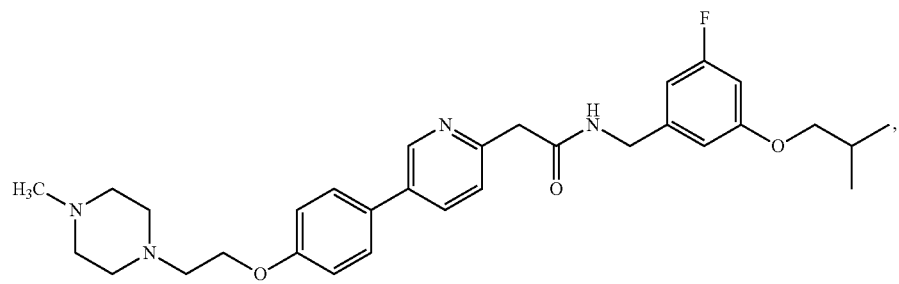
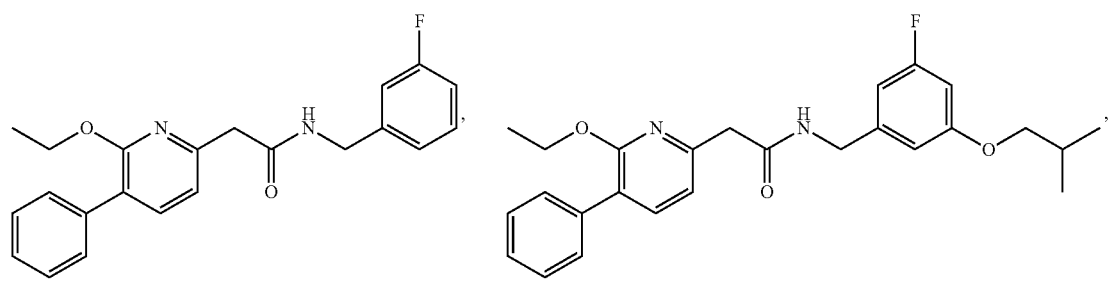
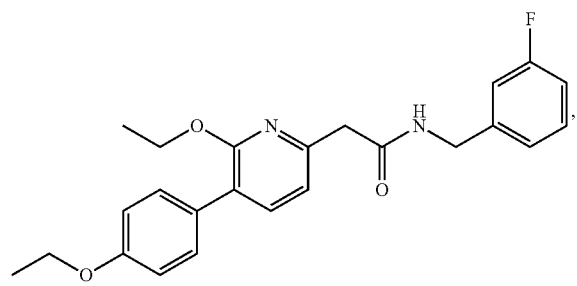
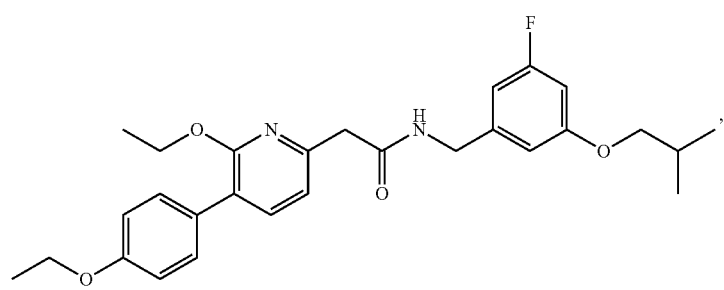

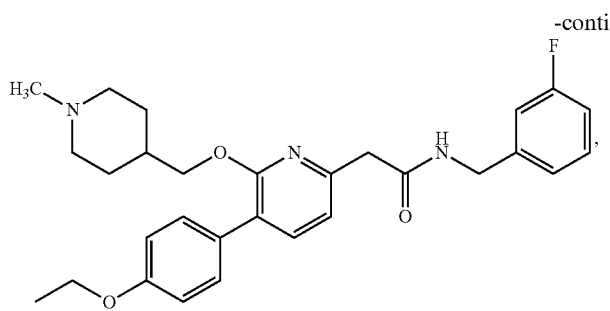
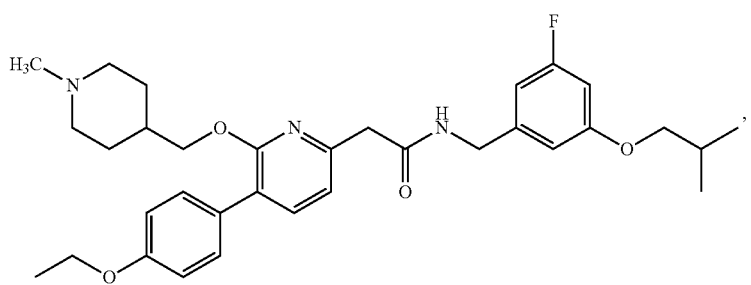
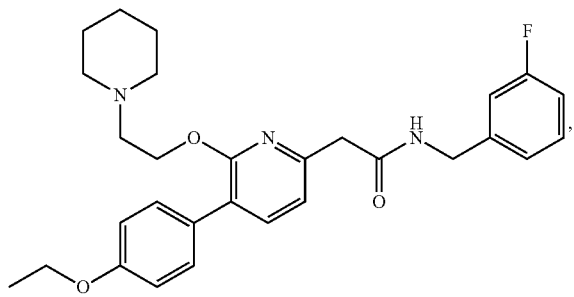
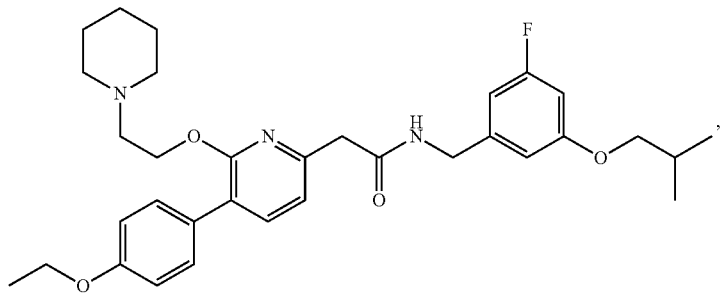
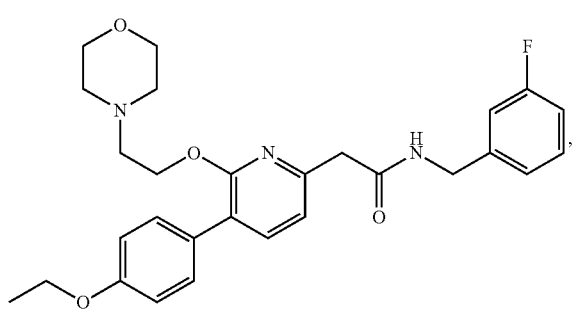

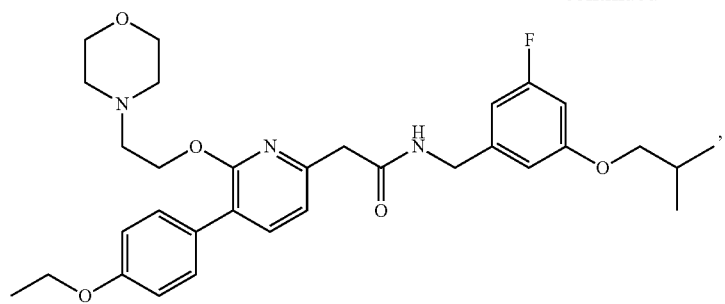
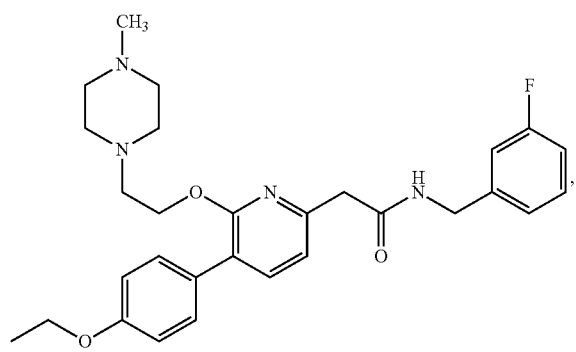
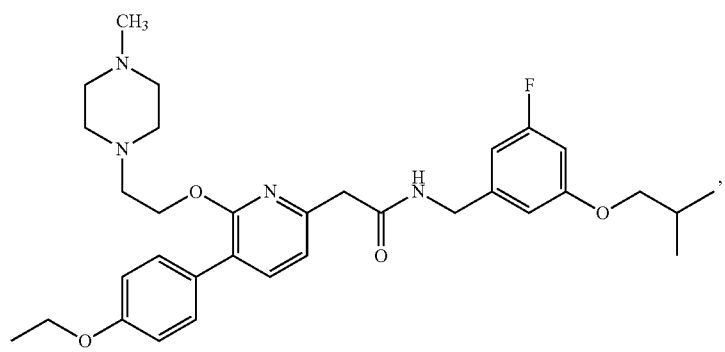
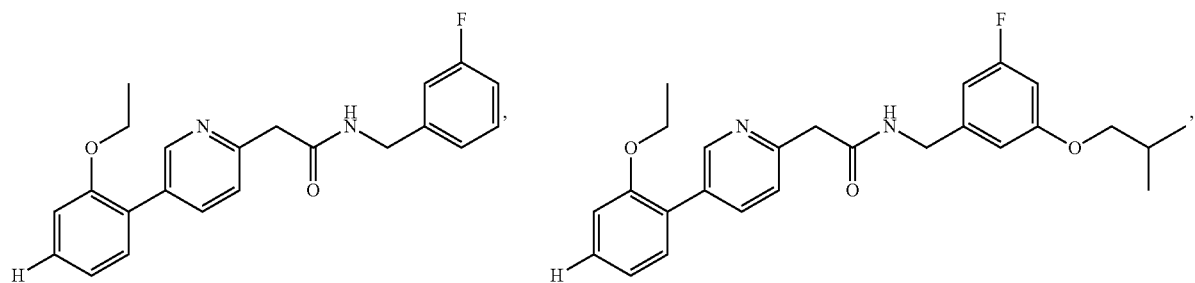
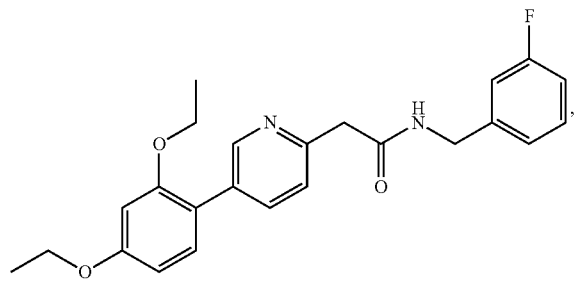

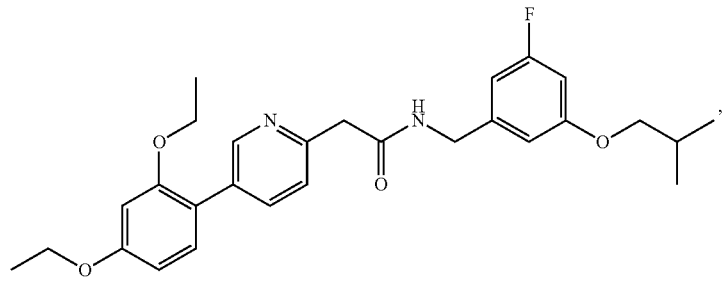
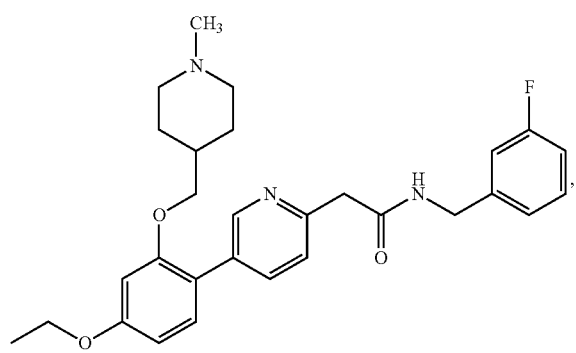
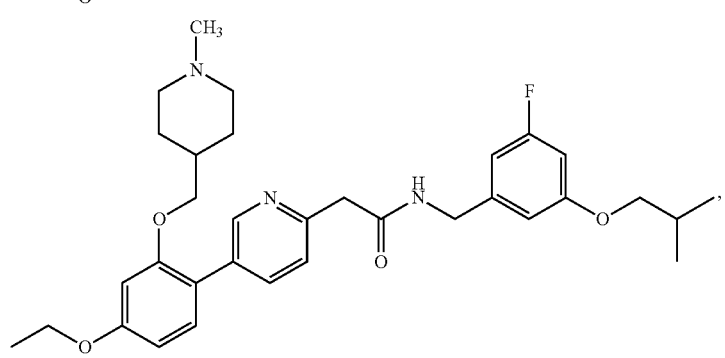
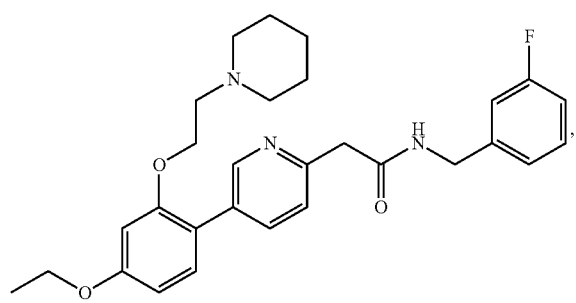
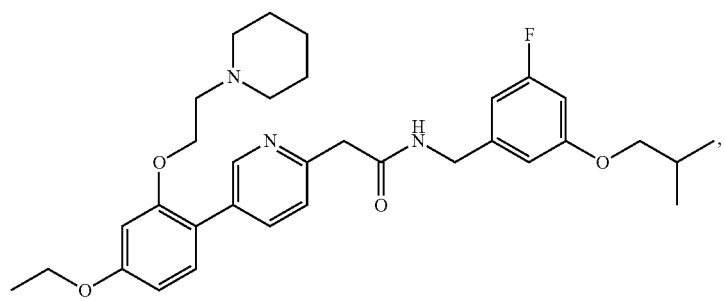

-continued
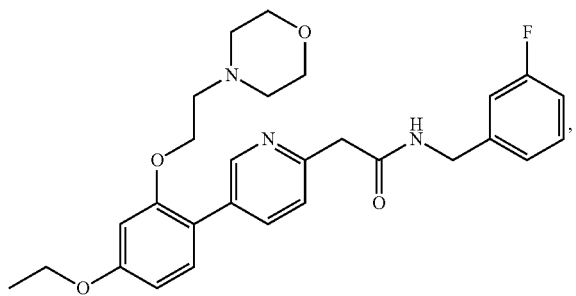
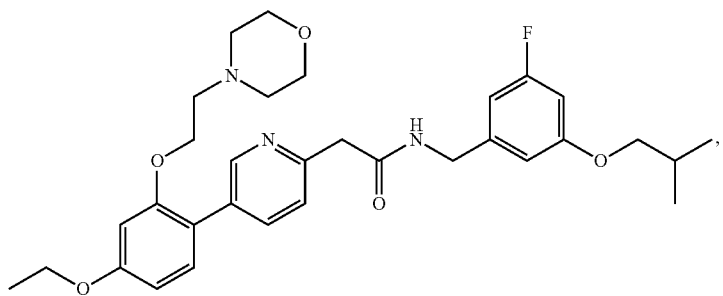
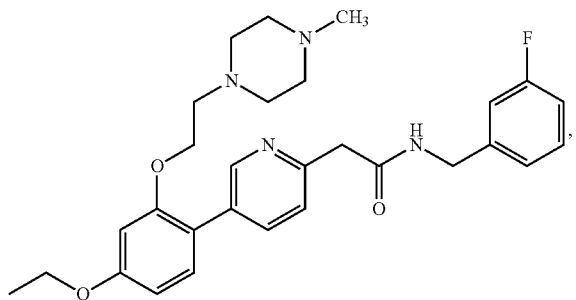
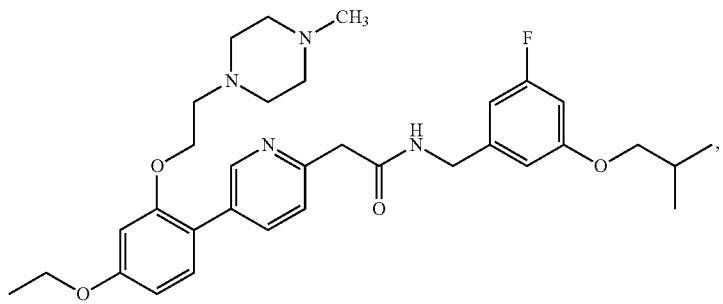
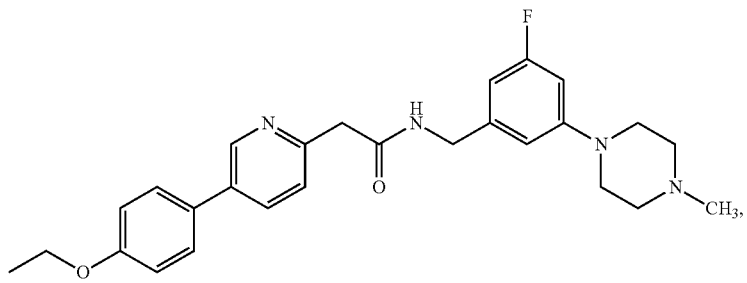

-continued
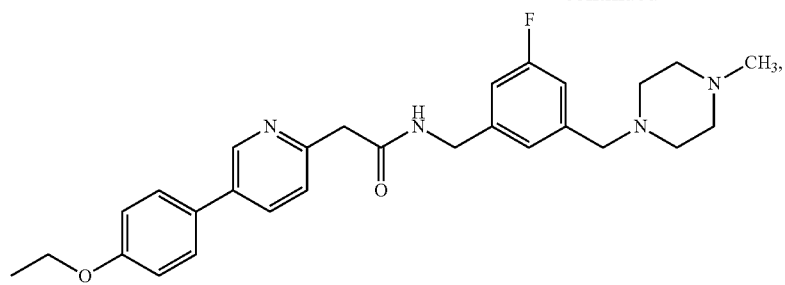
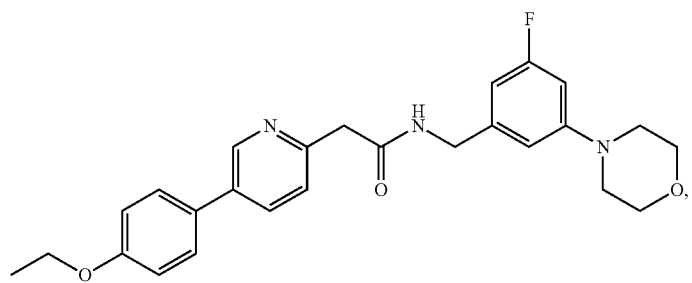
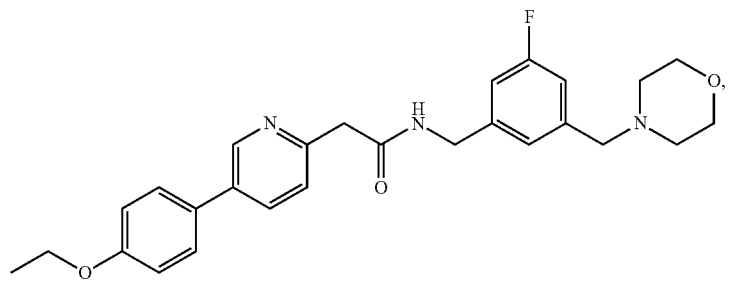
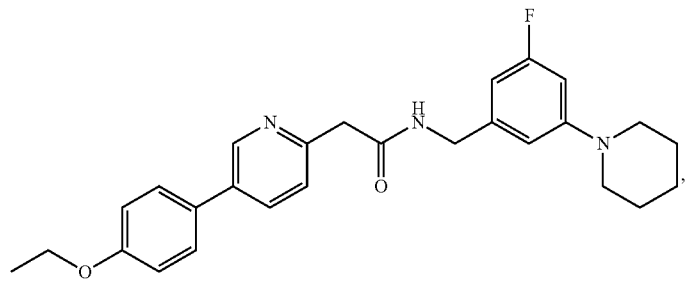
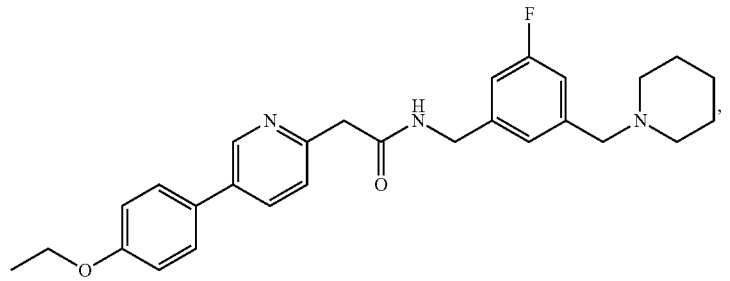
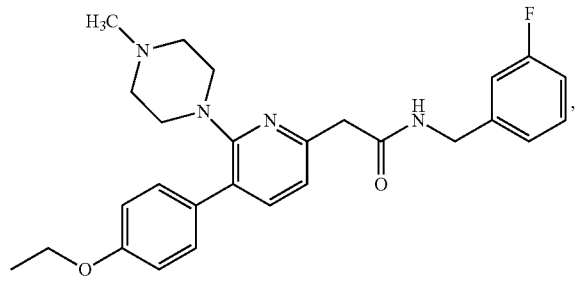

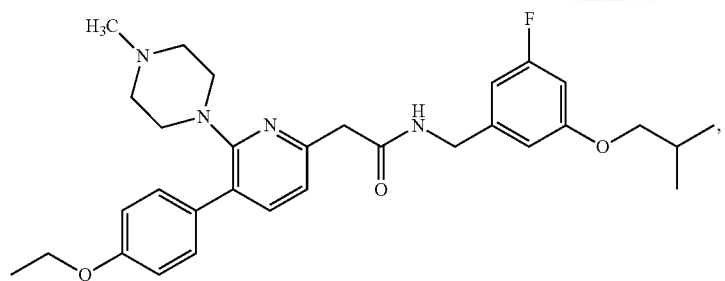
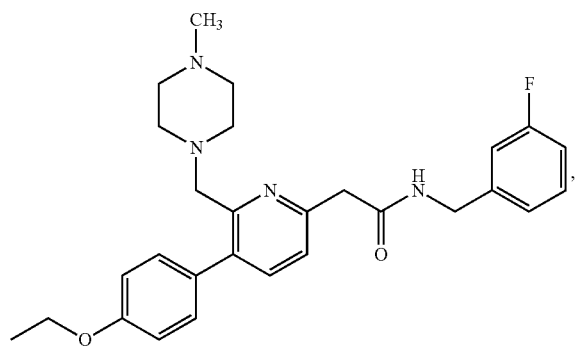
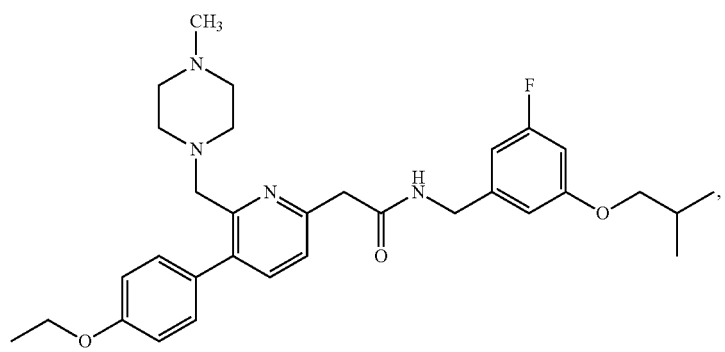
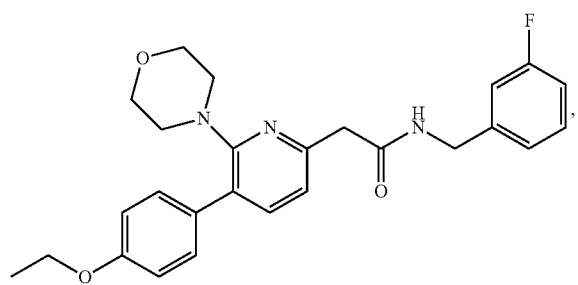
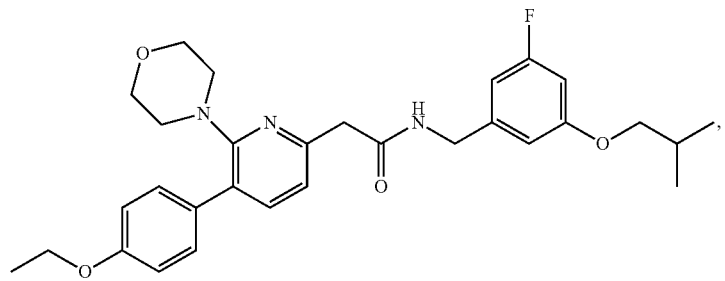

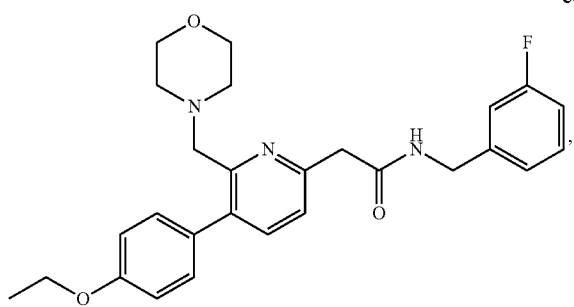
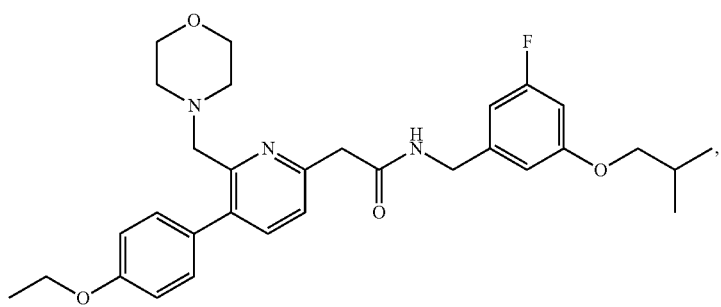
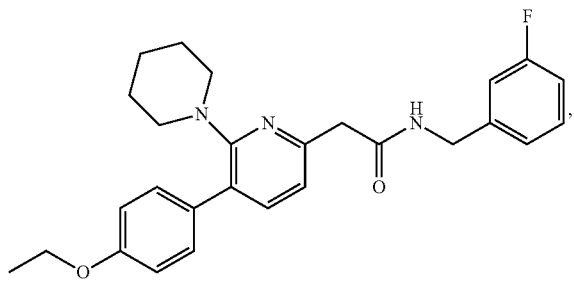
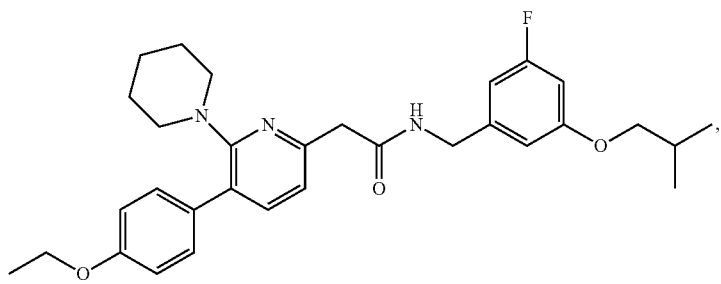
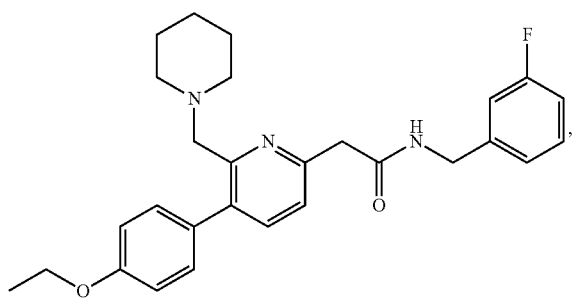

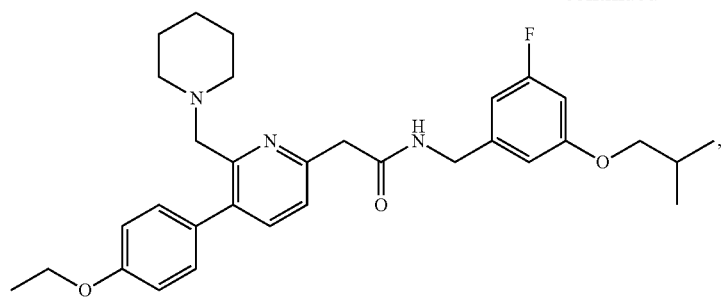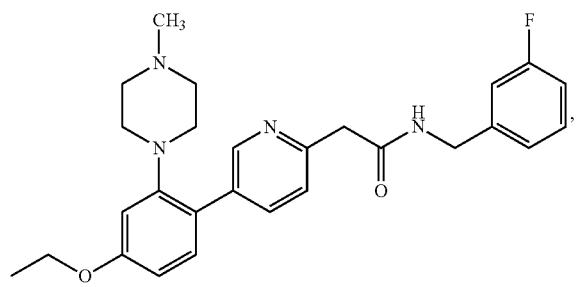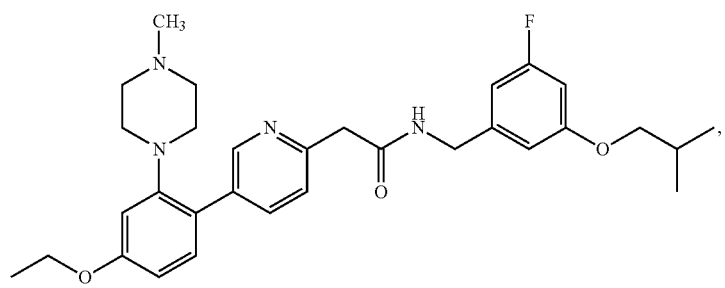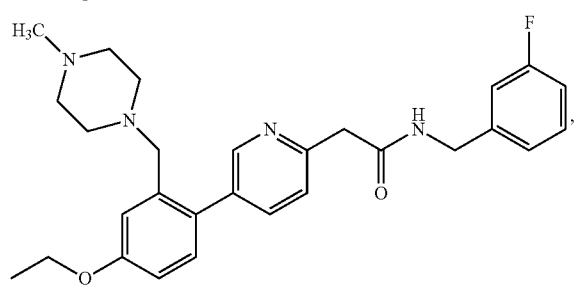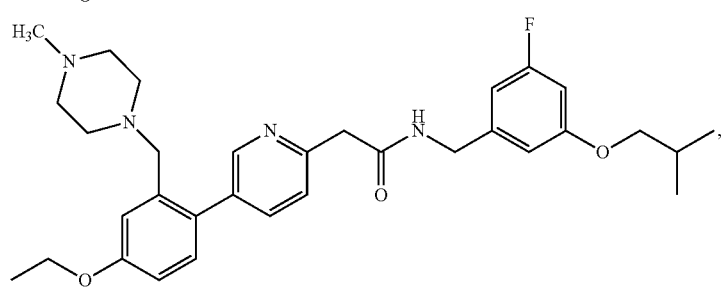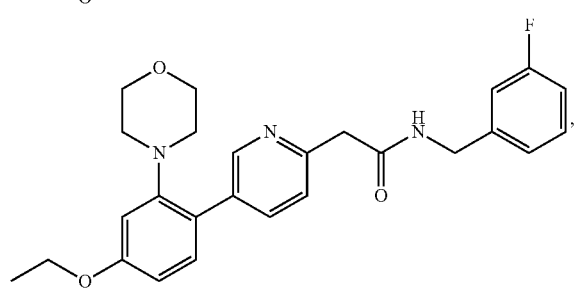

-continued
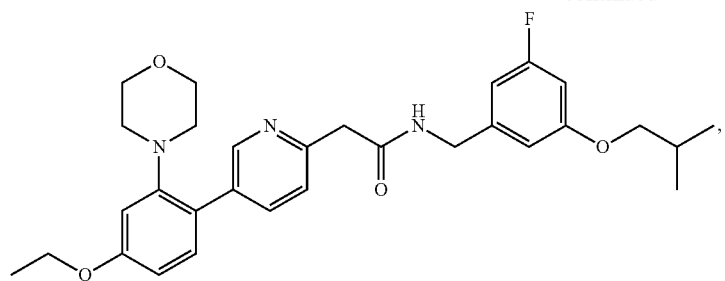
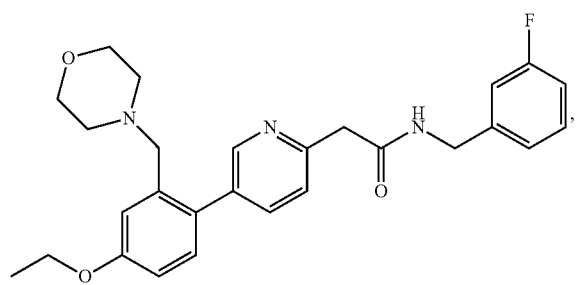
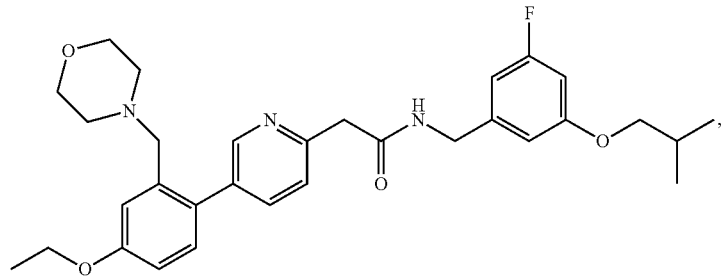
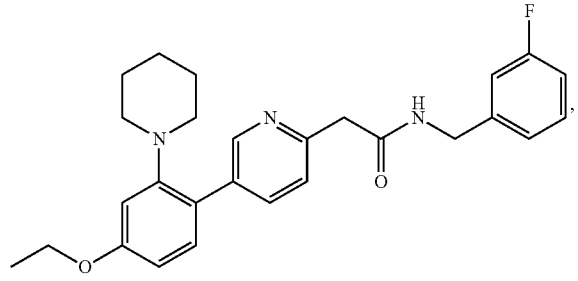
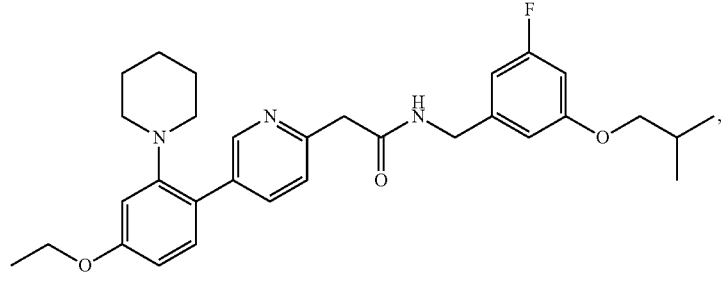
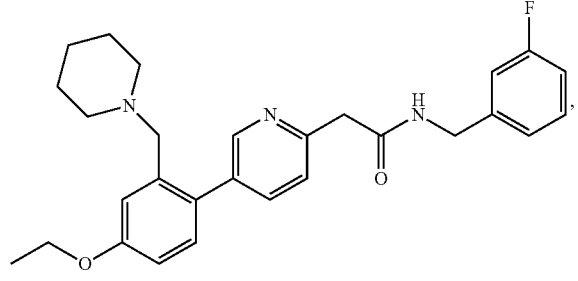

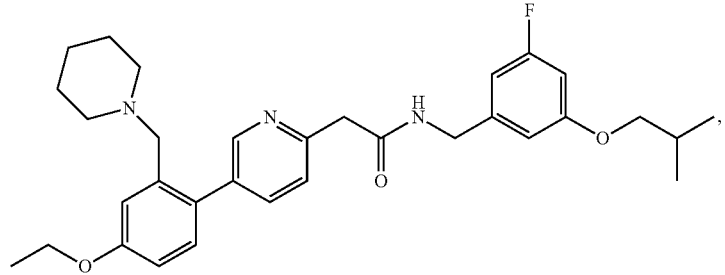
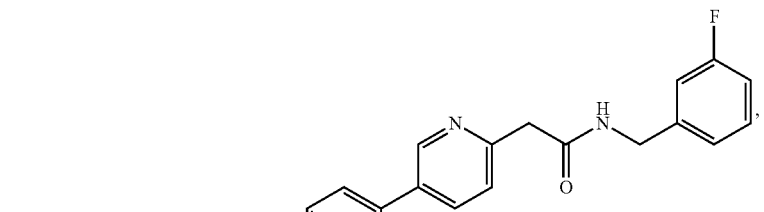
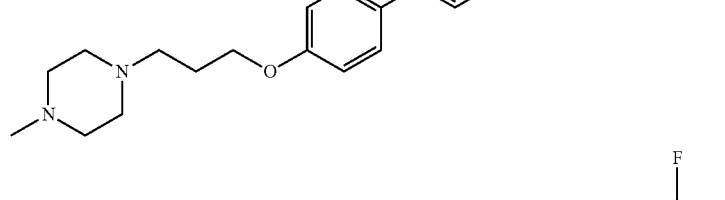
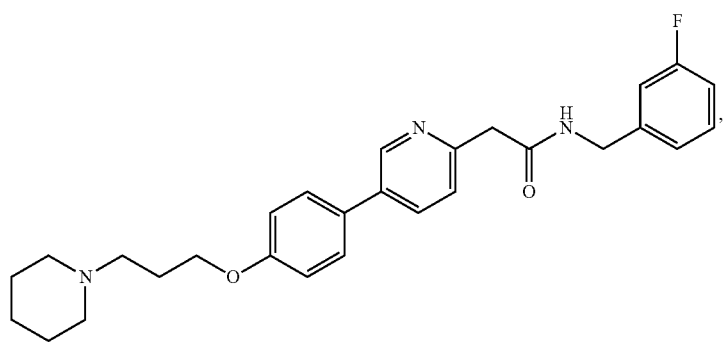
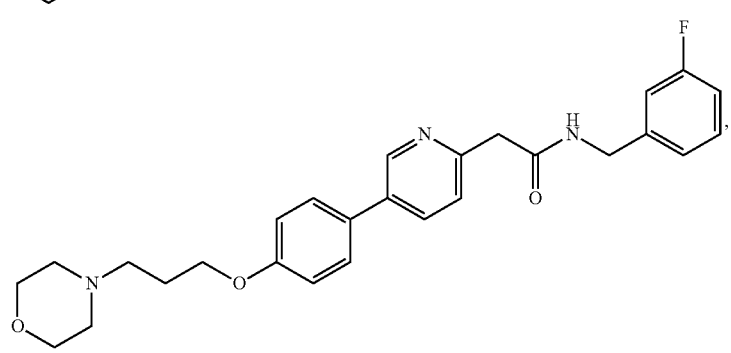
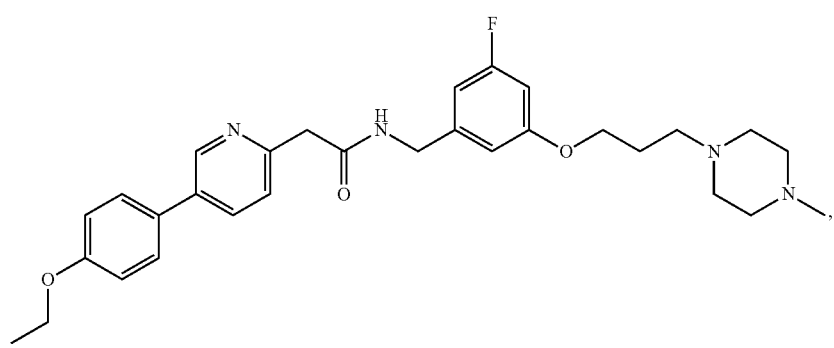

-continued
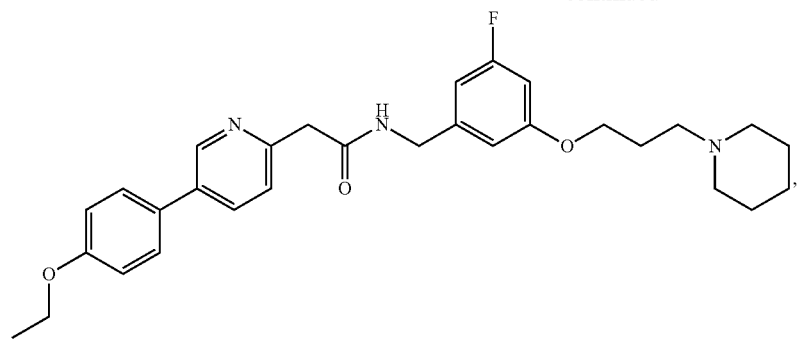
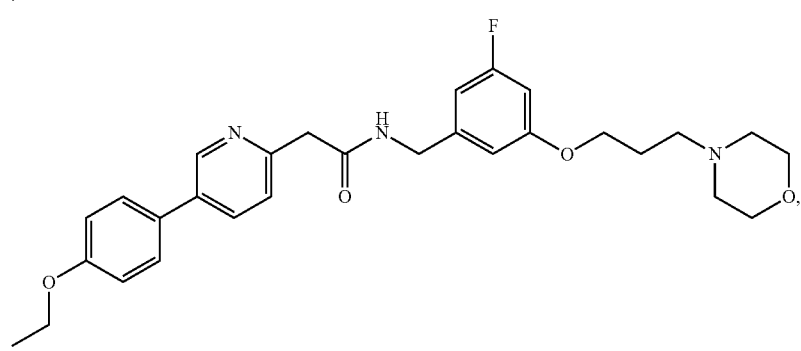
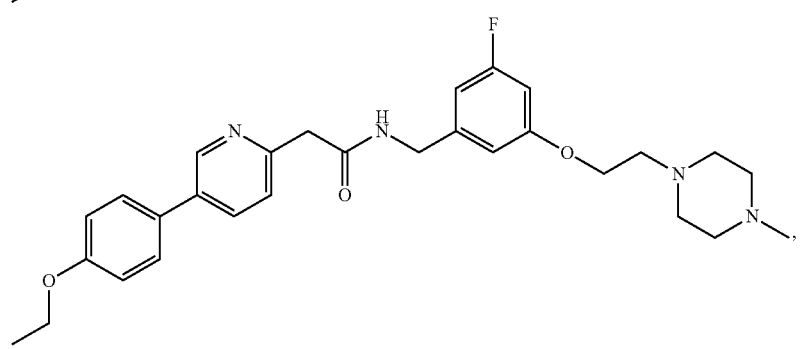
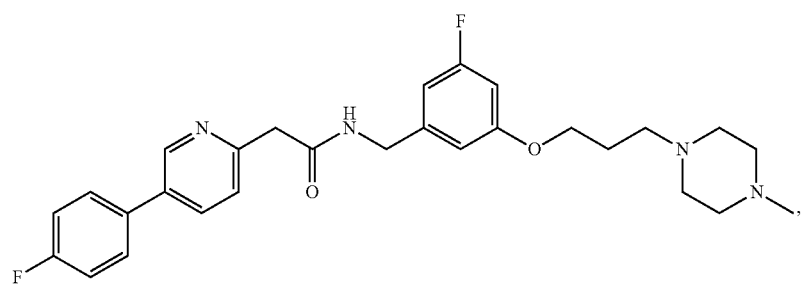
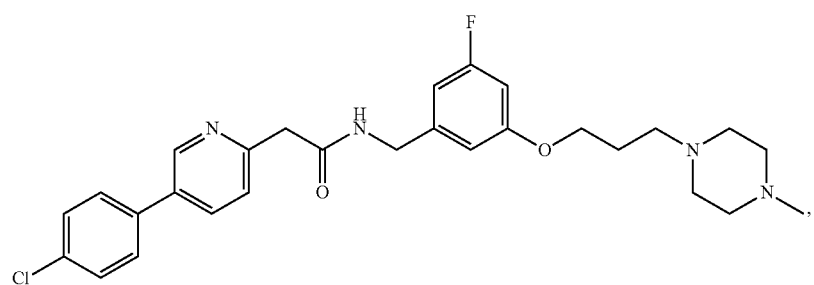

-continued
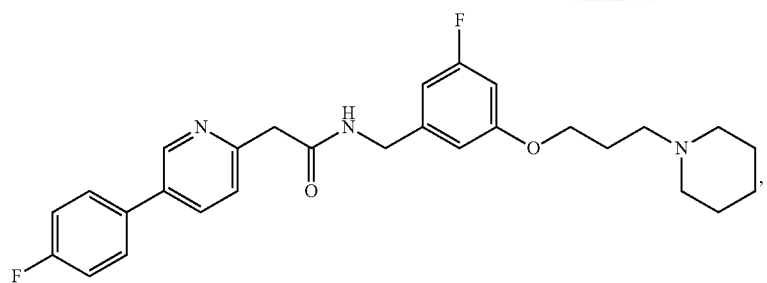
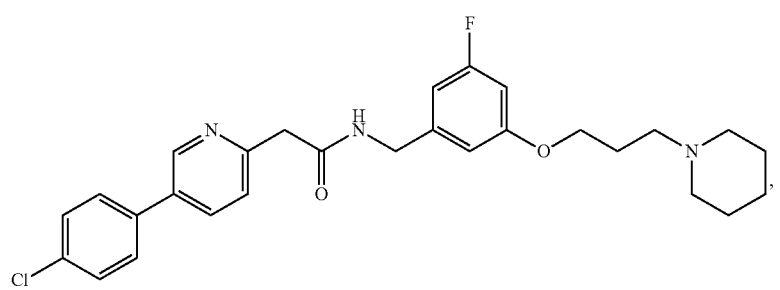
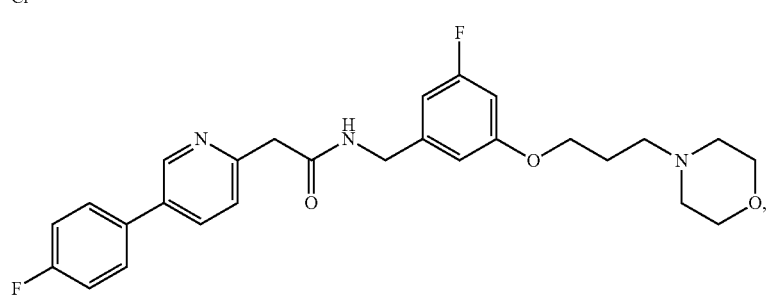
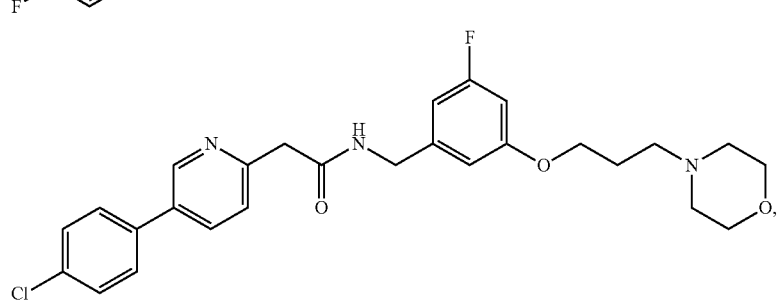
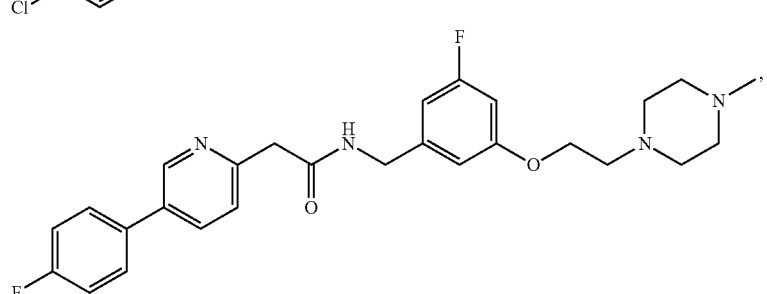
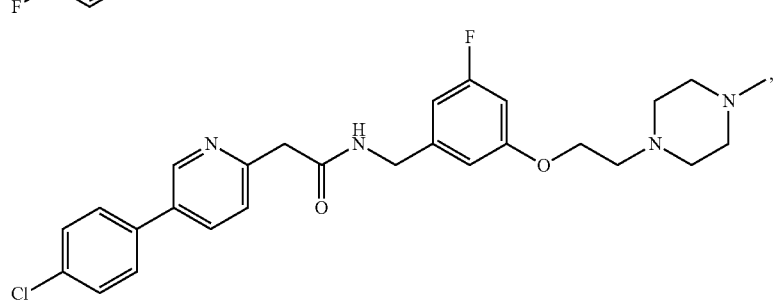

-continued
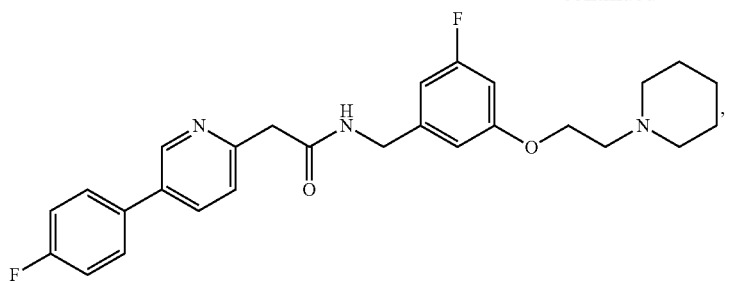
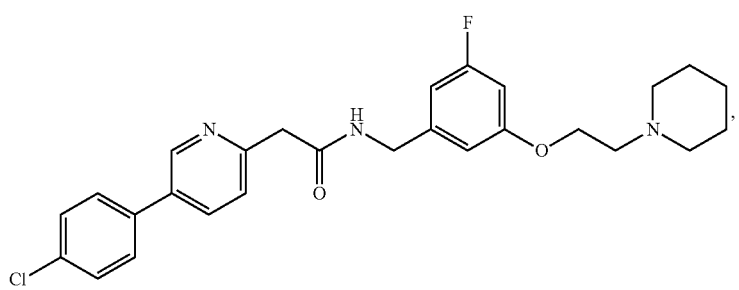
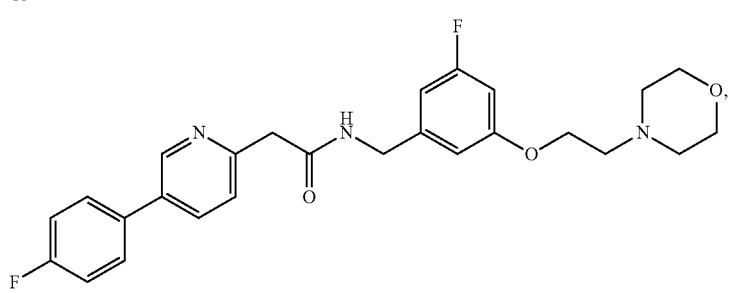
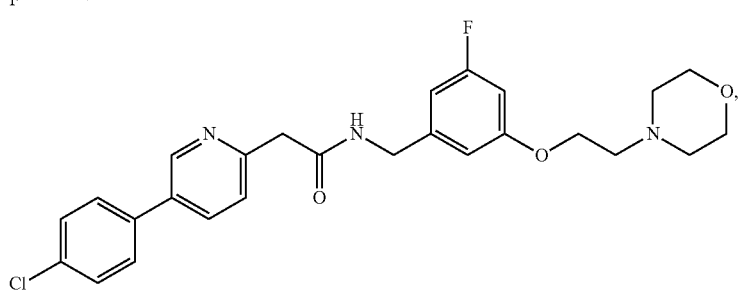
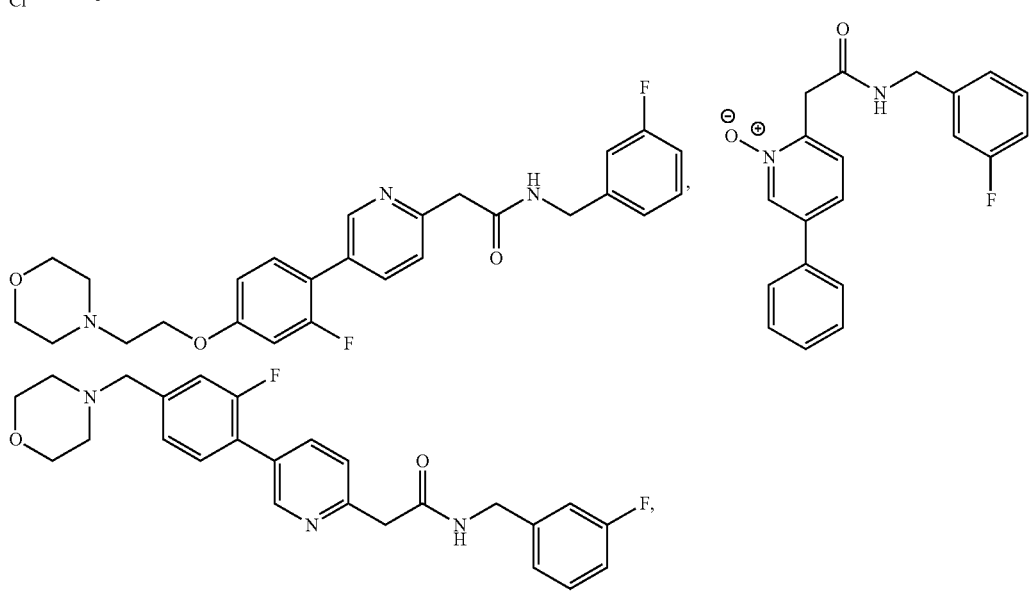

-continued
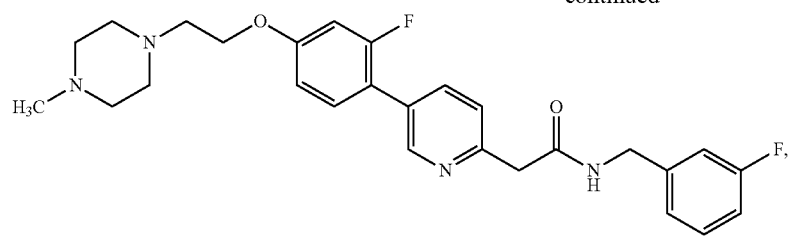
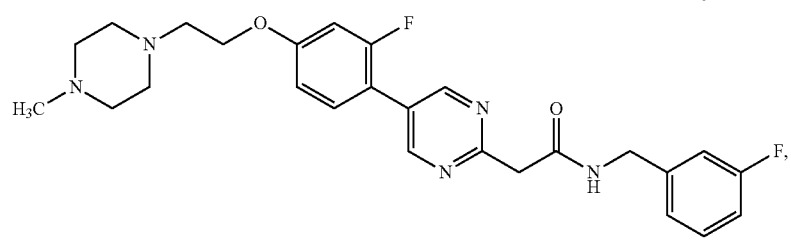
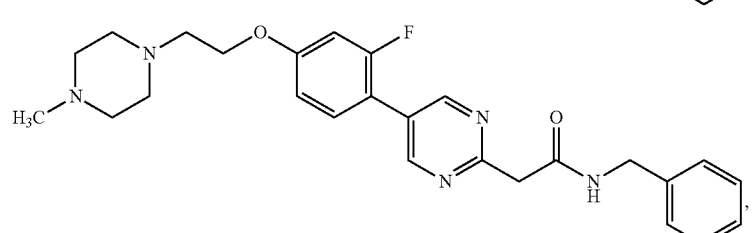
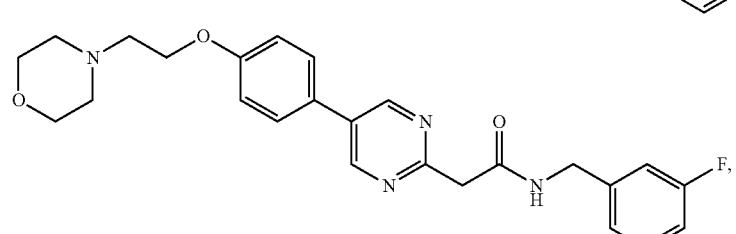
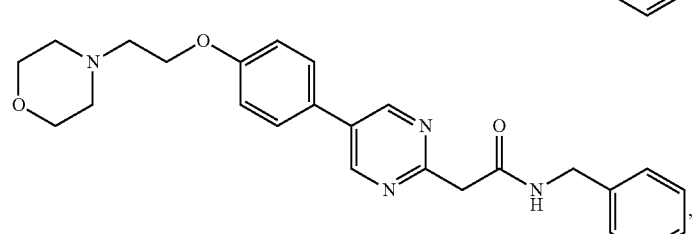
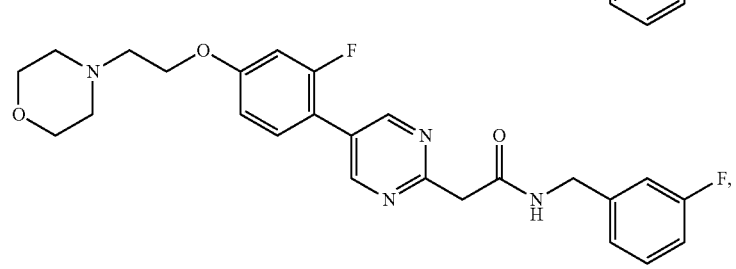
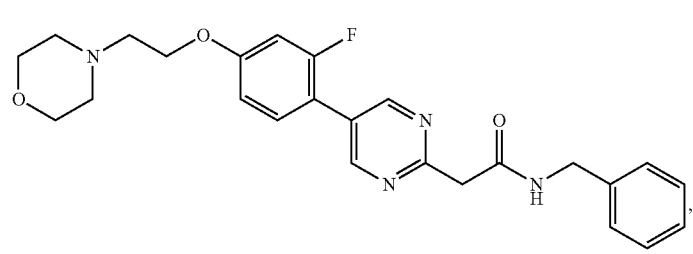

-continued
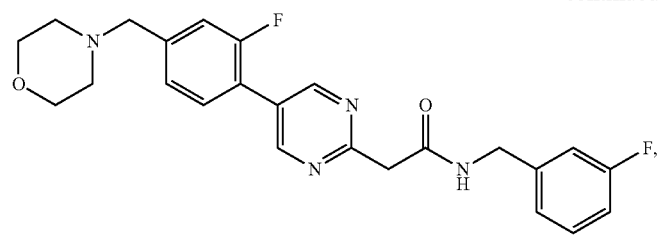
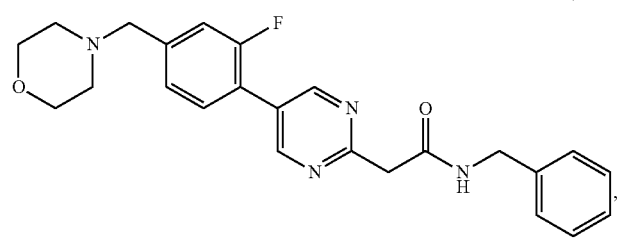
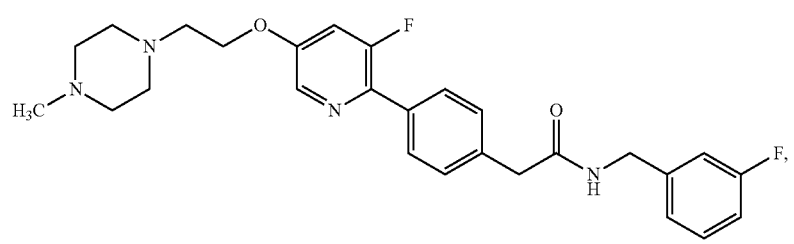
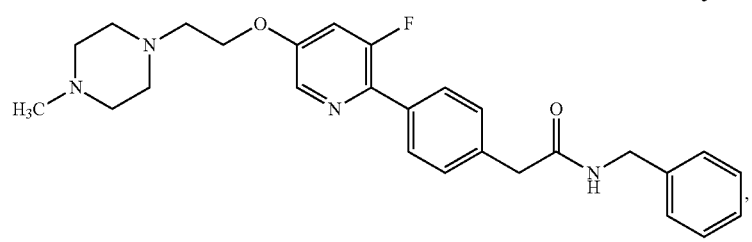
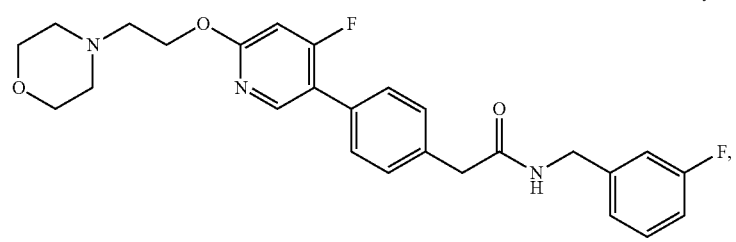
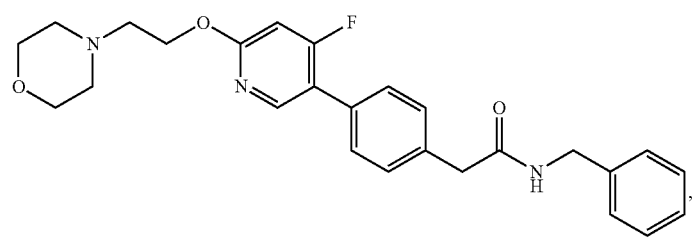
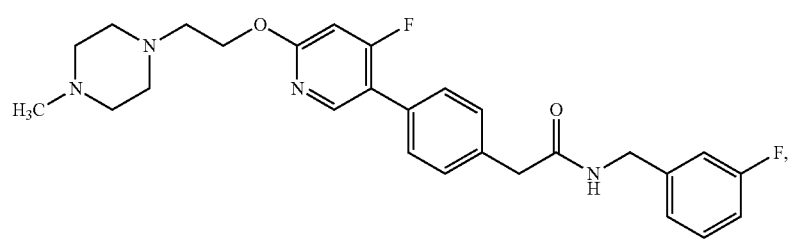

-continued
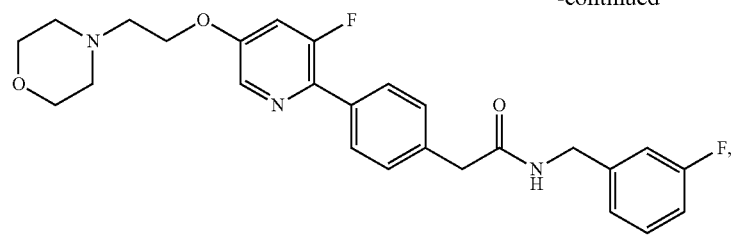
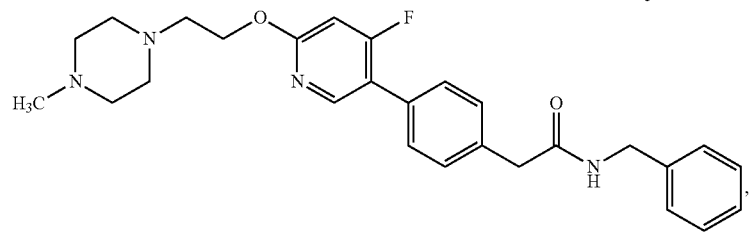
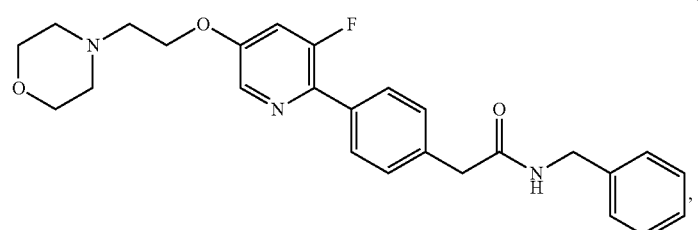
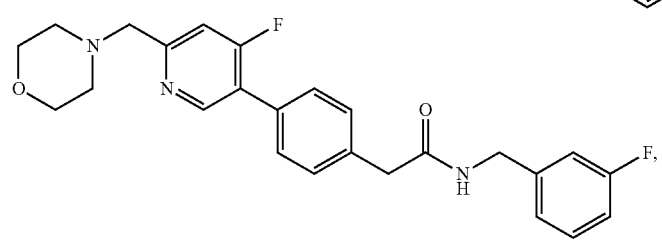
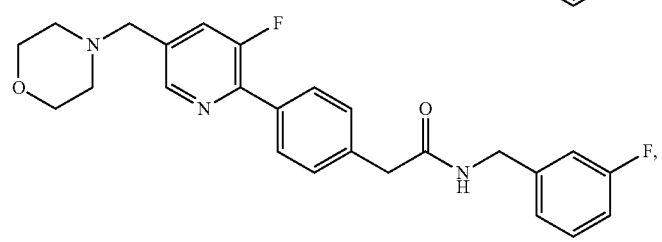
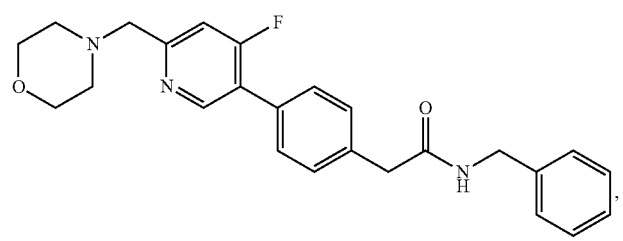
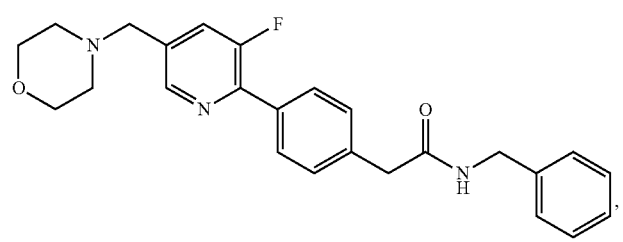

-continued
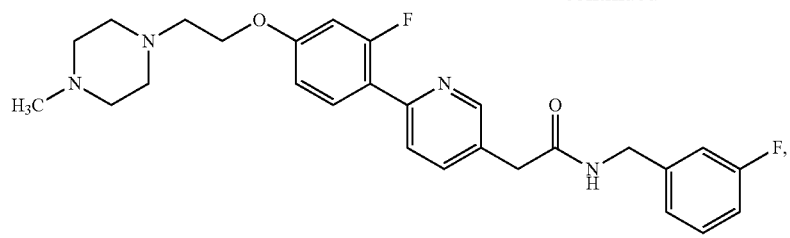
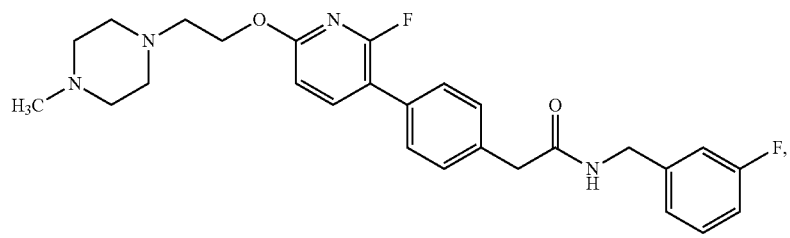
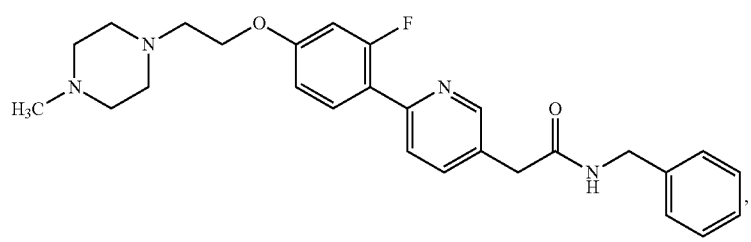
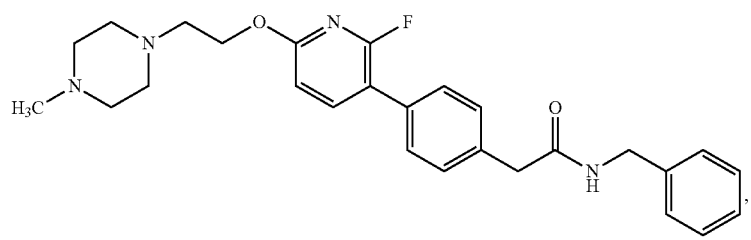
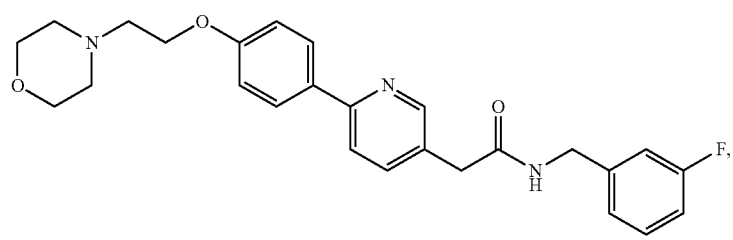
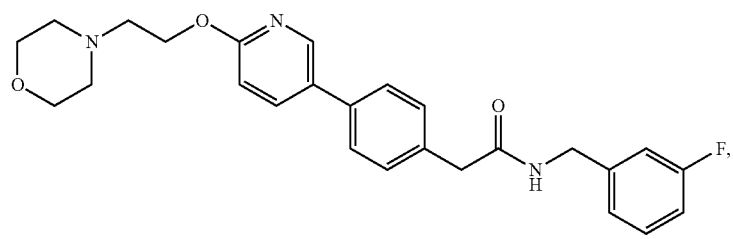
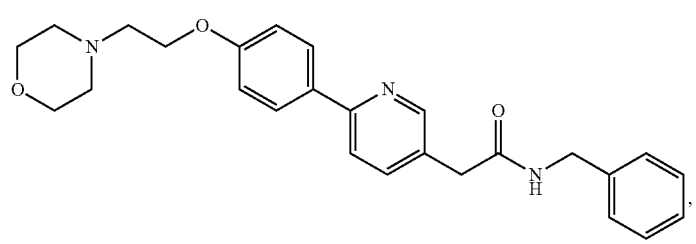

-continued
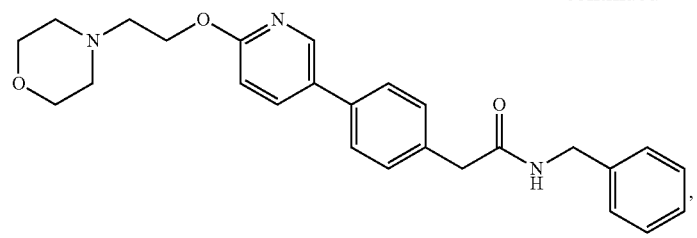
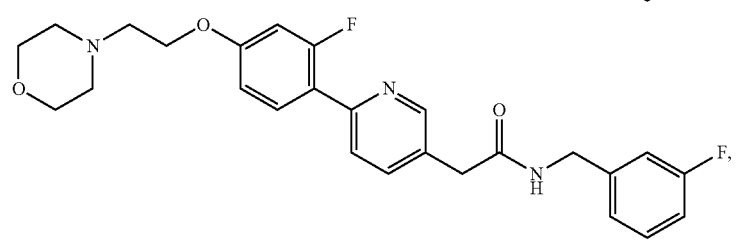
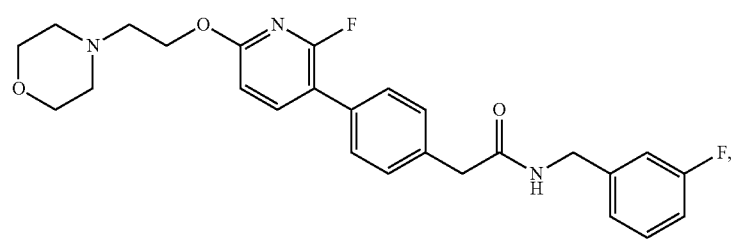
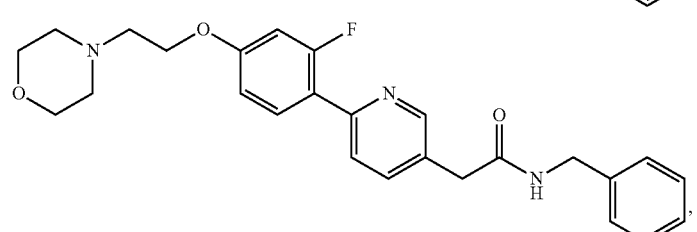
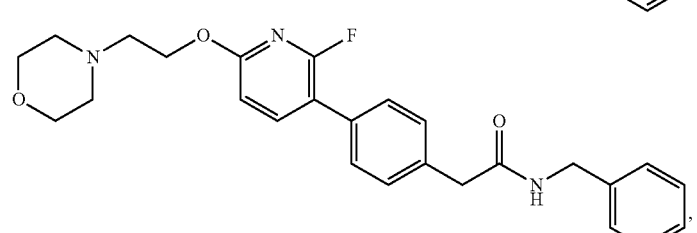
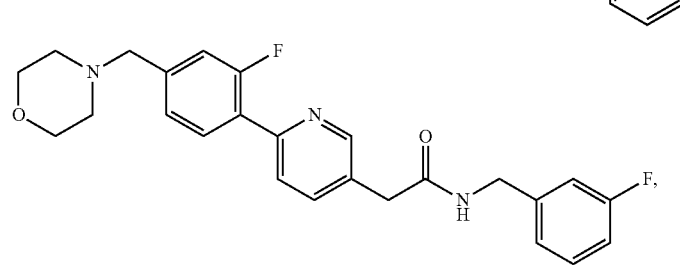
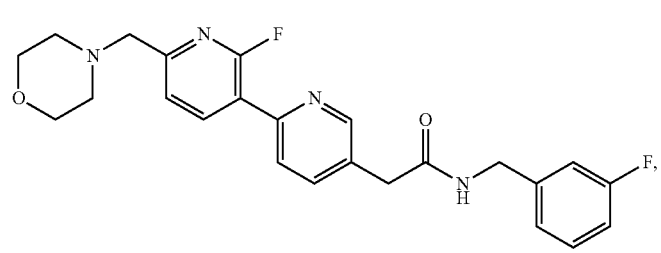

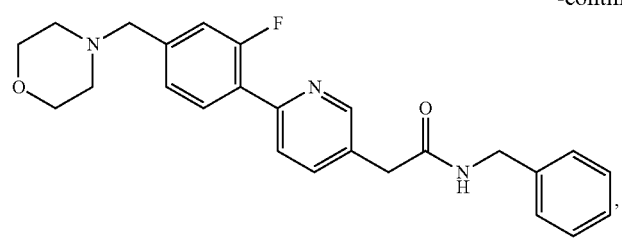
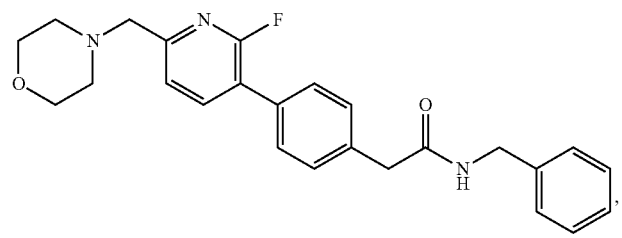
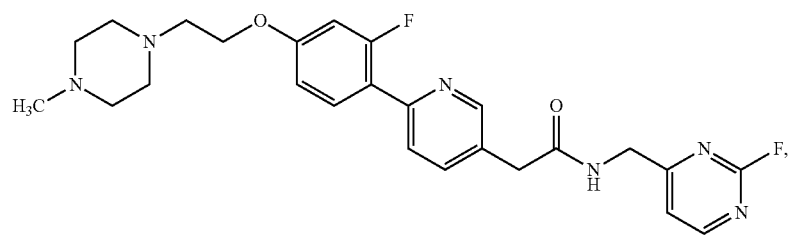
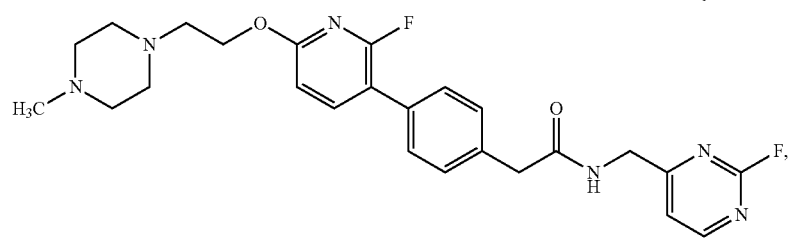
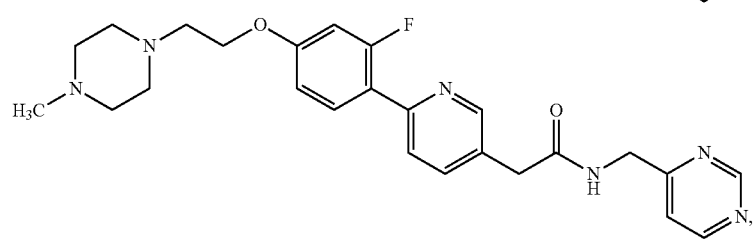
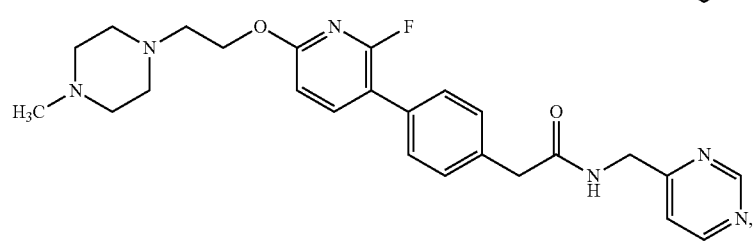
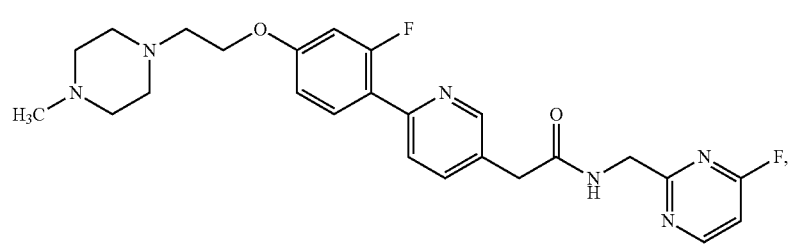

-continued
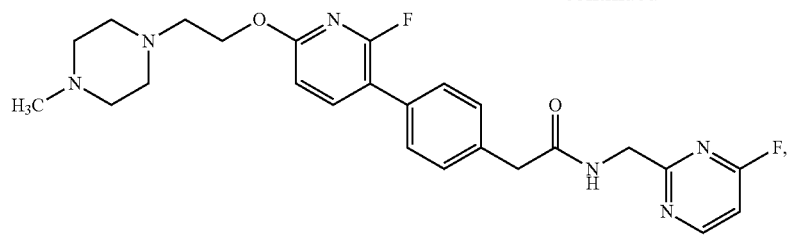
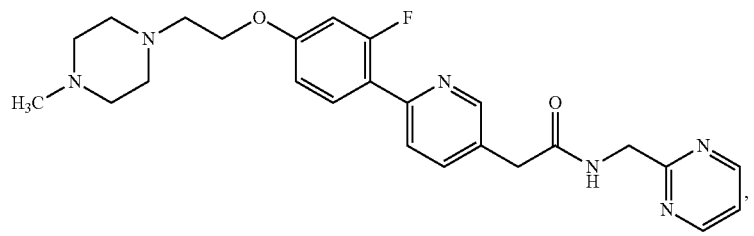
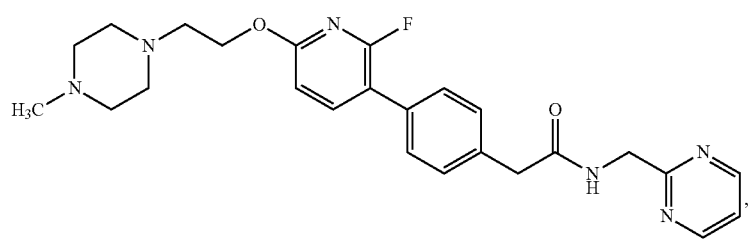
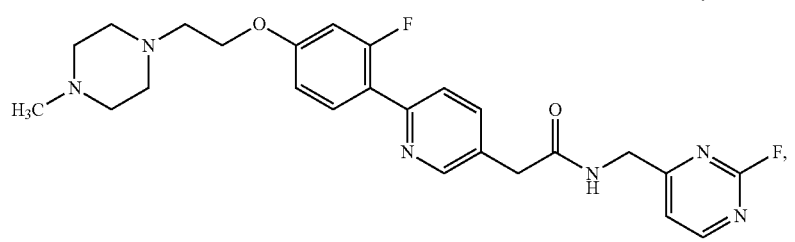
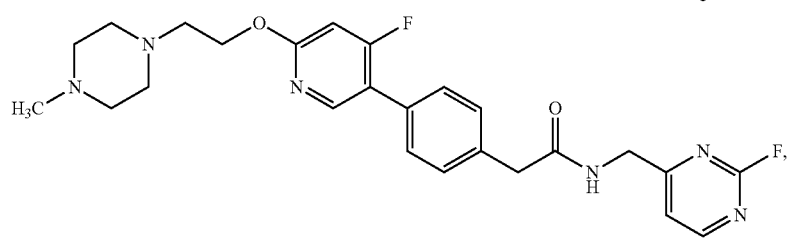
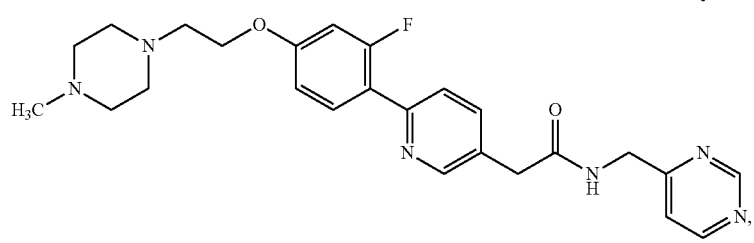
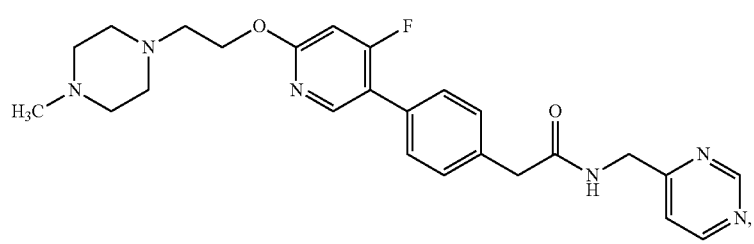

-continued

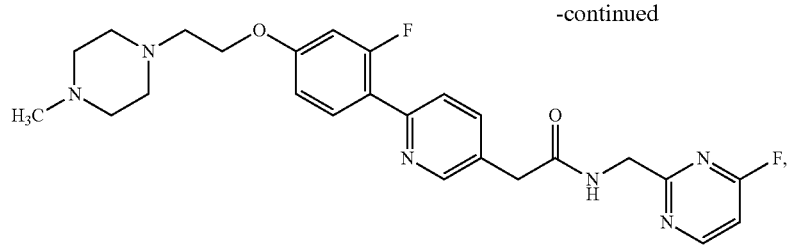

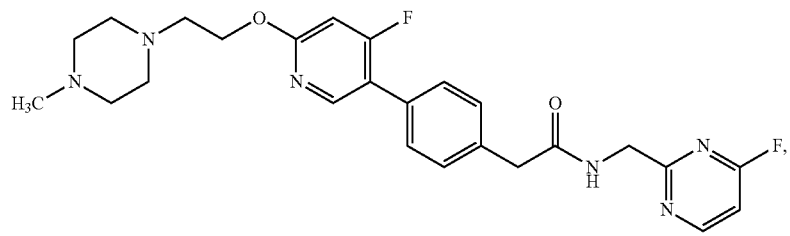

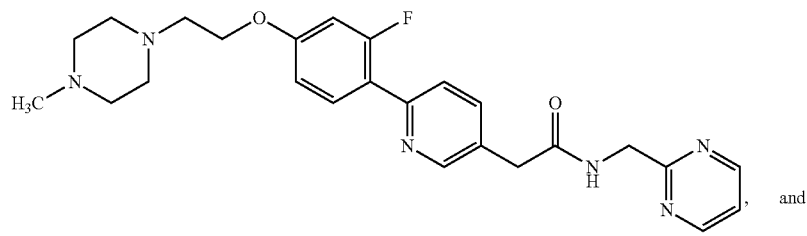

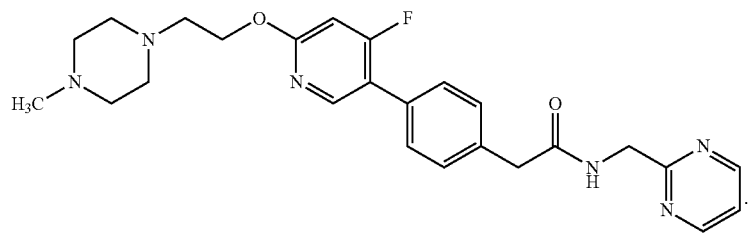

12. A compound according to Formula II:

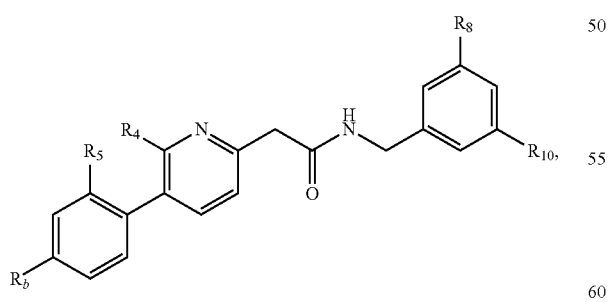

(II)

or a pharmaceutically acceptable salt, tautomer, or prodrug thereof, wherein:

$R_b$, $R_4$, $R_5$, $R_8$, and $R_{10}$ are, independently, hydrogen, hydroxyl, halogen, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, $C_1$, $C_2$, $C_3$, $C_4$, $C_5$, or $C_6$ alkyl-O-lower ($C_1$, $C_2$, $C_3$, $C_4$, $C_5$, or $C_6$) alkyl, COOH, COO-lower ($C_1$, $C_2$, $C_3$, $C_4$, $C_5$, or $C_6$) alkyl, $SO_2H$, or $SO_2$-lower ($C_1$, $C_2$, $C_3$, $C_4$, $C_5$, or $C_6$) alkyl,

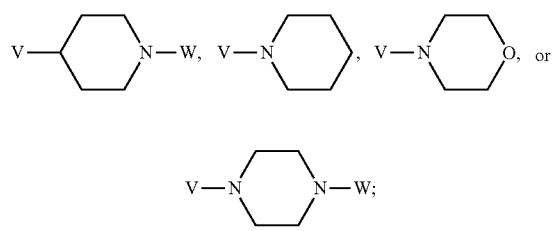

W is H, $C_1$, $C_2$, $C_3$, $C_4$, $C_5$, or $C_6$ alkyl, or $C_1$, $C_2$, $C_3$, $C_4$, $C_5$, or $C_6$ alkyl-aryl; and V is a bond, —$CH_2$—, —$CH_2CH_2$—, —$CH_2CH_2CH_2$—, —O—$CH_2$—, —$OCH_2CH_2$—, or —$OCH_2CH_2CH_2$—.

13. The compound of claim 1, having the formula:
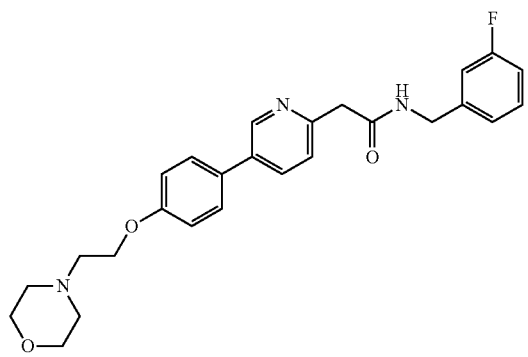 [SMILES: O=C(Cc1ccc(-c2ccc(OCCN3CCOCC3)cc2)cn1)NCc1cccc(F)c1]
or a pharmaceutically acceptable salt, tautomer or prodrug thereof.
14. A composition comprising the compound according to claim 13 and at least one pharmaceutically acceptable excipient.
15. The compound of claim 1, having the formula:
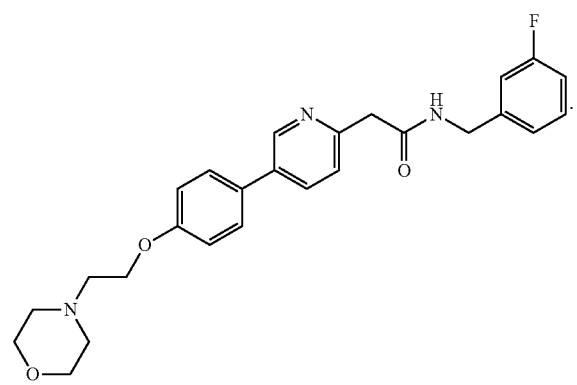 [SMILES: O=C(Cc1ccc(-c2ccc(OCCN3CCOCC3)cc2)cn1)NCc1cccc(F)c1]
16. A compound selected from:
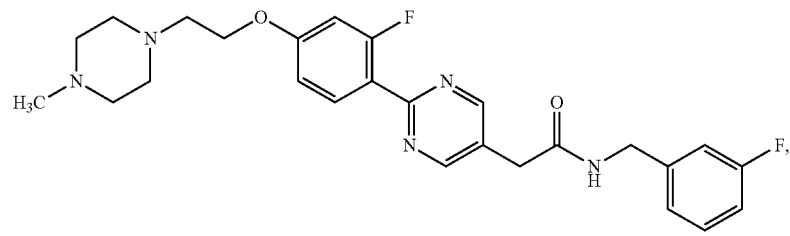
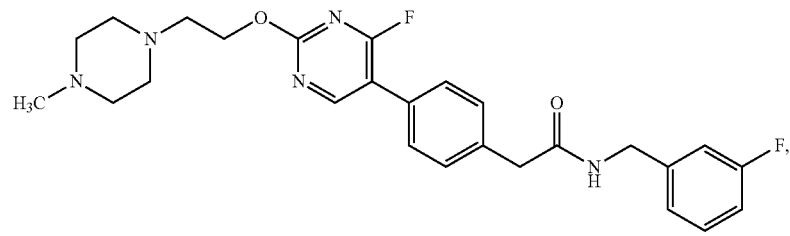
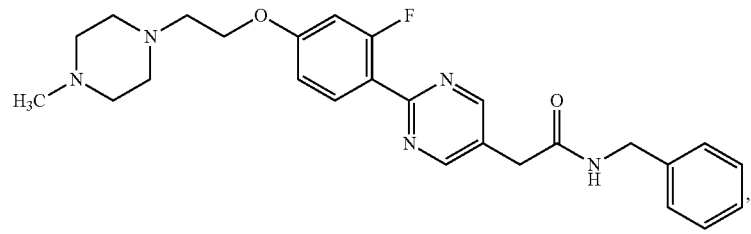
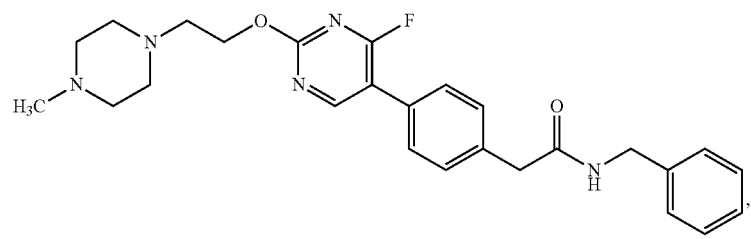

-continued
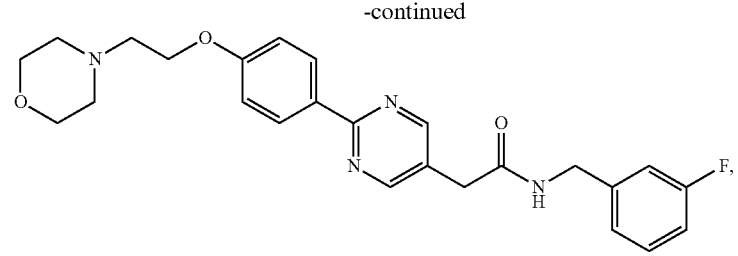
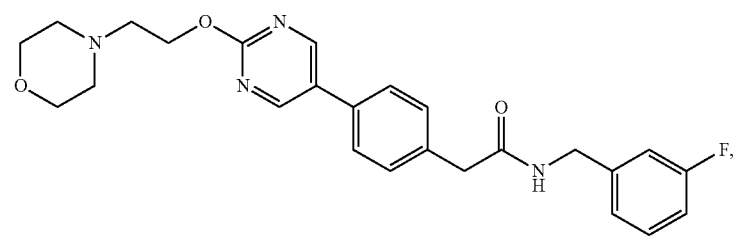
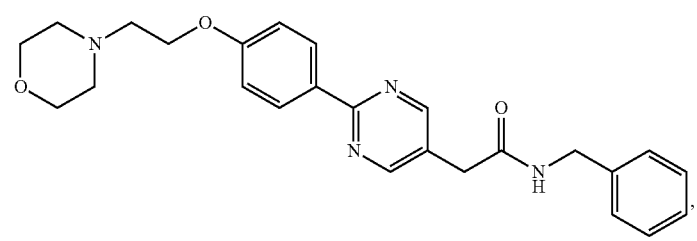
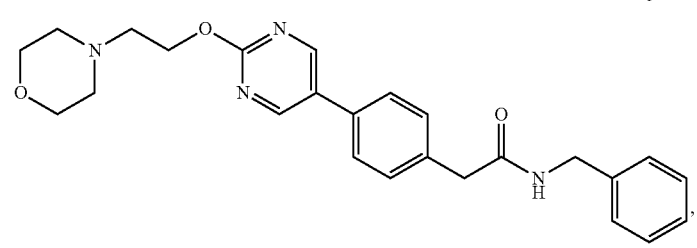
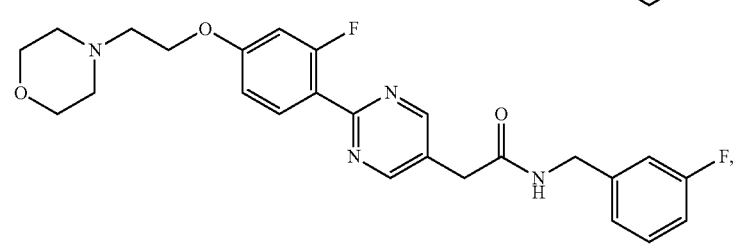
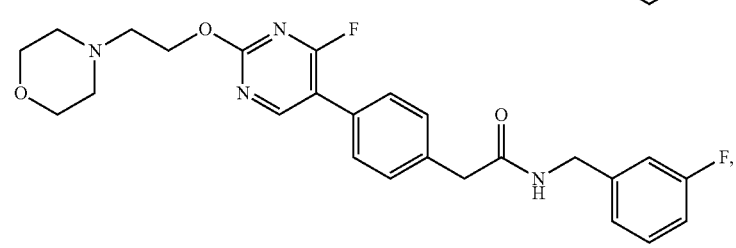
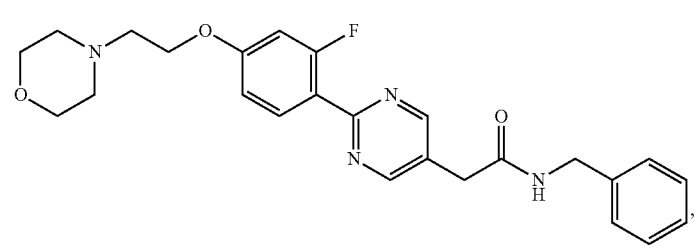

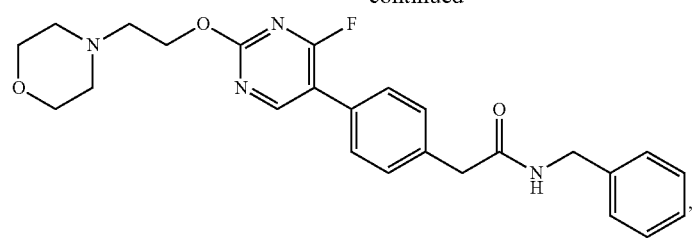
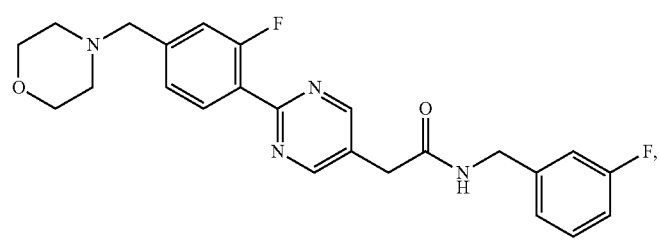
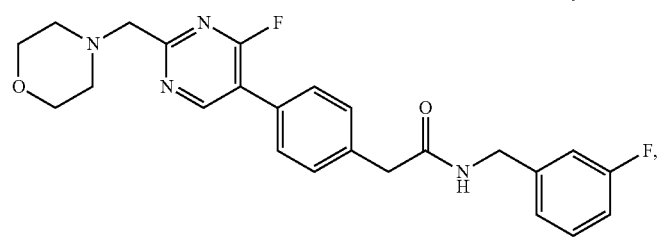
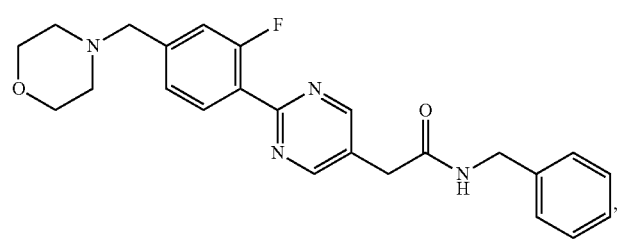
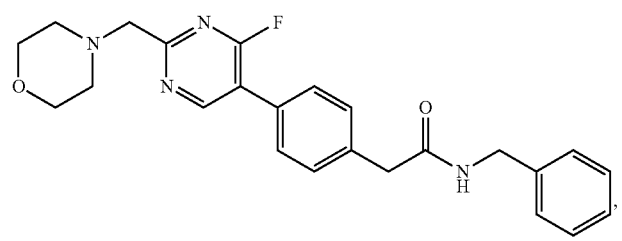
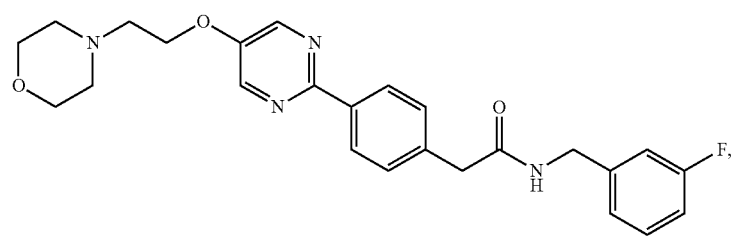
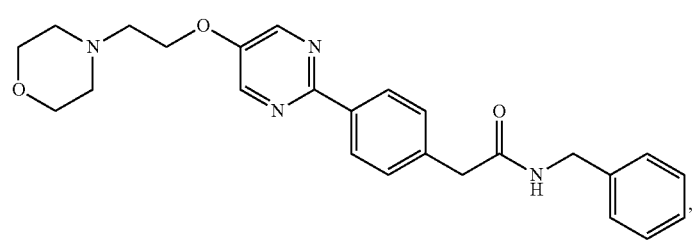

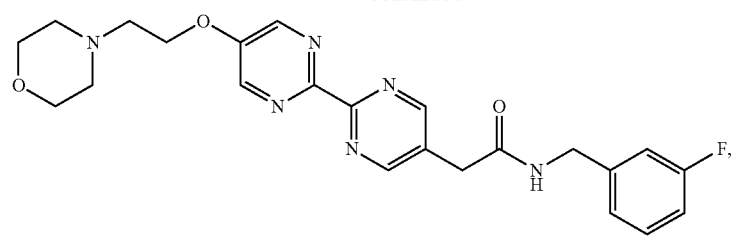
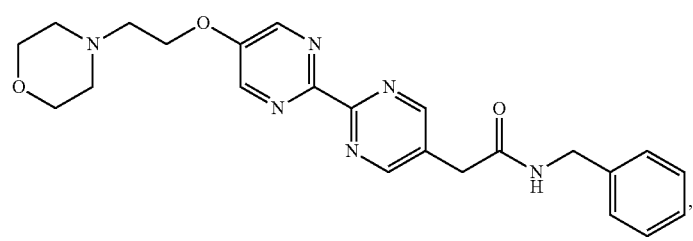
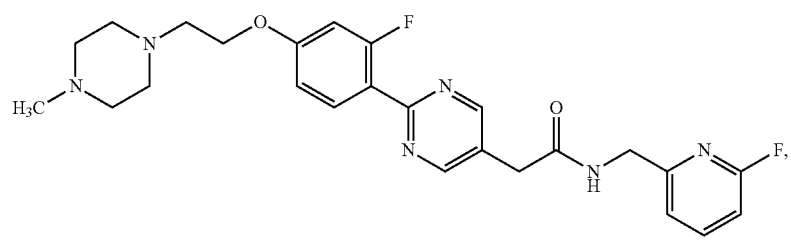
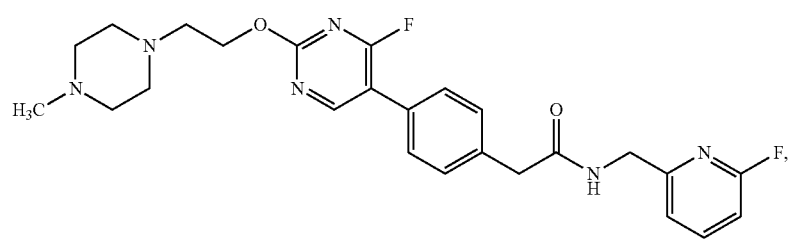
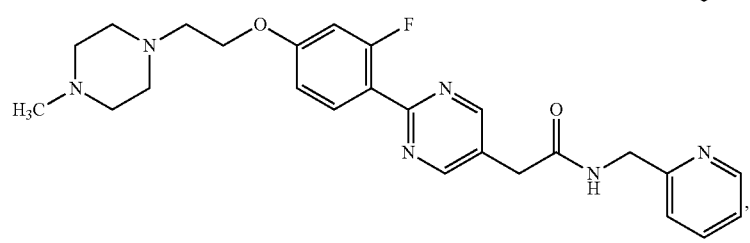
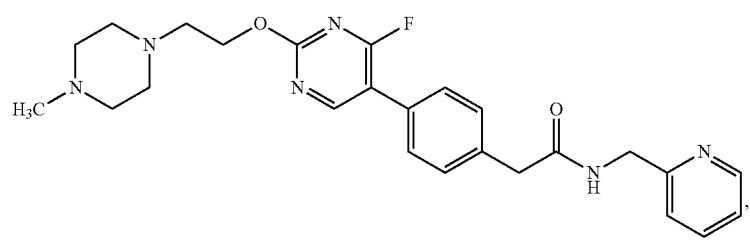
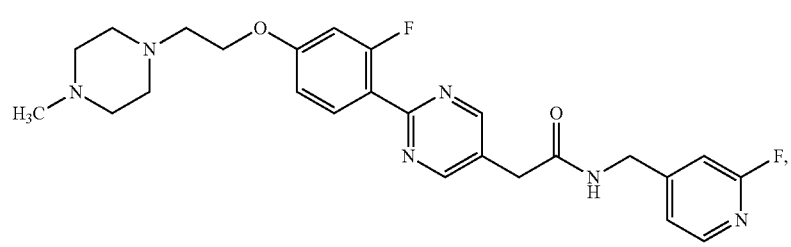

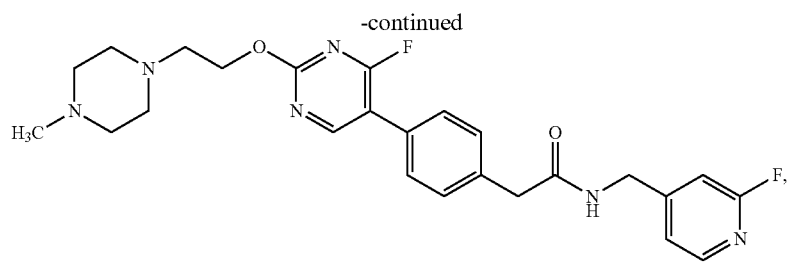
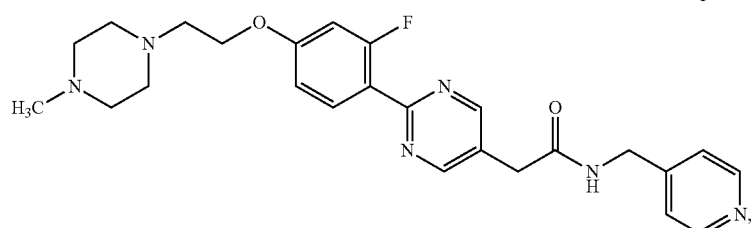
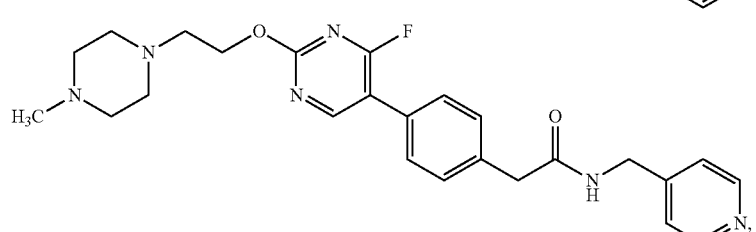
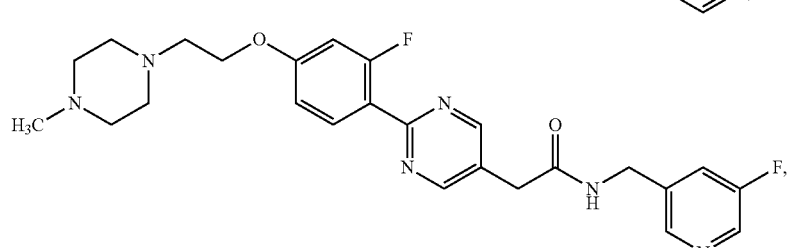
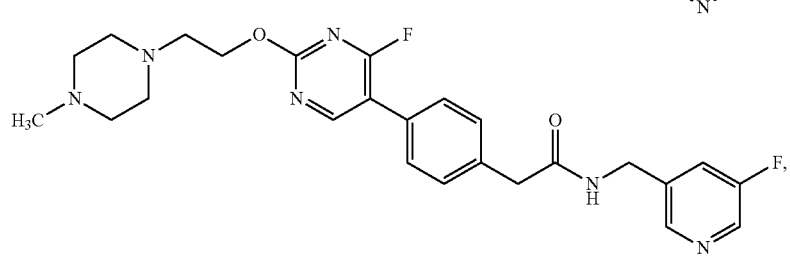
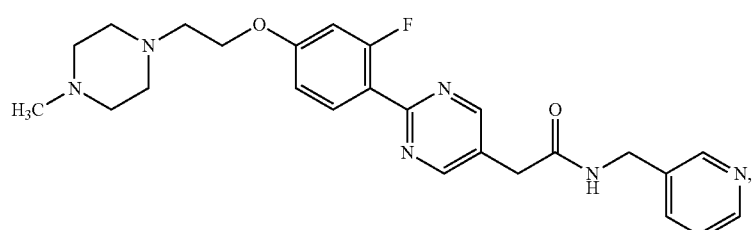
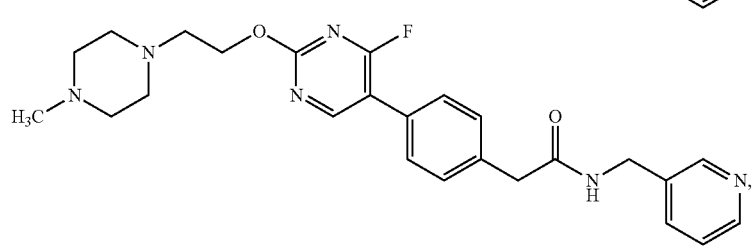

-continued
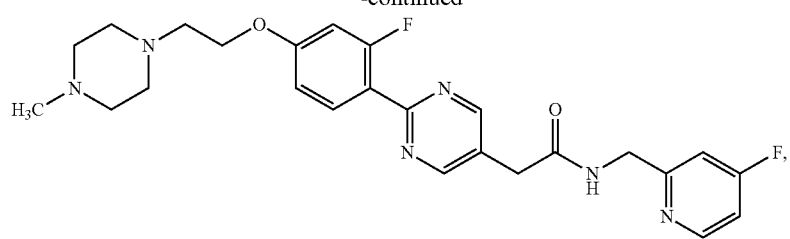
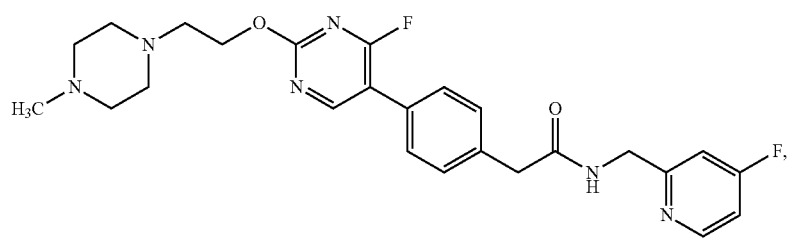
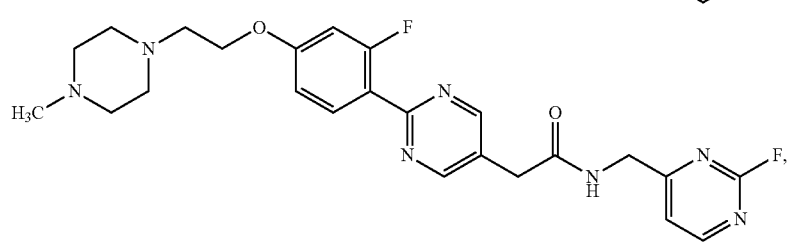
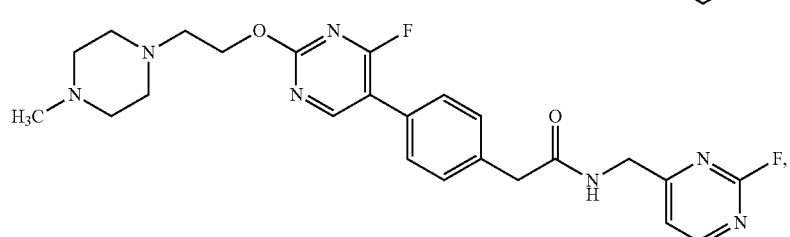
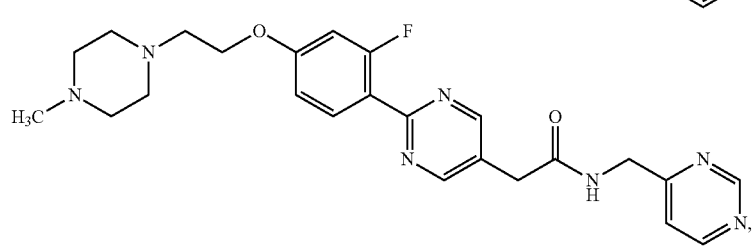
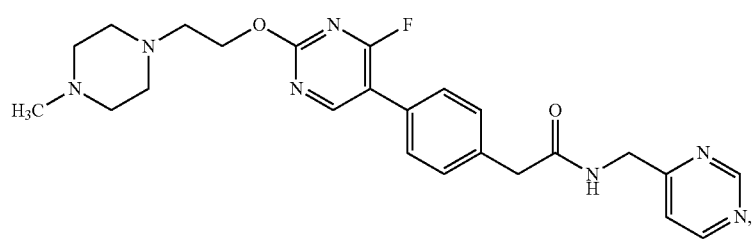
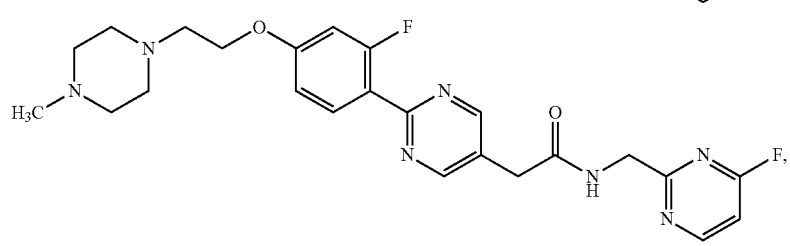

-continued
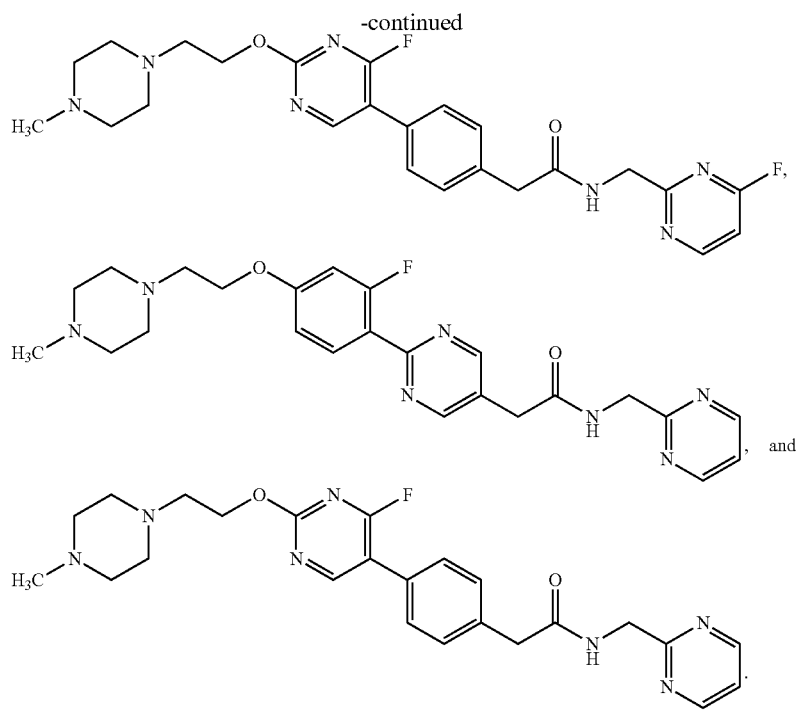
* * * * *